US010144730B2

(12) United States Patent
Gray et al.

(10) Patent No.: US 10,144,730 B2
(45) Date of Patent: Dec. 4, 2018

(54) INHIBITORS OF C-JUN-N-TERMINAL KINASE (JNK)

(71) Applicant: Dana-Farber Cancer Institute, Inc., Boston, MA (US)

(72) Inventors: Nathanael Gray, Boston, MA (US); Tinghu Zhang, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/188,545

(22) Filed: Jun. 21, 2016

(65) Prior Publication Data

US 2016/0368910 A1 Dec. 22, 2016

Related U.S. Application Data

(63) Continuation of application No. 14/358,606, filed as application No. PCT/US2012/065618 on Nov. 16, 2012, now Pat. No. 9,382,239.

(60) Provisional application No. 61/561,078, filed on Nov. 17, 2011.

(51) Int. Cl.
| A61K 31/506 | (2006.01) |
| C07D 417/06 | (2006.01) |
| A61K 31/437 | (2006.01) |
| A61K 31/444 | (2006.01) |
| C07D 401/04 | (2006.01) |
| C07D 403/04 | (2006.01) |
| C07D 403/06 | (2006.01) |
| C07D 471/04 | (2006.01) |
| C07D 417/04 | (2006.01) |

(52) U.S. Cl.
CPC .......... *C07D 417/06* (2013.01); *A61K 31/437* (2013.01); *A61K 31/444* (2013.01); *C07D 401/04* (2013.01); *C07D 403/04* (2013.01); *C07D 403/06* (2013.01); *C07D 417/04* (2013.01); *C07D 471/04* (2013.01); *Y02A 50/414* (2018.01)

(58) Field of Classification Search
CPC .. C07D 411/06; C07D 239/26; C07D 239/28; C07D 403/06; C07D 403/12
See application file for complete search history.

(56) References Cited

U.S. PATENT DOCUMENTS

| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |

(Continued)

FOREIGN PATENT DOCUMENTS

| CA | 2486101 A1 | 11/2003 |
| CA | 2503646 A1 | 5/2004 |

(Continued)

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
CAS Abstract GB 796,524 (1958).*
Z. Wang et al., 18 Bioorganic & Medicinal Chemistry, 4202-4211 (2010).*
B. Stanovinik et al.,91 Advances in Heterocyclic Chemistry, 1-134 (2006).*
T. Zhang et al., 19 Chemistry & Biology, 140-154 (Jan. 26, 2012).*
Z. Wang et al., 19 Drug Discovery Today, 145-150 (2014).*
U.K. Marelli et al., 3 Frontiers in Oncology, 1-12 (2013).*
W. Matsuyama et al., 172 The Journal of Immunology, 2332-2340 (2004).*

(Continued)

*Primary Examiner* — Alexander R Pagano
(74) *Attorney, Agent, or Firm* — Wolf, Greenfield & Sacks, P.C.

(57) ABSTRACT

The present invention provides novel compounds according to Formula (I):

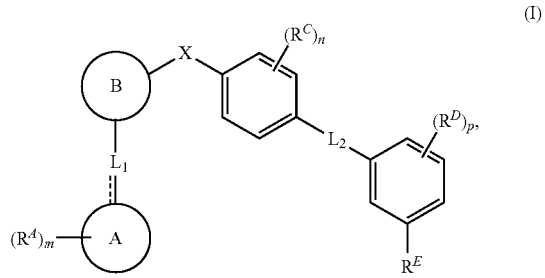

where Ring A, Ring B, X, $L_1$, $L_2$, $R^A$, $R^C$, $R^D$, $R^E$, m, n, and p are as defined herein. Compounds of the present invention are contemplated useful for the prevention and treatment of a variety of human diseases associated with kinase activity, for example, proliferative diseases, neurodegenerative diseases, metabolic disorders, inflammatory diseases, and cardiovascular diseases.

39 Claims, 19 Drawing Sheets

(56) References Cited

U.S. PATENT DOCUMENTS

| | | | |
|---|---|---|---|
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 * | 7/2016 | Gray ............... A61K 31/437 |
| 9,505,784 B2 | 11/2016 | Choi et al. |
| 9,670,165 B2 | 6/2017 | Cohen et al. |
| 9,758,522 B2 | 9/2017 | Gray et al. |
| 9,862,688 B2 | 1/2018 | Gray et al. |
| 2003/0139416 A1 | 7/2003 | Buchanan et al. |
| 2004/0106634 A1 | 6/2004 | Satoh et al. |
| 2004/0235892 A1 | 11/2004 | Yujia et al. |
| 2005/0026914 A1 | 2/2005 | Buchanan et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2010/0056524 A1 | 3/2010 | Mciver et al. |
| 2010/0197688 A1 | 8/2010 | Nantermet et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2017/0044111 A1 | 2/2017 | Gray et al. |
| 2017/0044112 A1 | 2/2017 | Gray et al. |

FOREIGN PATENT DOCUMENTS

| | | | |
|---|---|---|---|
| CA | 2526430 A1 | 12/2004 |
| CA | 2550128 A1 | 6/2005 |
| CA | 2563212 A1 | 10/2005 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| GB | 796524 A | * | 6/1958 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/06138 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |

(56) References Cited

FOREIGN PATENT DOCUMENTS

| | | |
|---|---|---|
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 2000/50032 A1 | 8/2000 |
| WO | WO 00/61186 A1 | 10/2000 |
| WO | WO 2001/02369 A2 | 1/2001 |
| WO | WO 01/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 2002/083653 A1 | 10/2002 |
| WO | WO 02/096905 A1 | 12/2002 |
| WO | WO 02/102800 A1 | 12/2002 |
| WO | WO 03/018021 A1 | 3/2003 |
| WO | WO 03/018022 A1 | 3/2003 |
| WO | WO 03/026664 A1 | 4/2003 |
| WO | WO 03/051847 A1 | 6/2003 |
| WO | WO 2003/078403 A2 | 9/2003 |
| WO | WO 03/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/039796 A1 | 5/2004 |
| WO | WO 2004/078757 A2 | 9/2004 |
| WO | WO 2004/087699 A2 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 | 7/2008 |
| WO | WO 2008/112913 | 9/2008 |
| WO | WO 2008/124393 | 10/2008 |
| WO | WO 2008/144253 | 11/2008 |
| WO | WO 2008/151183 | 12/2008 |
| WO | WO 2009/017822 | 2/2009 |
| WO | WO 2009/028655 | 3/2009 |
| WO | WO 2009/032694 | 3/2009 |
| WO | WO 2009/145360 | 12/2009 |
| WO | WO 2009/152027 A1 | 12/2009 |
| WO | WO 2009/155017 | 12/2009 |
| WO | WO 2010/008847 | 1/2010 |
| WO | WO 2010/051781 | 5/2010 |
| WO | WO 2010/125799 | 11/2010 |
| WO | WO 2010/144909 | 12/2010 |
| WO | WO 2011/115725 A2 | 9/2011 |
| WO | WO 2013/014162 | 1/2013 |
| WO | WO 2013/040436 | 3/2013 |
| WO | WO 2013/074986 | 5/2013 |
| WO | WO 2013/136070 | 9/2013 |
| WO | WO 2013/154778 | 10/2013 |
| WO | WO 2014/063061 | 4/2014 |
| WO | WO 2014/063068 | 4/2014 |
| WO | WO 2015/013635 A2 | 1/2015 |
| WO | WO 2015/058126 | 4/2015 |
| WO | WO 2015/058140 | 4/2015 |
| WO | WO 2015/117087 A1 | 8/2015 |
| WO | WO 2015/154022 | 10/2015 |
| WO | WO 2015/164604 | 10/2015 |
| WO | WO 2015/164614 | 10/2015 |
| WO | WO 2016/014542 | 1/2016 |
| WO | WO 2016/014551 | 1/2016 |
| WO | WO 2016/023014 | 2/2016 |
| WO | WO 2016/105528 | 6/2016 |

OTHER PUBLICATIONS

G. Fan et al., The Journal of Biological Chemistry, 24788-24793 (1996).*
J.A. Bloom et al., 21 Genes & Development, 2593-2606 (2007).*
S. Hirai et al., 26 The Journal of Neuroscience, 11992-12002 (2006).*
A. Itoh et al, 383 Biochemical and Biophysical Research Communications, 258-262 (2009).*
X. Chen, 28 The Journal of Neuroscience, 672-680 (2008).*
A. Sengupta et al., The Journal of Cell Biology, 751-764 (2011).*
J.E. Shin et al., 74 Neuron, 1015-1022 (2012).*
N. Beeler et al., 80 Brain Research Bulletin, 274-281 (2009).*
K. Fernandes et al., 46 Neurobiology of Disease, 393-401 (2012).*
S. Akira et al, 4 Nature Reviews | Immunology, 499-511 (2004).*
R. Srivastava et al., 72 Cancer Research, 6209-6216 (2012).*
J.P. Powers et al., 16 Bioorganic & Medicinal Chemistry Letters, 2842-2845 (2006).*
E-H Joh et al., 82 Biochemical Pharmacology, 278-286 (2011).*
Z. Wang et al., 9 Current Topics in Medicinal Chemistry, 724-737 (2009).*
K Kanakaraj et al., Journal of Experimental Medicine, 2073-2079 (1998).*
C. Wietek et al., IRAK-4: A New Drug Target in Inflammation, Sepsis, and Autoimmunity, 2 Molecular interventions, 212 (2002).*
G. Roberts et al., 65 Cancer Research, 957-966 (2005).*
S. Attoub et al., 62 Cancer Research, 4879-4883 (2002).*
B.P. Rubin et al., 61 Cancer Research, 8118-8121 (2001).*
R.D. Carvajal et al., 305 Journal of the American Medical Association, 2327-2334 (2011).*
A. Yasuda et al., 5 Molecular Cancer, 1-10 (2006) (pancreatic cancer cell lines).*
G. Di Lorenzo et al., 30 European Journal of Surgical Oncology, 987-992 (2004).*
International Search Report and Written Opinion for PCT/US2012/065618, dated Mar. 19, 2013.
International Preliminary Report on Patentability for PCT/US2012/065618, dated May 30, 2014.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.

(56) References Cited

OTHER PUBLICATIONS

International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Invitation to Pay Additional Fees for PCT/US2015/041360, dated Sep. 24, 2015.
International Search Report and Written Opinion for PCT/US2015/041360, dated Dec. 16, 2015.
International Preliminary Report on Patentability for PCT/US2015/041360, dated Feb. 2, 2017.
International Search Report and Written Opinion for PCT/US2015/41348, dated Oct. 28, 2015.
International Preliminary Report on Patentability for PCT/US2015/41348, dated Feb. 2, 2017.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Search Report and Written Opinion for PCT/US2016/037086, dated Sep. 2, 2016.
Invitation to Pay Additional Fees for PCT/US2016/024345, dated Aug. 9, 2016.
International Search Report and Written Opinion for PCT/US2016/024345, dated Oct. 6, 2016.
Invitation to Pay Additional Fees for PCT/US2016/051118, dated Dec. 1, 2016.
International Search Report and Written Opinion from PCT/US2016/051118, dated Mar. 13, 2017.
International Search Report and Written Opinion from PCT/US2011/025423, dated Nov. 5, 2012.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
CAS Registry No. 1334419-59-8, STN Entry Date Dec. 30, 2013.
PubChem-CID-68365059. Available at https://pubchem.ncbi.nlm.nih.gov/compound/68365059. Accessed Jun. 17, 2016.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. OpthamoL Apr. 1990;108(4):573-6.
Berge et al., Pharmaceutical salts. J. Pharmaceutical Sciences 1977 66:1-19.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chiarugi et al., Cox-2, iNOS and p53 as play-makers of tumor angiogenesis. International Journal of Molecular Medicine 1998;2:715-9.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials. 16 pages.
Chong et al., Positive and negative regulation of Raf kinase activity and function by phosphorylation EMBO J. Jul. 16, 2001;20(14):3716-27.
Christensen et al., Targeting transcriptional addictions in small cell lung cancer with a covalent CDK7 inhibitor. Cancer Cell. Dec. 8, 2014;26(6):909-22.
Davies et al., Mutations of the BRAF gene in human cancer Nature. Jun. 27, 2002;417(6892):94954. Epub Jun. 9, 2002.
Davis et al., Comprehensive analysis of kinase inhibitor selectivity. Nat Biotechnol Oct. 30, 2011;29(10:1046-51. doi: 10.1038/nbt. 1990.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Ercan et al., Reactivation of ERK signaling causes resistance to EGFR kinase inhibitors. Cancer Discov. Oct. 2012;2(10):934-47.
Fernandez et al., Neovascularization produced by angiotensin I.Journal of Laboratory and Medicine 1985;105(2):141-5.
Filippakopoulos et al., Selective inhibition of BET bromodomains. Nature. Dec. 23, 2010;468(7327):1067-73.
Fleisher et al., Improved oral drug delivery: solubility limitations overcome by the use of prodrugs. Advanced Drug Delivery Reviews 1996;19:115-30.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hla et al., Human cyclooxygenase-2 cDNA. Proceedings of the National Academy of Sciences 1992;89(16):7384-8.

(56) References Cited

OTHER PUBLICATIONS

Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kantarjian et al., Dasatinib versus imatinib in newly diagnosed chronic-phase chronic myeloid leukemia. N Engl J Med. Jun. 17, 2010;362(24):2260-70.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Lee et al., BRAF mutations in non-Hodgkin's lymphoma. Br J Cancer. Nov. 17, 2003;89(10):1958-60.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Mukaiyama et al., The unexpected and the unpredictable in organic synthesis. Tetrahedron Jul. 1999;55(29):8609-70.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sharma et al., A chromatin-mediated reversible drug-tolerant state in cancer cell subpopulations. Cell. Apr. 2, 2010;141(1):69-80.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Terai et al., Activation of the FGF2-FGFR1 autocrine pathway: a novel mechanism of acquired resistance to gefitinib in NSCLC. Mol Cancer Res. Jul. 2013;11(7):759-67.
Tsujii et al., Cyclooxygenase regulates angiogenesis induced by colon cancer cells. Cell. May 29, 1998;93(5):705-16.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Zebisch et al., Back to the roots: the remarkable RAF oncogene story Cell Mol Life Sci. Jun. 2006;63(11):1314-30.
Zhang et al., Discovery of potent and selective covalent inhibitors of JNK. Chem Biol. Jan. 27, 2012;19(1):140-54. doi: 10.1016/j.chembiol.2011.11.010.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
International Preliminary Report on Patentability PCT/US2015/000297, dated Jul. 6, 2017.
International Search Report and Written Opinion for PCT/US2016/051118, dated Mar. 13, 2017.
Invitation to Pay Additional Fees for PCT/US2011/025423, dated May 31, 2011.
International Preliminary Report on Patentability PCT/US2011/025423, dated Nov. 29, 2012.
GenBank Accession No. M80629. Lapidot-Lifson et al., Dec. 31, 1994. 2 pages.
GenBank Accession No. NP_001790. Yang et al., Oct. 6, 2016. 4 pages.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.

(56) References Cited

OTHER PUBLICATIONS

Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Cappuzzo et al., Increased MET gene copy number negatively affects survival of surgically resected non-small-cell lung cancer patients. J Clin Oncol. Apr. 1, 2009;27(10):1667-74. doi: 10.1200/X0.2008.19.1635. Epub Mar. 2, 2009.
Chen et al., Cdk12 and Cdk13 regulate axonal elongation through a common signaling pathway that modulates Cdk5 expression. Exp Neural. Nov. 2014;261:10-21. doi: 10.1016/j.expneurol.2014.06.024. Epub Jul. 3, 2014.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Christensen et al., Cytoreductive antitumor activity of PF-2341066, a novel inhibitor of anaplastic lymphoma kinase and c-Met, in experimental models of anaplastic large-cell lymphoma. Mal Cancer Ther. Dec. 2007;6(12 Pt 1):3314-22.
Christian et al., Flavopiridol in chronic lymphocytic leukemia: a concise review. Clin Lymphoma Myeloma. 2009;9 Suppl 3:8179-85. doi: 10.3816/CLM.2009.s.009.
Desai et al., Effects of phosphorylation by CAK on cyclin binding by CDC2 and CDK2. Mol Cell Biol. Jan. 1995;15(1):345-50.
Drapkin et al., Human cyclin-dependent kinase-activating kinase exists in three distinct complexes. Proc Natl Acad Sci USA. Jun. 25, 1996;93(13):6488-93.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Kaldis et al., Analysis of CAK activities from human cells. Eur J Biochem. Jul. 2000;267(13):4213-21.
Kauraniemi et al., New amplified and highly expressed genes discovered in the ERBB2 amplicon in breast cancer by cDNA microarrays. Cancer Res. Nov. 15, 2001;61(22):8235-40.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Larochelle et al., Requirements for Cdk7 in the assembly of Cdkl/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Marques et al., A new subfamily of high molecular mass CDC2-related kinases with PITAI/VRE motifs. Biochem Biophys Res Commun. Dec. 29, 2000;279(3):832-7.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Serizawa et al., Association of Cdk-activating kinase subunits with transcription factor TFIIH. Nature. Mar. 16, 1995;374(6519):280-2.
Shiekhattar et al., Cdk-activating kinase complex is a component of human transcription factor TFIIH. Nature. Mar. 16, 1995;374(6519):283-7.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wilen et al., Strategies in optical resolutions. Tetrahedron 33:2725 (1977).
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al. Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
International Preliminary Report on Patentability for PCT/US/2016/037086, dated Dec. 21, 2017.
International Preliminary Report on Patentability for PCT/US2016/024345, dated Oct. 12, 2017.

\* cited by examiner

| Kinase Family | Kinase | Labeling Site | JNK-IN-6 | JNK-IN-7 | JNK-IN-8 | JNK-IN-11 | JNK-IN-12 |
|---|---|---|---|---|---|---|---|
| CMCG | JNK1,JNK2,JNK3 | Lys2 | 27.3 | 99.7 | 93.7 | 99.8 | 98.6 |
|  | p38a | Lys2 | 32.6 | 16.4 | 13.2 | 95.9 | 12.2 |
|  | p38a | Other | 12.4 | 14.7 | 3.9 | 98.9 | 55.3 |
|  | GSK3A | Lys2 | 6.8 | 20.4 | 10.6 | 40.7 | 77.7 |
|  | GSK3B | Lys2 | 23.6 | 12.3 | -8.5 | 67.1 | 82.6 |
|  | PFTAIRE1 | Lys1 | -6 | 75.3 | 38.1 | 12.8 | 38.3 |
|  | CDK9 | Lys2 | -7.6 | 16.6 | 34.1 | 23.4 | 62.4 |
| AGC | ROCK1 | Other | 24.4 | -11.9 | 10 | 8.2 | 7.9 |
|  | ROCK1,ROCK2 | Lys2 | 11.6 | -21.5 | -17.1 | 33.9 | 71.9 |
| Lipid | PIP5K3 | ATP | 16.8 | 99.8 | 18.7 | 99.3 | 23.6 |
|  | PIK3C3 | ATP | 26.5 | 77.5 | 18.1 | 8.9 | 23.3 |
|  | PIK3C3 | ATP | 3.1 | 74.2 | 6.4 | -11 | 30.2 |
|  | PIP4K2C | ATP | -4.7 | 11.5 | 1.9 | -4.4 | 61.4 |
|  | PIP4K2C | ATP | 35.7 | 84.3 | 32.2 | 24.3 | 85.3 |
|  | DNAPK | ATP | 51.1 | 17.4 | 34.9 | 23.3 | 76.2 |
|  | DNAPK | ATP | 31.7 | 18.4 | 10.5 | -9.4 | 89.3 |
|  | ITPK1 | ATP | 27 | -0.2 | 24.6 | -0.7 | 60.1 |
| CAMK | PKD2 | Lys1 | 12 | 13.6 | 4.9 | 40.9 | 80.9 |
|  | PKD1 | Lys1 | 28.7 | 2 | 8.6 | 29.4 | 83.2 |
|  | PKD1,PKD2 | Lys2 | 15.9 | 18.2 | -3 | 10.4 | 75.4 |
|  | MARK1 | Lys1 | 23.9 | 7.9 | 8.9 | 18.6 | 88.7 |
|  | MARK2 | Lys1 | 13.4 | 23.6 | 9.6 | 20.8 | 61.7 |
|  | MARK3 | Lys2 | 22.9 | 26.5 | 13.9 | 0.4 | 80.3 |
|  | MARK2,MARK3 | Lys2 | -7.3 | -13.5 | -1.2 | -27.8 | 83.7 |
|  | PHKg2 | Lys1 | 28 | -7 | -0.8 | -7.6 | 86.2 |
| CK1 | CK1a | Lys2 | 19.5 | -20.2 | -13.6 | 61.1 | 34.5 |
|  | CK1d,CK1e | Lys2 | 32.4 | 8.4 | -21.8 | 88.4 | 10.1 |
| Other | AurA | ATP Loop | 9.9 | 20.9 | -8 | 68.2 | 81 |
|  | AurA,AurB,AurC | Lys2 | 4.9 | 19.1 | -11.3 | 53.8 | 77.4 |
|  | IKKa | Lys2 | 27.3 | -9.2 | 4.9 | -7.3 |  |
|  | IKKb | Lys2 | 33.4 | -10.1 | -6.5 | -11.2 |  |
| STE | ZC2/TNIK,ZC3/MINK | Lys2 | 52.8 | 31 | 45.1 | 75.9 | 57.9 |
|  | ZC1/HGK,ZC2/TNIK,ZC3/MINK | Lys2 | 8.8 | 8.3 | -11.3 | 65.1 | 70.4 |
|  | ZC2/TNIK | Lys1 | -15.9 | 20.9 | 9.9 | 80 | 37.3 |
|  | TAO2 | Lys2 | 22.5 | -3.7 | -21.6 | 42.6 | 77.4 |
|  | MAP2K1,MAP2K2 | Lys2 | 24.3 | 3.2 | 3.2 | -10.4 | 83.3 |
|  | TAO1,TAO3 | Lys1 | 35.8 | 13.1 | 2.9 | 34.1 | 99.6 |
| TK | ABL,ARG | Lys1 | -1.4 | 1.9 | -2.7 | 56.1 | 50.3 |
| TKL | IRAK1 | Lys2 | -4.6 | 80 | 0.8 | 5.4 | 37.9 |
|  | ZAK | Lys1 | 3 | 15.5 | -7.8 | 84.4 | 27.9 |
|  | BRAF | Lys2 | 8.9 | 7 | -23.7 | 27.8 | 52.9 |
|  | RAF1 | Lys2 | -20.2 | -7.3 | -41.4 | 25.5 | -169.4 |

Key:
- >90% Inhibition
- 75-90% Inhibition
- 50-75% Inhibition
- 35-50% Inhibition
- No change
- >100% increase in probe labeling

Labeling Site Key:
- LYS1: Conserved Lysine 1
- LYS2: Conserved Lysine 2
- ATP Loop: ATP binding loop
- ATP: ATP site in non-canonical kinase (e.g. lipid kinase)
- Other: Labeling of residue outside of the protein kinase domain, possibly not in ATP binding site

Fig. 9

| | | | | | | | | | | | | | | | | |
|---|---|---|---|---|---|---|---|---|---|---|---|---|---|---|---|---|
| RNAseL | L | F | V | C | V | T | L | C | E | Q | T | L | E | A | C | L | D | V | H | R |
| CASK | L | Y | M | V | F | E | F | M | D | G | A | - | D | L | C | F | E | I | V | K |
| PFTAIRE1 | E | T | L | T | L | V | F | E | Y | V | H | T | D | L | C | Q | Y | M | D | K |
| JNK1 | Q | D | V | Y | I | V | M | E | L | M | D | A | N | L | C | Q | V | I | Q | M |
| JNK3 | Q | D | V | Y | L | V | M | E | L | M | D | A | N | L | C | Q | V | I | Q | M |
| JNK2 | Q | D | V | Y | L | V | M | E | L | M | D | A | N | L | C | Q | V | I | H | M |
| MARKps26 | L | C | L | I | T | K | H | A | S | E | K | F | V | N | T | C | S | Q | Q | Q |
| SPEG2 | Y | L | V | L | I | A | E | S | C | G | N | R | E | L | L | C | G | L | S | D |
| Obscn2 | H | L | V | L | I | L | E | L | C | S | G | P | E | L | L | P | C | L | A | E |
| Trio | S | Y | I | L | V | L | E | M | A | D | Q | G | R | L | L | D | C | V | V | R |
| TSSK3 | K | I | C | L | V | M | E | L | A | E | G | G | D | V | F | D | C | V | L | N |
| BMPR2 | Y | L | L | V | M | E | Y | Y | P | N | G | S | L | C | K | Y | L | S | L | H |
| MISR2 | P | L | L | V | L | E | L | H | P | K | G | S | L | C | H | Y | L | T | Q | Y |
| MAST1 | L | C | M | V | M | E | Y | V | E | G | G | D | C | A | T | L | L | K | N | I |
| MAST2 | L | C | M | V | M | E | Y | V | E | G | G | D | C | A | T | L | L | K | N | I |
| MAST3 | L | C | M | V | M | E | Y | V | E | G | G | D | C | A | T | L | L | K | N | M |
| MAST4 | L | C | M | V | M | E | Y | V | E | G | G | D | C | A | T | L | M | K | N | M |
| DRAK1 | E | M | I | L | V | L | E | Y | A | A | G | G | E | I | F | D | Q | C | V | A |
| DRAK2 | E | I | I | L | I | L | E | Y | A | A | G | G | E | I | F | S | L | C | L | P |
| GPRK6ps | L | C | L | V | LTT | L | M | N | G | G | D | L | N | F | H | I | C | H | M |
| MYT1 | - | I | L | Y | L | Q | T | E | L | C | G | P | S | L | Q | Q | H | C | E | A |
| STLK5 | L | W | V | V | T | S | F | M | A | Y | G | S | A | K | D | L | I | C | T | H |
| BMPR1Aps2 | L | Y | L | I | T | D | Y | H | E | N | G | S | L | Y | D | F | L | K | C | A |
| IRAK1 | Y | C | L | V | Y | G | F | L | P | N | G | S | L | E | D | R | L | H | C | Q |
| IRAK3 | F | C | L | I | Y | P | Y | M | R | N | G | T | L | F | D | R | L | Q | C | V |
| IRAK4 | L | C | L | V | Y | V | Y | M | P | N | G | S | L | L | D | R | L | S | C | L |
| BLK | I | Y | I | V | T | E | Y | M | A | R | G | C | L | L | D | F | L | K | T | D |
| BMX | I | Y | I | V | T | E | Y | I | S | N | G | C | L | L | N | Y | L | R | S | H |
| BTK | I | F | I | I | T | E | Y | M | A | N | G | C | L | L | N | Y | L | R | E | M |
| EGFR | V | Q | L | I | T | Q | L | M | P | F | G | C | L | L | D | Y | V | R | E | H |
| HER2/ErbB2 | V | Q | L | V | T | Q | L | M | P | Y | G | C | L | L | D | H | V | R | E | N |
| HER4/ErbB4 | I | Q | L | V | T | Q | L | M | P | H | G | C | L | L | E | Y | V | H | E | H |
| ITK | I | C | L | V | F | E | F | M | E | H | G | C | L | S | D | Y | L | R | T | Q |
| JAK3 | L | R | L | V | M | E | Y | L | P | S | G | C | L | R | D | F | L | Q | R | H |
| LKB1 | Q | K | M | Y | M | V | M | E | Y | C | V | C | G | M | Q | E | M | L | D | S |
| MAP2K7 | V | F | I | A | M | E | L | M | G | - | T | C | A | E | K | L | K | K | R | M |
| TEC | I | Y | I | V | T | E | F | M | E | R | G | C | L | L | N | F | L | R | Q | R |
| TXK | L | Y | I | V | T | E | F | M | E | N | G | C | L | L | N | Y | L | R | E | N |
| CHK1 | G | N | I | Q | Y | L | F | L | E | Y | C | S | G | G | E | L | F | D | R | I |
| EphB3 | V | M | I | L | T | E | F | M | E | N | C | A | L | D | S | F | L | R | L | N |
| PRKXps | L | C | R | L | M | E | Y | V | P | G | C | E | L | F | S | Y | L | R | N | R | gatekeeper amino acid residues

Fig. 10

| | JNK-IN-7 | JNK-IN-8 | JNK-IN-11 | JNK-IN-12 |
|---|---|---|---|---|
| AAK1 | 18 | 69 | 100 | 100 |
| ABL1(E255K)-phosphorylated | 43 | 100 | 12 | 100 |
| ABL1(F317I)-nonphosphorylated | 100 | 87 | 60 | 100 |
| ABL1(F317I)-phosphorylated | 100 | 100 | 65 | 100 |
| ABL1(F317L)-nonphosphorylated | 43 | 65 | 22 | 100 |
| ABL1(F317L)-phosphorylated | 67 | 61 | 27 | 100 |
| ABL1(H396P)-nonphosphorylated | 6.6 | 42 | 1.6 | 93 |
| ABL1(H396P)-phosphorylated | 95 | 60 | 11 | 100 |
| ABL1(M351T)-phosphorylated | 42 | 81 | 14 | 69 |
| ABL1(Q252H)-nonphosphorylated | 35 | 100 | 5.4 | 100 |
| ABL1(Q252H)-phosphorylated | 45 | 56 | 7.5 | 100 |
| ABL1(T315I)-nonphosphorylated | 88 | 100 | 6 | 100 |
| ABL1(T315I)-phosphorylated | 75 | 92 | 76 | 100 |
| ABL1(Y253F)-phosphorylated | 39 | 71 | 1.6 | 100 |
| ABL1-nonphosphorylated | 32 | 97 | 11 | 100 |
| ABL1-phosphorylated | 52 | 100 | 24 | 100 |
| ABL2 | 79 | 97 | 21 | 100 |
| ACVR1 | 70 | 100 | 3.8 | 100 |
| ACVR1B | 86 | 88 | 8.4 | 96 |
| ACVR2A | 43 | 100 | 5.1 | 79 |
| ACVR2B | 56 | 100 | 9.6 | 100 |
| ACVRL1 | 100 | 96 | 22 | 100 |
| ADCK3 | 58 | 100 | 0 | 82 |
| ADCK4 | 69 | 93 | 0 | 48 |
| AKT1 | 87 | 100 | 100 | 66 |
| AKT2 | 96 | 100 | 100 | 100 |
| AKT3 | 100 | 100 | 80 | 100 |
| ALK | 100 | 85 | 100 | 100 |
| AMPK-alpha1 | 92 | 100 | 100 | 100 |
| AMPK-alpha2 | 81 | 84 | 90 | 100 |
| ANKK1 | 50 | 75 | 73 | 100 |
| ARK5 | 37 | 100 | 83 | 100 |
| ASK1 | 100 | 100 | 100 | 100 |
| ASK2 | 100 | 92 | 100 | 100 |
| AURKA | 67 | 100 | 28 | 100 |
| AURKB | 63 | 82 | 85 | 83 |
| AURKC | 33 | 95 | 84 | 76 |
| AXL | 100 | 77 | 58 | 100 |
| BIKE | 3.8 | 94 | 100 | 51 |
| BLK | 100 | 65 | 5.9 | 100 |
| BMPR1A | 46 | 100 | 66 | 100 |
| BMPR1B | 43 | 92 | 47 | 100 |
| BMPR2 | 64 | 77 | 100 | 50 |
| BMX | 70 | 100 | 76 | 88 |
| BRAF | 95 | 90 | 43 | 57 |
| BRAF(V600E) | 60 | 100 | 21 | 32 |

Fig. 11

| JNK-IN-7 | | JNK-IN-8 | | JNK-IN-11 | | JNK-IN-12 | |
|---|---|---|---|---|---|---|---|
| Kinase | IC50 (nM) (enzymatic) | Kinase | IC50 (nM) (enzymatic) | Kinase | IC50 (nM) (enzymatic) | Kinase | IC50 (nM) (enzymatic) |
| JNK1 | 1.5 | JNK1 | 4.7 | JNK1 | 1.3 | JNK1 | 1.3 |
| JNK2 | 2 | JNK2 | 18.7 | JNK2 | 0.5 | JNK2 | 11.3 |
| JNK3 | 0.7 | JNK3 | 1 | JNK3 | 0.5 | JNK3 | 1.1 |
| IRAK1 | 14.1 | MNK2 | 238 | EGFR(L861Q) | 2.1 | IRAK1 | 37.6 |
| KIT | 2410 | FMS | 287 | EGFR(L858R) | 24.9 | HIPK4 | 57.1 |
| HIPK1 | 5010 | HIPK4 | 8970 | DDR1 | 56.1 | AKT2 | 89.9 |
| Kinase | Kd (nM, Ambit) | KIT | >10000 | CSNK1E | 82.9 | AKT1 | >370 |
| YSK4 | 48 | MET (M250T) | >10000 | CSNK1G2 | 161 | AKT3 | >370 |
| ERK3 | 22 | PDGFRB | 7500 | PDGFRB | 1030 | SLK | 884 |
| RIOK2 | 30 | PRKX | | KIT | 1320 | Kinase | Kd (nM, Ambit) |
| PIP5K2C | 32 | Kinase | Kd (nM, Ambit) | Kinase | Kd (nM, Ambit) | KIT(V559D, T670I) | 160 |
| CDKL5 | 34 | KIT(V559D) | 92 | EGFR(G719C) | 2.6 | | |
| KIT (L576P) | 40 | KIT(V559D,T670I) | 56 | EGFR(E746-A750del) | 7 | | |
| KIT (V559D) | 48 | MYLK4 | 4000 | KIT(V559D) | 82 | | |
| ICK | 54 | RIOK2 | 120 | PFCDPK1 | 14 | | |
| DRAK1 | 100 | | | DMPK2 | 18 | | |
| DYRK2 | 120 | | | CIT | 95 | | |
| BIKE | 190 | | | ERBB2 | 230 | | |
| | | | | PRKD3 | 240 | | |

Fig. 12

| Kinase | JNK-IN-7 IC50 (nM) (enzymatic) | Kinase | JNK-IN-8 IC50 (nM) (enzymatic) | Kinase | JNK-IN-11 IC50 (nM) (enzymatic) | Kinase | JNK-IN-12 IC50 (nM) (enzymatic) |
|---|---|---|---|---|---|---|---|
| JNK1 | 41 | JNK1 | 34.5 | JNK1 | 39 | JNK1 | 327 |
| JNK2 | 25 | JNK2 | 436 | JNK2 | 23 | JNK2 | 490 |
| JNK3 | 13 | JNK3 | 426 | JNK3 | 84 | JNK3 | 354 |
| IRAK1 | 175 | YES1 | 1284 | HER4 | 28.9 | TAK1 | 866 |
| ERK8 | 183 | TAK1 | 7723 | GSK3b | 32 | GSK3b | 84 |
| NUAK1 | 144 | | | EPHB4 | 121 | MLK1 | 104 |
| HIPK1 | 7613 | | | BRK | 60 | VEGFR | 134 |
| TAK1 | 833 | | | TAK1 | 351 | CAMK1 | 900 |
| JAK2 | 2514 | | | RIPK2 | 42 | PKB beta | 970 |
| Aurora | 1656 | | | MLK1 | 45 | | |
| CLK2 | 299 | | | EPHB2 | 138 | | |
| CK2 | 506 | | | VEGFR | 18 | | |
| GSK3b | 933 | | | SAPK2a | 63 | | |
| GCK | 20480 | | | | | | |
| RIPK2 | 729 | | | | | | |

Fig. 13

INHIBITORS OF C-JUN-N-TERMINAL KINASE (JNK)

RELATED APPLICATIONS

The present application is a continuation of and claims priority under 35 U.S.C. § 120 to U.S. application Ser. No. 14/358,606, filed May 15, 2014, which is a national stage filing under 35 U.S.C. § 371 of international PCT application, PCT/US2012/065618, filed Nov. 16, 2012, which claims priority under 35 U.S.C. § 119(e) to U.S. provisional patent application, U.S. Ser. No. 61/561,078, filed Nov. 17, 2011, each of which is incorporated herein by reference.

This invention was made with government support under grant numbers CA148164, HG005693, HG006097, U54 HG006907-01, and NS057135 awarded by the National Institutes of Health. The government has certain rights in the invention.

BACKGROUND OF THE INVENTION

In mammalian cells, the MAPK (Mitogen-Activated Protein Kinase) signaling system is comprised of, at least, four distinct signaling modules defined by a core of MAP4K, MAP3K, MAP2K and MAPKs that are named after the "terminal" MAPK kinase in each pathway: ERK1/2, JNK1/2/3, p38alpha/beta, and ERK5 (Chang et al., 2001; Johnson et al., 2002; Pearson et al., 2001; and Raman et al., 2007). JNKs (c-Jun $NH_2$-terminal kinase) become highly activated after cells are exposed to stress conditions such as cytokines, osmotic stress, hypoxia, and UV light, and are poorly activated by exposure to growth factors or mitogens (Derijard et al., 1994; and Pulverer et al., 1991). There are three distinct genes Jnk1, Jnk2, and Jnk3 that are alternatively spliced to yield approximately ten different proteins with the predominant isoforms: JNK1 and JNK2 expressed ubiquitously, and JNK3 expressed primarily in the nervous system (Derijard et al., 1994; Kallunki et al., 1994; Sluss et al., 1994; and Mohit et al., 1995). JNKs are activated by phosphorylation at the activation T-loop residues Thr183/Tyr185 by the MAP2Ks: MKK4 and MKK7, and are deactivated by MAP kinase phosphatases including MKP1 and MKP5. Signaling through the JNK-pathway is organized through binding to "scaffolding" proteins such as JIP which assemble signaling complexes containing MAP3K, MAP2K, and MAPKs in addition to transcription factors such as c-Jun, ATF2, and Elk1 which are phosphorylated by JNK. As JNKs comprise a central node in the inflammatory signaling network, it is not surprising that hyperactivation of JNK signaling is a very common finding in a number of disease states including cancer, inflammatory, and neurodegenerative diseases. A significant body of genetic and pharmacological evidence has been generated that suggest that inhibitors of JNK signaling may provide a promising therapeutic strategy. JNK3 knockout mice exhibit amelioration of neurodegeneration in animal models of Parkinson's and Alzheimer's disease (Kyriakis et al., 2001; Zhang et al., 2005; and Hunot et al., 2004). JNK1 phosphorylates IRS-1, a key molecule in the insulin-sensing pathway which down-regulates insulin signaling, and JNK1 knockout mice are resistant to diet-induced obesity (Aguirre et al., 2000 and 2002; Hirosumi et al., 2002; and Sabio et al., 2010). JNK2, often in concert with JNK1, has been implicated in the pathology of autoimmune disorders such as rheumatoid arthritis (Han et al., 2002) and asthma (Wong, W. S., 2005; Pelaia et al., 2005; Blease et al., 2003; Chialda et al., 2005); A recent study suggests that JNK2 may play a role in vascular disease and atherosclerosis as well (Osto et al., 2008). Yet, to date, no direct JNK inhibitors have been approved for use in humans.

Numerous small molecules from a variety of scaffolds such as indazoles, aminopyrazoles, aminopyridines, pyridine carboxamides, benzothien-2-ylamides and benzothiazol-2-yl acetonitriles, quinoline derivatives, and aminopyrimidines have been reported to act as selective ATP-competitive JNK inhibitors (LoGrasso and Kamenecka, 2008). However, despite this apparent plethora of reported JNK inhibitors, many exhibit poor kinase selectivity and/or do not inhibit the phosphorylation of well characterized substrates of JNK in cells. For example, one of the earliest and still most widely utilized inhibitors is the anthrapyrazolone, SP-600125 (Bennett et al., 2001) (FIG. 1) which exhibits exceptionally low specificity for JNK (Bain et al., 2007) and should only be used in combination with other approaches such as gene deletions or siRNA mediated depletion to rule-out a JNK role in a particular process (Inesta-Vaquera et al., 2010). Other reported JNK inhibitors such as AS601245 (Gaillard et al., 2005) only inhibit c-Jun phosphorylation at high concentrations which is likely due to a combination of limited cell penetration, ATP concentration, and differences between biochemical and cellular sensitivities to JNK inhibitors.

SUMMARY OF THE INVENTION

The mitogen activated c-Jun-N-terminal kinases (JNKs, such as JNK1, JNK2, and JNK3) are key enzymes in signaling modules that transduce and integrate extracellular stimuli into coordinated cellular response. Irreversible JNK inhibitors, such as JNK-IN-7, were discovered to form a covalent bond with a cysteine residue conserved in JNKs. Some irreversible JNK inhibitors, such as JNK-IN-8, are selective JNK inhibitors that inhibit c-Jun phosphorylation, a direct JNK substrate, in cells in a manner that was dependent on covalent modification of the conserved cysteine residue. Extensive biochemical, cellular, and pathway-based profiling were used to establish the JNK selectivity of these compounds and suggested their applicability as versatile pharmacological probes of JNK-mediated biological phenomena.

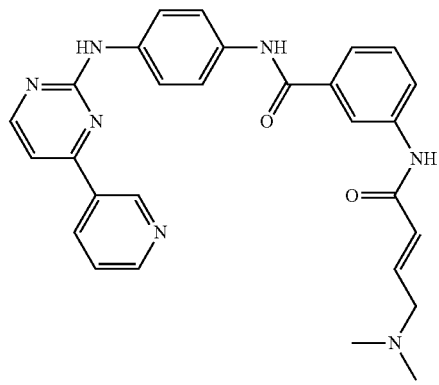

(JNK-IN-7)

(JNK-IN-8)

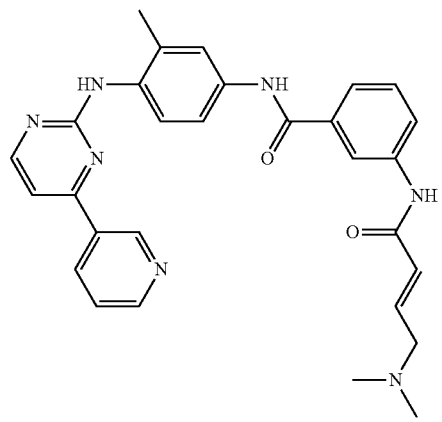

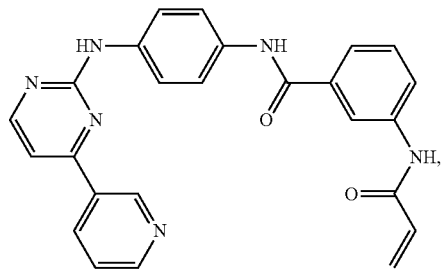
(JNK-IN-5)

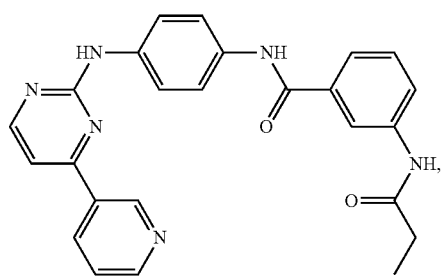
(JNK-IN-6)

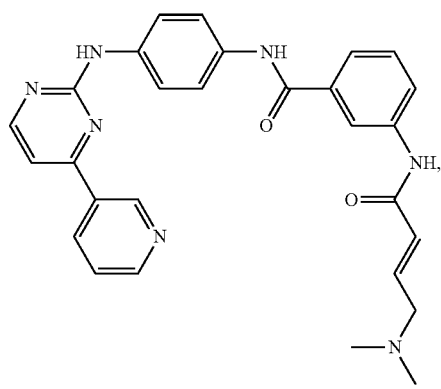
(JNK-IN-7)

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of JNK and as therapeutics for the prevention and treatment of diseases associated with JNK activity. In certain embodiments, the inventive compounds are used for the prevention and treatment of proliferative diseases (e.g., cancer and benign neoplasms), neurodegenerative diseases, metabolic disorders, inflammatory diseases, and cardiovascular diseases.

In one aspect, the present invention provides compounds of Formula (I):

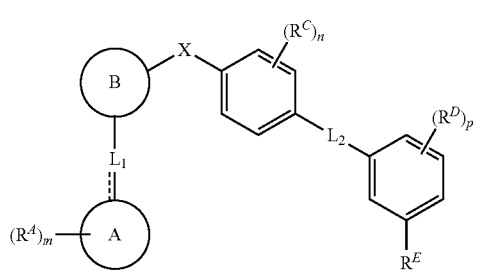
(I)

and pharmaceutically acceptable salts, solvates, hydrates, polymorphs, co-crystals, tautomers, stereoisomers, isotopically labeled derivatives, and prodrugs thereof, wherein Ring A, Ring B, X, $L^1$, $L^2$, $R^A$, $R^C$, $R^D$, $R^E$, m, n, and p are as defined herein.

Exemplary compounds of Formulae (I) include, but are not limited to:

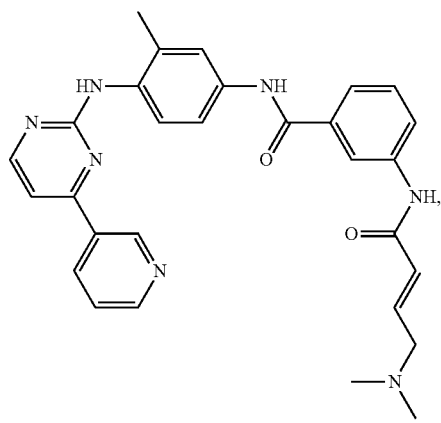
(JNK-IN-8)

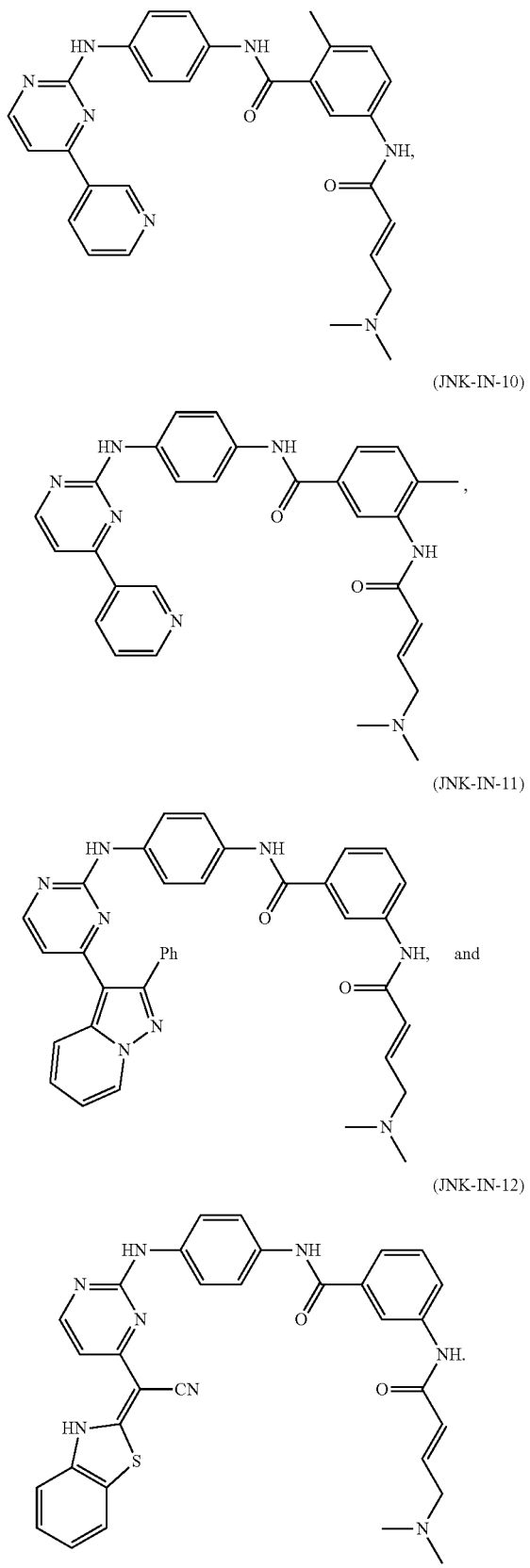

In another aspect, the present invention provides pharmaceutical compositions comprising a compound of Formulae (I) and pharmaceutically acceptable salts, solvates, hydrates, polymorphs, co-crystals, tautomers, stereoisomers, isotopically labeled derivatives, and prodrugs thereof, and optionally a pharmaceutically acceptable excipient.

In still another aspect, the invention provides methods and compositions for the treatment of diseases of a subject. The diseases being treated by the inventive methods include JNK-associated diseases. Inhibition of other therapeutic targets and their associated diseases, such as CDK7 and CDK7-associated diseases, are contemplated herein. Exemplary diseases include, but are not limited to, neurodegenerative diseases, metabolic disorders, inflammatory diseases, cardiovascular diseases, and proliferative diseases (e.g., cancer and benign neoplasms). The methods of the invention include administering to a subject in need of treatment of a disease a therapeutically effective amount of a compound of the present invention. The compound of the present invention may be, e.g., JNK-IN-5, JNK-IN-6, JNK-IN-7, JNK-IN-8, JNK-IN-9, JNK-IN-10, JNK-IN-11, and JNK-IN-12, or a pharmaceutically acceptable salt, solvate, hydrate, polymorph, co-crystal, tautomer, stereoisomer, isotopically labeled derivative, or prodrug thereof.

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGrawHill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, a "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

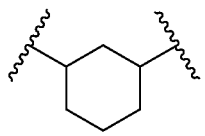 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

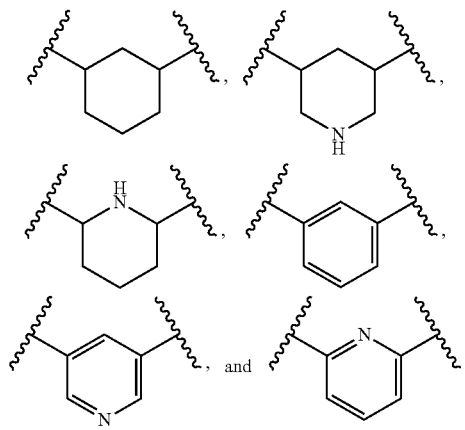

are all examples of a hydrocarbon chain. In contrast, in certain embodiments

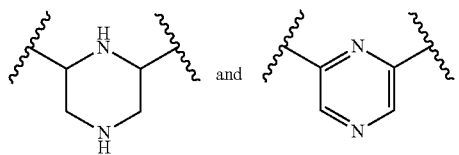 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straightchain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straightchain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6\ 14}$ aryl.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, p-teridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0,1,2,3,4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl) $^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{16}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methan-sulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$ R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-climethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethylbenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, benzoyl (Bz), phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and claims. The invention is not intended to be limited in any manner by the above exemplary listing of substituents.

Other definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

A "subject" to which administration is contemplated includes, but is not limited to, humans (i.e., a male or female of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal, such as a transgenic mouse or transgenic pig.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

"Treat," "treating," and "treatment" contemplate an action that occurs while a subject is suffering from a condition and that reduces the severity of the condition or retards or slows the progression of the condition ("therapeutic treatment"), and also contemplates an action that occurs before a subject begins to suffer from the condition and that inhibits or reduces the severity of the condition ("prophylactic treatment").

As used herein, "condition," "disease," and "disorder" are used interchangeably.

An "effective amount" of a compound of the present invention refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of the present invention is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of the present invention is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

BRIEF DESCRIPTION OF THE DRAWINGS

FIG. 9 illustrates the cellular kinase selectivity as assessed using the KiNativ™ technology. Percent inhibition of kinase labeling by ATP-biotin that results from incubating A375 cells with the inhibitors for 3 hours at a concentration of 1 µM is indicated (larger numbers indicate stronger binding to the kinase).

FIG. 10 shows the sequence alignment of kinases that possess a potentially reactive cysteine (highlighted) that is at least five residues N- and C-terminal to C154 of JNK3. Kinase sequences were retrieved from the human KinBase, and kinome-wide sequence alignment was performed with ClustalX. The gatekeeper amino acid residues are also highlighted.

FIG. 11 shows the Kinome Scan™ (DiscoverRx) profiles for the irreversible JNK inhibitors.

FIG. 12 shows the enzymatic $IC_{50}$'s or dissociation constants ($K_d$) for the potential additional kinase targets. For JNK-IN-7 and JNK-IN-11, the kinases with the score below 5 were tested; and for JNK-IN-8 and JNK-IN-12, kinases with score below 1 were tested. Scores were obtained from the profiling against a 400 kinase panel using Kinome Scan™ technology as illustrated in FIG. 11.

FIG. 13 shows the biochemical $IC_{50}$'s for additional kinase targets selected based upon the result of screening a panel of 105 kinases at a concentration of 1 µM (Dundee Kinase panel).

(FIG. 15A), JNK-IN-8 (FIG. 15B), and JNK-IN-11 (FIG. 15C) following anisomycin stimulation of HEK293-IL1R cells.

FIG. 16B shows the inhibition of anisomycin-stimulated c-Jun phosphorylation with varying concentrations and incubation times of JNK-IN-8 in HEK293-ILR1 cells.

DETAILED DESCRIPTION OF CERTAIN EMBODIMENTS OF THE INVENTION

Figure 1:
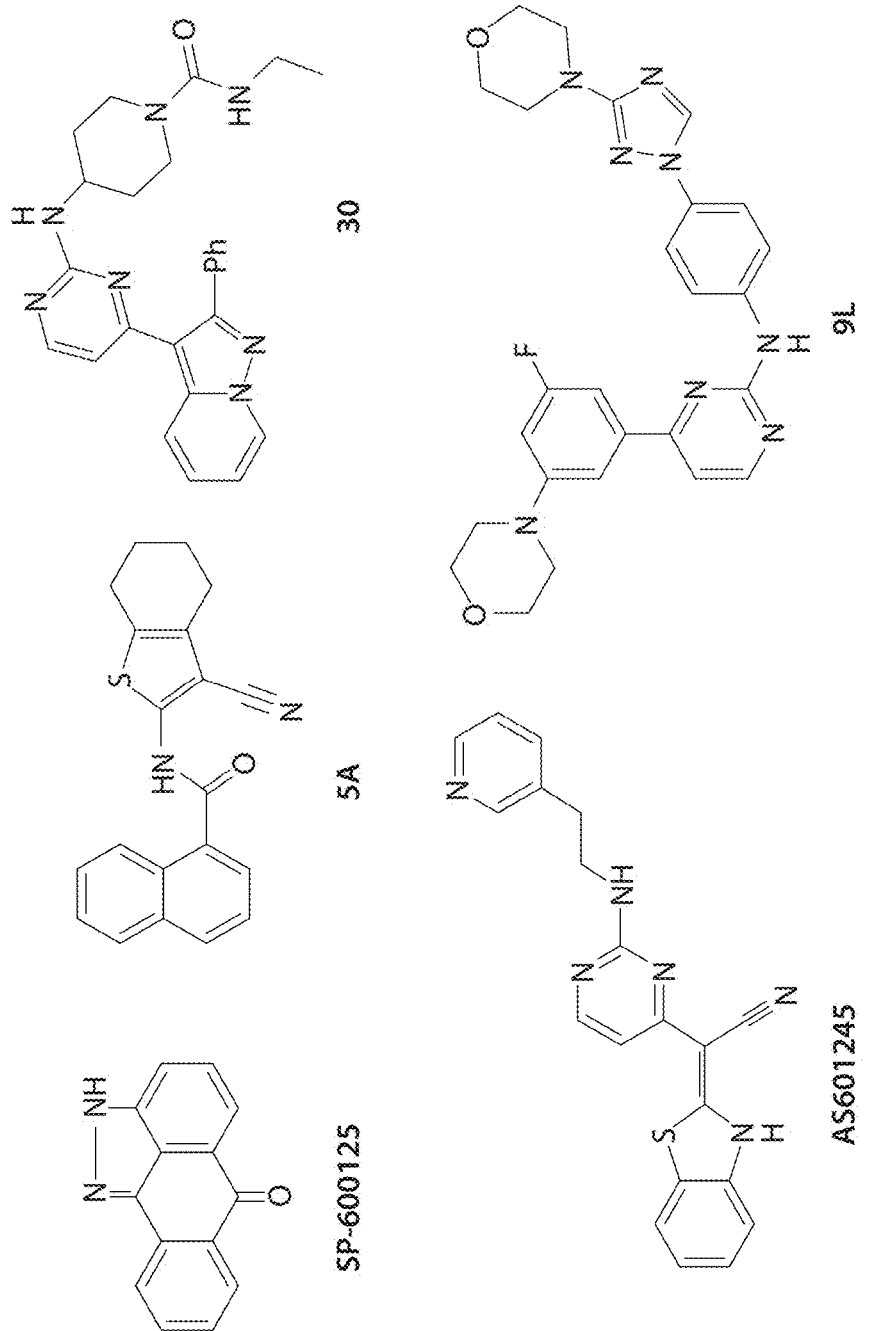
FIG. 1 includes the chemical structures of representative JNK inhibitors.

The present invention provides compounds that inhibit a kinase, and pharmaceutical compositions thereof, for the prevention and treatment of a disease of a subject. In certain embodiments, the compounds inhibit c-Jun-N-terminal kinase (JNK). In certain embodiments, the compounds irreversibly inhibit JNK. The present invention further provides methods of using the compounds described herein, e.g., as biological probes to study the inhibition of JNK activity, and as therapeutics, e.g., in the prevention and treatment of diseases associated with JNK activity. In certain embodiments, the diseases include, but are not limited to, proliferative diseases (e.g., cancer and benign neoplasms), neurodegenerative diseases, metabolic disorders, inflammatory diseases, and cardiovascular diseases.

Compounds

In one aspect of the present invention, provided are compounds of Formula (I):

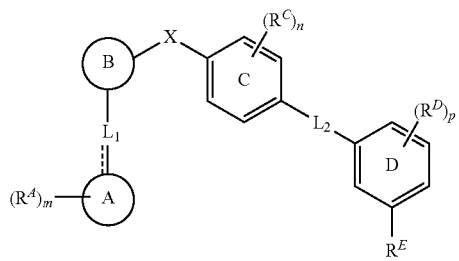

and pharmaceutically acceptable salts, solvates, hydrates, polymorphs, co-crystals, tautomers, stereoisomers, isotopically labeled derivatives, prodrugs, and compositions thereof;
wherein:
Ring A is a carbocyclic, heterocyclic, heteroaryl, or aryl ring;
each instance of $R^A$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A1})_2$, and $-SR^{A1}$, wherein each occurrence of $R^{A1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{A1}$ groups are joined to form an optionally substituted heterocyclic ring;
m is 0, 1, 2, 3, or 4;
Ring B is a group of the formula:

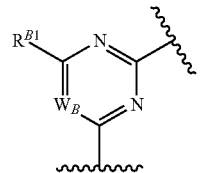

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B1a}$, $-N(R^{B1a})_2$, and $-SR^{B1a}$, wherein each occurrence of $R^{B1a}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{B1a}$ groups are joined to form an optionally substituted heterocyclic ring;
$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B2a}$, $-N(R^{N2a})_2$, and $-SR^{B2a}$, wherein each occurrence of $R^{B2a}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{B2a}$ groups are joined to form an optionally substituted heterocyclic ring;
optionally wherein $R^{B1}$ and $R^{B2}$ are joined to form an optionally substituted carbocyclyl, optionally substituted heterocyclyl, optionally substituted heteroaryl, or optionally substituted aryl ring;
$L_1$ is a bond directly attaching Ring A to Ring B, or $L_1$ is $=C(R^{L1a})-$, $-O-$, $-S-$, $-NR^{L1b}-$, $-NR^{L1b}C(=O)-$, $-C(=O)NR^{L1b}-$, $-SC(=O)-$, $-C(=O)S-$, $-OC(=O)-$, $-C(=O)O-$, $-NR^{L1b}C(=S)-$, —C(=S)NR$^{L1b}$—, trans-CH=CH—, cis-CH=CH—, —S(=O)$_2$O—, —OS(=O)$_2$—, —S(=O)$_2$NR$^{L1b}$—, —NR$^{L1b}$S(=O)$_2$—, or an optionally substituted C$_{1-4}$ hydrocarbon chain, optionally wherein one methylene unit of the hydrocarbon chain is replaced with =C(R$^{L1a}$)—, —O—, —S—, —NR$^{L1b}$—, —NR$^{L1b}$C(=O)—, —(=O)NR$^{L1b}$—, —SC(=O)—, —C(=O)S—, —OC(=O)—, —C(=O)O—, —NR$^{L1b}$C(=S)—, —C(=S)NR$^{L1b}$—, trans-CH=CH—, cis-CH=CH—, —S(=O)$_2$O—, —OS(=O)$_2$—, —S(=O)$_2$NR$^{L1b}$—, or —NR$^{L1b}$S(=O)$_2$—, wherein R$^{L1a}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, or —NO$_2$, and R$^{L1b}$ is hydrogen, C$_{1-6}$ alkyl, or a nitrogen protecting group;

==== represents a single or double bond;

X is an optionally substituted C$_{1-4}$ hydrocarbon chain, optionally wherein one or more carbon units of the hydrocarbon chain is replaced with —O—, —S—, or —NR$^X$—, wherein R$^X$ is hydrogen, C$_{1-6}$ alkyl, or a nitrogen protecting group;

L$_2$ is a bond, —O—, —S—, —NR$^{L2a}$—, —NR$^{L2a}$C(=O)—, —C(=O)NR$^{L2a}$—, —SC(=O)—, —C(=O)S—, —OC(=O)—, —C(=O)O—, —NR$^{L2a}$C(=S)—, —C(=S)NR$^{L2a}$—, trans-CR$^{L2b}$=CR$^{L2b}$—, cis-CR$^{L2b}$=CR$^{L2b}$—, C≡C—, —OC(R$^{L2b}$)$_2$—, —C(R$^{L2b}$)$_2$O—, —NR$^{L2a}$C(R$^{L2b}$)$_2$—, —C(R$^{L2b}$)$_2$NR$^{L2a}$—, —SC(R$^{L2b}$)$_2$—, —C(R$^{L2b}$)$_2$S—, —(=O)$_2$O—, —OS(=O)$_2$—, —S(=O)$_2$NR$^{L2a}$—, —NR$^{L2a}$S(=O)$_2$—, or an optionally substituted C$_{1-4}$ hydrocarbon chain, optionally wherein one or more carbon units of the hydrocarbon chain is replaced with —O—, —S—, —NR$^{L2a}$—, —NR$^{L2a}$C(=O)—, —C(=O)NR$^{L2a}$—, —SC(=O)—, —C(=O)S—, —OC(=O)—, —C(=O)O—, —NR$^{L2a}$C(=S)—, —C(=S)NR$^{L2a}$—, trans-CR$^{L2b}$=CR$^{L2b}$—, cis-CR$^{L2b}$=CR$^{L2b}$—, —C≡C—, —S(=O)$_2$O—, —OS(=O)$_2$—, —S(=O)$_2$NR$^{L2a}$—, or —NR$^{L2a}$S(=O)$_2$—, wherein R$^{L2a}$ is hydrogen, C$_{1-6}$ alkyl, or a nitrogen protecting group, and wherein each occurrence of R$^{L2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L2b}$ groups are joined to form an optionally substituted carbocyclic or optionally substituted heterocyclic ring;

each instance of R$^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1}$)$_2$, and —SR$^{C1}$, wherein each occurrence of R$^{C1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{C1}$ groups are joined to form an optionally substituted heterocyclic ring;

n is 0, 1, 2, 3, or 4;

each instance of R$^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$, wherein each occurrence of R$^{D1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{D1}$ groups are joined to form an optionally substituted heterocyclic ring;

p is 0, 1, 2, 3, or 4;

R$^E$ is a group of the formula:

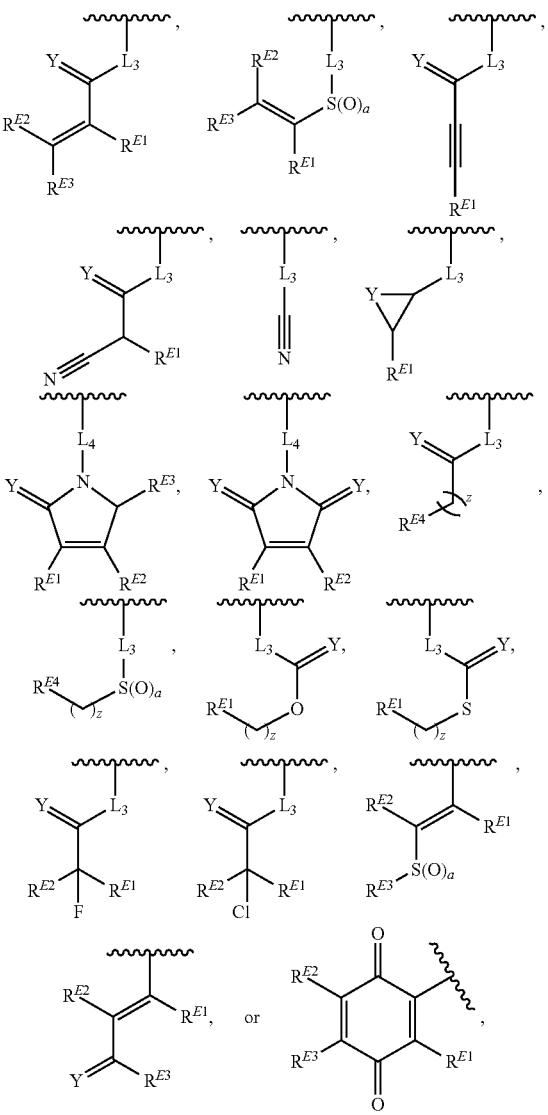

wherein:

L$_3$ is a bond, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —OC(R$^{L3b}$)$_2$—, —C(R$^{L3b}$)$_2$O—, —NR$^{L3a}$C(R$^{L3b}$)$_2$—, —C(R$^{L3b}$)$_2$NR$^{L3a}$—, —SC(R$^{L3b}$)$_2$—, —C(R$^{L3b}$)$_2$S—, —S(=O)$_2$O—, —OS(=O)$_2$—, —S(=O)$_2$NR$^{L3a}$—, —NR$^{L3a}$S(=O)$_2$—, or an optionally substituted C$_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, C$_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

L$_4$ is a bond or an optionally substituted C$_{1-4}$ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)$_2$, —CH$_2$SR$^{E2a}$, —OR$^{E2a}$, —N(R$^{E2a}$)$^2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

optionally wherein R$^{E1}$ and R$^{E3}$ or R$^{E2}$ and R$^{E3}$ or R$^{E1}$ and R$^{E2}$ are joined to form an optionally substituted carbocyclic or optionally substituted heterocyclic ring;

R$^{E4}$ is a leaving group;

Y is O, S, or NR$^{E5}$, wherein R$^{E5}$ is hydrogen, C$_{1-6}$ alkyl, or a nitrogen protecting group;

a is 1 or 2; and z is 0, 1, 2, 3, 4, 5, or 6.

Compounds of Formula (I) include a substituted or unsubstituted carbocyclic, heterocyclic, heteroaryl, or aryl ring as Ring A. Ring A may be substituted with one or more substitutents R$^A$. In certain embodiments, Ring A is a carbocyclic ring. In certain embodiments, Ring A is a monocyclic carbocyclic ring. In certain embodiments, Ring A is a bicyclic carbocyclic ring. In certain embodiments, Ring A is a tricyclic carbocyclic ring. In certain embodiments, Ring A is a substituted carbocyclic ring. In certain embodiments, Ring A is an unsubstituted carbocyclic ring. In certain embodiments, Ring A is a saturated carbocyclic ring. In certain embodiments, Ring A is an unsaturated carbocyclic ring. In certain embodiments, Ring A is a carbocyclic ring fused with one or more carbocyclic, heterocyclic, aryl, or heteroaryl groups wherein the point of attachment is on the carbocyclic ring.

In certain embodiments, Ring A is

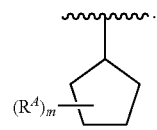

In certain embodiments, Ring A is

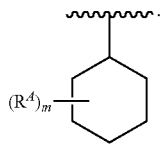

In certain embodiments, Ring A is

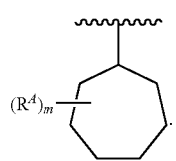

In certain embodiments, Ring A is

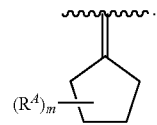

In certain embodiments, Ring A is
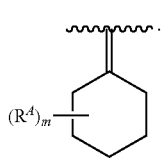
In certain embodiments, Ring A is
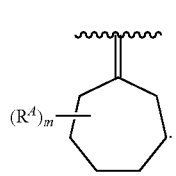
In certain embodiments, Ring A is
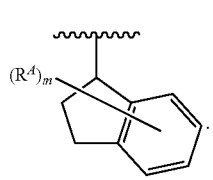
In certain embodiments, Ring A is
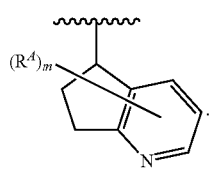
In certain embodiments, Ring A is
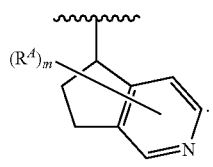
In certain embodiments, Ring A is
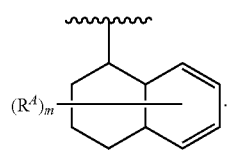
In certain embodiments, Ring A is
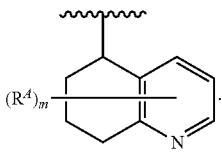
In certain embodiments, Ring A is
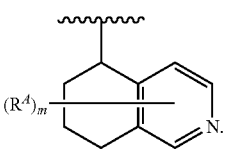
In certain embodiments, Ring A is
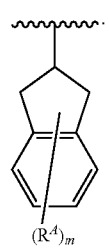
In certain embodiments, Ring A is
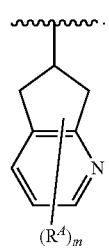
In certain embodiments, Ring A is

In certain embodiments, Ring A is

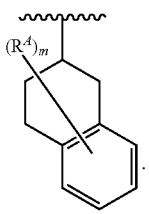

In certain embodiments, Ring A is

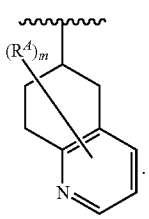

In certain embodiments, Ring A is

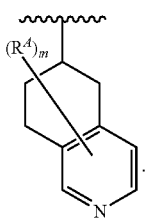

In certain embodiments, Ring A is a heterocyclic ring. In certain embodiments, Ring A is a monocyclic heterocyclic ring. In certain embodiments, Ring A is a bicyclic heterocyclic ring. In certain embodiments, Ring A is a tricyclic heterocyclic ring. In certain embodiments, Ring A is a substituted heterocyclic ring. In certain embodiments, Ring A is an unsubstituted heterocyclic ring. In certain embodiments, Ring A is a saturated heterocyclic ring. In certain embodiments, Ring A is an unsaturated heterocyclic ring. In certain embodiments, Ring A is a heterocyclic ring fused with one or more carbocyclic, heterocyclic, aryl, or heteroaryl groups wherein the point of attachment is on the heterocyclic ring.

In certain embodiments, Ring A is

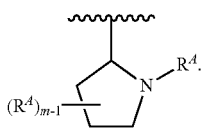

In certain embodiments, Ring A is

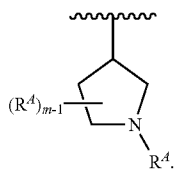

In certain embodiments, Ring A is

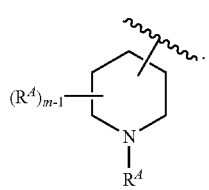

In certain embodiments, Ring A is

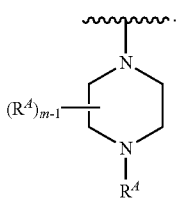

In certain embodiments, Ring A is

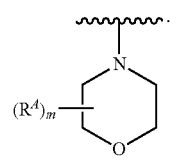

In certain embodiments, Ring A is

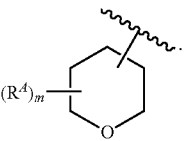

In certain embodiments, Ring A is

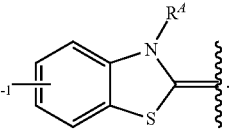

In certain embodiments, Ring A is

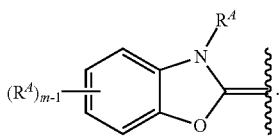

In certain embodiments, Ring A is an aryl ring. In certain embodiments, Ring A is a monocyclic aryl ring. In certain embodiments, Ring A is a bicyclic aryl ring. In certain embodiments, Ring A is a tricyclic aryl ring. In certain embodiments, Ring A is a substituted aryl ring. In certain embodiments, Ring A is an unsubstituted aryl ring. In certain embodiments, Ring A is substituted phenyl. In certain embodiments, Ring A is unsubstituted phenyl. In certain embodiments, Ring A is an aryl ring fused with one or more carbocyclic, heterocyclic, aryl, or heteroaryl groups wherein the point of attachment is on the aryl ring. In certain embodiments, Ring A is substituted naphthyl. In certain embodiments, Ring A is unsubstituted naphthyl.

In certain embodiments, Ring A is

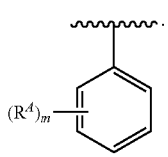

In certain embodiments, Ring A is

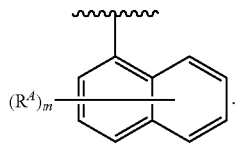

In certain embodiments, Ring A is

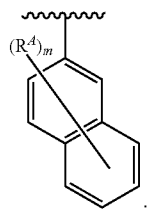

Ring A of Formula (I) may also be an optionally substituted heteroaryl ring. In certain embodiments, Ring A is a substituted heteroaryl ring. In certain embodiments, Ring A is an unsubstituted heteroaryl ring. In certain embodiments, Ring A is a monocyclic heteroaryl ring. In certain embodiments, Ring A is a 5-membered monocyclic heteroaryl ring. In certain embodiments, Ring A is a 5-membered monocyclic heteroaryl ring with one heteroatom selected from the group consisting of S, N, and O. In certain embodiments, Ring A is a 5-membered monocyclic heteroaryl ring with two heteroatoms selected from the group consisting of S, N, and O. In certain embodiments, Ring A is a 5-membered monocyclic heteroaryl ring with three heteroatoms selected from the group consisting of S, N, and O. In certain embodiments, Ring A is substituted pyrrolyl. In certain embodiments, Ring A is unsubstituted pyrrolyl. In certain embodiments, Ring A is substituted furanyl. In certain embodiments, Ring A is unsubstituted furanyl. In certain embodiments, Ring A is substituted thienyl. In certain embodiments, Ring A is unsubstituted thienyl. In certain embodiments, Ring A is substituted pyrazolyl. In certain embodiments, Ring A is unsubstituted pyrazolyl. In certain embodiments, Ring A is substituted imidazolyl. In certain embodiments, Ring A is unsubstituted imidazolyl. In certain embodiments, Ring A is substituted oxazolyl. In certain embodiments, Ring A is unsubstituted oxazolyl. In certain embodiments, Ring A is substituted isoxazolyl. In certain embodiments, Ring A is unsubstituted isoxazolyl. In certain embodiments, Ring A is substituted thiazolyl. In certain embodiments, Ring A is unsubstituted thiazolyl. In certain embodiments, Ring A is substituted isothiazolyl. In certain embodiments, Ring A is unsubstituted isothiazolyl. In certain embodiments, Ring A is substituted triazolyl. In certain embodiments, Ring A is unsubstituted triazolyl. In certain embodiments, Ring A is substituted oxadiazolyl. In certain embodiments, Ring A is unsubstituted oxadiazolyl. In certain embodiments, Ring A is substituted thiadiazolyl. In certain embodiments, Ring A is unsubstituted thiadiazolyl. In certain embodiments, Ring A is a 6-membered monocyclic heteroaryl ring. In certain embodiments, Ring A is a 6-membered monocyclic heteroaryl ring with one heteroatom selected from the group consisting of S, N, and O. In certain embodiments, Ring A is a 6-membered monocyclic heteroaryl ring with two heteroatoms selected from the group consisting of S, N, and O. In certain embodiments, Ring A is a 6-membered monocyclic heteroaryl ring with three heteroatoms selected from the group consisting of S, N, and O. In certain embodiments, Ring A is substituted pyridyl. In certain embodiments, Ring A is unsubstituted pyridyl. In certain embodiments, Ring A is substituted pyridazinyl. In certain embodiments, Ring A is unsubstituted pyridazinyl. In certain embodiments, Ring A is substituted pyrimidinyl. In certain embodiments, Ring A is unsubstituted pyrimidinyl. In certain embodiments, Ring A is substituted pyrazinyl. In certain embodiments, Ring A is unsubstituted pyrazinyl. In certain embodiments, Ring A is substituted triazinyl. In certain embodiments, Ring A is unsubstituted triazinyl. In certain embodiments, Ring A is an optionally substituted heteroaryl ring fused with one or more optionally substituted carbocyclic, optionally substituted heterocyclic, optionally substituted aryl, or optionally substituted heteroaryl groups wherein the point of attachment is on any one of the heteroaryl ring, or carbocyclic, heterocyclic, aryl, or heteroaryl groups, as valency permits. In certain embodiments, Ring A is a bicyclic heteroaryl ring. In certain embodiments, Ring A is an optionally substituted heteroaryl ring fused with an optionally substituted phenyl ring. In certain embodiments, Ring A is substituted indolyl. In certain embodiments, Ring A is unsubstituted indolyl. In certain embodiments, Ring A is substituted isoindolyl. In certain embodiments, Ring A is unsubstituted isoindolyl. In certain embodiments, Ring A is substituted indazolyl. In certain embodiments, Ring A is unsubstituted indazolyl. In certain embodiments, Ring A is substituted benzothienyl. In certain embodiments, Ring A is unsubstituted benzothienyl. In certain embodiments, Ring A is substituted isobenzothienyl. In certain embodiments, Ring A is unsubstituted isobenzothienyl. In certain embodiments, Ring A is substituted benzofuranyl. In certain embodiments, Ring A is unsubstituted benzofuranyl. In certain embodiments, Ring A is substituted benzoisofuranyl. In certain embodiments, Ring A is unsubstituted benzoisofuranyl. In certain embodiments, Ring A is substituted benzimidazolyl. In certain embodiments, Ring A is unsubstituted benzimidazolyl. In certain embodiments, Ring A is substituted benzoxazolyl. In certain embodiments, Ring A is unsubstituted benzoxazolyl. In certain embodiments, Ring A is substituted benzisoxazolyl. In certain embodiments, Ring A is unsubstituted benzisoxazolyl. In certain embodiments, Ring A is substituted benzothiazolyl. In certain embodiments, Ring A is unsubstituted benzothiazolyl. In certain embodiments, Ring A is substituted benzisothiazolyl. In certain embodiments, Ring A is unsubstituted benzisothiazolyl. In certain embodiments, Ring A is substituted benzotriazolyl. In certain embodiments, Ring A is unsubstituted benzotriazolyl. In certain embodiments, Ring A is substituted benzoxadiazolyl. In certain embodiments, Ring A is unsubstituted benzoxadiazolyl. In certain embodiments, Ring A is substituted quinolinyl. In certain embodiments, Ring A is unsubstituted quinolinyl. In certain embodiments, Ring A is substituted isoquinolinyl. In certain embodiments, Ring A is unsubstituted isoquinolinyl. In certain embodiments, Ring A is substituted cinnolinyl. In certain embodiments, Ring A is unsubstituted cinnolinyl. In certain embodiments, Ring A is substituted quinoxalinyl. In certain embodiments, Ring A is unsubstituted quinoxalinyl. In certain embodiments, Ring A is substituted phthalazinyl. In certain embodiments, Ring A is unsubstituted phthalazinyl. In certain embodiments, Ring A is substituted quinazolinyl. In certain embodiments, Ring A is unsubstituted quinazolinyl. In certain embodiments, Ring A is a tricyclic heteroaryl ring.

In certain embodiments, Ring A is

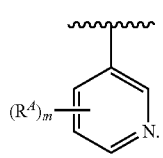

In certain embodiments, Ring A is

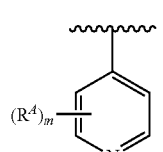

In certain embodiments, Ring A is

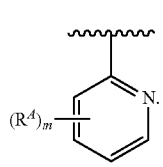

In certain embodiments, Ring A is

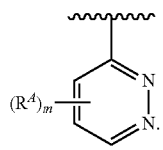

In certain embodiments, Ring A is

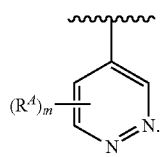

In certain embodiments, Ring A is

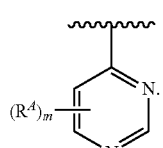

In certain embodiments, Ring A is

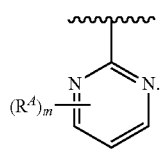

In certain embodiments, Ring A is

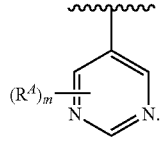

In certain embodiments, Ring A is

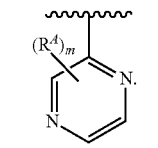

In certain embodiments, Ring A is

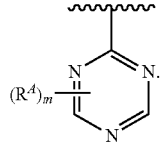

In certain embodiments, Ring A is

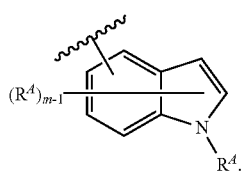

In certain embodiments, Ring A is

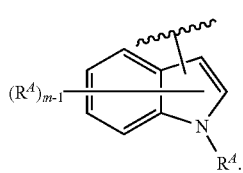

In certain embodiments, Ring A is

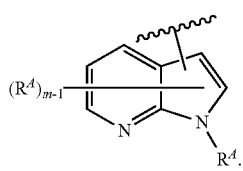

In certain embodiments, Ring A is

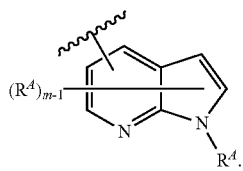

In certain embodiments, Ring A is

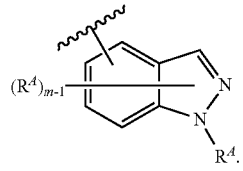

In certain embodiments, Ring A is

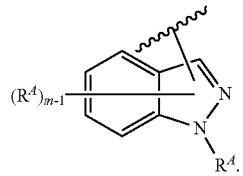

In certain embodiments, Ring A is

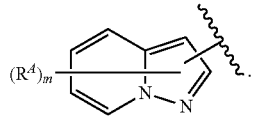

In certain embodiments, Ring A is

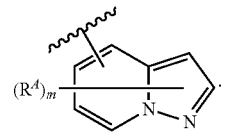

In certain embodiments, Ring A is

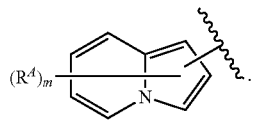

In certain embodiments, Ring A is

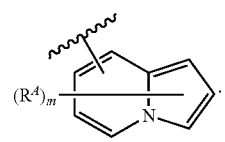

In certain embodiments, Ring A is

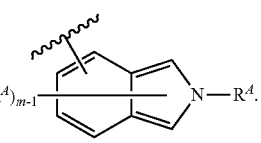

In certain embodiments, Ring A is

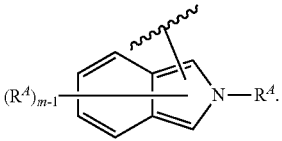

In certain embodiments, Ring A is

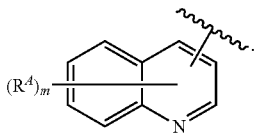

In certain embodiments, Ring A is

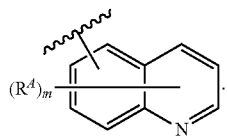

In certain embodiments, Ring A is

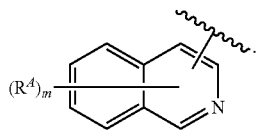

In certain embodiments, Ring A is

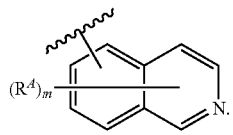

In certain embodiments, Ring A is

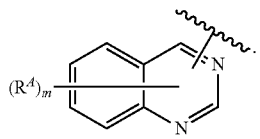

In certain embodiments, Ring A is

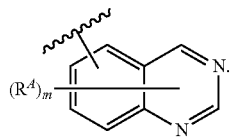

In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is acyl. In certain embodiments, at least one $R^A$ is acetyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is butyl. In certain embodiments, at least one $R^A$ is substituted alkenyl. In certain embodiments, at least one $R^A$ is unsubstituted alkenyl. In certain embodiments, at least one $R^A$ is substituted alkynyl. In certain embodiments, at least one $R^A$ is unsubstituted alkynyl. In certain embodiments, at least one $R^A$ is substituted carbocyclyl. In certain embodiments, at least one $R^A$ is unsubstituted carbocyclyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted heteroaryl. In certain embodiments, at least one $R^A$ is unsubstituted heteroaryl. In certain embodiments, at least one $R^A$ is substituted pyridyl. In certain embodiments, at least one $R^A$ is unsubstituted pyridyl. In certain embodiments, at least one $R^A$ is $-OR^{A1}$. In certain embodiments, at least one $R^A$ is $-N(R^{A1})_2$. In certain embodiments, at least one $R^A$ is $-SR^{A1}$.

In certain embodiments, when $R^A$ is $-OR^{A1}$, $-N(R^{A1})_2$, or $-SR^{A1}$, at least one $R^{A1}$ is H. In certain embodiments, at least one $R^{A1}$ is acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is substituted alkenyl. In certain embodiments, at least one $R^{A1}$ is unsubstituted alkenyl. In certain embodiments, at least one $R^{A1}$ is substituted alkynyl. In certain embodiments, at least one $R^{A1}$ is unsubstituted alkynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is an oxygen protecting group when attached to an oxygen atom. In certain embodiments, at least one $R^{A1}$ is a sulfur protecting group when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring.

Ring A may be unsubstituted or substituted with one or more $R^A$. In certain embodiments, Ring A is unsubstituted, and thus m is 0. In certain embodiments, m is 1. In certain embodiments, m is 2. In certain embodiments, m is 3. In certain embodiments, m is 4.

Compounds of Formula (I) include a substituted or unsubstituted heteroaryl ring as Ring B. Ring B may be substituted with one substituent $R^{B1}$ or two substituents $R^{B1}$ and $R^{B2}$.

In certain embodiments, Ring B is

[chemical structure: triazine ring with R^B1 substituent]

In certain embodiments, Ring B is

[chemical structure: pyrimidine ring with R^B1 and R^B2 substituents]

In certain embodiments, $R^{B1}$ is H. In certain embodiments, $R^{B1}$ is halogen. In certain embodiments, $R^{B1}$ is F. In certain embodiments, $R^{B1}$ is Cl. In certain embodiments, $R^{B1}$ is Br. In certain embodiments, $R^{B1}$ is I (iodine). In certain embodiments, $R^{B1}$ is acyl. In certain embodiments, $R^{B1}$ is acetyl. In certain embodiments, $R^{B1}$ is substituted alkyl. In certain embodiments, $R^{B1}$ is unsubstituted alkyl. In certain embodiments, $R^{B1}$ is $C_{1-6}$ alkyl. In certain embodiments, $R^{B1}$ is methyl. In certain embodiments, $R^{B1}$ is ethyl. In certain embodiments, $R^{B1}$ is propyl. In certain embodiments, $R^{B1}$ is butyl. In certain embodiments, $R^{B1}$ is substituted alkenyl. In certain embodiments, $R^{B1}$ is unsubstituted alkenyl. In certain embodiments, $R^{B1}$ is substituted alkynyl. In certain embodiments, $R^{B1}$ is unsubstituted alkynyl. In certain embodiments, $R^{B1}$ is substituted carbocyclyl. In certain embodiments, $R^{B1}$ is unsubstituted carbocyclyl. In certain embodiments, $R^{B1}$ is substituted heterocyclyl. In certain embodiments, $R^{B1}$ is unsubstituted heterocyclyl. In certain embodiments, $R^{B1}$ is substituted aryl. In certain embodiments, $R^{B1}$ is unsubstituted aryl. In certain embodiments, $R^{B1}$ is substituted phenyl. In certain embodiments, $R^{B1}$ is unsubstituted phenyl. In certain embodiments, $R^{B1}$ is substituted heteroaryl. In certain embodiments, $R^{B1}$ is unsubstituted heteroaryl. In certain embodiments, $R^{B1}$ is substituted pyridyl. In certain embodiments, $R^{B1}$ is unsubstituted pyridyl. In certain embodiments, $R^{B1}$ is —$OR^{B1a}$. In certain embodiments, $R^{B1}$ is —$N(R^{B1a})_2$. In certain embodiments, $R^{B1}$ is —$SR^{B1a}$.

In certain embodiments, at least one $R^{B1a}$ is H. In certain embodiments, at least one $R^{B1a}$ is acyl. In certain embodiments, at least one $R^{B1a}$ is acetyl. In certain embodiments, at least one $R^{B1a}$ is substituted alkyl. In certain embodiments, at least one $R^{B1a}$ is unsubstituted alkyl. In certain embodiments, at least one $R^{B1a}$ is $C_{1-6}$ alkyl. In certain embodiments, at least one $R^{B1a}$ is methyl. In certain embodiments, at least one $R^{B1a}$ is ethyl. In certain embodiments, at least one $R^{B1a}$ is propyl. In certain embodiments, at least one $R^{B1a}$ is butyl. In certain embodiments, at least one $R^{B1a}$ is substituted alkenyl. In certain embodiments, at least one $R^{B1a}$ is unsubstituted alkenyl. In certain embodiments, at least one $R^{B1a}$ is substituted alkynyl. In certain embodiments, at least one $R^{B1a}$ is unsubstituted alkynyl. In certain embodiments, at least one $R^{B1a}$ is substituted carbocyclyl. In certain embodiments, at least one $R^{B1a}$ is unsubstituted carbocyclyl. In certain embodiments, at least one $R^{B1a}$ is substituted heterocyclyl. In certain embodiments, at least one $R^{B1a}$ is unsubstituted heterocyclyl. In certain embodiments, at least one $R^{B1a}$ is substituted aryl. In certain embodiments, at least one $R^{B1a}$ is unsubstituted aryl. In certain embodiments, at least one $R^{B1a}$ is substituted phenyl. In certain embodiments, at least one $R^{B1a}$ is unsubstituted phenyl. In certain embodiments, at least one $R^{B1a}$ is substituted heteroaryl. In certain embodiments, at least one $R^{B1a}$ is unsubstituted heteroaryl. In certain embodiments, at least one $R^{B1a}$ is substituted pyridyl. In certain embodiments, at least one $R^{B1a}$ is unsubstituted pyridyl. In certain embodiments, at least one $R^{B1a}$ is a nitrogen protecting group when attached to a nitrogen atom. In certain embodiments, at least one $R^{B1a}$ is an oxygen protecting group when attached to an oxygen atom. In certain embodiments, at least one $R^{B1a}$ is a sulfur protecting group when attached to a sulfur atom. In certain embodiments, two $R^{B1a}$ groups are joined to form a substituted heterocyclic ring. In certain embodiments, two $R^{B1a}$ groups are joined to form an unsubstituted heterocyclic ring.

In certain embodiments, $R^{B2}$ is H. In certain embodiments, $R^{B2}$ is halogen. In certain embodiments, $R^{B2}$ is F. In certain embodiments, $R^{B2}$ is Cl. In certain embodiments, $R^{B2}$ is Br. In certain embodiments, $R^{B2}$ is I (iodine). In certain embodiments, $R^{B2}$ is acyl. In certain embodiments, $R^{B2}$ is acetyl. In certain embodiments, $R^{B2}$ is substituted alkyl. In certain embodiments, $R^{B2}$ is unsubstituted alkyl. In certain embodiments, $R^{B2}$ is $C_{1-6}$ alkyl. In certain embodiments, $R^{B2}$ is methyl. In certain embodiments, $R^{B2}$ is ethyl. In certain embodiments, $R^{B2}$ is propyl. In certain embodiments, $R^{B2}$ is butyl. In certain embodiments, $R^{B2}$ is substituted alkenyl. In certain embodiments, $R^{B2}$ is unsubstituted alkenyl. In certain embodiments, $R^{B2}$ is substituted alkynyl. In certain embodiments, $R^{B2}$ is unsubstituted alkynyl. In certain embodiments, $R^{B2}$ is substituted carbocyclyl. In certain embodiments, $R^{B2}$ is unsubstituted carbocyclyl. In certain embodiments, $R^{B2}$ is substituted heterocyclyl. In certain embodiments, $R^{B2}$ is unsubstituted heterocyclyl. In certain embodiments, $R^{B2}$ is substituted aryl. In certain embodiments, $R^{B2}$ is unsubstituted aryl. In certain embodiments, $R^{B2}$ is substituted phenyl. In certain embodiments, $R^{B2}$ is unsubstituted phenyl. In certain embodiments, $R^{B2}$ is substituted heteroaryl. In certain embodiments, $R^{B2}$ is unsubstituted heteroaryl. In certain embodiments, $R^{B2}$ is substituted pyridyl. In certain embodiments, $R^{B2}$ is unsubstituted pyridyl. In certain embodiments, $R^{B2}$ is —$OR^{B2a}$. In certain embodiments, $R^{B2}$ is —$N(R^{B2a})_2$. In certain embodiments, $R^{B2}$ is —$SR^{B2a}$.

In certain embodiments, at least one $R^{B2a}$ is H. In certain embodiments, at least one $R^{B2a}$ is acyl. In certain embodiments, at least one $R^{B2a}$ is acetyl. In certain embodiments, at least one $R^{B2a}$ is substituted alkyl. In certain embodiments, at least one $R^{B2a}$ is unsubstituted alkyl. In certain embodiments, at least one $R^{B2a}$ is $C_{1-6}$ alkyl. In certain embodiments, at least one $R^{B2a}$ is methyl. In certain embodiments, at least one $R^{B2a}$ is ethyl. In certain embodiments, at least one $R^{B2a}$ is propyl. In certain embodiments, at least one $R^{B2a}$ is butyl. In certain embodiments, at least one $R^{B2a}$ is substituted alkenyl. In certain embodiments, at least one $R^{B2a}$ is unsubstituted alkenyl. In certain embodiments, at least one $R^{B2a}$ is substituted alkynyl. In certain embodiments, at least one $R^{B2a}$ is unsubstituted alkynyl. In certain embodiments, at least one $R^{B2a}$ is substituted carbocyclyl. In certain embodiments, at least one $R^{B2a}$ is unsubstituted carbocyclyl. In certain embodiments, at least one $R^{B2a}$ is substituted heterocyclyl. In certain embodiments, at least one $R^{B2a}$ is unsubstituted heterocyclyl. In certain embodiments, at least one $R^{B2a}$ is substituted aryl. In certain embodiments, at least one $R^{B2a}$ is unsubstituted aryl. In certain embodiments, at least one $R^{B2a}$ is substituted phenyl. In certain embodiments, at least one $R^{B2a}$ is unsubstituted phenyl. In certain embodiments, at least one $R^{B2a}$ is substituted heteroaryl. In certain embodiments, at least one $R^{B2a}$ is unsubstituted heteroaryl. In certain embodiments, at least one $R^{B2a}$ is substituted pyridyl. In certain embodiments, at least one $R^{B2a}$ is unsubstituted pyridyl. In certain embodiments, at least one $R^{B2a}$ is a nitrogen protecting group when attached to a nitrogen atom. In certain embodiments, at least one $R^{B2a}$ is an oxygen protecting group when attached to an oxygen atom. In certain embodiments, at least one $R^{B2a}$ is a sulfur protecting group when attached to a sulfur atom. In certain embodiments, two $R^{B2a}$ groups are joined to form a substituted heterocyclic ring. In certain embodiments, two $R^{B2a}$ groups are joined to form an unsubstituted heterocyclic ring.

In certain embodiments, $R^{B1}$ and $R^{B2}$ are joined to form a substituted carbocyclic ring. In certain embodiments, $R^{B1}$ and $R^{B2}$ are joined to form an unsubstituted carbocyclic ring. In certain embodiments, $R^{B1}$ and $R^{B2}$ are joined to form a substituted heterocyclic ring. In certain embodiments, $R^{B1}$ and $R^{B2}$ are joined to form an unsubstituted heterocyclic ring. In certain embodiments, $R^{B1}$ and $R^{B2}$ are joined to form a substituted heteroaryl ring. In certain embodiments, $R^{B1}$ and $R^{B2}$ are joined to form an unsubstituted heteroaryl ring. In certain embodiments, $R^{B1}$ and $R^{B2}$ are joined to form a substituted pyridyl ring. In certain embodiments, $R^{B1}$ and $R^{B2}$ are joined to form an unsubstituted pyridyl ring. In certain embodiments, $R^{B1}$ and $R^{B2}$ are joined to form a substituted aryl ring. In certain embodiments, $R^{B1}$ and $R^{B2}$ are joined to form an unsubstituted aryl ring. In certain embodiments, $R^{B1}$ and $R^{B2}$ are joined to form a substituted phenyl ring. In certain embodiments, $R^{B1}$ and $R^{B2}$ are joined to form an unsubstituted phenyl ring.

In certain embodiments, Ring B is a group selected from the group consisting of:

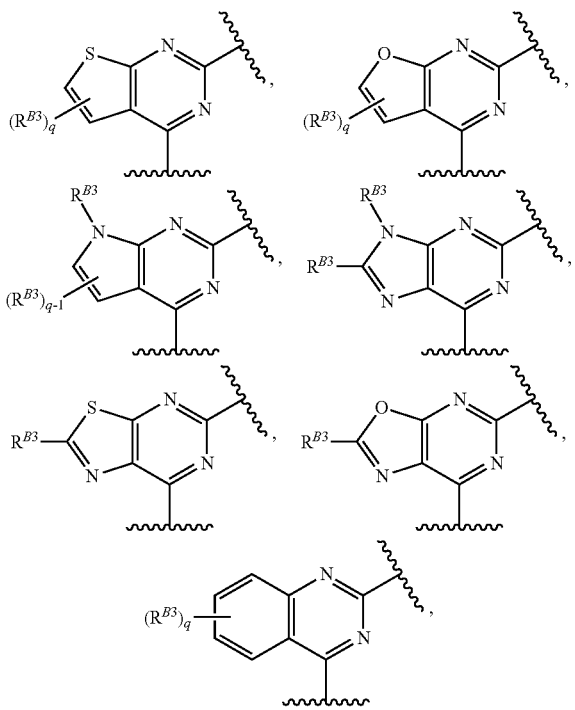

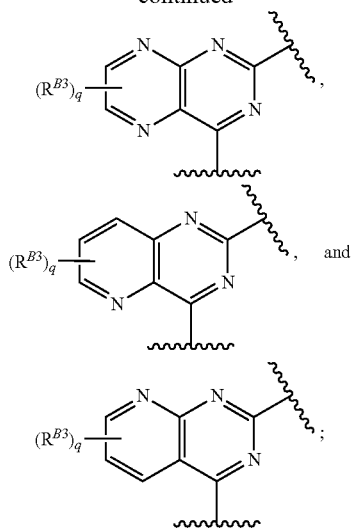

wherein:

$R^{B3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B3a}$, $-N(R^{B3a})_2$, and $-SR^{B3a}$, wherein each occurrence of $R^{B3a}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{B3a}$ groups are joined to form an optionally substituted heterocyclic ring; and q is 0, 1, 2, or 3.

In certain embodiments, $R^{B3}$ is H. In certain embodiments, $R^{B3}$ is halogen. In certain embodiments, $R^{B3}$ is F. In certain embodiments, $R^{B3}$ is Cl. In certain embodiments, $R^{B3}$ is Br. In certain embodiments, $R^{B3}$ is I (iodine). In certain embodiments, $R^{B3}$ is acyl. In certain embodiments, $R^{B3}$ is acetyl. In certain embodiments, $R^{B3}$ is substituted alkyl. In certain embodiments, $R^{B3}$ is unsubstituted alkyl. In certain embodiments, $R^{B3}$ is $C_{1-6}$ alkyl. In certain embodiments, $R^{B3}$ is methyl. In certain embodiments, $R^{B3}$ is ethyl. In certain embodiments, $R^{B3}$ is propyl. In certain embodiments, $R^{B3}$ is butyl. In certain embodiments, $R^{B3}$ is substituted alkenyl. In certain embodiments, $R^{B3}$ is unsubstituted alkenyl. In certain embodiments, $R^{B3}$ is substituted alkynyl. In certain embodiments, $R^{B3}$ is unsubstituted alkynyl. In certain embodiments, $R^{B3}$ is substituted carbocyclyl. In certain embodiments, $R^{B3}$ is unsubstituted carbocyclyl. In certain embodiments, $R^{B3}$ is substituted heterocyclyl. In certain embodiments, $R^{B3}$ is unsubstituted heterocyclyl. In certain embodiments, $R^{B3}$ is substituted aryl. In certain embodiments, $R^{B3}$ is unsubstituted aryl. In certain embodiments, $R^{B3}$ is substituted phenyl. In certain embodiments, $R^{B3}$ is unsubstituted phenyl. In certain embodiments, $R^{B3}$ is substituted heteroaryl. In certain embodiments, $R^{B3}$ is unsubstituted heteroaryl. In certain embodiments, $R^{B3}$ is substituted pyridyl. In certain embodiments, $R^{B3}$ is unsubstituted pyridyl. In certain embodiments, $R^{B3}$ is —$OR^{B3a}$. In certain embodiments, $R^{B3}$ is —$N(R^{B3a})_2$. In certain embodiments, $R^{B3}$ is —$SR^{B3a}$.

In certain embodiments, at least one $R^{B3a}$ is H. In certain embodiments, at least one $R^{B3a}$ is acyl. In certain embodiments, at least one $R^{B3a}$ is acetyl. In certain embodiments, at least one $R^{B3a}$ is substituted alkyl. In certain embodiments, at least one $R^{B3a}$ is unsubstituted alkyl. In certain embodiments, at least one $R^{B3a}$ is $C_{1-6}$ alkyl. In certain embodiments, at least one $R^{B3a}$ is methyl. In certain embodiments, at least one $R^{B3a}$ is ethyl. In certain embodiments, at least one $R^{B3a}$ is propyl. In certain embodiments, at least one $R^{B3a}$ is butyl. In certain embodiments, at least one $R^{B3a}$ is substituted alkenyl. In certain embodiments, at least one $R^{B3a}$ is unsubstituted alkenyl. In certain embodiments, at least one $R^{B3a}$ is substituted alkynyl. In certain embodiments, at least one $R^{B3a}$ is unsubstituted alkynyl. In certain embodiments, at least one $R^{B3a}$ is substituted carbocyclyl. In certain embodiments, at least one $R^{B3a}$ is unsubstituted carbocyclyl. In certain embodiments, at least one $R^{B3a}$ is substituted heterocyclyl. In certain embodiments, at least one $R^{B3a}$ is unsubstituted heterocyclyl. In certain embodiments, at least one $R^{B3a}$ is substituted aryl. In certain embodiments, at least one $R^{B3a}$ is unsubstituted aryl. In certain embodiments, at least one $R^{B3a}$ is substituted phenyl. In certain embodiments, at least one $R^{B3a}$ is unsubstituted phenyl. In certain embodiments, at least one $R^{B3a}$ is substituted heteroaryl. In certain embodiments, at least one $R^{B3a}$ is unsubstituted heteroaryl. In certain embodiments, at least one $R^{B3a}$ is substituted pyridyl. In certain embodiments, at least one $R^{B3a}$ is unsubstituted pyridyl. In certain embodiments, at least one $R^{B3a}$ is a nitrogen protecting group when attached to a nitrogen atom. In certain embodiments, at least one $R^{B3a}$ is an oxygen protecting group when attached to an oxygen atom. In certain embodiments, at least one $R^{B3a}$ is a sulfur protecting group when attached to a sulfur atom. In certain embodiments, two $R^{B3a}$ groups are joined to form a substituted heterocyclic ring. In certain embodiments, two $R^{B3a}$ groups are joined to form an unsubstituted heterocyclic ring.

Ring B may be unsubstituted or substituted with one or more $R^{B3}$. In certain embodiments, Ring B is unsubstituted, and thus q is 0. In certain embodiments, q is 1. In certain embodiments, q is 2. In certain embodiments, q is 3.

$L_1$ is a divalent linker moiety. $L_1$ may contain 0-4 carbon or hetero atoms in the backbone of $L_1$. $L_1$ may be saturated or unsaturated. $L_1$ may be substituted or unsubstituted. In certain embodiments, $L_1$ is a bond directly attaching Ring A to Ring B. In certain embodiments, $L_1$ is a single bond. In certain embodiments, $L_1$ is a double bond. In certain embodiments, $L_1$ is —O—. In certain embodiments, $L_1$ is —S—. In certain embodiments, $L_1$ is —$NR^{L1b}$—. In certain embodiments, $L_1$ is —NH—. In certain embodiments, $L_1$ is —$NR^{L1b}C(=O)$—. In certain embodiments, $L_1$ is —NHC(=O)—. In certain embodiments, $L_1$ is —$C(=O)NR^{L1b}$—. In certain embodiments, $L_1$ is —C(=O)NH—. In certain embodiments, $L_1$ is —SC(=O)—. In certain embodiments, $L_1$ is —C(=O)S—. In certain embodiments, $L_1$ is —OC(=O)—. In certain embodiments, $L_1$ is —C(=O)O—. In certain embodiments, $L_1$ is —$NR^{L1b}C(=S)$—. In certain embodiments, $L_1$ is —NHC(=S)—. In certain embodiments, $L_1$ is —$C(=S)NR^{L1b}$—. In certain embodiments, $L_1$ is —C(=S)NH—. In certain embodiments, $L_1$ is trans-CH=CH—. In certain embodiments, $L_1$ is cis-CH=CH—. In certain embodiments, $L_1$ is —$S(=O)_2O$—. In certain embodiments, $L_1$ is —$OS(=O)_2$—. In certain embodiments, $L_1$ is —$S(=O)_2NR^{L1b}$—. In certain embodiments, $L_1$ is —$S(=O)_2NH$—. In certain embodiments, $L_1$ is —$NR^{L1b}S(=O)_2$—. In certain embodiments, $L_1$ is —$NHS(=O)_2$—. In certain embodiments, $L_1$ is an unsubstituted $C_{1-4}$ hydrocarbon chain. In certain embodiments, $L_1$ is a substituted $C_{1-4}$ hydrocarbon chain. In certain embodiments, $L_1$ is a substituted or unsubstituted $C_{1-4}$ hydrocarbon chain, wherein one methylene unit of the hydrocarbon chain is replaced with =$C(R^{L1a})$—, —O—, —S—, —$NR^{L1b}$—, —$NR^{L1b}C(=O)$—, —$C(=O)NR^{L1b}$—, —SC(=O)—, —C(=O)S—, —OC(=O)—, —C(=O)O—, —$NR^{L1b}C(=S)$—, —$C(=S)NR^{L1b}$—, trans-CH=CH—, cis-CH=CH—, —$S(=O)_2O$—, —$OS(=O)_2$—, —$S(=O)_2NR^{L1b}$—, or —$NR^{L1b}S(=O)_2$—. In certain embodiments, $L_1$ is —$OCH_2$—. In certain embodiments, $L_1$ is —$NCH_2$—. In certain embodiments, $L_1$ is —$CH_2$—.

In certain embodiments, with respect to Formula (I), ==== between $L_1$ and Ring A is a single bond. In certain embodiments, with respect to Formula (I), ==== is a double bond.

X is a divalent linker moiety. X may be an optionally substituted $C_{1-4}$ hydrocarbon chain, optionally wherein one or more carbon units of the hydrocarbon chain is replaced with —O—, —S—, or —$NR^X$—. In certain embodiments, X is a $C_1$ hydrocarbon chain, optionally wherein the carbon unit of the hydrocarbon chain is replaced with —O—, —S—, or —$NR^X$—. In certain embodiments, X is —O—. In certain embodiments, X is —S—. In certain embodiments, X is —$NR^X$—. In certain embodiments, X is —NH—. In certain embodiments, X is —$C(R^X)_2$—. In certain embodiments, X is —$CH_2$—. In certain embodiments, when X is —$NR^X$— or —$C(R^X)_2$—, $R^X$ is H. In certain embodiments, $R^X$ is substituted alkyl. In certain embodiments, $R^X$ is unsubstituted alkyl. In certain embodiments, $R^X$ is $C_{1-6}$ alkyl. In certain embodiments, $R^X$ is methyl. In certain embodiments, $R^X$ is ethyl. In certain embodiments, $R^X$ is propyl. In certain embodiments, $R^X$ is butyl. In certain embodiments, when X is —$NR^X$—, $R^X$ is a nitrogen protecting group. In certain embodiments, $R^X$ is BOC. In certain embodiments, $R^X$ is Cbz. In certain embodiments, $R^X$ is Fmoc. In certain embodiments, $R^X$ is Bn. In certain embodiments, X is a $C_2$ hydrocarbon chain, optionally wherein one or two carbon units of the hydrocarbon chain is replaced with —O—, —S—, or —$NR^X$—. In certain embodiments, X is a $C_3$ hydrocarbon chain, optionally wherein one or more carbon units of the hydrocarbon chain is replaced with —O—, —S—, or —$NR^X$—. In certain embodiments, X is a $C_4$ hydrocarbon chain, optionally wherein one or more carbon units of the hydrocarbon chain is replaced with —O—, —S—, or —$NR^X$—.

In compounds of Formula (I), $L_2$ is a divalent linker moiety. $L_2$ may contain 0-4 carbon or hetero atoms in the backbone of $L_2$. $L_2$ may be saturated or unsaturated. $L_2$ may be substituted or unsubstituted. $L_2$ may be branched or unbranched. In certain embodiments, $L_2$ is a bond. In certain embodiments, $L_2$ is —O—. In certain embodiments, $L_2$ is —S—. In certain embodiments, $L_2$ is —$NR^{L2a}$—. In certain embodiments, $L_2$ is —NH—. In certain embodiments, $L_2$ is —$NR^{L2a}C(=O)$—. In certain embodiments, $L_2$ is —NHC(=O)—. In certain embodiments, $L_2$ is —$C(=O)NR^{L2a}$—. In certain embodiments, $L_2$ is —C(=O)NH—. In certain embodiments, $L_2$ is —SC(=O)—. In certain embodiments, $L_2$ is —C(=O)S—. In certain embodiments, $L_2$ is —OC(=O)—. In certain embodiments, $L_2$ is —C(=O)O—. In certain embodiments, $L_2$ is —$NR^{L2a}C(=S)$—. In certain embodiments, $L_2$ is —NHC(=S)—. In certain embodiments, $L_2$ is —$C(=S)NR^{L2a}$—. In certain embodiments, $L_2$ is —C(=S)NH—. In certain embodiments, $L_2$ is trans- $CR^{L2b}=CR^{L2b}$—. In certain embodiments, $L_2$ is trans-CH=CH—. In certain embodiments, $L_2$ is cis-$CR^{L2b}=CR^{L2b}$—. In certain embodiments, $L_2$ is cis-CH=CH—. In certain embodiments, $L_2$ is —C≡C—. In certain embodiments, $L_2$ is —OC($R^{L2b}$)$_2$—. In certain embodiments, $L_2$ is —OCH$_2$—. In certain embodiments, $L_2$ is —C($R^{L2b}$)$_2$O—. In certain embodiments, $L_2$ is —CH$_2$O—. In certain embodiments, $L_2$ is —$NR^{L2a}$C($R^{L2b}$)$_2$—. In certain embodiments, $L_2$ is —$NR^{L2a}$CH$_2$—. In certain embodiments, $L_2$ is —NHCH$_2$—. In certain embodiments, $L_2$ is —C($R^{L2b}$)$_2$$NR^{L2a}$—. In certain embodiments, $L_2$ is —CH$_2$$NR^{L2a}$—. In certain embodiments, $L_2$ is —CH$_2$NH—. In certain embodiments, $L_2$ is —SC($R^{L2b}$)$_2$—. In certain embodiments, $L_2$ is —SCH$_2$—. In certain embodiments, $L_2$ is —C($R^{L2b}$)$_2$S—. In certain embodiments, $L_2$ is —CH$_2$S—. In certain embodiments, $L_2$ is —S(=O)$_2$O—. In certain embodiments, $L_2$ is —OS(=O)$_2$—. In certain embodiments, $L_2$ is —S(=O)$_2$$NR^{L2a}$—. In certain embodiments, $L_2$ is —S(=O)$_2$NH—. In certain embodiments, $L_2$ is —$NR^{L2a}$S(=O)$_2$—. In certain embodiments, $L_2$ is —NHS(=O)$_2$—. In certain embodiments, $L_2$ is a substituted $C_{1-4}$ hydrocarbon chain. In certain embodiments, $L_2$ is an unsubstituted $C_{1-4}$ hydrocarbon chain. In certain embodiments, $L_2$ is a substituted $C_2$ hydrocarbon chain. In certain embodiments, $L_2$ is an unsubstituted $C_2$ hydrocarbon chain. In certain embodiments, $L_2$ is a substituted $C_3$ hydrocarbon chain. In certain embodiments, $L_2$ is an unsubstituted $C_3$ hydrocarbon chain. In certain embodiments, $L_2$ is a substituted $C_4$ hydrocarbon chain. In certain embodiments, $L_2$ is an unsubstituted $C_4$ hydrocarbon chain. In certain embodiments, $L_2$ is an optionally substituted $C_{1-4}$ hydrocarbon chain, wherein one or more carbon units of the hydrocarbon chain is replaced with —O—, —S—, —$NR^{L2a}$—, —$NR^{L2a}$C(=O)C(=O)—, —C(=O)$NR^{L2a}$—, —SC(=O)—, —C(=O)S—, —OC(=O)—, —C(=O)O—, —$NR^{L2a}$C(=S)—, —C(=S)$NR^{L2a}$—, trans-$CR^{L2b}=CR^{L2b}$—, cis-$CR^{L2b}=CR^{L2b}$—, —C≡C—, —S(=O)$_2$O—, —OS(=O)$_2$—, —S(=O)$_2$$NR^{L2a}$—, or —$NR^{L2a}$S(=O)$_2$—.

In certain embodiments, $R^{L2a}$ is H. In certain embodiments, $R^{L2a}$ is substituted alkyl. In certain embodiments, $R^{L2a}$ is unsubstituted alkyl. In certain embodiments, $R^{L2a}$ is $C_{1-6}$ alkyl. In certain embodiments, $R^{L2a}$ is methyl. In certain embodiments, $R^{L2a}$ is ethyl. In certain embodiments, $R^{L2a}$ is propyl. In certain embodiments, $R^{L2a}$ is butyl. In certain embodiments, $R^{L2a}$ is a nitrogen protecting group. In certain embodiments, $R^{L2a}$ is Bn, BOC, Cbz, Fmoc, trifluoroacetyl, triphenylmethyl, or Ts.

In certain embodiments, at least one $R^{L2b}$ is H. In certain embodiments, at least one $R^{L2b}$ is halogen. In certain embodiments, at least one $R^{L2b}$ is F. In certain embodiments, at least one $R^{L2b}$ is Cl. In certain embodiments, at least one $R^{L2b}$ is Br. In certain embodiments, at least one $R^{L2b}$ is I (iodine). In certain embodiments, at least one $R^{L2b}$ is substituted alkyl. In certain embodiments, at least one $R^{L2b}$ is unsubstituted alkyl. In certain embodiments, at least one $R^{L2b}$ is $C_{1-6}$ alkyl. In certain embodiments, at least one $R^{L2b}$ is methyl. In certain embodiments, at least one $R^{L2b}$ is ethyl. In certain embodiments, at least one $R^{L2b}$ is propyl. In certain embodiments, at least one $R^{L2b}$ is butyl. In certain embodiments, at least one $R^{L2b}$ is substituted alkenyl. In certain embodiments, at least one $R^{L2b}$ is unsubstituted alkenyl. In certain embodiments, at least one $R^{L2b}$ is vinyl. In certain embodiments, at least one $R^{L2b}$ is substituted alkynyl. In certain embodiments, at least one $R^{L2b}$ is unsubstituted alkynyl. In certain embodiments, at least one $R^{L2b}$ is ethynyl. In certain embodiments, at least one $R^{L2b}$ is substituted carbocyclyl. In certain embodiments, at least one $R^{L2b}$ is unsubstituted carbocyclyl. In certain embodiments, at least one $R^{L2b}$ is substituted heterocyclyl. In certain embodiments, at least one $R^{L2b}$ is unsubstituted heterocyclyl. In certain embodiments, at least one $R^{L2b}$ is substituted aryl. In certain embodiments, at least one $R^{L2b}$ is unsubstituted aryl. In certain embodiments, at least one $R^{L2b}$ is substituted phenyl. In certain embodiments, at least one $R^{L2b}$ is unsubstituted phenyl. In certain embodiments, at least one $R^{L2b}$ is substituted heteroaryl. In certain embodiments, at least one $R^{L2b}$ is unsubstituted heteroaryl. In certain embodiments, at least one $R^{L2b}$ is substituted pyridyl. In certain embodiments, at least one $R^{L2b}$ is unsubstituted pyridyl. In certain embodiments, two $R^{L2b}$ groups are joined to form a substituted carbocyclic ring. In certain embodiments, two $R^{L2b}$ groups are joined to form an unsubstituted carbocyclic ring. In certain embodiments, two $R^{L2b}$ groups are joined to form a substituted heterocyclic ring. In certain embodiments, two $R^{L2b}$ groups are joined to form an unsubstituted heterocyclic ring.

Ring C is a para-phenylene moiety. Ring C may be unsubstituted or substituted with one or more substituents $R^C$. In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is acyl. In certain embodiments, at least one $R^C$ is acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is substituted alkynyl. In certain embodiments, at least one $R^C$ is unsubstituted alkynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is —$OR^{C1}$. In certain embodiments, at least one $R^C$ is —N($R^{C1}$)$_2$—. In certain embodiments, at least one $R^C$ is —$SR^{C1}$.

In certain embodiments, when $R^C$ is —$OR^{C1}$, —N($R^{C1}$)$_2$, or —$SR^{C1}$, at least one $R^{C1}$ is H. In certain embodiments, at least one $R^{C1}$ is acyl. In certain embodiments, at least one $R^{C1}$ is acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is substituted alkynyl. In certain embodiments, at least one $R^{C1}$ is unsubstituted alkynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is an oxygen protecting group when attached to an oxygen atom. In certain embodiments, at least one $R^{C1}$ is a sulfur protecting group when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

Ring C may be unsubstituted or substituted with one or more $R^C$. In certain embodiments, Ring C is unsubstituted, and thus n is 0. In certain embodiments, n is 1. In certain embodiments, n is 2. In certain embodiments, n is 3. In certain embodiments, n is 4.

In certain embodiments, $R^C$ is substituted alkyl; and n is 1. In certain embodiments, $R^C$ is unsubstituted alkyl; and n is 1.

Ring D is a meta-phenylene moiety. Ring D may be unsubstituted or substituted with one or more substituents $R^D$. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is acyl. In certain embodiments, at least one $R^D$ is acetyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is ethyl. In certain embodiments, at least one $R^D$ is propyl. In certain embodiments, at least one $R^D$ is butyl. In certain embodiments, at least one $R^D$ is substituted alkenyl. In certain embodiments, at least one $R^D$ is unsubstituted alkenyl. In certain embodiments, at least one $R^D$ is substituted alkynyl. In certain embodiments, at least one $R^D$ is unsubstituted alkynyl. In certain embodiments, at least one $R^D$ is substituted carbocyclyl. In certain embodiments, at least one $R^D$ is unsubstituted carbocyclyl. In certain embodiments, at least one $R^D$ is substituted heterocyclyl. In certain embodiments, at least one $R^D$ is unsubstituted heterocyclyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted heteroaryl. In certain embodiments, at least one $R^D$ is unsubstituted heteroaryl. In certain embodiments, at least one $R^D$ is substituted pyridyl. In certain embodiments, at least one $R^D$ is unsubstituted pyridyl. In certain embodiments, at least one $R^D$ is $-OR^{D1}$. In certain embodiments, at least one $R^D$ is $-N(R^{D1})_2$. In certain embodiments, at least one $R^D$ is $-SR^{D1}$.

In certain embodiments, at least one $R^{D1}$ is H. In certain embodiments, at least one $R^{D1}$ is acyl. In certain embodiments, at least one $R^{D1}$ is acetyl. In certain embodiments, at least one $R^{D1}$ is substituted alkyl. In certain embodiments, at least one $R^{D1}$ is unsubstituted alkyl. In certain embodiments, at least one $R^{D1}$ is $C_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is substituted alkenyl. In certain embodiments, at least one $R^{D1}$ is unsubstituted alkenyl. In certain embodiments, at least one $R^{D1}$ is substituted alkynyl. In certain embodiments, at least one $R^{D1}$ is unsubstituted alkynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is a nitrogen protecting group when attached to a nitrogen atom. In certain embodiments, at least one $R^{D1}$ is an oxygen protecting group when attached to an oxygen atom. In certain embodiments, at least one $R^{D1}$ is a sulfur protecting group when attached to a sulfur atom. In certain embodiments, two $R^{D1}$ groups are joined to form a substituted heterocyclic ring. In certain embodiments, two $R^{D1}$ groups are joined to form an unsubstituted heterocyclic ring.

Ring D may be unsubstituted or substituted with one or more $R^D$. In certain embodiments, Ring D is unsubstituted, and thus p is 0. In certain embodiments, p is 1. In certain embodiments, p is 2. In certain embodiments, p is 3. In certain embodiments, p is 4.

In certain embodiments, $R^D$ is substituted alkyl; and p is 1. In certain embodiments, $R^D$ is unsubstituted alkyl; and p is 1.

$R^E$ is a substituent on Ring D, meta to $L_2$. In certain embodiments, $R^E$ is:

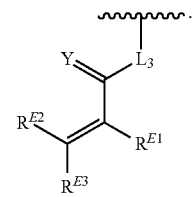

In certain embodiments, $R^E$ is a group selected from the group consisting of:

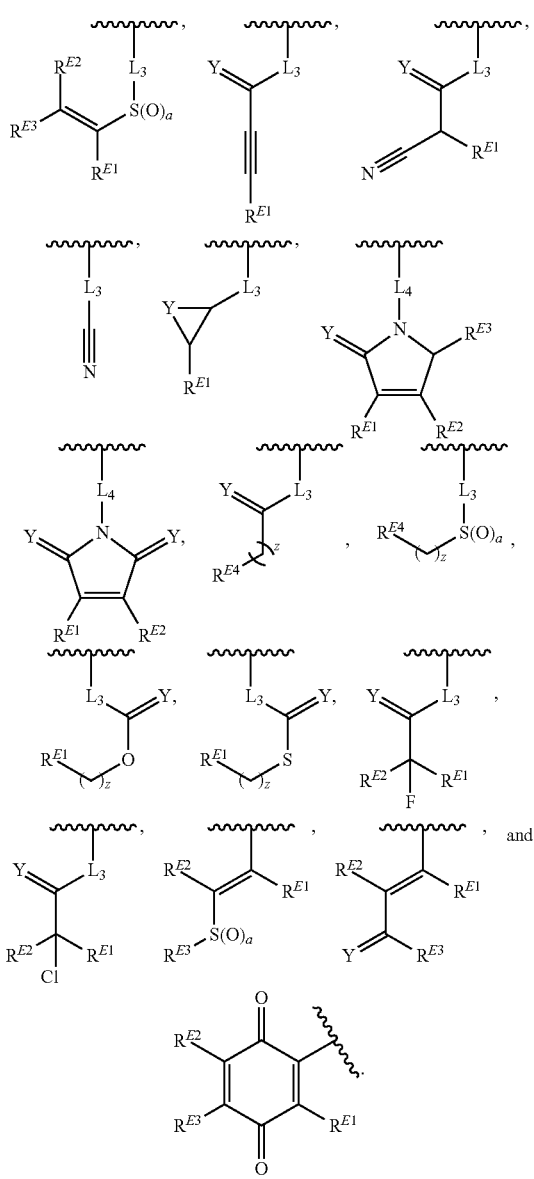

In compounds of Formula (I), $L_3$ is a divalent linker moiety. $L_3$ may contain 0-4 carbon or hetero atoms in the backbone of $L_3$. $L_3$ may be saturated or unsaturated. $L_3$ may be substituted or unsubstituted. $L_3$ may be branched or unbranched. In certain embodiments, $L_3$ is a bond. In certain embodiments, $L_3$ is —O—. In certain embodiments, $L_3$ is —S—. In certain embodiments, $L_3$ is —$NR^{L3a}$—. In certain embodiments, $L_3$ is —NH—. In certain embodiments, $L_3$ is —$NR^{L3a}$C(=O)—. In certain embodiments, $L_3$ is —NHC(=O)—. In certain embodiments, $L_3$ is —C(=O)$NR^{L3a}$—. In certain embodiments, $L_3$ is —C(=O)NH—. In certain embodiments, $L_3$ is —SC(=O)—. In certain embodiments, $L_3$ is —C(=O)S—. In certain embodiments, $L_3$ is —OC(=O)—. In certain embodiments, $L_3$ is —C(=O)O—. In certain embodiments, $L_3$ is —$NR^{L3a}$C(=S)—. In certain embodiments, $L_3$ is —NHC(=S)—. In certain embodiments, $L_3$ is —C(=S)$NR^{L3a}$—. In certain embodiments, $L_3$ is —C(=S)NH—. In certain embodiments, $L_3$ is trans-$CR^{L3b}$=$CR^{L3b}$—. In certain embodiments, $L_3$ is trans-CH=CH—. In certain embodiments, $L_3$ is cis-$CR^{L3b}$=$CR^{L3b}$—. In certain embodiments, $L_3$ is cis-CH=CH—. In certain embodiments, $L_3$ is —C≡C—. In certain embodiments, $L_3$ is —OC($R^{L3b}$)$_2$—. In certain embodiments, $L_3$ is —$OCH_2$—. In certain embodiments, $L_3$ is —C($R^{L3b}$)$_2$O—. In certain embodiments, $L_3$ is —$CH_2$O—. In certain embodiments, $L_3$ is —$NR^{L3a}$C($R^{L3b}$)$^2$—. In certain embodiments, $L_3$ is —$NR^{L3a}CH_2$—. In certain embodiments, $L_3$ is —$NHCH_2$—. In certain embodiments, $L_3$ is —C($R^{L3b}$)$_2NR^{L3a}$—. In certain embodiments, $L_3$ is —$CH_2NR^{L3a}$—. In certain embodiments, $L_3$ is —$CH_2$NH—. In certain embodiments, $L_3$ is —SC($R^{L3b}$)$_2$—. In certain embodiments, $L_3$ is —$SCH_2$—. In certain embodiments, $L_3$ is —C($R^{L3b}$)$_2$S—. In certain embodiments, $L_3$ is —$CH_2$S—. In certain embodiments, $L_3$ is —S(=O)$_2$O—. In certain embodiments, $L_3$ is —OS(=O)$_2$—. In certain embodiments, $L_3$ is —S(=O)$_2NR^{L3a}$—. In certain embodiments, $L_3$ is —S(=O)$_2$NH—. In certain embodiments, $L_3$ is —$NR^{L3a}$S(=O)$_2$—. In certain embodiments, $L_3$ is —NHS(=O)$_2$—. In certain embodiments, $L_3$ is a substituted $C_{1-4}$ hydrocarbon chain. In certain embodiments, $L_3$ is an unsubstituted $C_{1-4}$ hydrocarbon chain. In certain embodiments, $L_3$ is a substituted $C_2$ hydrocarbon chain. In certain embodiments, $L_3$ is an unsubstituted $C_2$ hydrocarbon chain. In certain embodiments, $L_3$ is a substituted $C_3$ hydrocarbon chain. In certain embodiments, $L_3$ is an unsubstituted $C_3$ hydrocarbon chain. In certain embodiments, $L_3$ is a substituted $C_4$ hydrocarbon chain. In certain embodiments, $L_3$ is an unsubstituted $C_4$ hydrocarbon chain. In certain embodiments, $L_3$ is an optionally substituted $C_{1-4}$ hydrocarbon chain, wherein one or more carbon units of the hydrocarbon chain is replaced with —O—, —S—, —$NR^{L3a}$, —$NR^{L3a}$C(=O—, —C(=O)$NR^{L3a}$—, —SC(=O)—, —C(=O)S—, —OC(=O)—, —C(=O)O—, —$NR^{L3a}$C(=S)—, —C(=S)$NR^{L3a}$—, trans-$CR^{L3b}$=$CR^{L3b}$—, cis-$CR^{L3b}$=$CR^{L3b}$—, —C≡C—, —S(=O)$_2$O—, —OS(=O)$_2$—, —S(=O)$_2NR^{L3a}$—, or —$NR^{L3a}$S(=O)$_2$—.

In certain embodiments, $R^{L3a}$ is H. In certain embodiments, $R^{L3a}$ is substituted alkyl. In certain embodiments, $R^{L3a}$ is unsubstituted alkyl. In certain embodiments, $R^{L3a}$ is $C_{1-6}$ alkyl. In certain embodiments, $R^{L3a}$ is methyl. In certain embodiments, $R^{L3a}$ is ethyl. In certain embodiments, $R^{L3a}$ is propyl. In certain embodiments, $R^{L3a}$ is butyl. In certain embodiments, $R^{L3a}$ is a nitrogen protecting group. In certain embodiments, $R^{L3a}$ is Bn, BOC, Cbz, Fmoc, trifluoroacetyl, triphenylmethyl, or Ts.

In certain embodiments, at least one $R^{L3b}$ is H. In certain embodiments, at least one $R^{L3b}$ is halogen. In certain embodiments, at least one $R^{L3b}$ is F. In certain embodiments, at least one $R^{L3b}$ is Cl. In certain embodiments, at least one $R^{L3b}$ is Br. In certain embodiments, at least one $R^{L3b}$ is I (iodine). In certain embodiments, at least one $R^{L3b}$ is substituted alkyl. In certain embodiments, at least one $R^{L3b}$ is unsubstituted alkyl. In certain embodiments, at least one $R^{L3b}$ is $C_{1-6}$ alkyl. In certain embodiments, at least one $R^{L3b}$ is methyl. In certain embodiments, at least one $R^{L3b}$ is ethyl. In certain embodiments, at least one $R^{L3b}$ is propyl. In certain embodiments, at least one $R^{L3b}$ is butyl. In certain embodiments, at least one $R^{L3b}$ is substituted alkenyl. In certain embodiments, at least one $R^{L3b}$ is unsubstituted alkenyl. In certain embodiments, at least one $R^{L3b}$ is vinyl. In certain embodiments, at least one $R^{L3b}$ is substituted alkynyl. In certain embodiments, at least one $R^{L3b}$ is unsubstituted alkynyl. In certain embodiments, at least one $R^{L3b}$ is ethynyl. In certain embodiments, at least one $R^{L3b}$ is substituted carbocyclyl. In certain embodiments, at least one $R^{L3b}$ is unsubstituted carbocyclyl. In certain embodiments, at least one $R^{L3b}$ is substituted heterocyclyl. In certain embodiments, at least one $R^{L3b}$ is unsubstituted heterocyclyl. In certain embodiments, at least one $R^{L3b}$ is substituted aryl. In certain embodiments, at least one $R^{L3b}$ is unsubstituted aryl. In certain embodiments, at least one $R^{L3b}$ is substituted phenyl. In certain embodiments, at least one $R^{L3b}$ is unsubstituted phenyl. In certain embodiments, at least one $R^{L3b}$ is substituted heteroaryl. In certain embodiments, at least one $R^{L3b}$ is unsubstituted heteroaryl. In certain embodiments, at least one $R^{L3b}$ is substituted pyridyl. In certain embodiments, at least one $R^{L3b}$ is unsubstituted pyridyl. In certain embodiments, two $R^{L3b}$ groups are joined to form a substituted carbocyclic ring. In certain embodiments, two $R^{L3b}$ groups are joined to form an unsubstituted carbocyclic ring. In certain embodiments, two $R^{L3b}$ groups are joined to form a substituted heterocyclic ring. In certain embodiments, two $R^{L3b}$ groups are joined to form an unsubstituted heterocyclic ring.

$L_4$ is a divalent linker moiety. $L_4$ may contain 0-4 carbon or hetero atoms in the backbone of $L_4$. $L_4$ may be saturated or unsaturated. $L_4$ may be substituted or unsubstituted. $L_4$ may be branched or unbranched. In certain embodiments, $L_4$ is a bond. In certain embodiments, $L_4$ is a substituted $C_{1-4}$ hydrocarbon chain. In certain embodiments, $L_4$ is an unsubstituted $C_{1-4}$ hydrocarbon chain. In certain embodiments, $L_4$ is —$CH_2$—. In certain embodiments, $L_4$ is —$CH_2CH_2$—. In certain embodiments, $L_4$ is —CH=CH—. In certain embodiments, $L_4$ is —$(CH_2)_3$—. In certain embodiments, $L_4$ is —$(CH_2)_4$—.

In certain embodiments, $R^{E1}$ is H. In certain embodiments, $R^{E1}$ is halogen. In certain embodiments, $R^{E1}$ is F. In certain embodiments, $R^{E1}$ is Cl. In certain embodiments, $R^{E1}$ is Br. In certain embodiments, $R^{E1}$ is I (iodine). In certain embodiments, $R^{E1}$ is acyl. In certain embodiments, $R^{E1}$ is acetyl. In certain embodiments, $R^{E1}$ is substituted alkyl. In certain embodiments, $R^{E1}$ is unsubstituted alkyl. In certain embodiments, $R^{E1}$ is $C_{1-6}$ alkyl. In certain embodiments, $R^{E1}$ is methyl. In certain embodiments, $R^{E1}$ is ethyl. In certain embodiments, $R^{E1}$ is propyl. In certain embodiments, $R^{E1}$ is butyl. In certain embodiments, $R^{E1}$ is substituted alkenyl. In certain embodiments, $R^{E1}$ is unsubstituted alkenyl. In certain embodiments, $R^{E1}$ is substituted alkynyl. In certain embodiments, $R^{E1}$ is unsubstituted alkynyl. In certain embodiments, $R^{E1}$ is substituted carbocyclyl. In certain embodiments, $R^{E1}$ is unsubstituted carbocyclyl. In certain embodiments, $R^{E1}$ is substituted heterocyclyl. In certain embodiments, $R^{E1}$ is unsubstituted heterocyclyl. In certain embodiments, $R^{E1}$ is substituted aryl. In certain embodiments, $R^{E1}$ is unsubstituted aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is substituted pyridyl. In certain embodiments, $R^{E1}$ is unsubstituted pyridyl. In certain embodiments, $R^{E1}$ is —$OR^{E1a}$—. In certain embodiments, $R^{E1}$ is —$N(R^{E1a})_2$. In certain embodiments, $R^{E1}$ is —$SR^{E1a}$. In certain embodiments, $R^{E1}$ is —$CH_2OR^{E1a}$. In certain embodiments, $R^{E1}$ is —$CH_2N(R^{E1a})_2$. In certain embodiments, $R^{E1}$ is —$CH_2SR^{E1a}$.

In certain embodiments, at least one $R^{E1a}$ is H. In certain embodiments, at least one $R^{E1a}$ is acyl. In certain embodiments, at least one $R^{E1a}$ is acetyl. In certain embodiments, at least one $R^{E1a}$ is substituted alkyl. In certain embodiments, at least one $R^{E1a}$ is unsubstituted alkyl. In certain embodiments, at least one $R^{E1a}$ is $C_{1-6}$ alkyl. In certain embodiments, at least one $R^{E1a}$ is methyl. In certain embodiments, at least one $R^{E1a}$ is ethyl. In certain embodiments, at least one $R^{E1a}$ is propyl. In certain embodiments, at least one $R^{E1a}$ is butyl. In certain embodiments, at least one $R^{E1a}$ is substituted alkenyl. In certain embodiments, at least one $R^{E1a}$ is unsubstituted alkenyl. In certain embodiments, at least one $R^{E1a}$ is substituted alkynyl. In certain embodiments, at least one $R^{E1a}$ is unsubstituted alkynyl. In certain embodiments, at least one $R^{E1a}$ is substituted carbocyclyl. In certain embodiments, at least one $R^{E1a}$ is unsubstituted carbocyclyl. In certain embodiments, at least one $R^{E1a}$ is substituted heterocyclyl. In certain embodiments, at least one $R^{E1a}$ is unsubstituted heterocyclyl. In certain embodiments, at least one $R^{E1a}$ is substituted aryl. In certain embodiments, at least one $R^{E1a}$ is unsubstituted aryl. In certain embodiments, at least one $R^{E1a}$ is substituted phenyl. In certain embodiments, at least one $R^{E1a}$ is unsubstituted phenyl. In certain embodiments, at least one $R^{E1a}$ is substituted heteroaryl. In certain embodiments, at least one $R^{E1a}$ is unsubstituted heteroaryl. In certain embodiments, at least one $R^{E1a}$ is substituted pyridyl. In certain embodiments, at least one $R^{E1a}$ is unsubstituted pyridyl. In certain embodiments, at least one $R^{E1a}$ is a nitrogen protecting group when attached to a nitrogen atom. In certain embodiments, at least one $R^{E1a}$ is an oxygen protecting group when attached to an oxygen atom. In certain embodiments, at least one $R^{E1a}$ is a sulfur protecting group when attached to a sulfur atom. In certain embodiments, two $R^{E1a}$ groups are joined to form a substituted heterocyclic ring. In certain embodiments, two $R^{E1a}$ groups are joined to form an unsubstituted heterocyclic ring.

In certain embodiments, $R^{E2}$ is H. In certain embodiments, $R^{E2}$ is halogen. In certain embodiments, $R^{E2}$ is F. In certain embodiments, $R^{E2}$ is Cl. In certain embodiments, $R^{E2}$ is Br. In certain embodiments, $R^{E2}$ is I (iodine). In certain embodiments, $R^{E2}$ is acyl. In certain embodiments, $R^{E2}$ is acetyl. In certain embodiments, $R^{E2}$ is substituted alkyl. In certain embodiments, $R^{E2}$ is unsubstituted alkyl. In certain embodiments, $R^{E2}$ is $C_{1-6}$ alkyl. In certain embodiments, $R^{E2}$ is methyl. In certain embodiments, $R^{E2}$ is ethyl. In certain embodiments, $R^{E2}$ is propyl. In certain embodiments, $R^{E2}$ is butyl. In certain embodiments, $R^{E2}$ is substituted alkenyl. In certain embodiments, $R^{E2}$ is unsubstituted alkenyl. In certain embodiments, $R^{E2}$ is substituted alkynyl. In certain embodiments, $R^{E2}$ is unsubstituted alkynyl. In certain embodiments, $R^{E2}$ is substituted carbocyclyl. In certain embodiments, $R^{E2}$ is unsubstituted carbocyclyl. In certain embodiments, $R^{E2}$ is substituted heterocyclyl. In certain embodiments, $R^{E2}$ is unsubstituted heterocyclyl. In certain embodiments, $R^{E2}$ is substituted aryl. In certain embodiments, $R^{E2}$ is unsubstituted aryl. In certain embodiments, $R^{E2}$ is substituted phenyl. In certain embodiments, $R^{E2}$ is unsubstituted phenyl. In certain embodiments, $R^{E2}$ is substituted heteroaryl. In certain embodiments, $R^{E2}$ is unsubstituted heteroaryl. In certain embodiments, $R^{E2}$ is substituted pyridyl. In certain embodiments, $R^{E2}$ is unsubstituted pyridyl. In certain embodiments, $R^{E2}$ is —$OR^{E2a}$. In certain embodiments, $R^{E2}$ is —$N(R^{E2a})_2$. In certain embodiments, $R^{E2}$ is —$SR^{E2a}$. In certain embodiments, $R^{E2}$ is —$CH_2OR^{E2a}$. In certain embodiments, $R^{E2}$ is —$CH_2N(R^{E2a})_2$. In certain embodiments, $R^{E2}$ is —$CH_2SR^{E2a}$.

In certain embodiments, at least one $R^{E2a}$ is H. In certain embodiments, at least one $R^{E2a}$ is acyl. In certain embodiments, at least one $R^{E2a}$ is acetyl. In certain embodiments, at least one $R^{E2a}$ is substituted alkyl. In certain embodiments, at least one $R^{E2a}$ is unsubstituted alkyl. In certain embodiments, at least one $R^{E2a}$ is $C_{1-6}$ alkyl. In certain embodiments, at least one $R^{E2a}$ is methyl. In certain embodiments, at least one $R^{E2a}$ is ethyl. In certain embodiments, at least one $R^{E2a}$ is propyl. In certain embodiments, at least one $R^{E2a}$ is butyl. In certain embodiments, at least one $R^{E2a}$ is substituted alkenyl. In certain embodiments, at least one $R^{E2a}$ is unsubstituted alkenyl. In certain embodiments, at least one $R^{E2a}$ is substituted alkynyl. In certain embodiments, at least one $R^{E2a}$ is unsubstituted alkynyl. In certain embodiments, at least one $R^{E2a}$ is substituted carbocyclyl. In certain embodiments, at least one $R^{E2a}$ is unsubstituted carbocyclyl. In certain embodiments, at least one $R^{E2a}$ is substituted heterocyclyl. In certain embodiments, at least one $R^{E2a}$ is unsubstituted heterocyclyl. In certain embodiments, at least one $R^{E2a}$ is substituted aryl. In certain embodiments, at least one $R^{E2a}$ is unsubstituted aryl. In certain embodiments, at least one $R^{E2a}$ is substituted phenyl. In certain embodiments, at least one $R^{E2a}$ is unsubstituted phenyl. In certain embodiments, at least one $R^{E2a}$ is substituted heteroaryl. In certain embodiments, at least one $R^{E2a}$ is unsubstituted heteroaryl. In certain embodiments, at least one $R^{E2a}$ is substituted pyridyl. In certain embodiments, at least one $R^{E2a}$ is unsubstituted pyridyl. In certain embodiments, at least one $R^{E2a}$ is a nitrogen protecting group when attached to a nitrogen atom. In certain embodiments, at least one $R^{E2a}$ is an oxygen protecting group when attached to an oxygen atom. In certain embodiments, at least one $R^{E2a}$ is a sulfur protecting group when attached to a sulfur atom. In certain embodiments, two $R^{E2a}$ groups are joined to form a substituted heterocyclic ring. In certain embodiments, two $R^{E2a}$ groups are joined to form an unsubstituted heterocyclic ring.

In certain embodiments, $R^{E3}$ is H. In certain embodiments, $R^{E3}$ is halogen. In certain embodiments, $R^{E3}$ is F. In certain embodiments, $R^{E3}$ is Cl. In certain embodiments, $R^{E3}$ is Br. In certain embodiments, $R^{E3}$ is I (iodine). In certain embodiments, $R^{E3}$ is acyl. In certain embodiments, $R^{E3}$ is acetyl. In certain embodiments, $R^{E3}$ is substituted alkyl. In certain embodiments, $R^{E3}$ is unsubstituted alkyl. In certain embodiments, $R^{E3}$ is $C_{1-6}$ alkyl. In certain embodiments, $R^{E3}$ is methyl. In certain embodiments, $R^{E3}$ is ethyl. In certain embodiments, $R^{E3}$ is propyl. In certain embodiments, $R^{E3}$ is butyl. In certain embodiments, $R^{E3}$ is substituted alkenyl. In certain embodiments, $R^{E3}$ is unsubstituted alkenyl. In certain embodiments, $R^{E3}$ is substituted alkynyl. In certain embodiments, $R^{E3}$ is unsubstituted alkynyl. In certain embodiments, $R^{E3}$ is substituted carbocyclyl. In certain embodiments, $R^{E3}$ is unsubstituted carbocyclyl. In certain embodiments, $R^{E3}$ is substituted heterocyclyl. In certain embodiments, $R^{E3}$ is unsubstituted heterocyclyl. In certain embodiments, $R^{E3}$ is substituted aryl. In certain embodiments, $R^{E3}$ is unsubstituted aryl. In certain embodiments, $R^{E3}$ is substituted phenyl. In certain embodiments, $R^{E3}$ is unsubstituted phenyl. In certain embodiments, $R^{E3}$ is substituted heteroaryl. In certain embodiments, $R^{E3}$ is unsubstituted heteroaryl. In certain embodiments, $R^{E3}$ is substituted pyridyl. In certain embodiments, $R^{E3}$ is unsubstituted pyridyl. In certain embodiments, $R^{E3}$ is —$OR^{E3a}$. In certain embodiments, $R^{E3}$ is —$N(R^{E3a})_2$. In certain embodiments, $R^{E3}$ is —$SR^{E3a}$. In certain embodiments, $R^{E3}$ is —$CH_2OR^{E3a}$. In certain embodiments, $R^{E3}$ is —$CH_2N(R^{E3a})_2$. In certain embodiments, $R^{E3}$ is —$CH_2SR^{E3a}$.

In certain embodiments, at least one $R^{E3a}$ is H. In certain embodiments, at least one $R^{E3a}$ is acyl. In certain embodiments, at least one $R^{E3a}$ is acetyl. In certain embodiments, at least one $R^{E3a}$ is substituted alkyl. In certain embodiments, at least one $R^{E3a}$ is unsubstituted alkyl. In certain embodiments, at least one $R^{E3a}$ is $C_{1-6}$ alkyl. In certain embodiments, at least one $R^{E3a}$ is methyl. In certain embodiments, at least one $R^{E3a}$ is ethyl. In certain embodiments, at least one $R^{E3a}$ is propyl. In certain embodiments, at least one $R^{E3a}$ is butyl. In certain embodiments, at least one $R^{E3a}$ is substituted alkenyl. In certain embodiments, at least one $R^{E3a}$ is unsubstituted alkenyl. In certain embodiments, at least one $R^{E3a}$ is substituted alkynyl. In certain embodiments, at least one $R^{E3a}$ is unsubstituted alkynyl. In certain embodiments, at least one $R^{E3a}$ is substituted carbocyclyl. In certain embodiments, at least one $R^{E3a}$ is unsubstituted carbocyclyl. In certain embodiments, at least one $R^{E3a}$ is substituted heterocyclyl. In certain embodiments, at least one $R^{E3a}$ is unsubstituted heterocyclyl. In certain embodiments, at least one $R^{E3a}$ is substituted aryl. In certain embodiments, at least one $R^{E3a}$ is unsubstituted aryl. In certain embodiments, at least one $R^{E3a}$ is substituted phenyl. In certain embodiments, at least one $R^{E3a}$ is unsubstituted phenyl. In certain embodiments, at least one $R^{E3a}$ is substituted heteroaryl. In certain embodiments, at least one $R^{E3a}$ is unsubstituted heteroaryl. In certain embodiments, at least one $R^{E3a}$ is substituted pyridyl. In certain embodiments, at least one $R^{E3a}$ is unsubstituted pyridyl. In certain embodiments, at least one $R^{E3a}$ is a nitrogen protecting group when attached to a nitrogen atom. In certain embodiments, at least one $R^{E3a}$ is an oxygen protecting group when attached to an oxygen atom. In certain embodiments, at least one $R^{E3a}$ is a sulfur protecting group when attached to a sulfur atom. In certain embodiments, two $R^{E3a}$ groups are joined to form a substituted heterocyclic ring. In certain embodiments, two $R^{E3a}$ groups are joined to form an unsubstituted heterocyclic ring.

In compounds of Formula (I), $R^E$ may include a substituent $R^{E4}$. In certain embodiments, $R^{E4}$ is a leaving group. In certain embodiments, $R^{E4}$ is halogen. In certain embodiments, $R^{E4}$ is F. In certain embodiments, $R^{E4}$ is Cl. In certain embodiments, $R^{E4}$ is Br. In certain embodiments, $R^{E4}$ is I (iodine). In certain embodiments, $R^{E4}$ is —$OS(=O)_wR^{E4a}$. In certain embodiments, w is 1. In certain embodiments, w is 2. In certain embodiments, $R^{E4}$ is —OMs. In certain embodiments, $R^{E4}$ is —OTf. In certain embodiments, $R^{E4}$ is —OTs. In certain embodiments, $R^{E4}$ is —OBs. In certain embodiments, $R^{E4}$ is 2-nitrobenzenesulfonyloxy. In certain embodiments, $R^{E4}$ is —$OR^{E4a}$. In certain embodiments, $R^{E4}$ is —OMe. In certain embodiments, $R^{E4}$ is —$OCF_3$. In certain embodiments, $R^{E4}$ is —OPh. In certain embodiments, $R^{E4}$ is —$OC(=O)R^{E4a}$. In certain embodiments, $R^{E4}$ is —OC(=O)Me. In certain embodiments, $R^{E4}$ is —OC(=O)$CF_3$. In certain embodiments, $R^{E4}$ is —OC(=O)Ph. In certain embodiments, $R^{E4}$ is —OC(=O)Cl. In certain embodiments, $R^{E4}$ is —OC(=O)$OR^{E4a}$. In certain embodiments, $R^{E4}$ is —OC(=O)OMe. In certain embodiments, $R^{E4}$ is —OC(=O)O(t-Bu).

In certain embodiments, $R^{E4a}$ is substituted alkyl. In certain embodiments, $R^{E4a}$ is unsubstituted alkyl. In certain embodiments, $R^{E4a}$ is substituted alkenyl. In certain embodiments, $R^{E4a}$ is unsubstituted alkenyl. In certain embodiments, $R^{E4a}$ is substituted alkynyl. In certain embodiments, $R^{E4a}$ is unsubstituted alkynyl. In certain embodiments, $R^{E4a}$ is substituted carbocyclyl. In certain embodiments, $R^{E4a}$ is unsubstituted carbocyclyl. In certain embodiments, $R^{E4a}$ is substituted heterocyclyl. In certain embodiments, $R^{E4a}$ is unsubstituted heterocyclyl. In certain embodiments, $R^{E4a}$ is substituted aryl. In certain embodiments, $R^{E4a}$ is unsubstituted aryl. In certain embodiments, $R^{E4a}$ is substituted heteroaryl. In certain embodiments, $R^{E4a}$ is unsubstituted heteroaryl.

In certain embodiments, Y is O. In certain embodiments, Y is S. In certain embodiments, Y is $NR^{E5}$. In certain embodiments, Y is NH.

In certain embodiments, $R^{E5}$ is H. In certain embodiments, $R^{E5}$ is substituted alkyl. In certain embodiments, $R^{E5}$ is unsubstituted alkyl. In certain embodiments, $R^{E5}$ is $C_{1-6}$ alkyl. In certain embodiments, $R^{E5}$ is methyl. In certain embodiments, $R^{E5}$ is ethyl. In certain embodiments, $R^{E5}$ is propyl. In certain embodiments, $R^{E5}$ is butyl. In certain embodiments, $R^{E5}$ is a nitrogen protecting group. In certain embodiments, $R^{E5}$ is BOC. In certain embodiments, $R^{E5}$ is Cbz. In certain embodiments, $R^{E5}$ is Fmoc. In certain embodiments, $R^{E5}$ is Bn.

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, the compound of Formula (I) is of the formula:

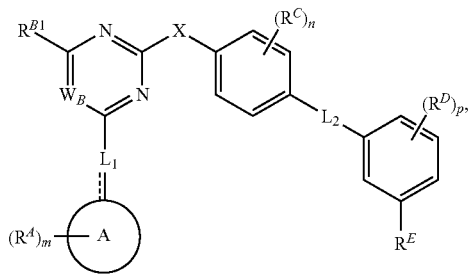

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

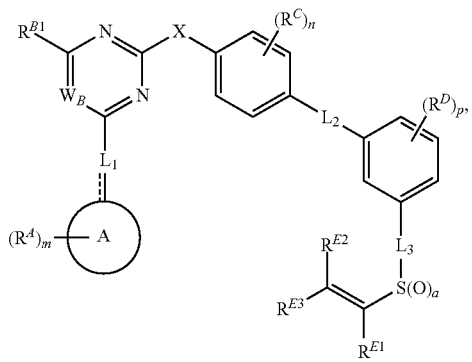

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

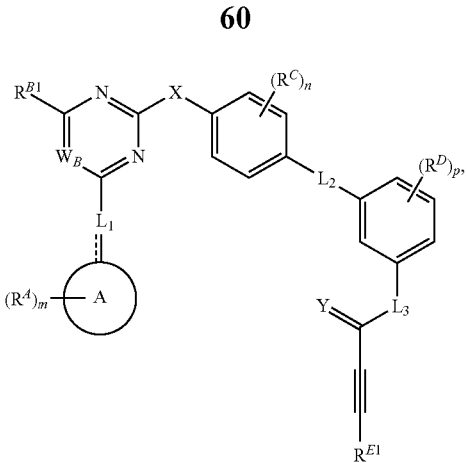

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

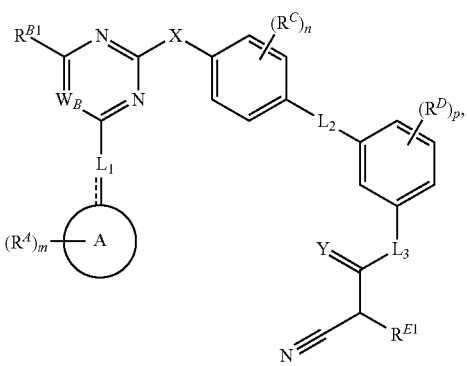

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

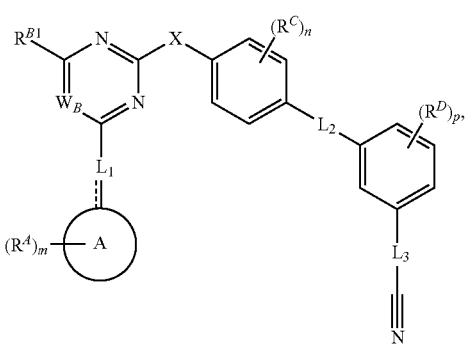

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

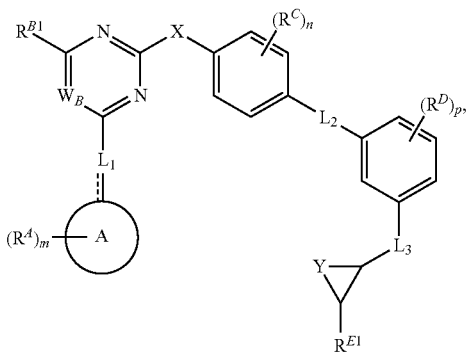

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

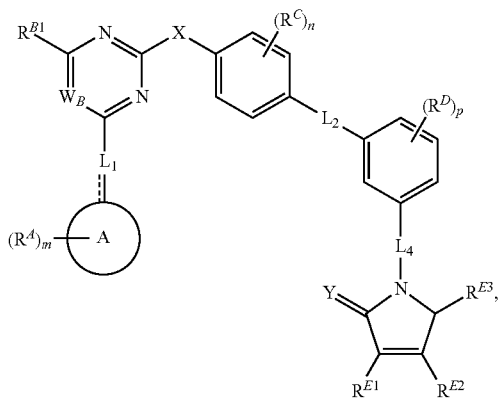

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

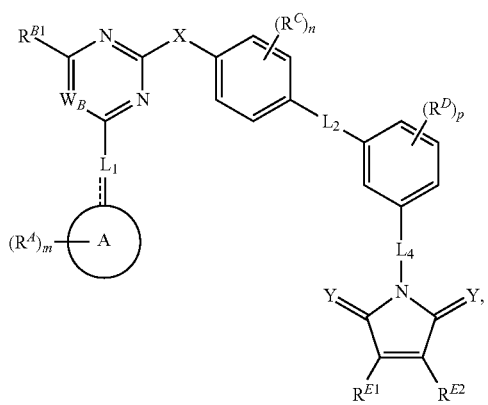

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

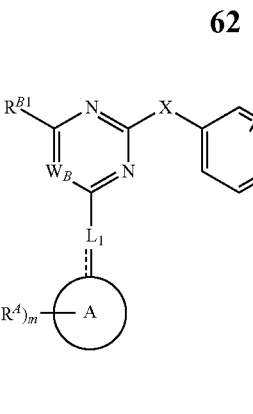

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

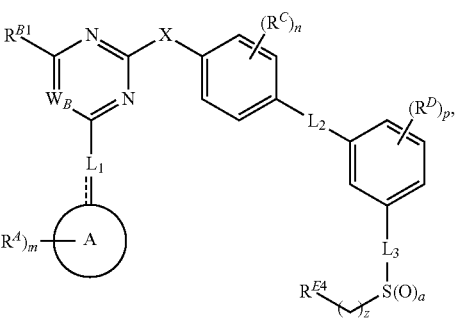

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

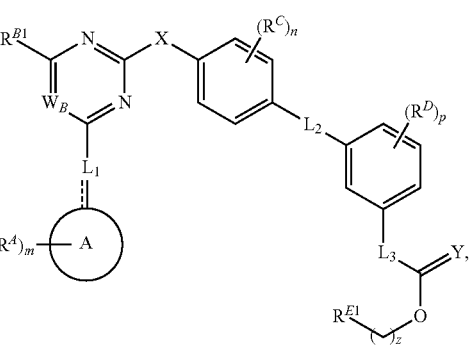

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

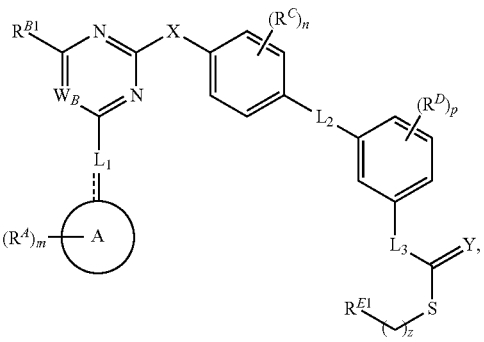

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

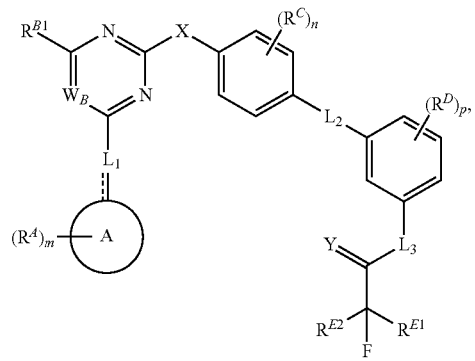

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

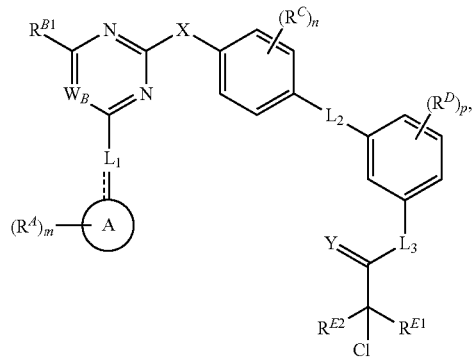

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

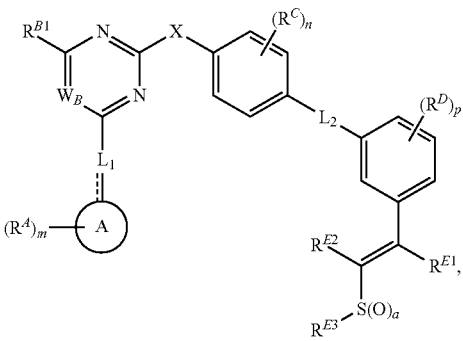

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

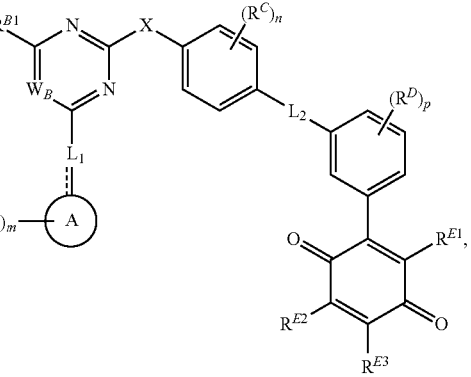

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

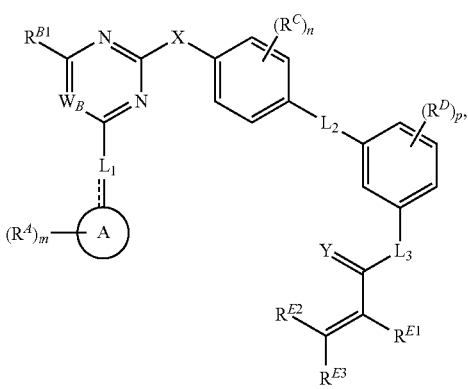
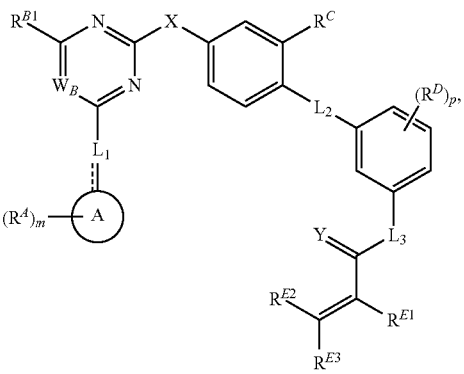
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
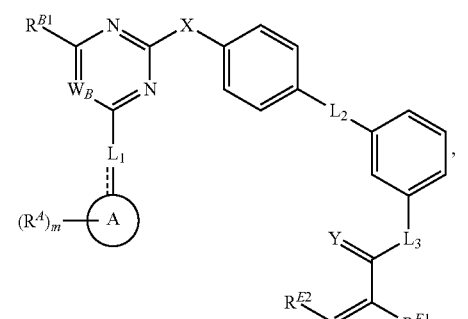
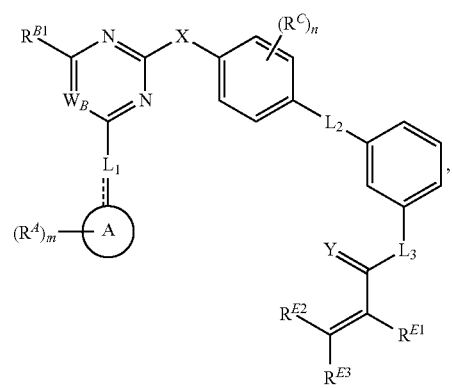
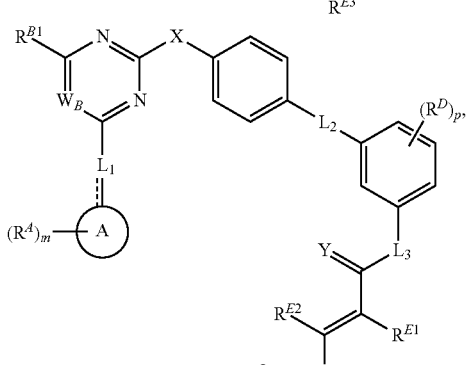
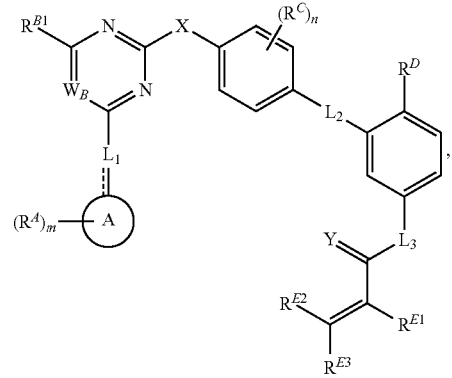
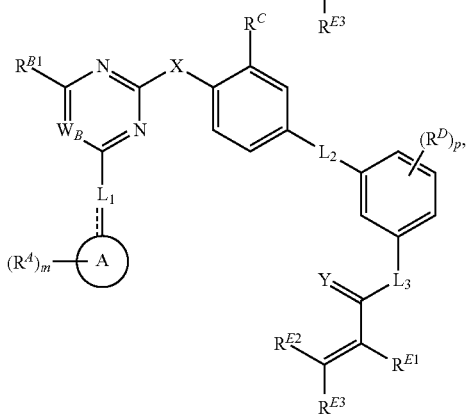
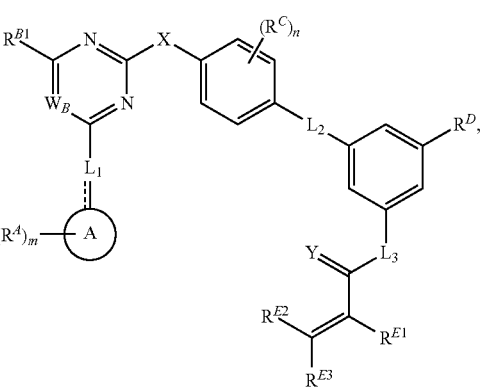

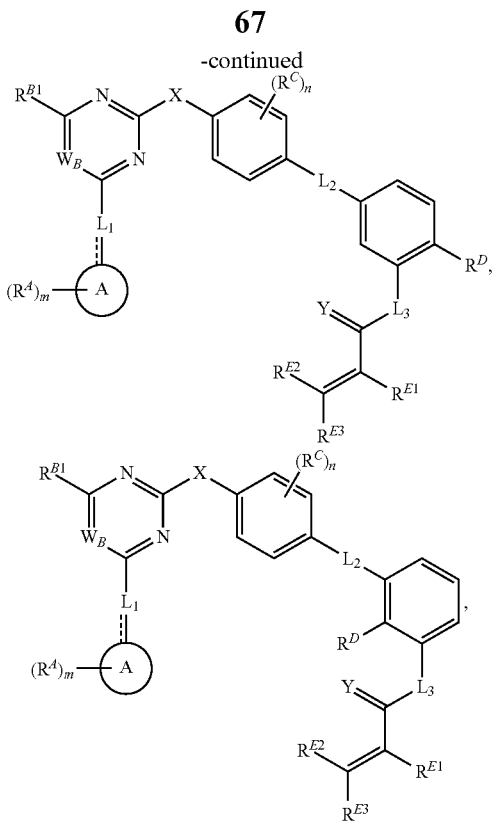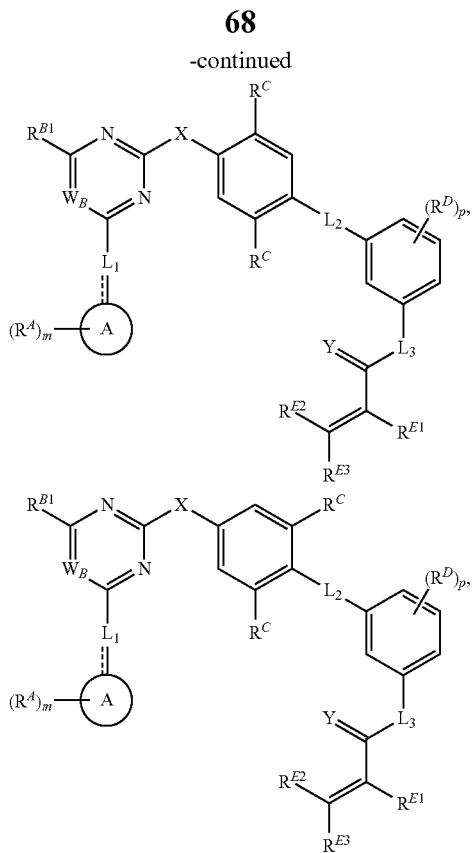

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

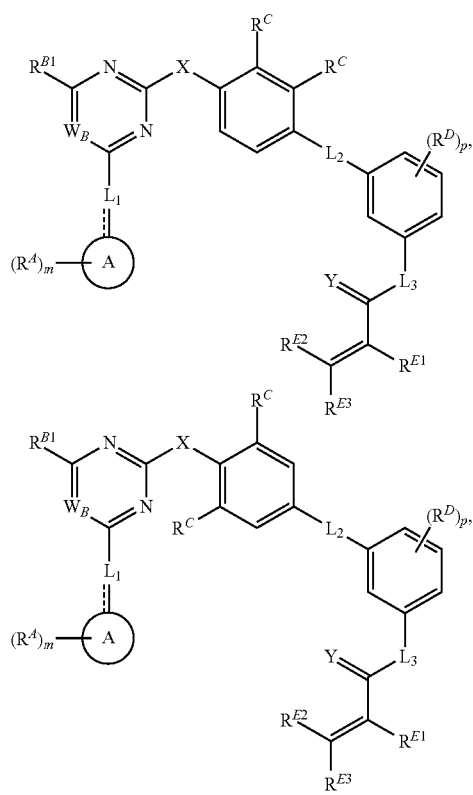

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

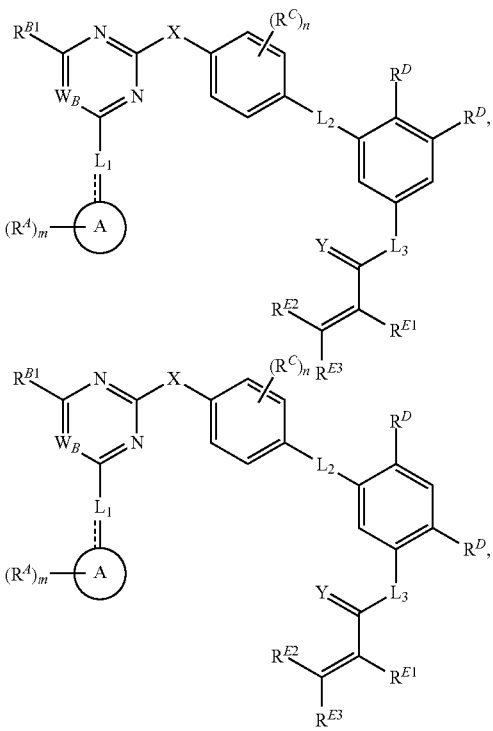

-continued

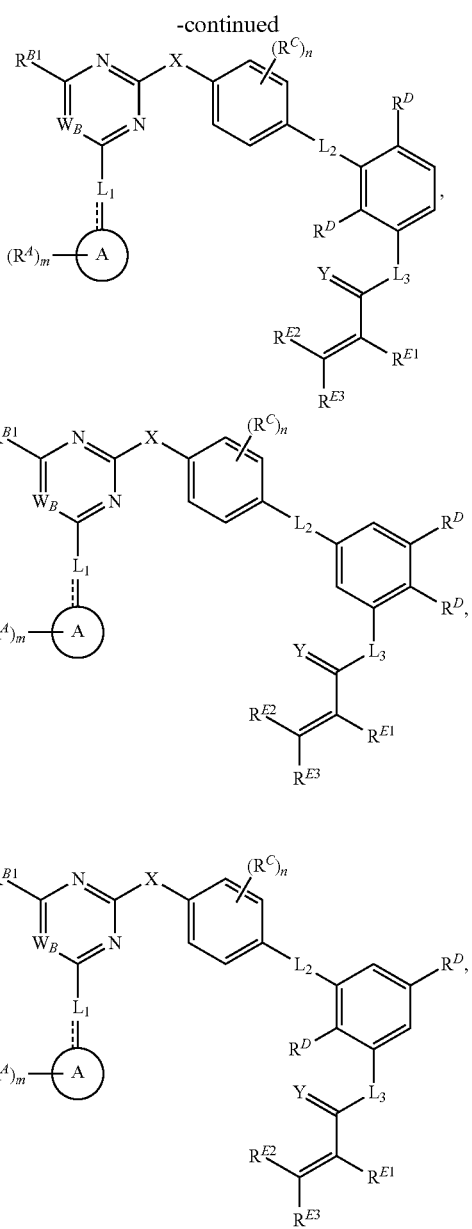

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

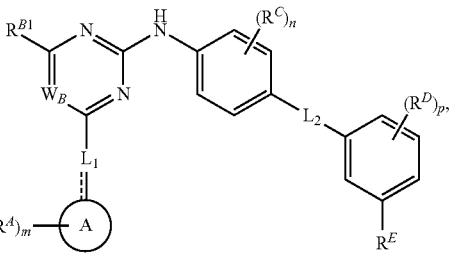

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

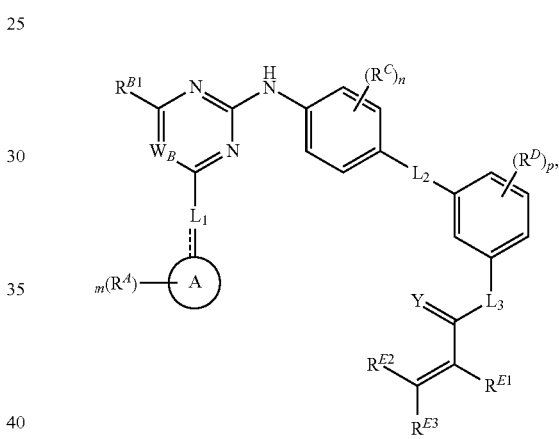

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

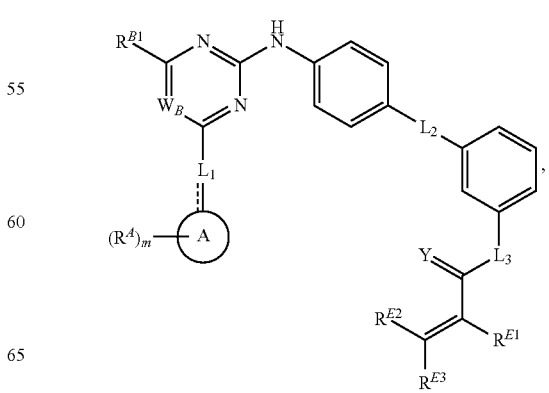

-continued
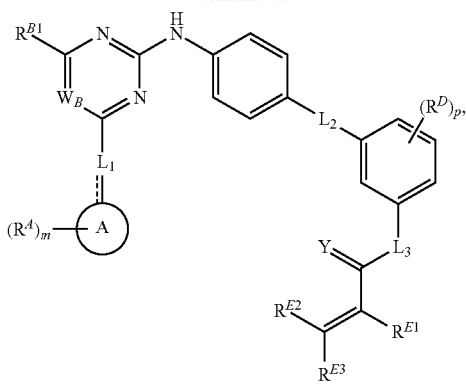
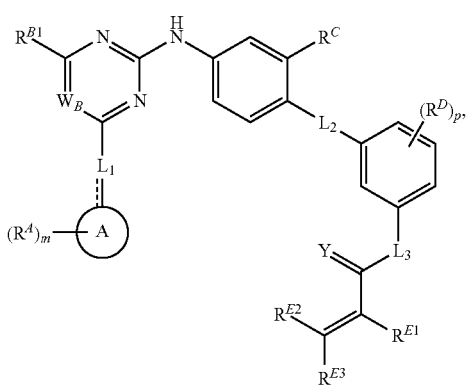
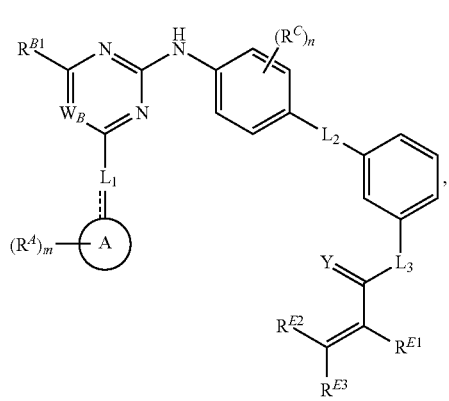
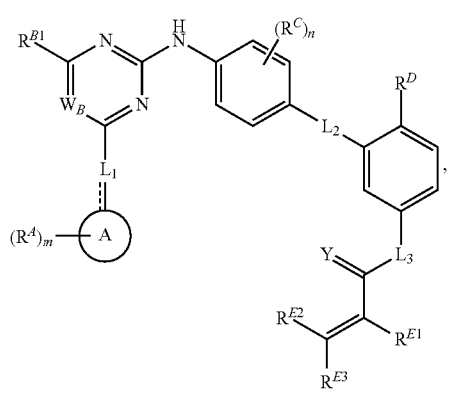
-continued
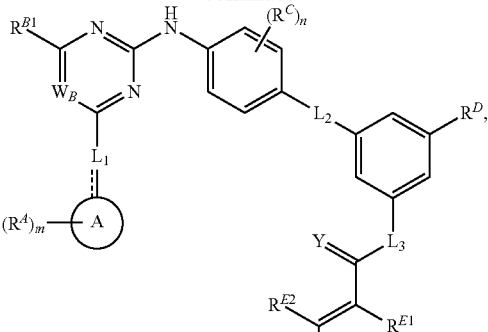
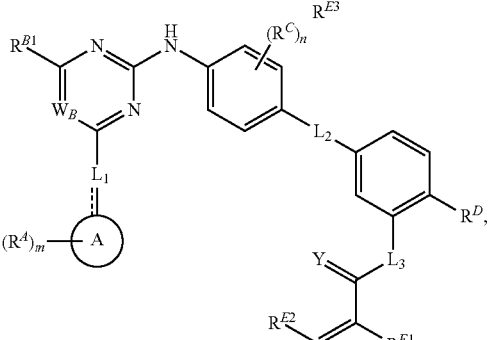
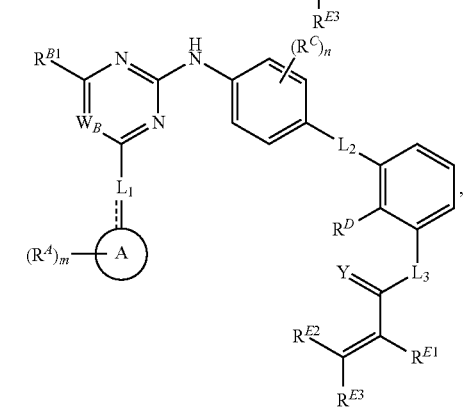
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
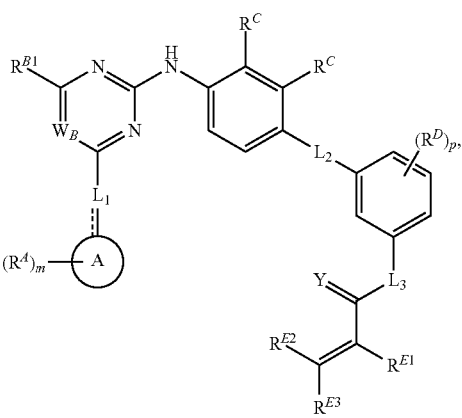

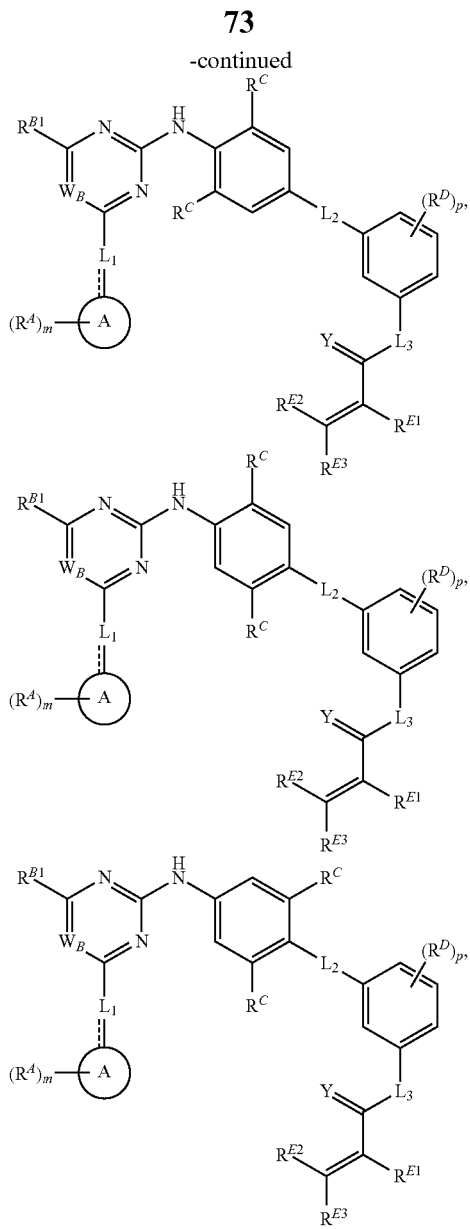
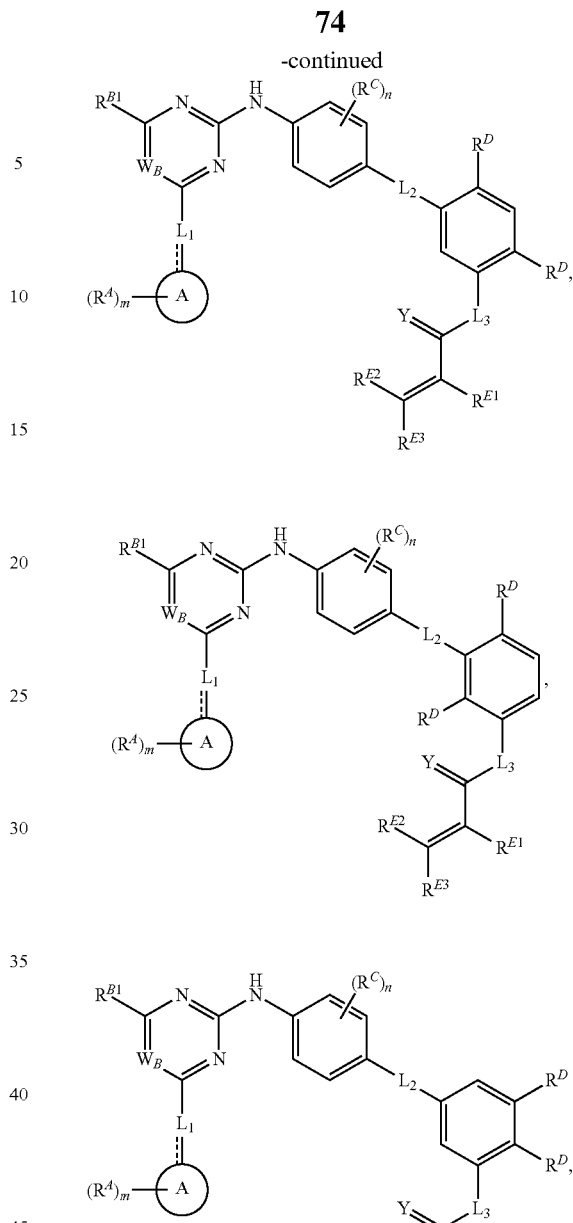
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
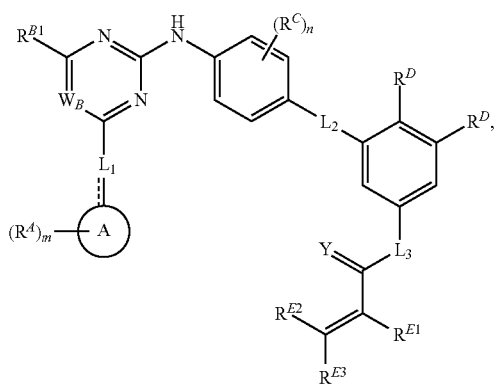

-continued

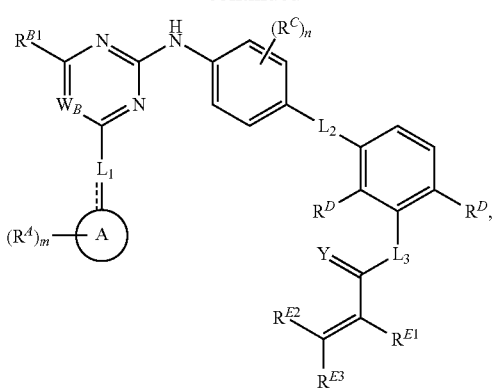

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

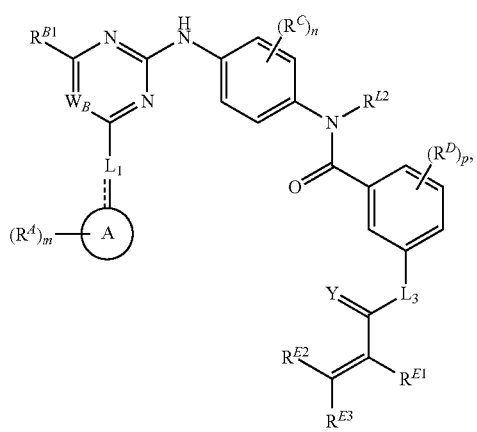

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

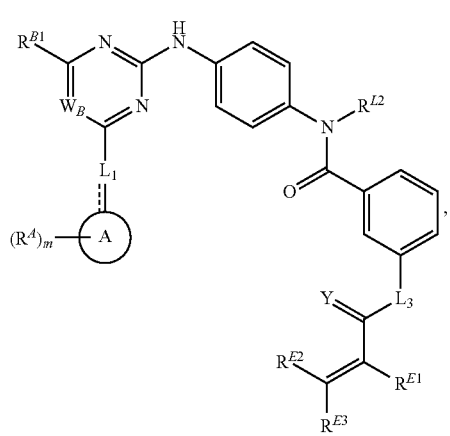

-continued

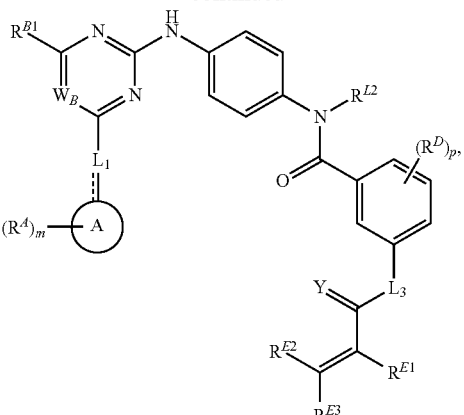

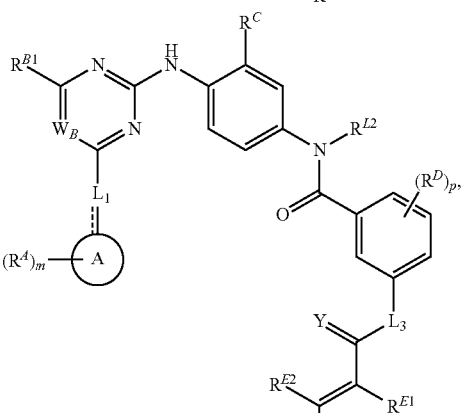

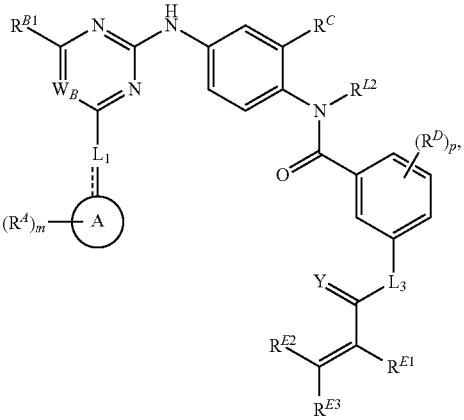

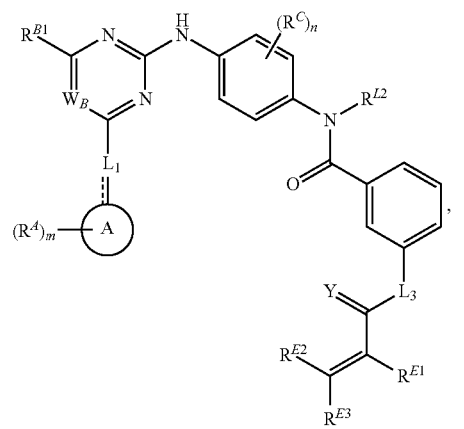

-continued
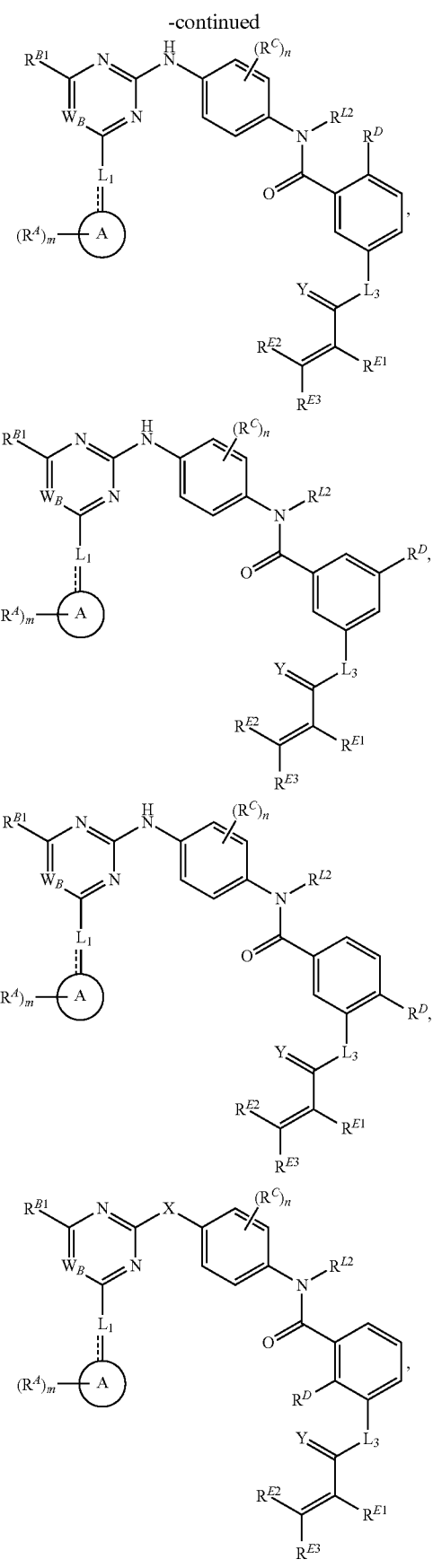
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
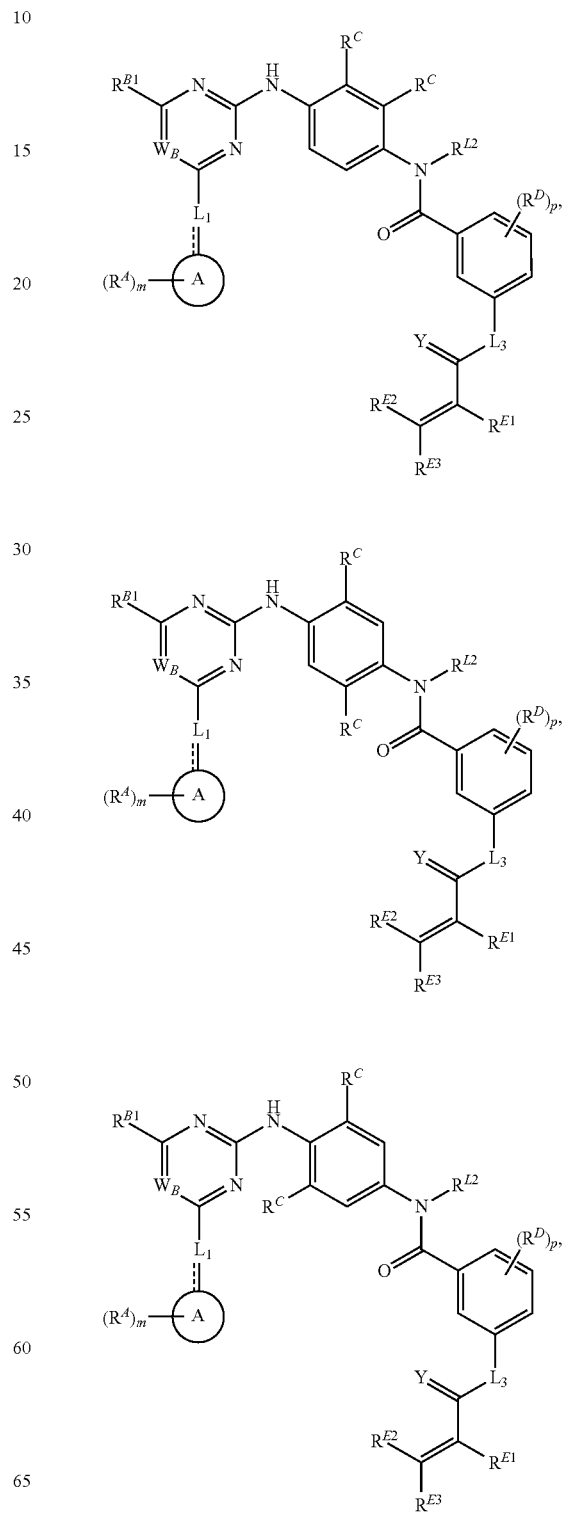

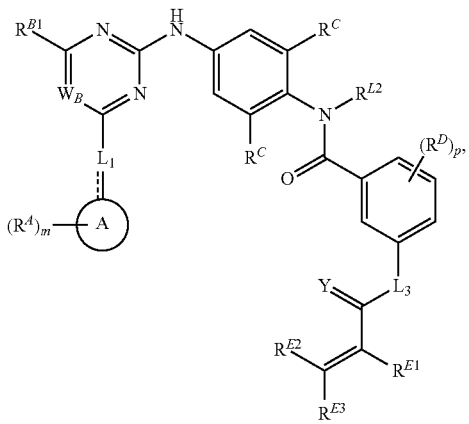
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
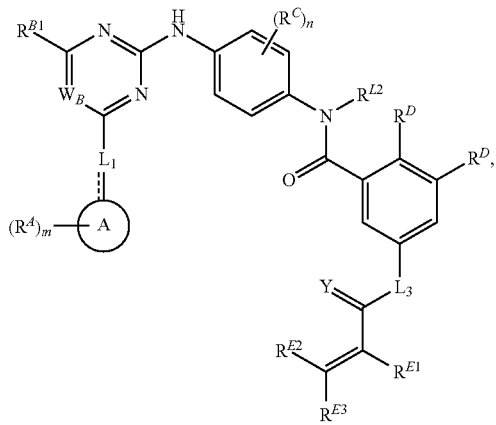
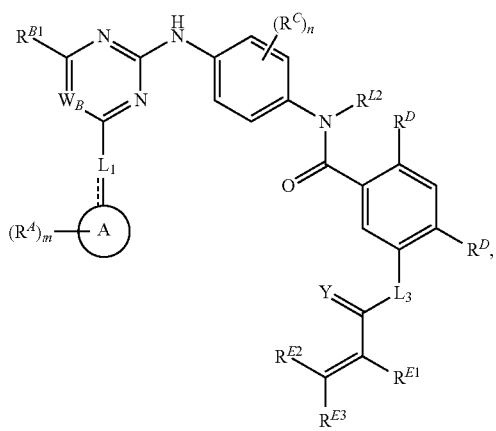
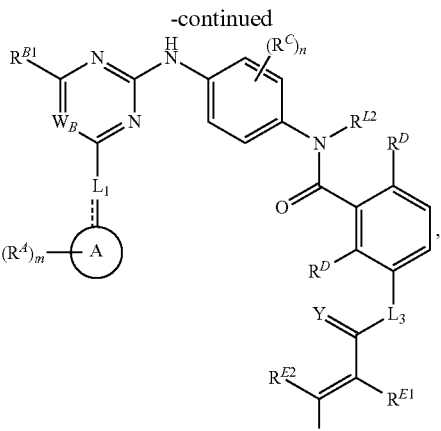
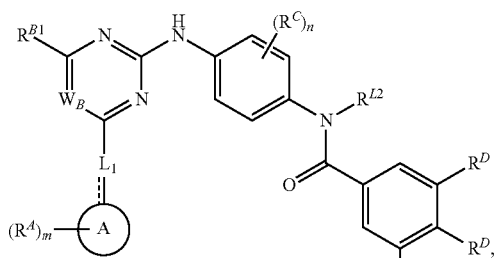
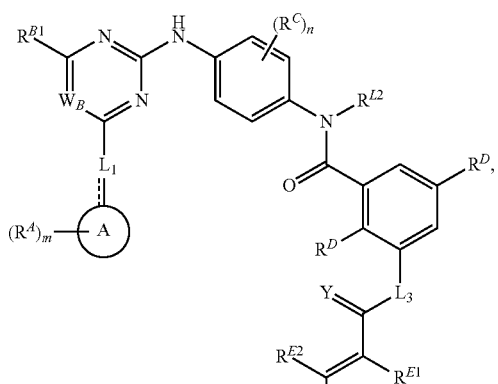
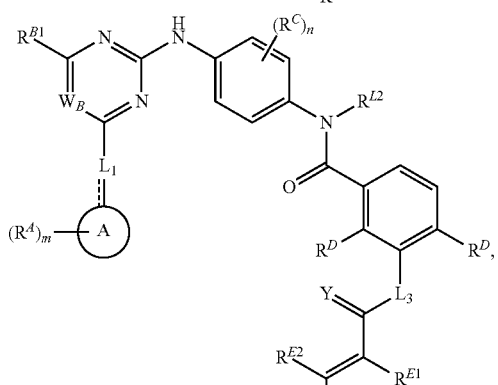

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

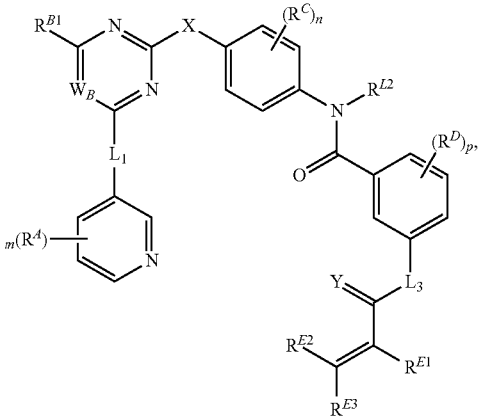

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

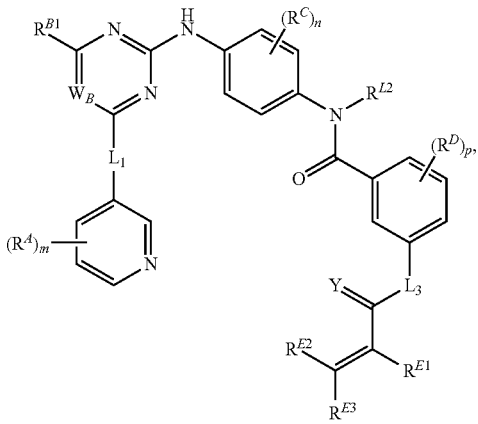

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

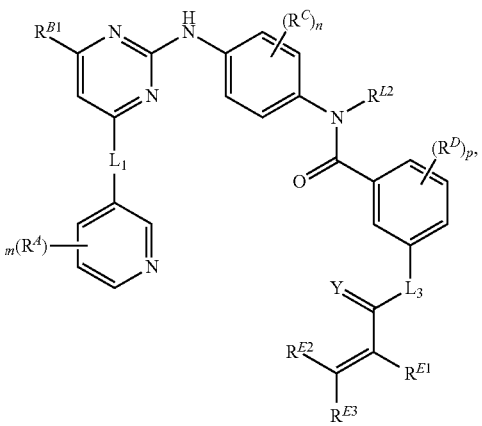

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

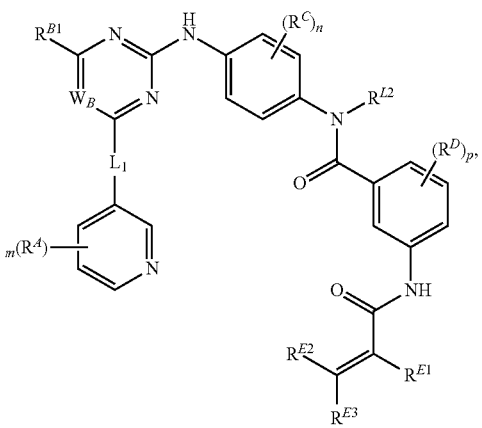

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

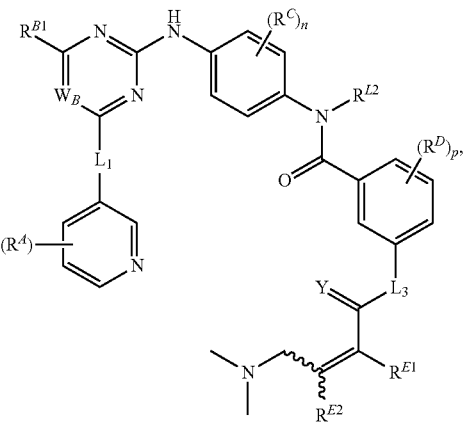

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

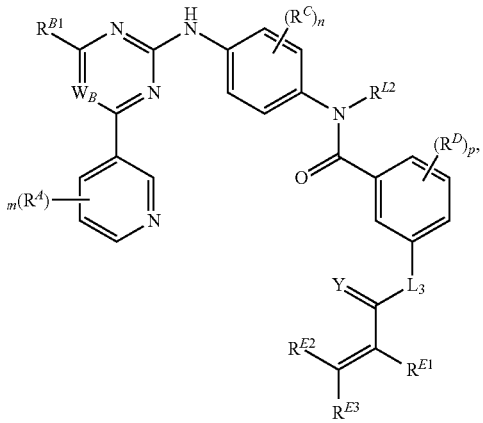
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
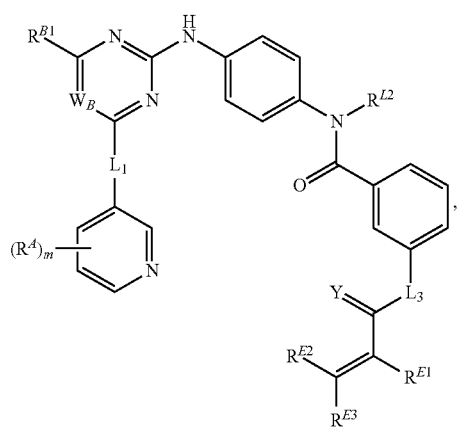
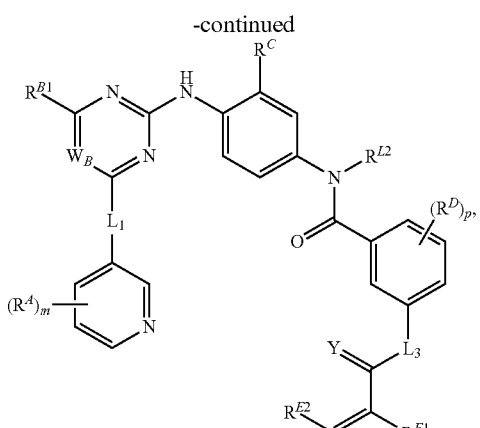
-continued
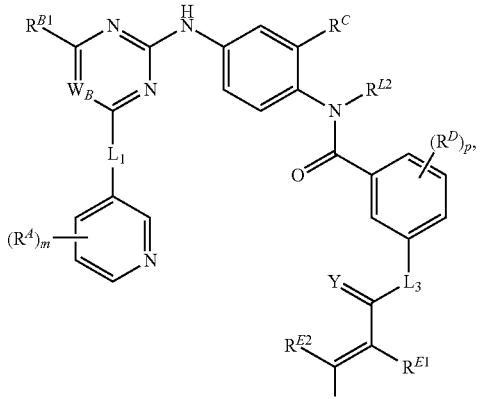
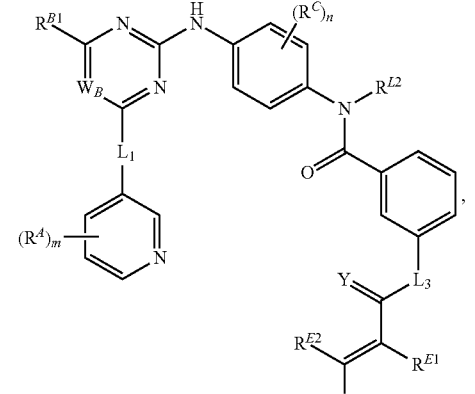
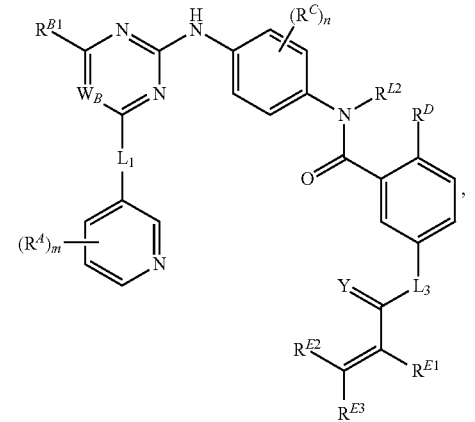

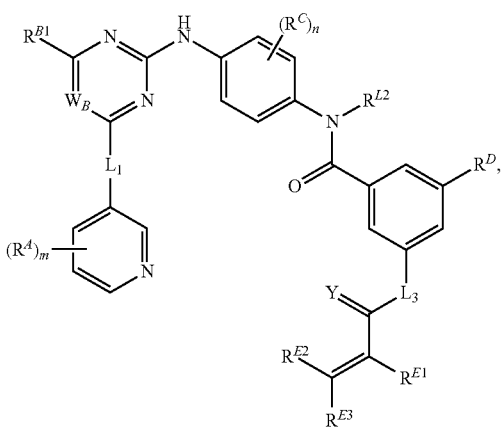
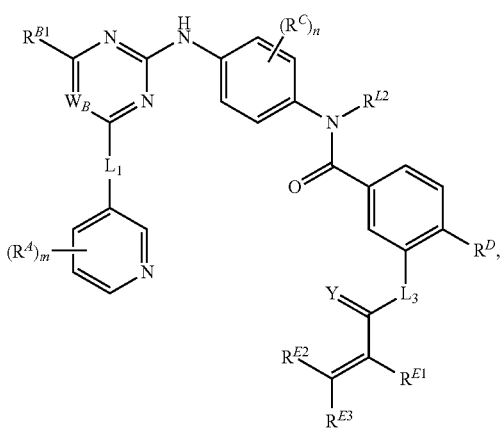
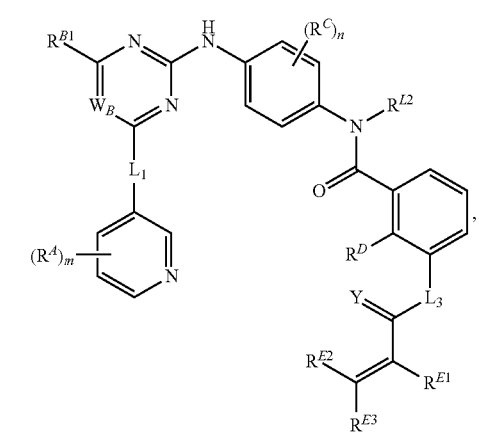
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
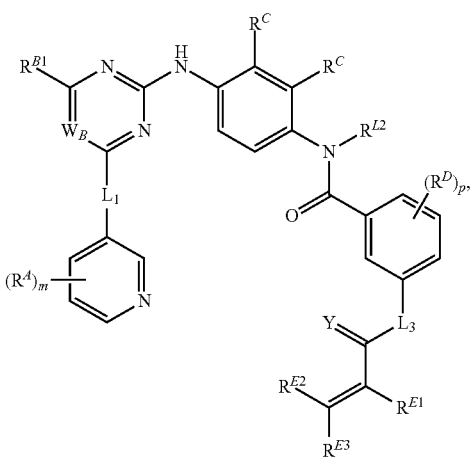
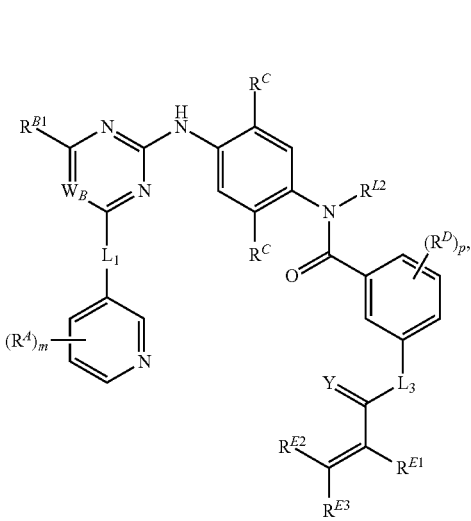
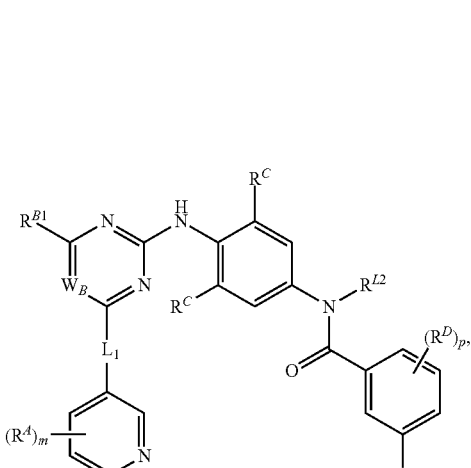

-continued
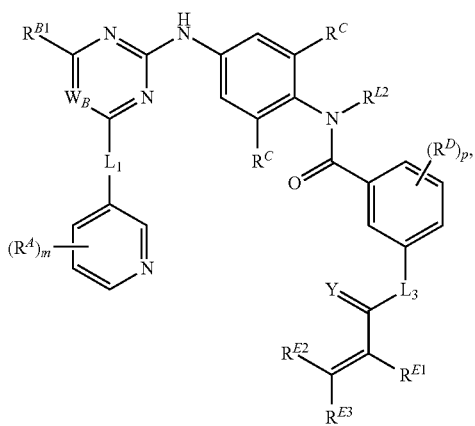
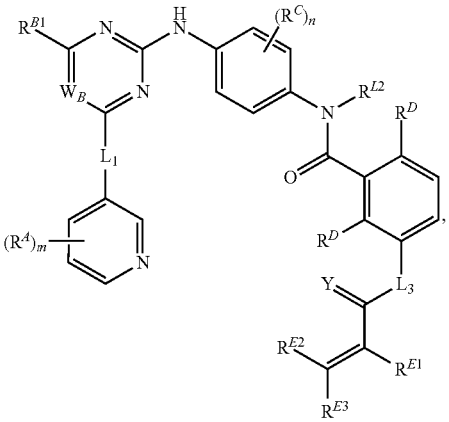
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
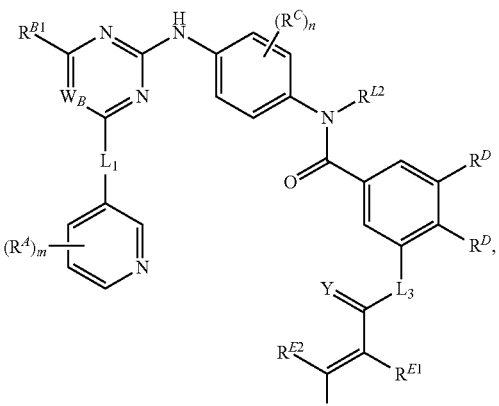
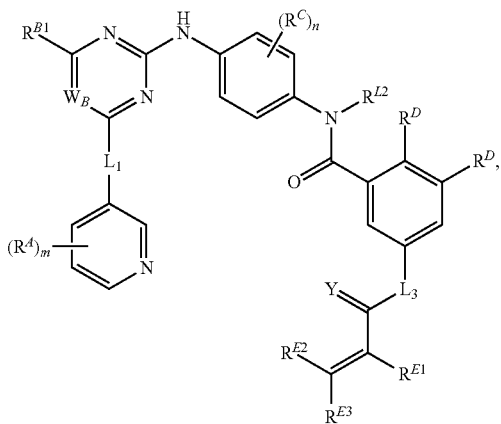
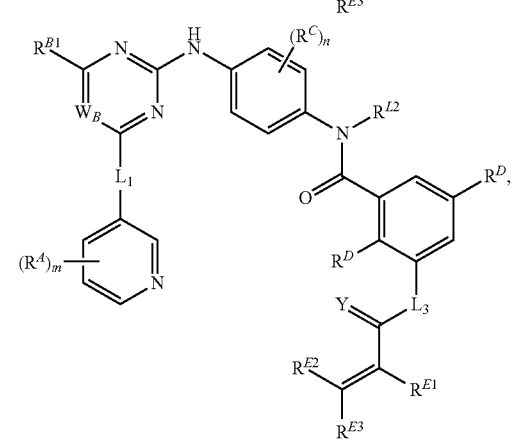
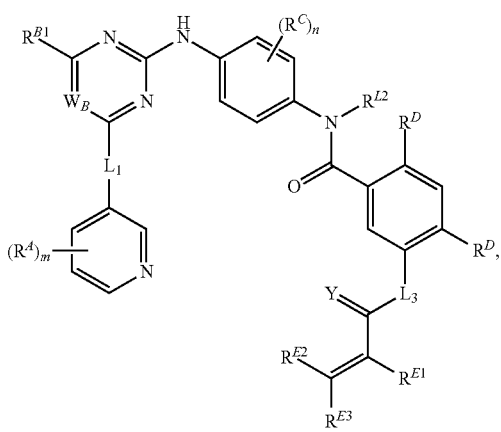
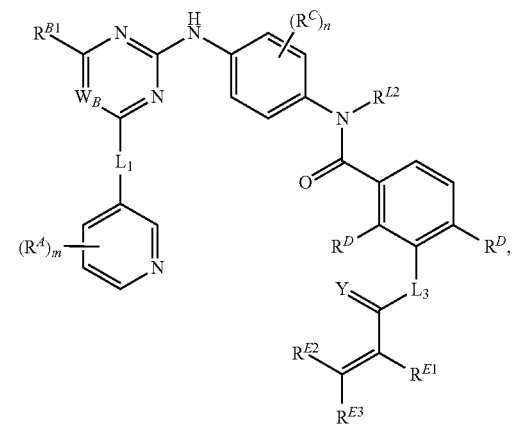

In certain embodiments, the compound of Formula (I) is of the formula:

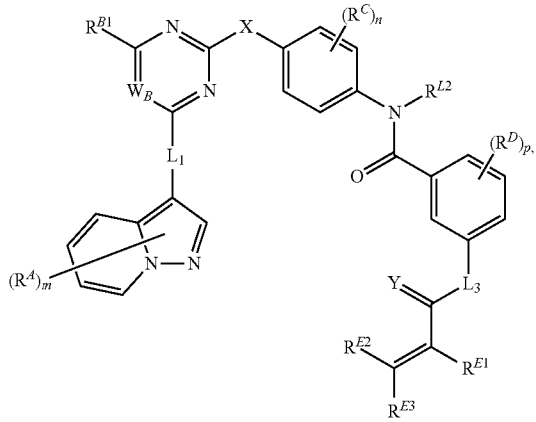

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

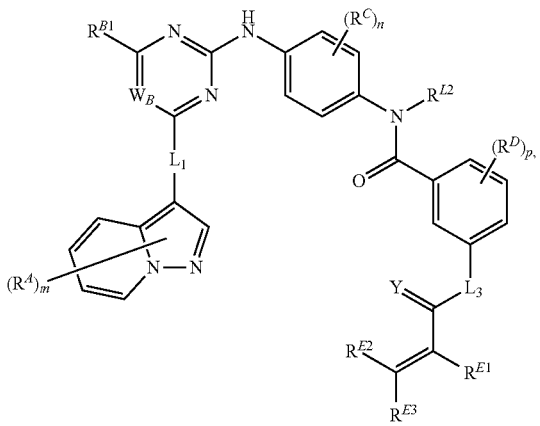

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

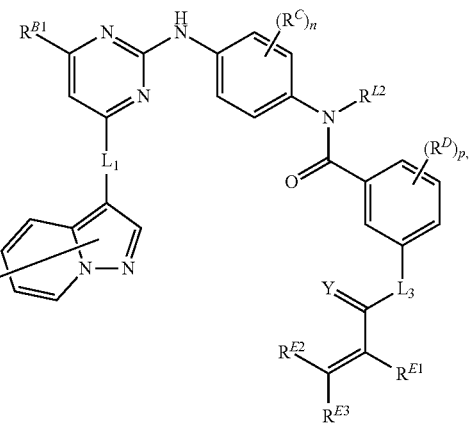

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

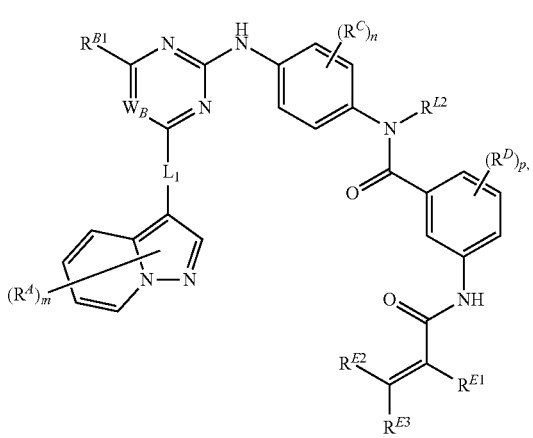

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

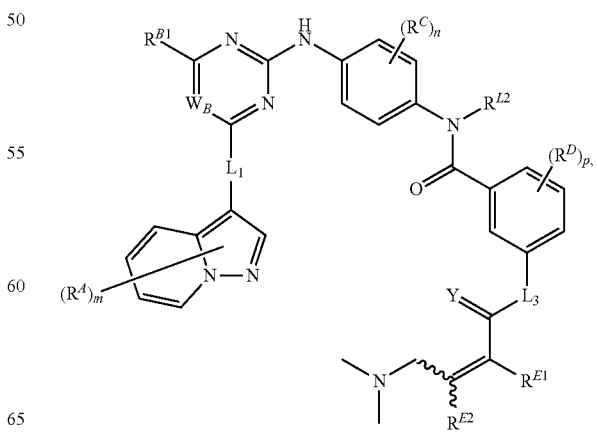

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

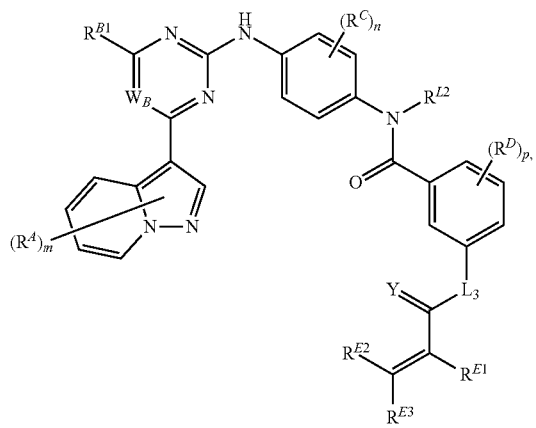

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

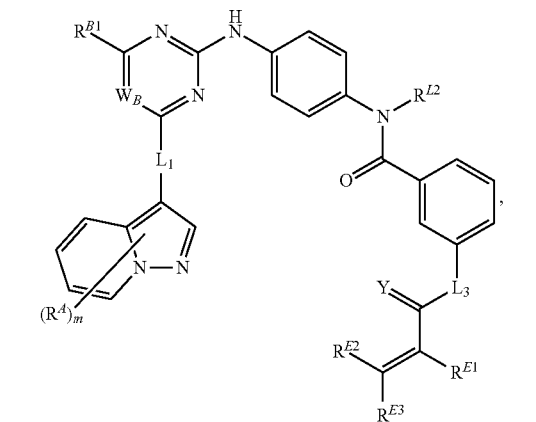

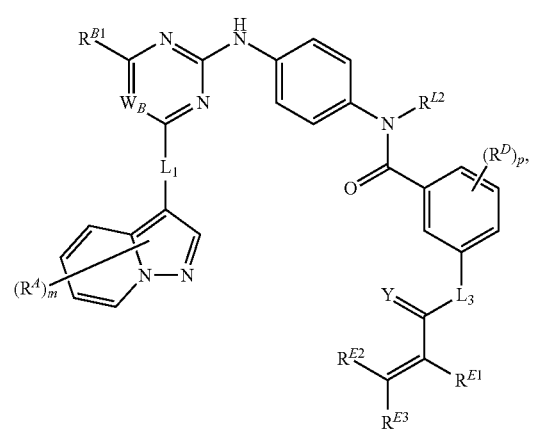

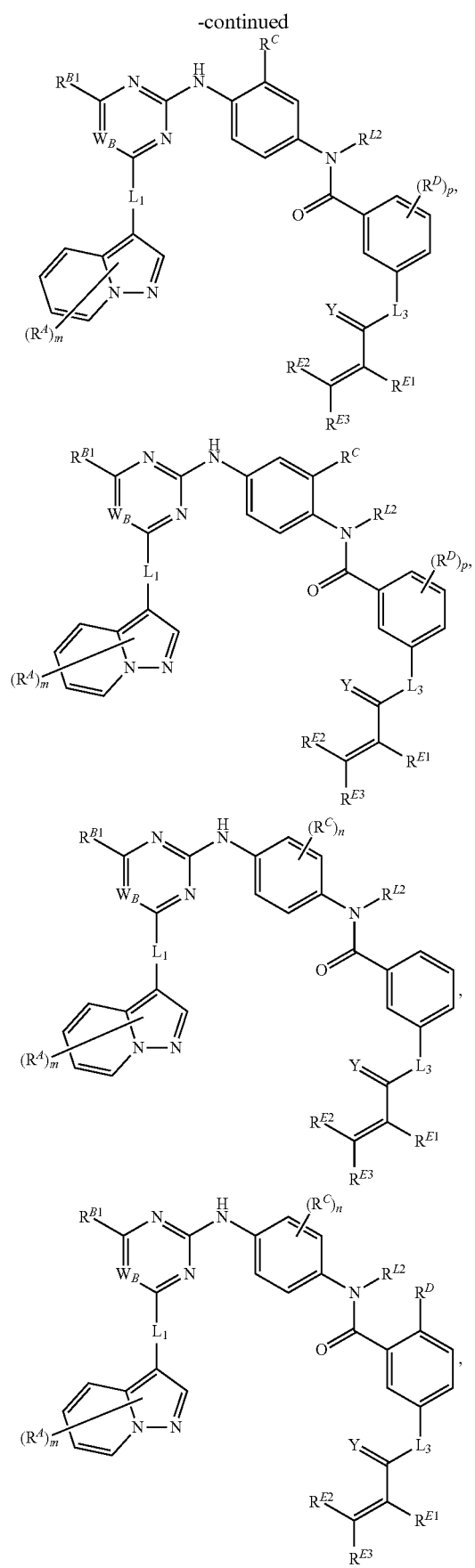

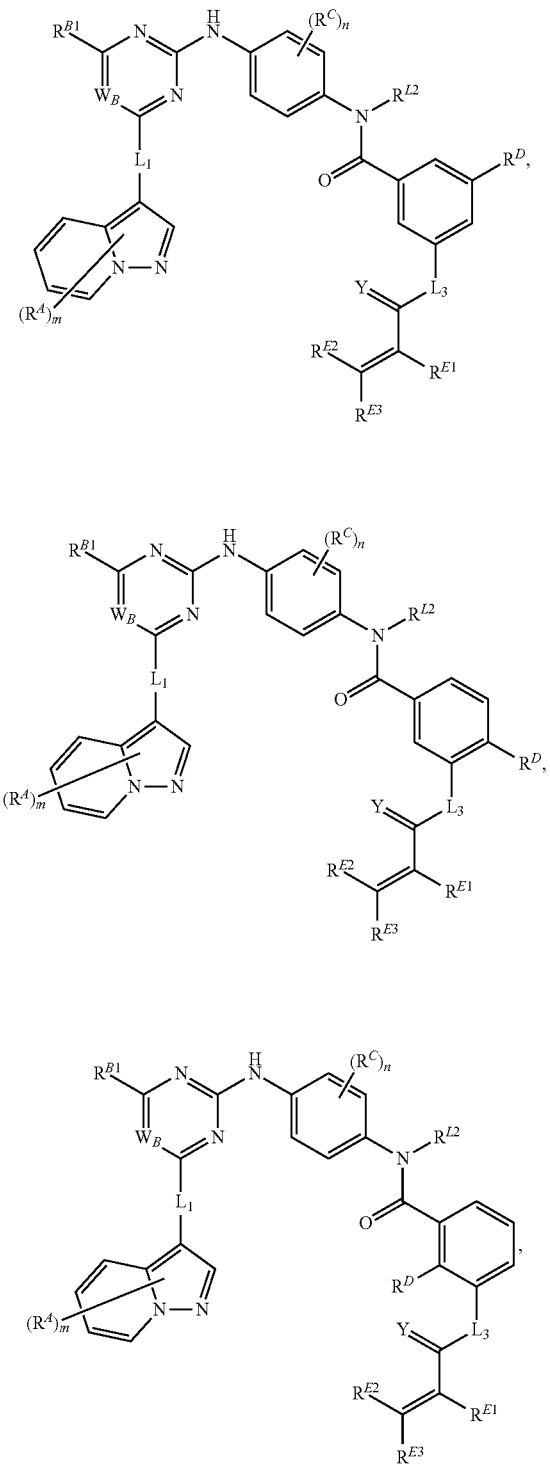
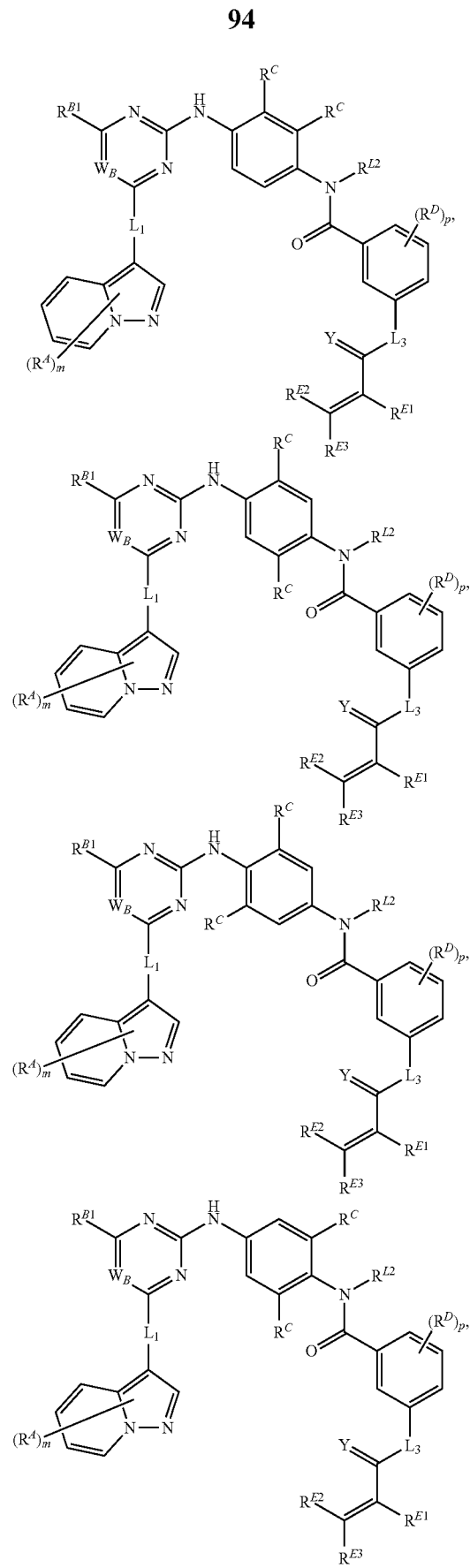
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

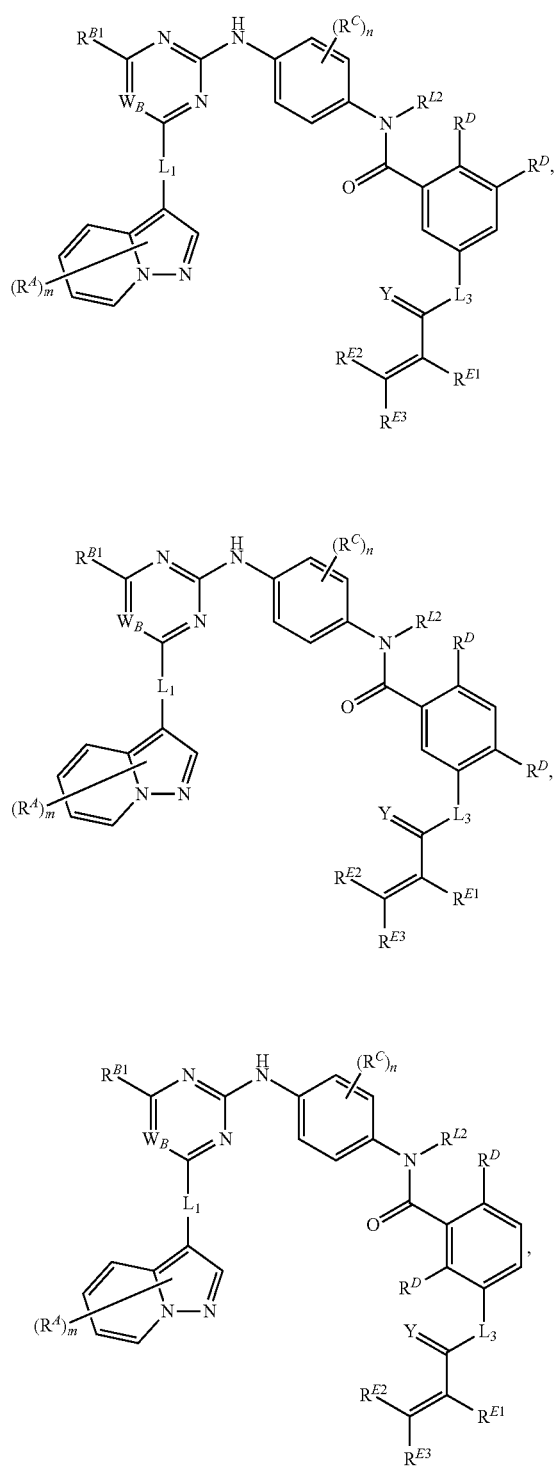

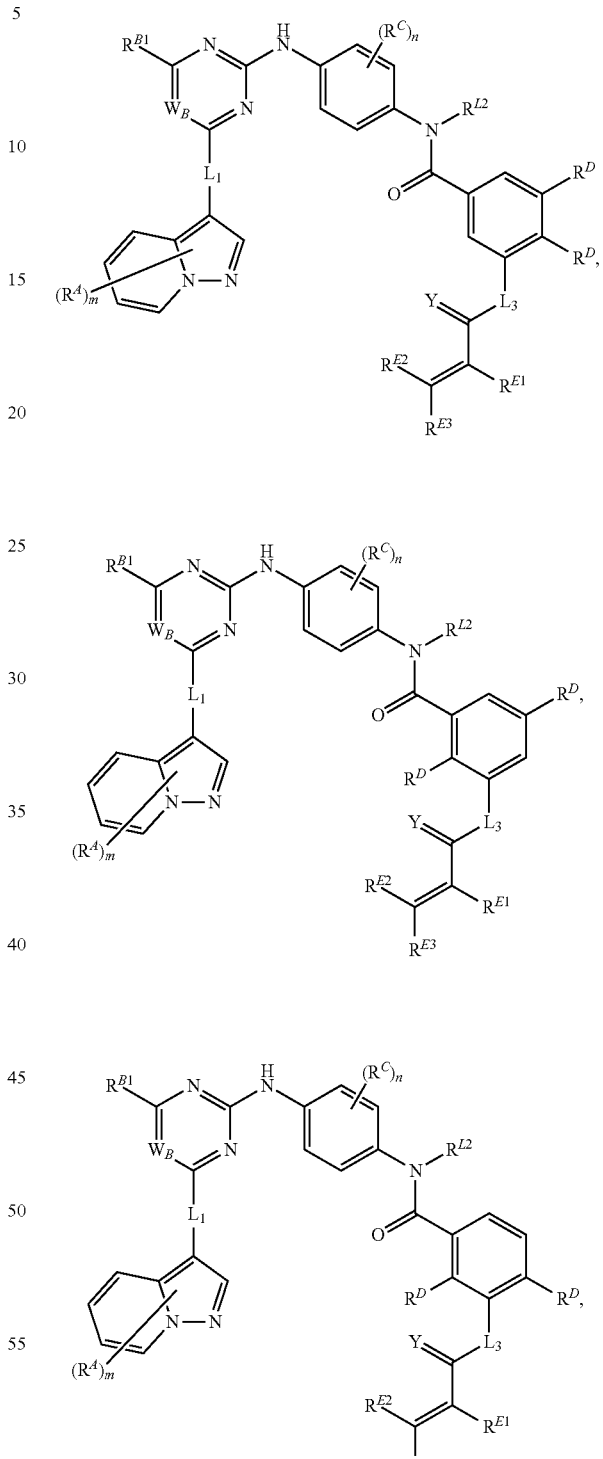

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

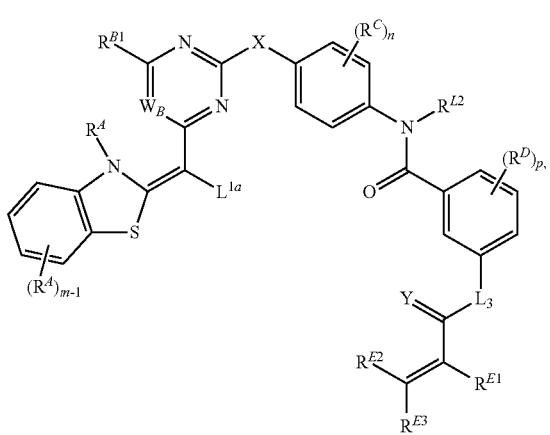

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

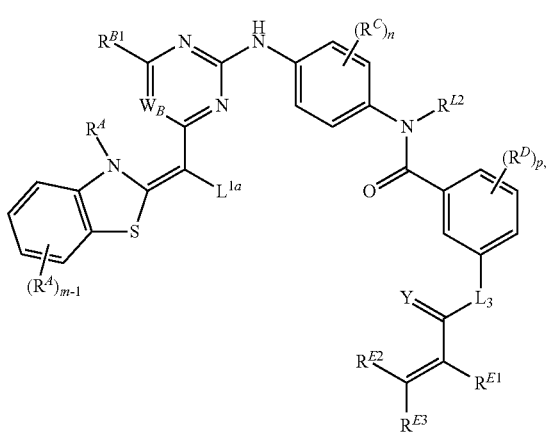

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

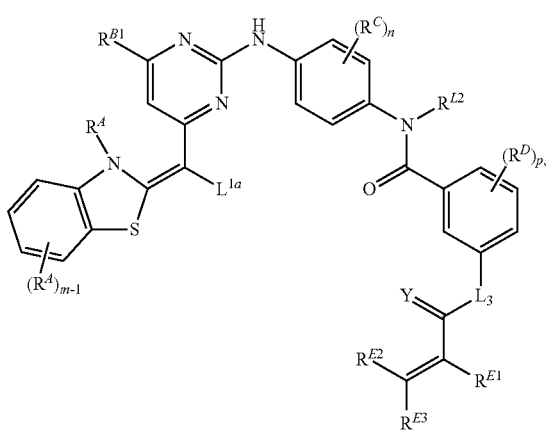

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

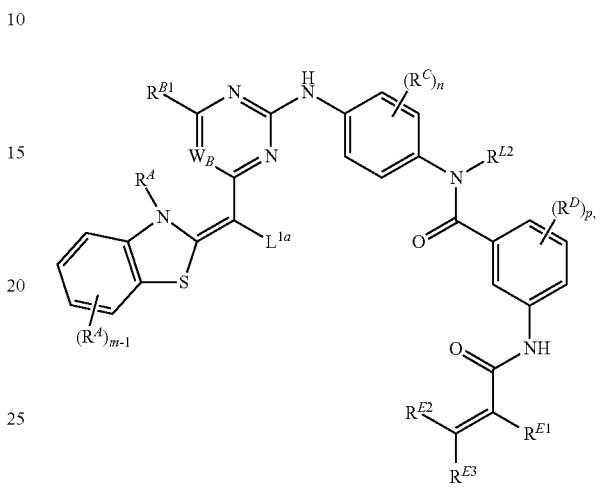

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

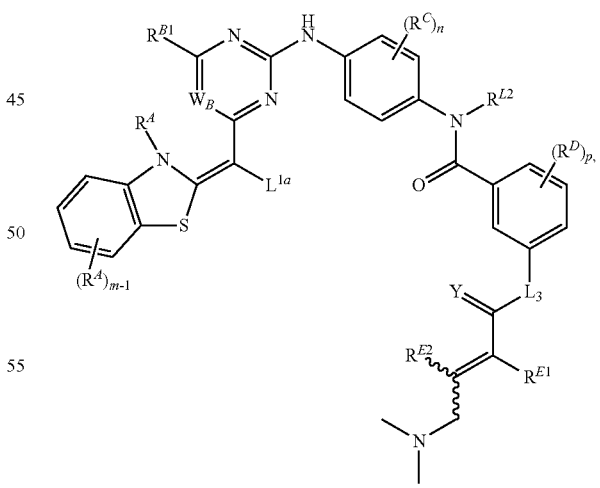

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

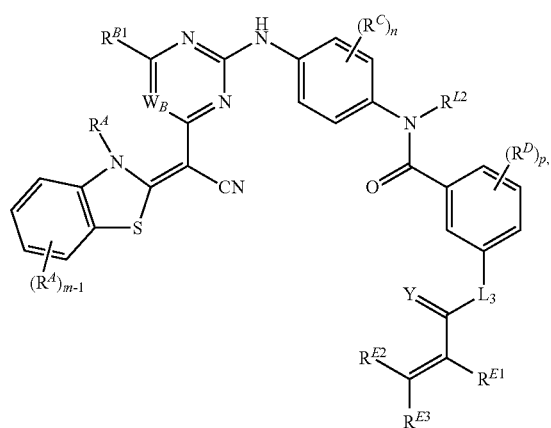
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
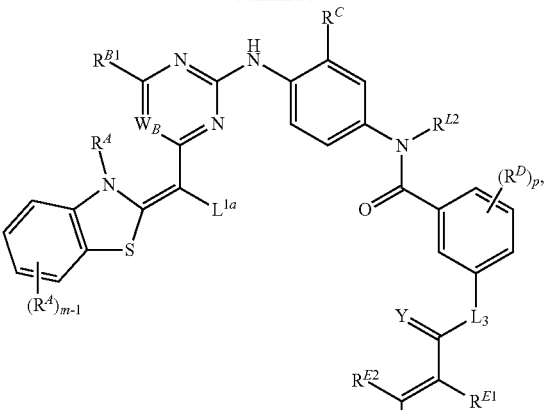
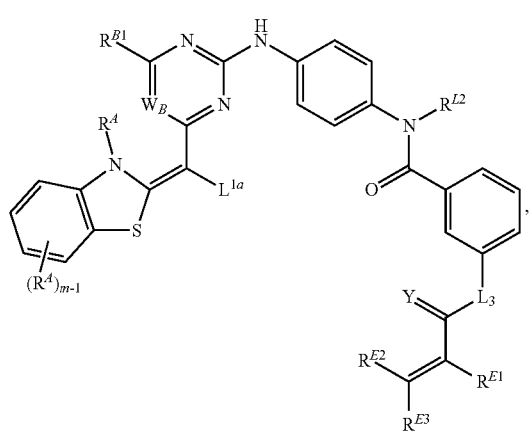
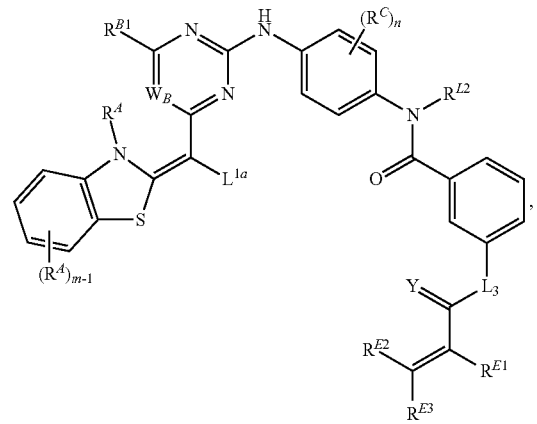
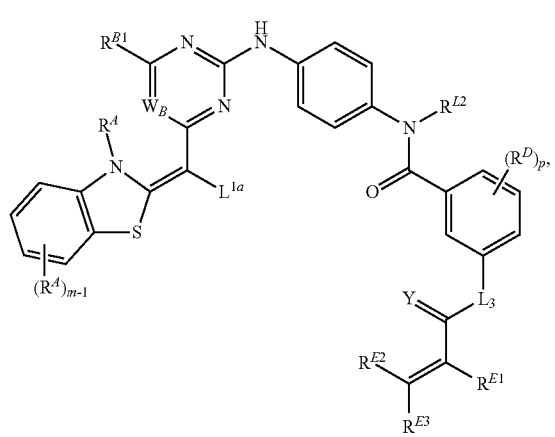
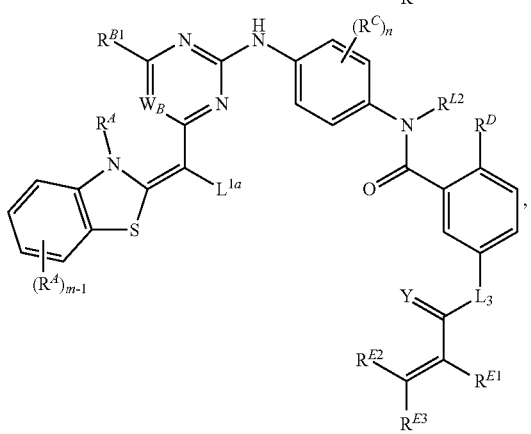

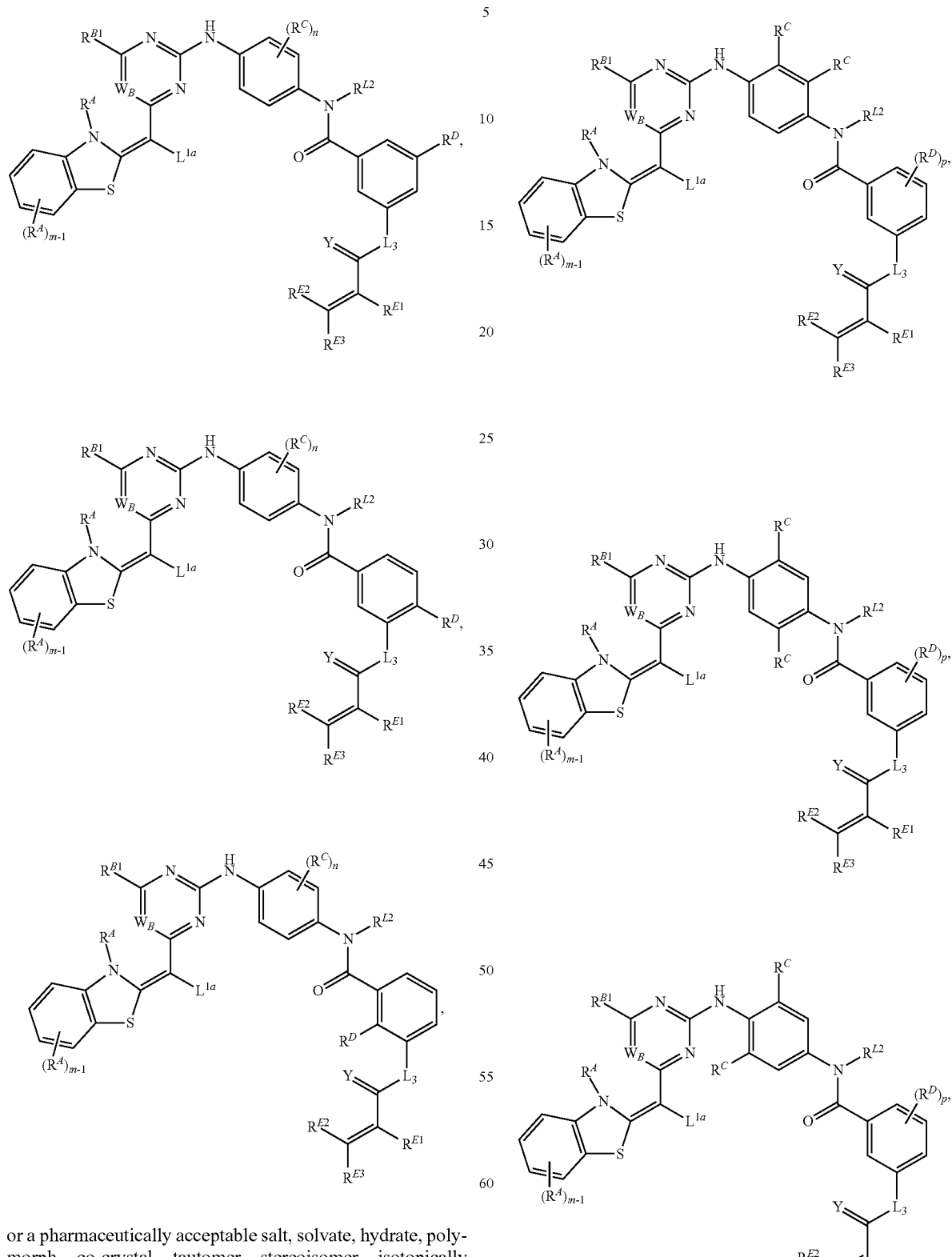
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:

103
-continued
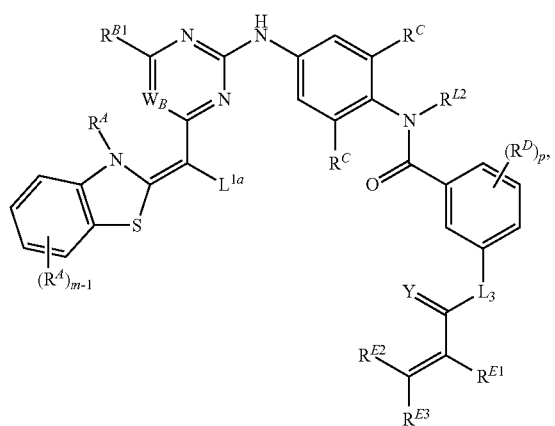
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
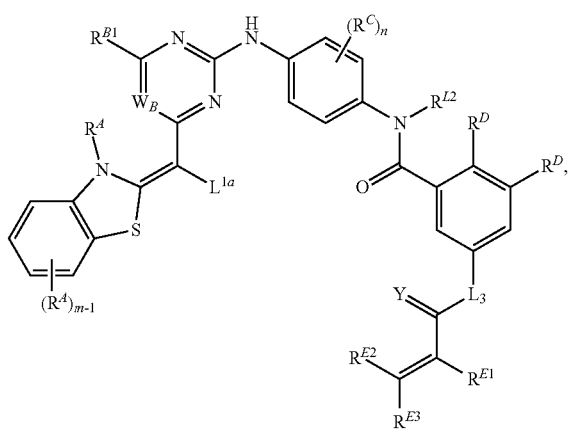
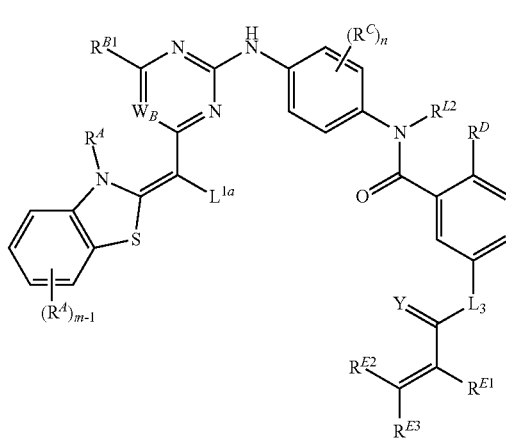
104
-continued
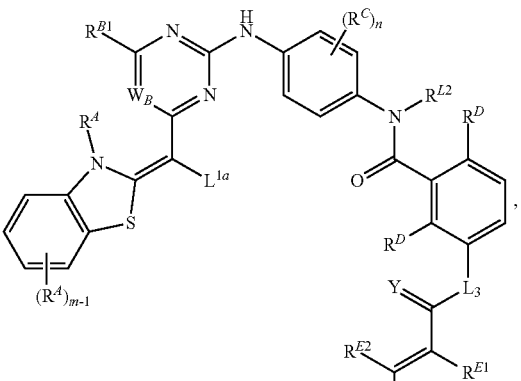

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

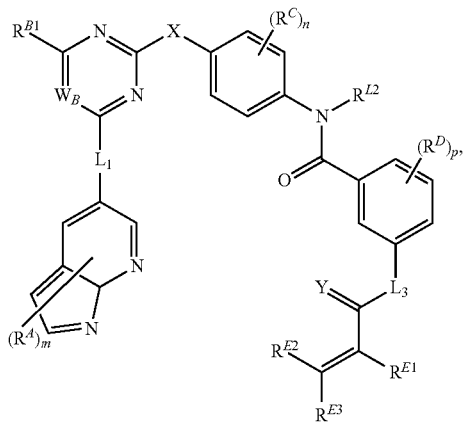

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

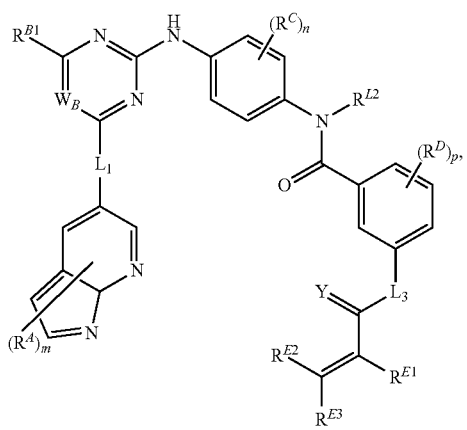

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

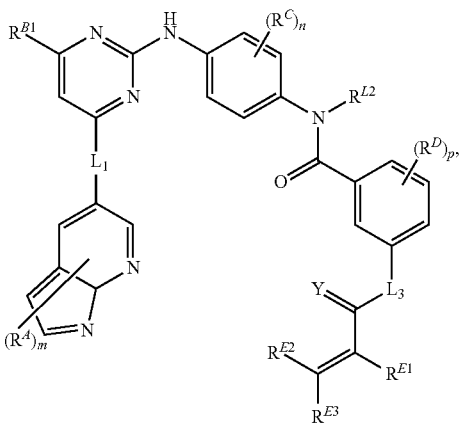

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

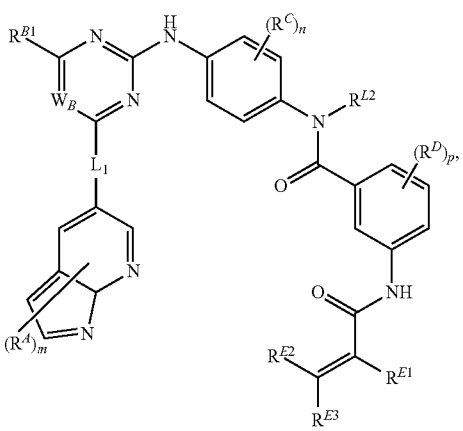

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

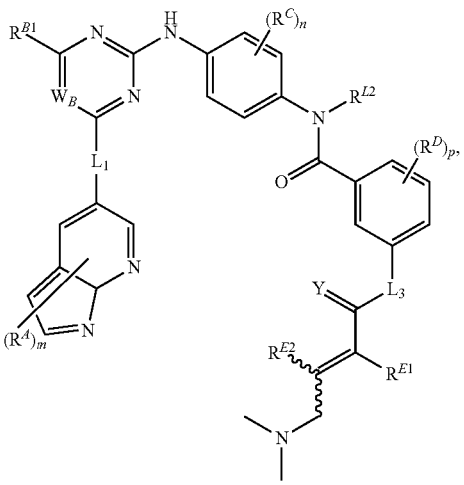

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

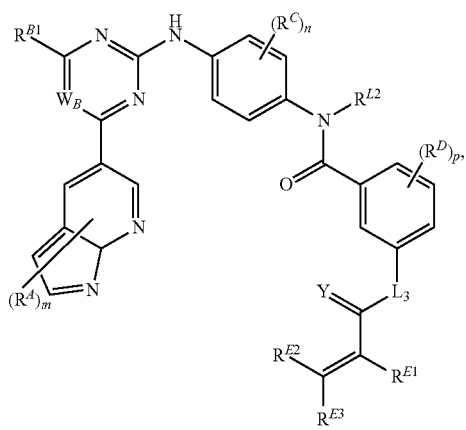

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

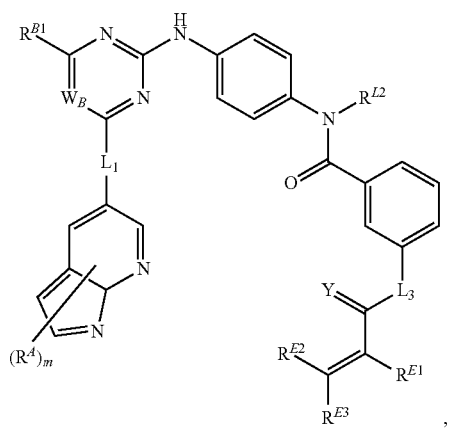

,

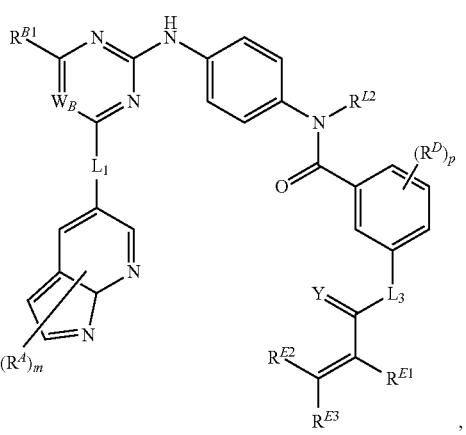

,

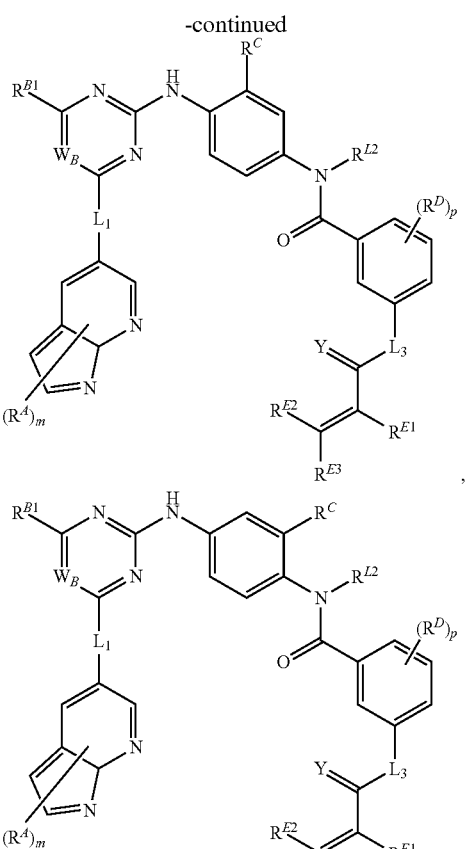

,

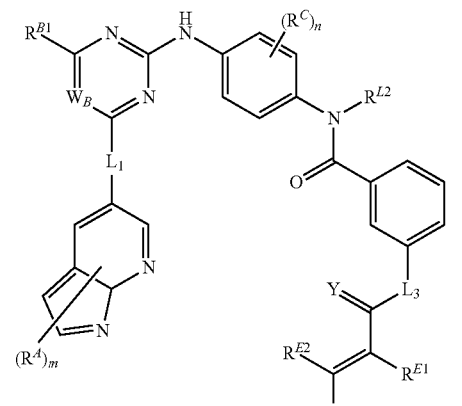

,

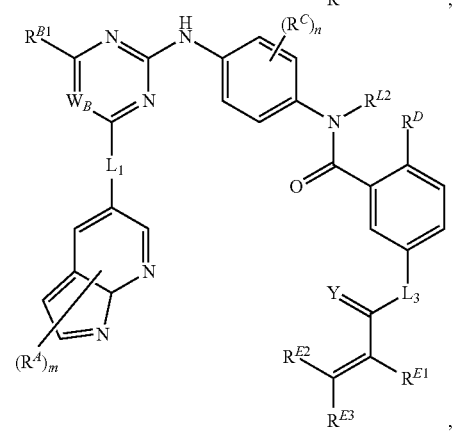

,

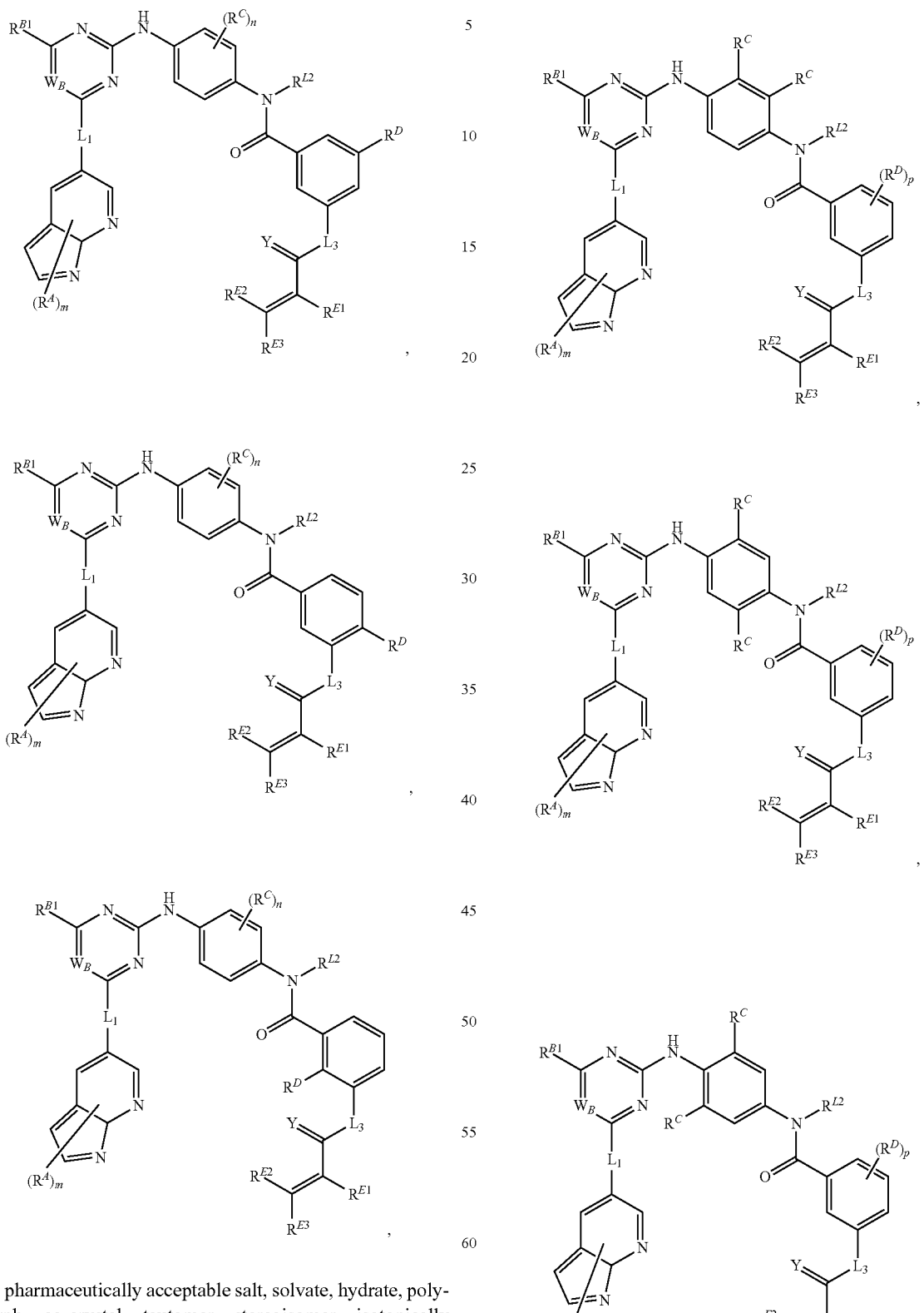
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:

-continued
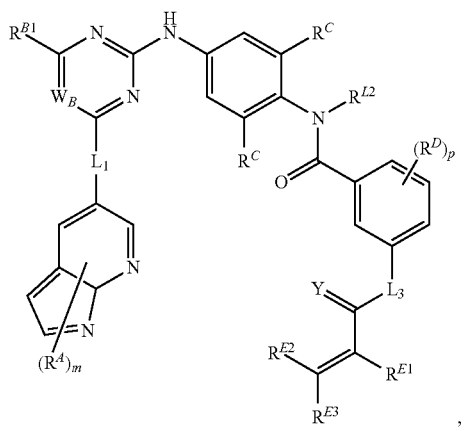
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
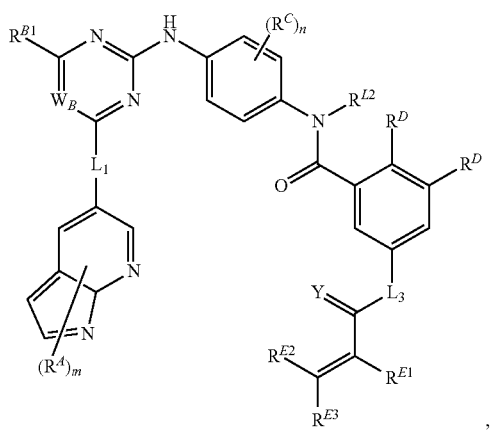
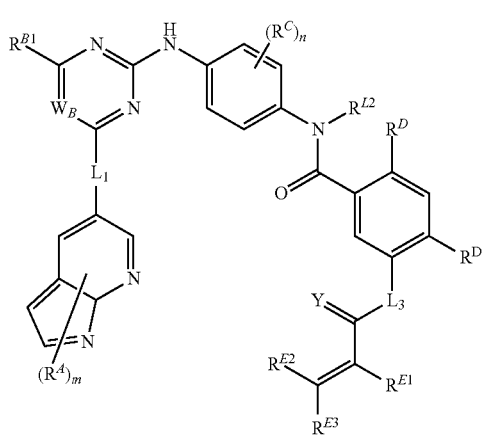
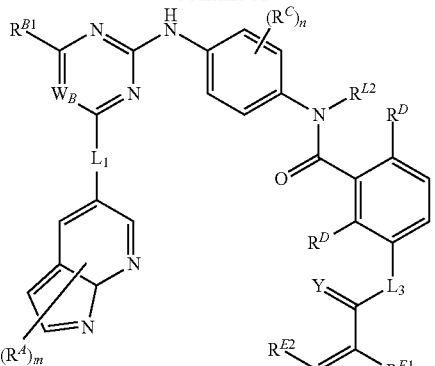
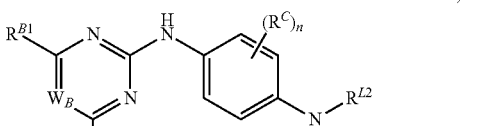
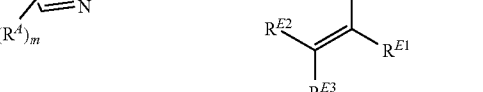
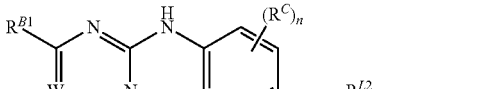
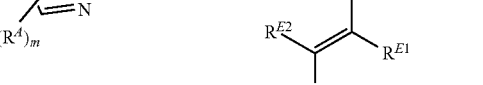
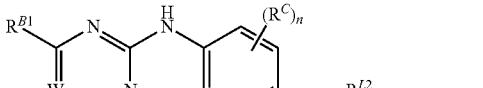

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

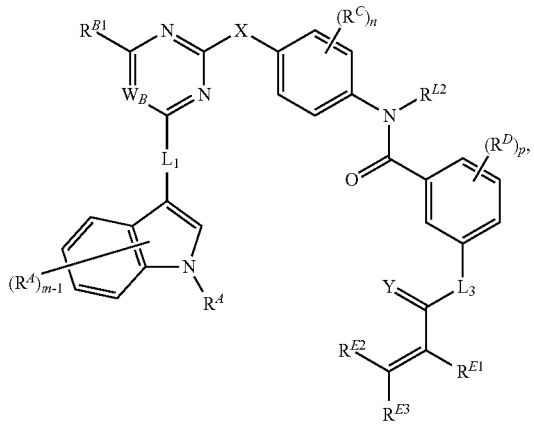

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

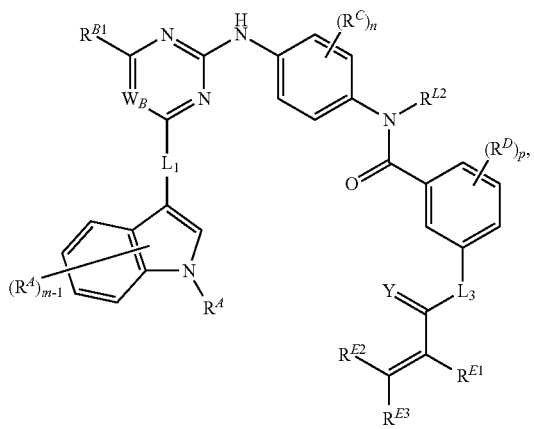

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

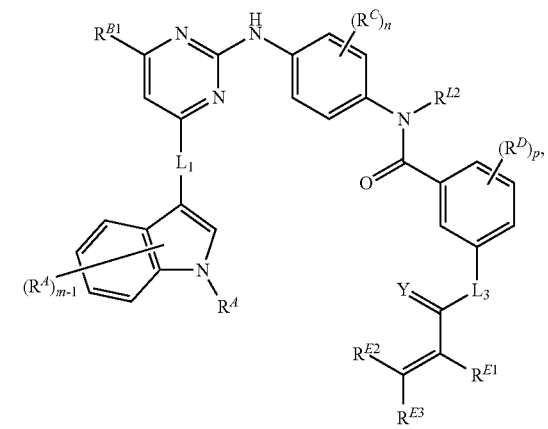

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

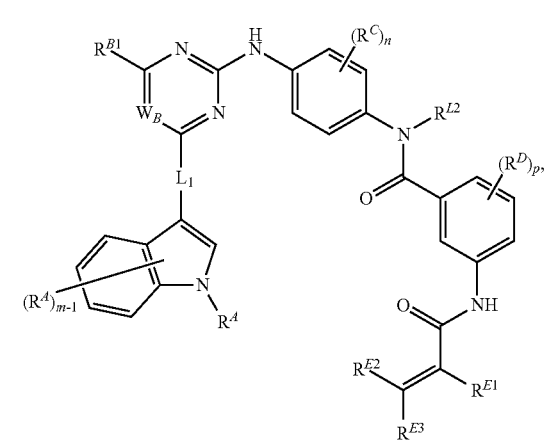

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

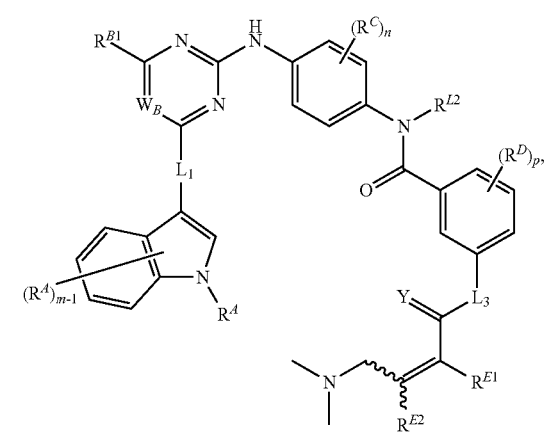

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

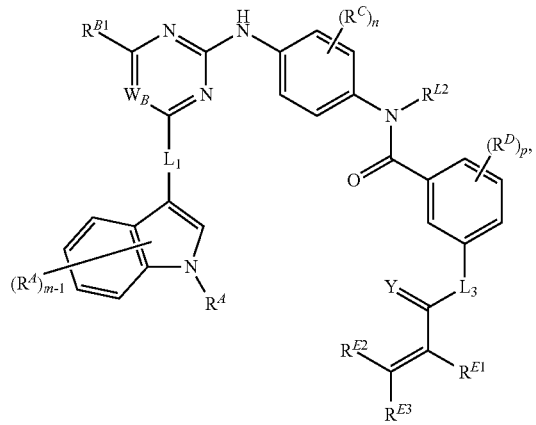

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

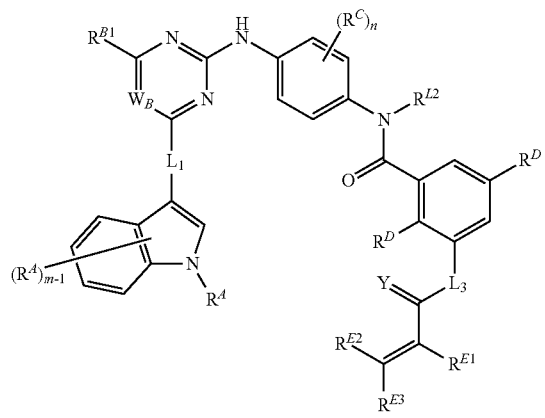

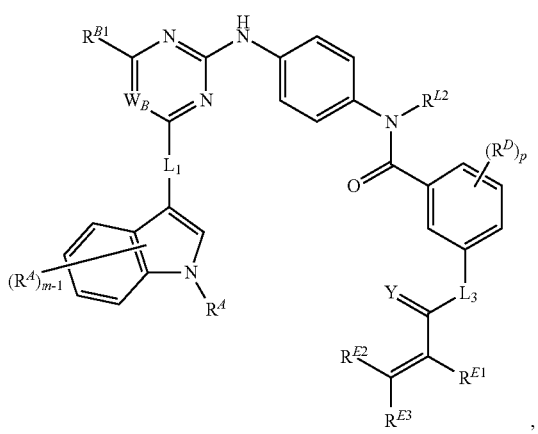

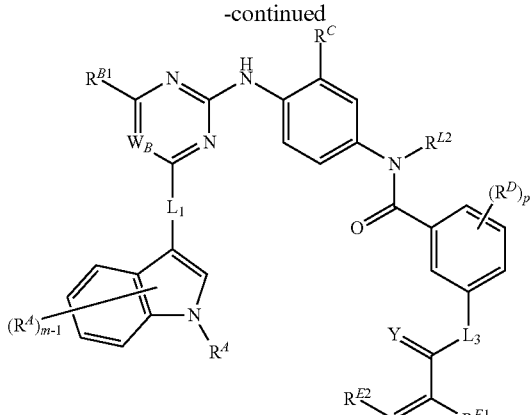

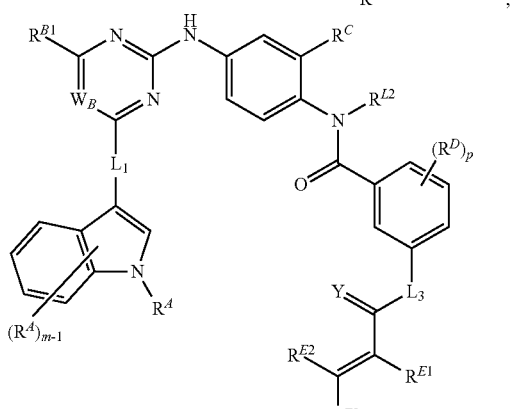

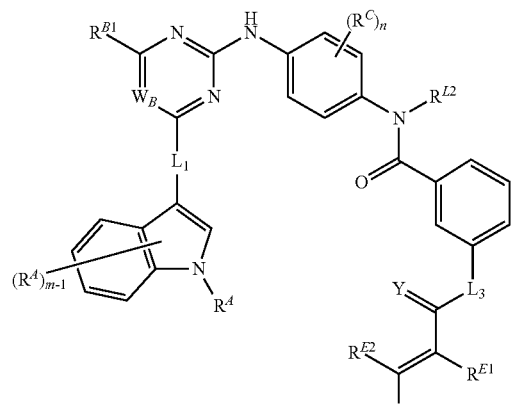

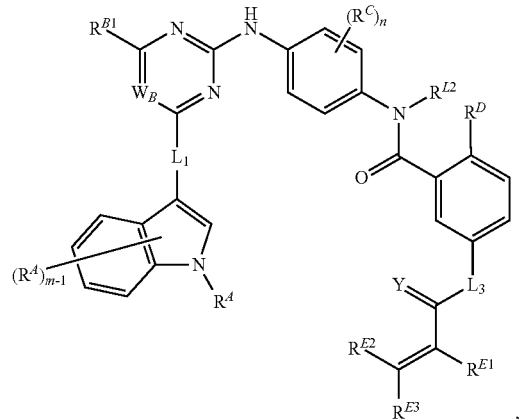

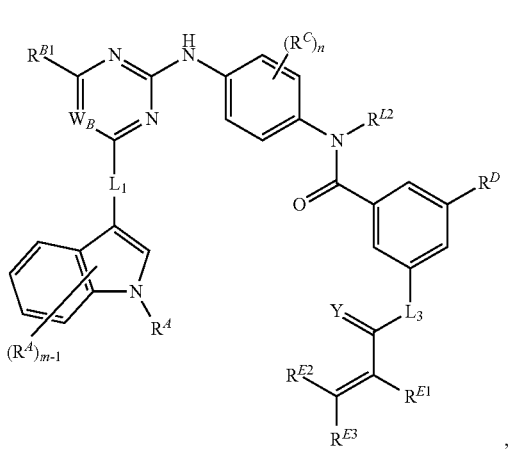
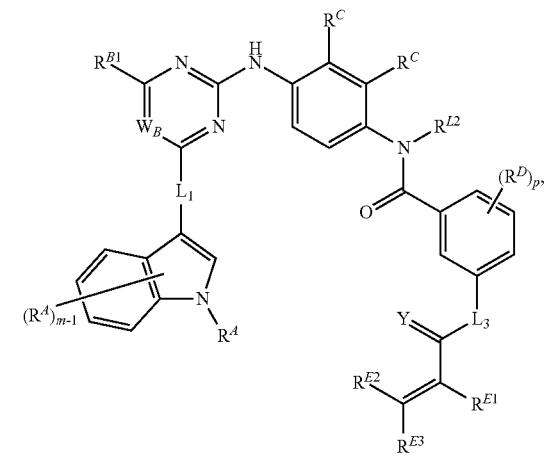
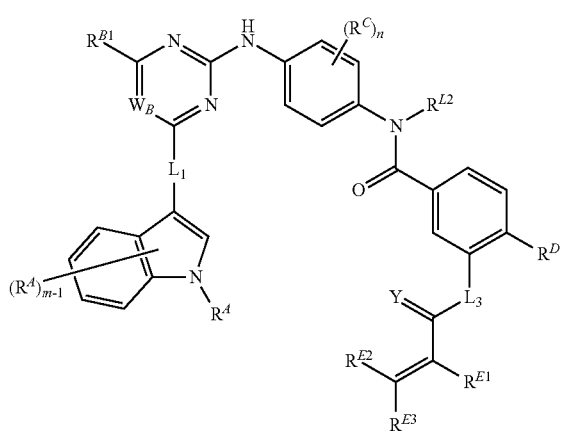
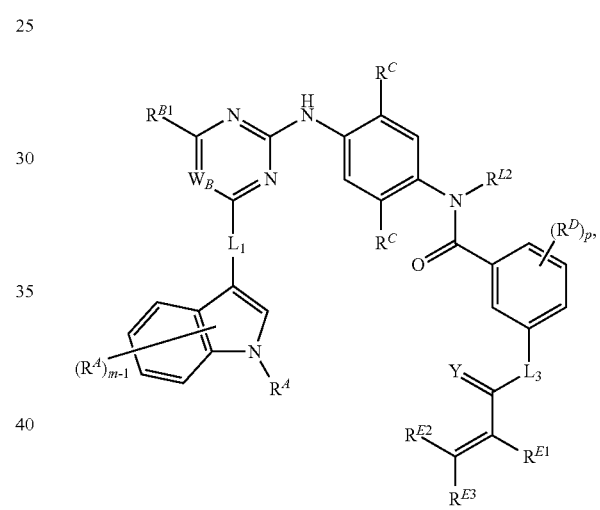
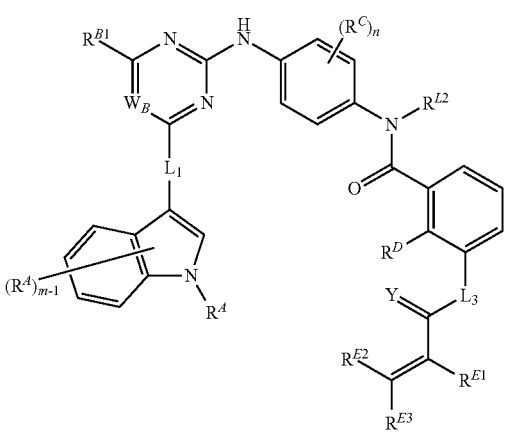
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
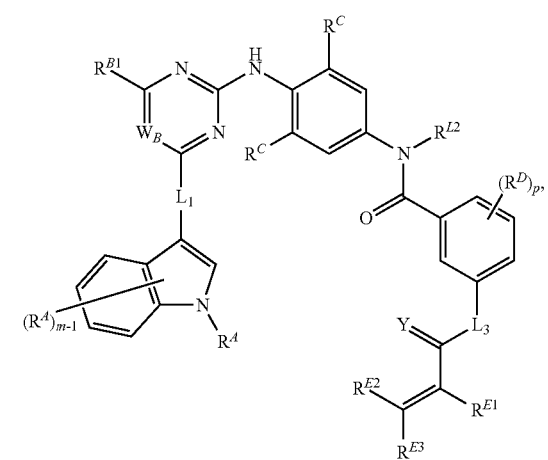

-continued
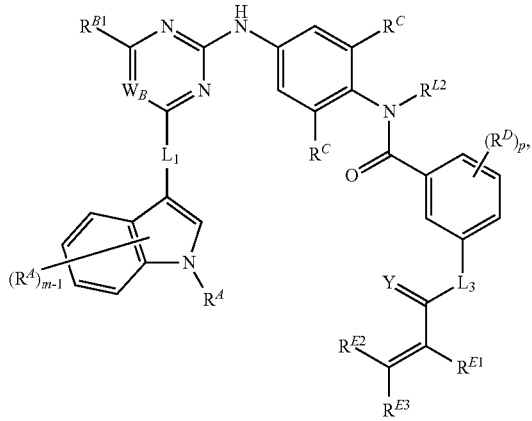
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
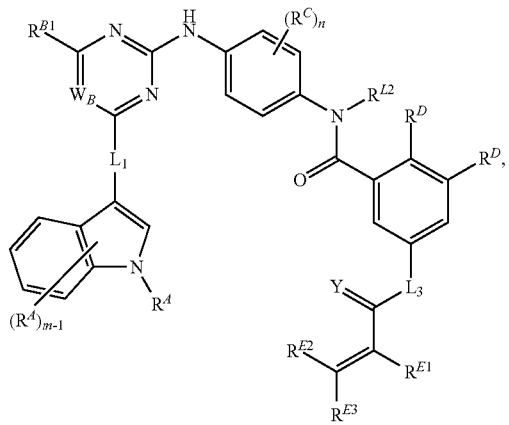
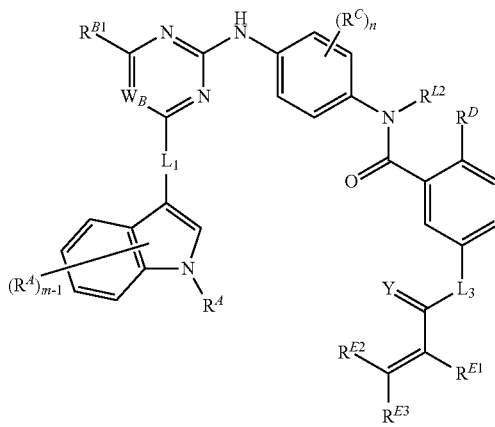
-continued
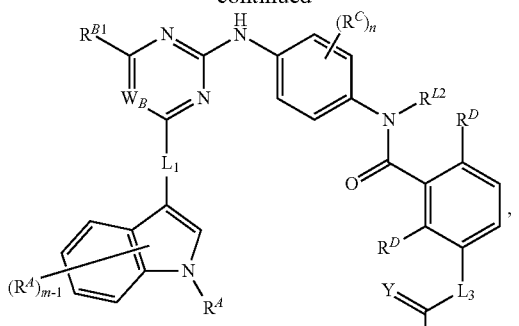
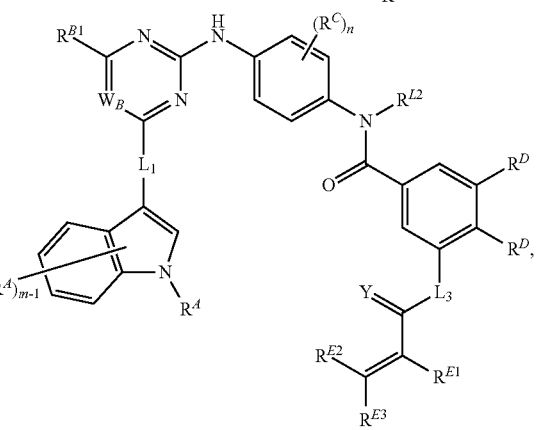
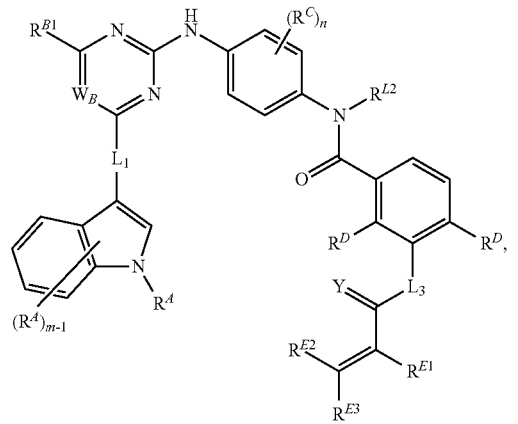

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

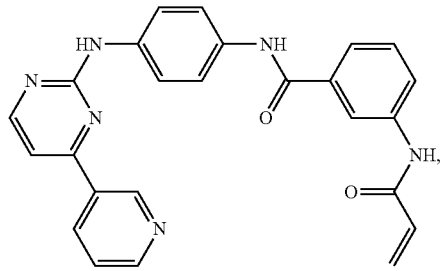
(JNK-IN-5)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

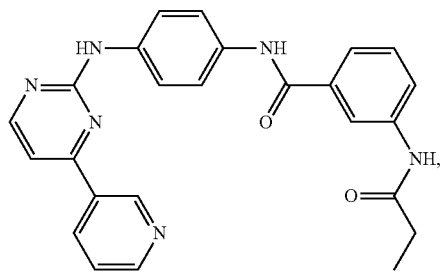
(JNK-IN-6)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

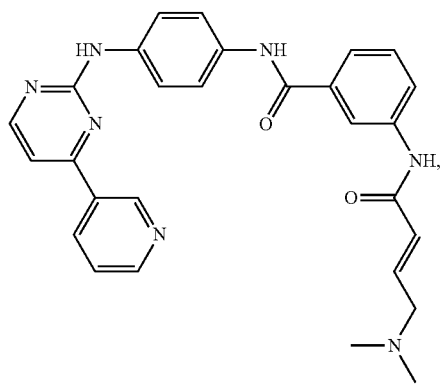
(JNK-IN-7)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

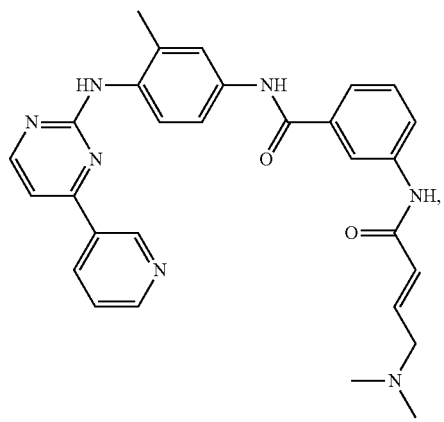
(JNK-IN-8)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

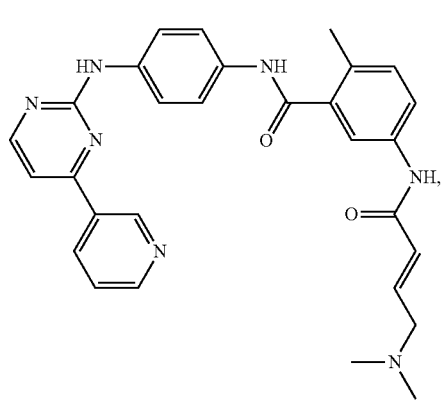
(JNK-IN-9)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

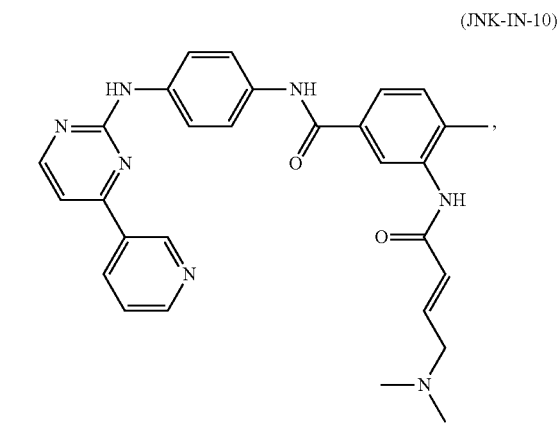 [SMILES: Cc1ccc(C(=O)Nc2ccc(Nc3nccc(-c4cccnc4)n3)cc2)cc1NC(=O)/C=C/CN(C)C]
(JNK-IN-10)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

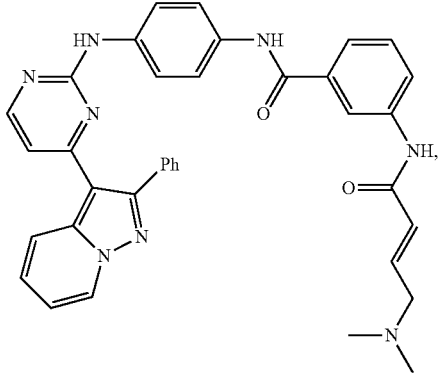

(JNK-IN-11)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

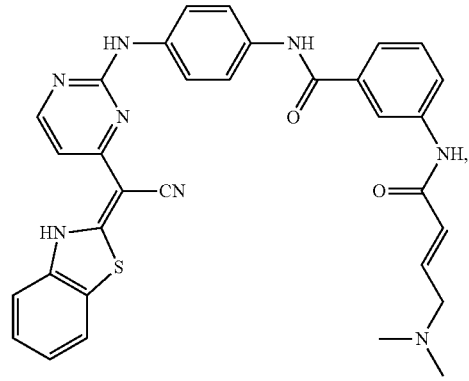

(JNK-IN-12)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

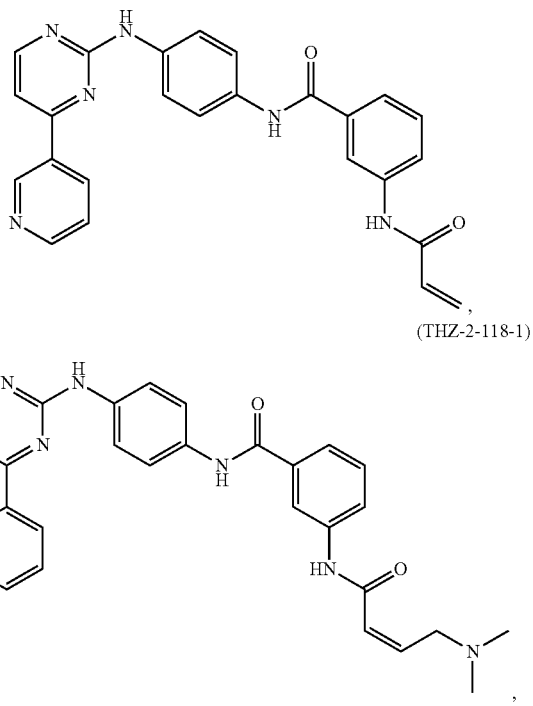

(THZ-2-117-1)

(THZ-2-118-1)

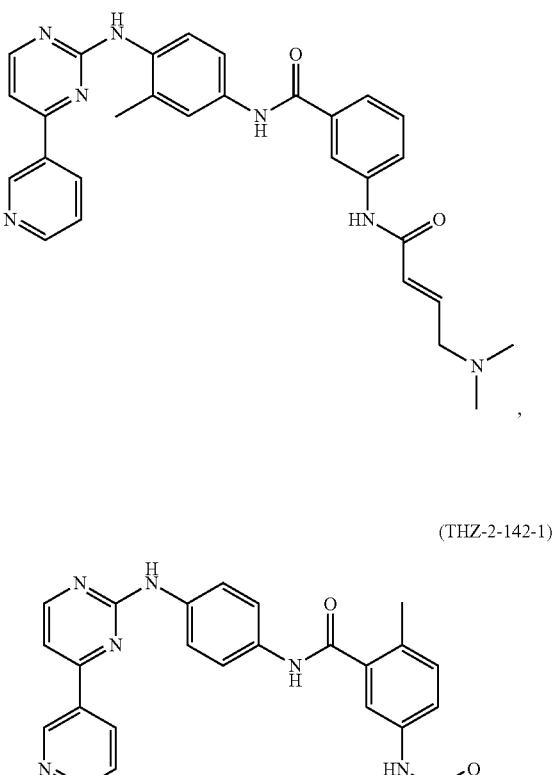

(THZ-2-140-2)

(THZ-2-142-1)

(THZ-2-143-1)
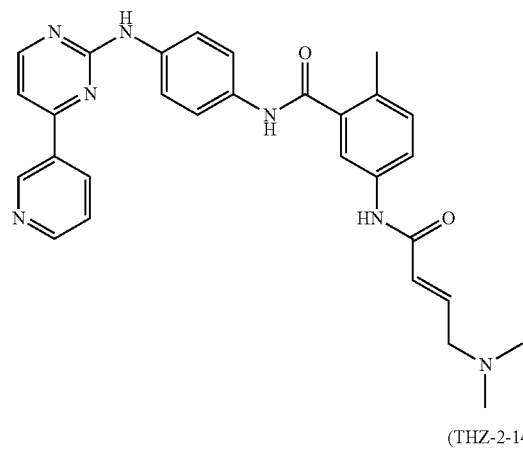
(THZ-2-144-1)
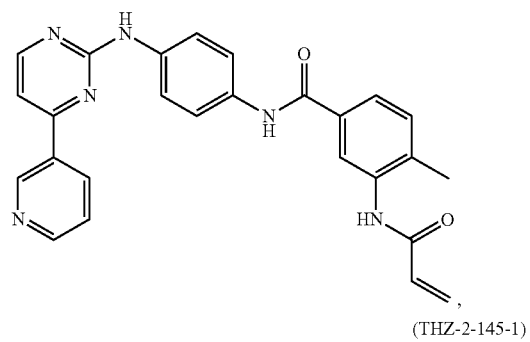
(THZ-2-145-1)
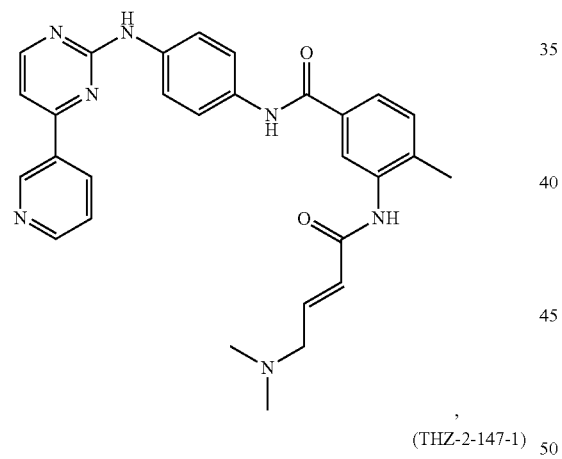
(THZ-2-147-1)
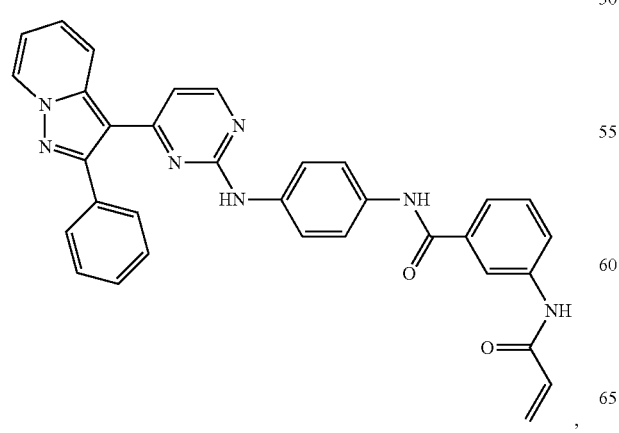
(THZ-2-148-1)
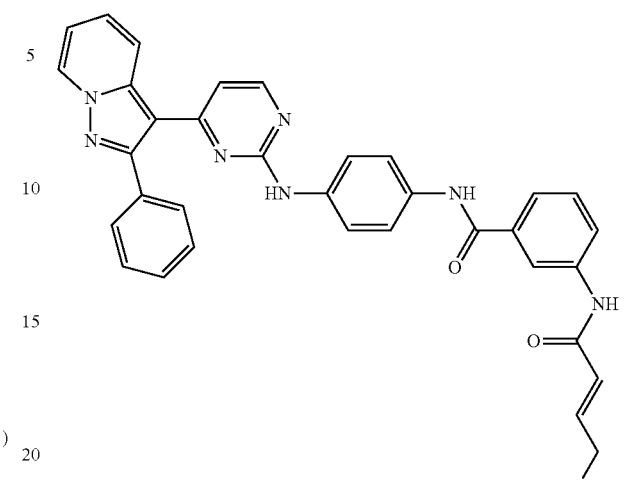
(THZ-3-06-1)
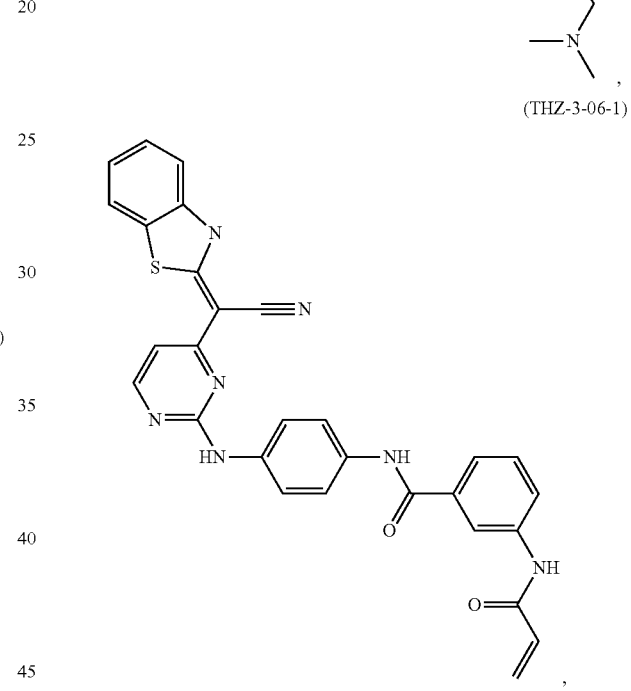
(THZ-3-07-1)
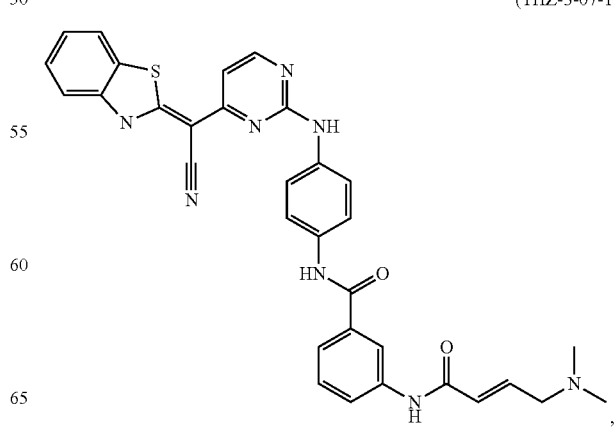

(THZ-3-11-1)

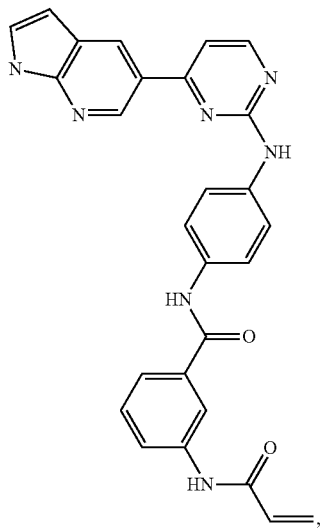

(THZ-3-30-1)

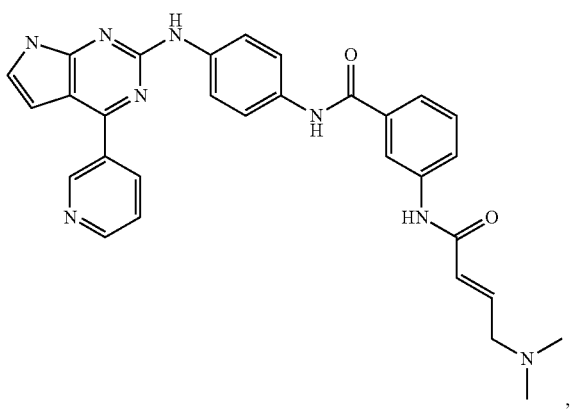

(THZ-3-39-1)

(THZ-3-46-1)

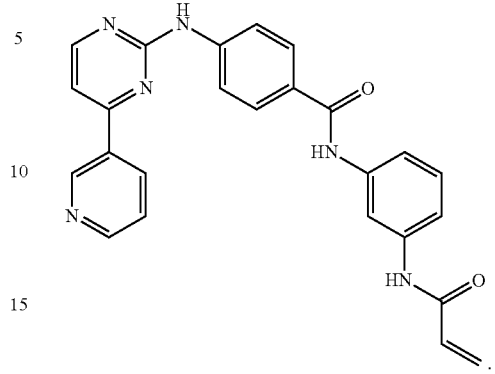

or a pharmaceutically acceptable salt, solvate, hydrate, polymorph, co-crystal, tautomer, stereoisomer, isotopically labeled derivative, or prodrug thereof.

In certain embodiments, the compounds of the present invention are the compounds described herein, and pharmaceutically acceptable salts, solvates, hydrates, polymorphs, co-crystals, tautomers, stereoisomers, isotopically labeled derivatives, or prodrugs thereof. In certain embodiments, the compounds of the present invention are the compounds of Formula (I), and pharmaceutically acceptable salts, solvates, hydrates, polymorphs, co-crystals, tautomers, stereoisomers, isotopically labeled derivatives, or prodrugs thereof. In certain embodiments, the compounds of the present invention are JNK-IN-5, JNK-IN-6, JNK-IN-7, JNK-IN-8, JNK-IN-9, JNK-IN-10, JNK-IN-11, JNK-IN-12, THZ-2-117-1, THZ-2-118-1, THZ-2-140-2, THZ-2-142-1, THZ-2-143-1, THZ-2-144-1, THZ-2-145-1, THZ-2-147-1, THZ-2-148-1, THZ-3-06-1, THZ-3-07-1, THZ-3-11-1, THZ-3-30-1, THZ-3-39-1, and THZ-3-46-1, and pharmaceutically acceptable salts, solvates, hydrates, polymorphs, co-crystals, tautomers, stereoisomers, isotopically labeled derivatives, or prodrugs thereof.

In certain embodiments, the compound of the present invention is of the formula:

(THZ-2-071-1)

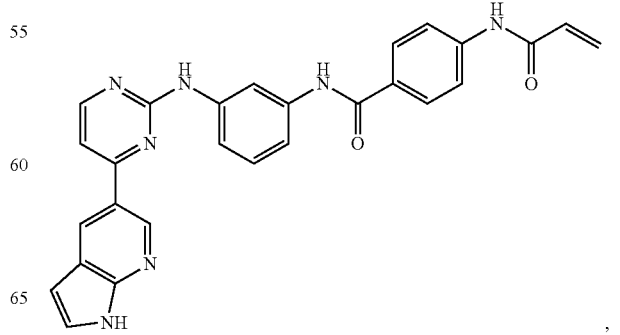

-continued (ZG-9)

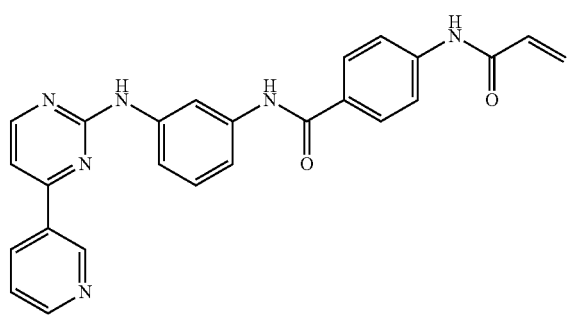

(ZG-10)

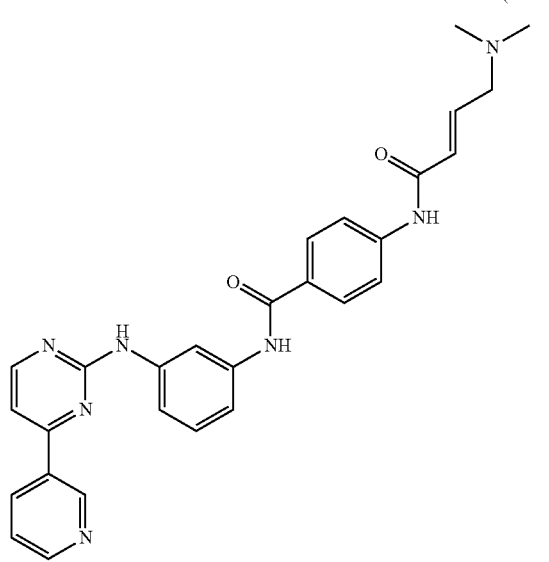

(ZG-6)

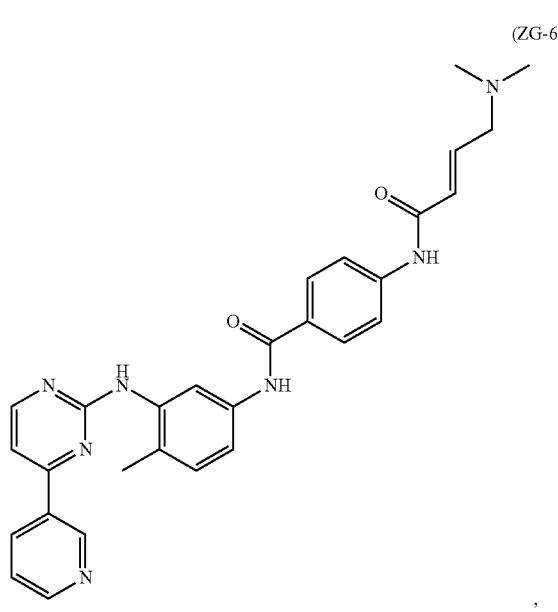

-continued (THZ-2-102-1)

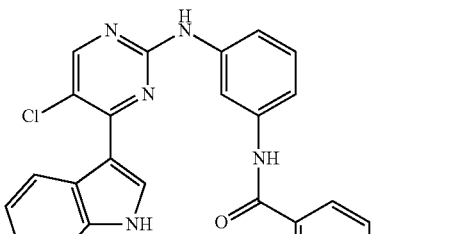

or a pharmaceutically acceptable salt, solvate, hydrate, polymorph, co-crystal, tautomer, stereoisomer, isotopically labeled derivative, or prodrug thereof. The compounds THZ-2-071-1, ZG-9, ZG-10, ZG-6, and THZ-2-102-1 may not have significant activity against JNK; however, these compounds may be useful in inhibiting other kinases.

The compounds of the invention bear multiple binding motifs to JNK. Ring A of the inventive compounds may be accommodated inside a hydrophobic pocket in the ATP-binding site of JNK. Functionalities on Ring A may bind to residues of JNK, such as to the "gatekeeper" methionine residue. Ring B of the compounds of the invention may bind to JNK kinase hinge residues, such as Leu148 and Met149. Functional groups of $R^E$ may form a hydrogen bond with JNK's Asn152 residue. This hydrogen bond may be important for positioning Ring D and orienting the Michael acceptor moiety proximal to Cys154 to facilitate covalent bond formation. In certain embodiments, the compounds of the invention non-covalently bind to JNK. In other embodiments, the compounds of the invention covalently attach to JNK. In certain embodiments, the covalent attachment of the compounds of the invention to JNK is irreversible. In other embodiments, the covalent attachment is reversible.

Pharmaceutical Compositions, Kits, and Administration

The present invention provides pharmaceutical compositions comprising a compound of the present invention, e.g., a compound of Formula (I), and pharmaceutically acceptable salts, solvates, hydrates, polymorphs, co-crystals, tautomers, stereoisomers, isotopically labeled derivatives, and prodrugs thereof, as described herein, and optionally a pharmaceutically acceptable excipient. In certain embodiments, the compound of the present invention, or a pharmaceutically acceptable salt thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™) polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-cancer agents, anti-diabetic agents, anti-inflammatory agents, immunosuppresant agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits for preventing and/or treating a disease of a subject. In certain embodiments, the kits include a first container comprising a compound, or a pharmaceutically acceptable salt, solvate, hydrate, polymorph, co-crystal, tautomer, stereoisomer, isotopically labeled derivative, prodrug, and composition thereof; and an instruction for administering the compound, or a pharmaceutically acceptable salt, solvate, hydrate, polymorph, co-crystal, tautomer, stereoisomer, isotopically labeled derivative, prodrug, and composition thereof, to a subject to prevent or treat a JNK-associated disease. In certain embodiments, the kits include a first container comprising a JNK inhibitor. In certain embodiments, the kits include a first container comprising an irreversible JNK inhibitor. In certain embodiments, the kits include a first container comprising a compound of the present invention. In certain embodiments, the kits include a first container comprising a compound of the present invention. In certain embodiments, the kits include a first container comprising a compound described herein. In certain embodiments, the kits include a first container comprising a compound selected from the group consisting of JNK-IN-5, JNK-IN-6, JNK-IN-7, JNK-IN-8, JNK-IN-9, JNK-IN-10, JNK-IN-11, and JNK-IN-12. In certain embodiments, the kits include a first container comprising a compound selected from the group consisting of THZ-2-117-1, THZ-2-118-1, THZ-2-140-2, THZ-2-142-1, THZ-2-143-1, THZ-2-144-1, THZ-2-145-1, THZ-2-147-1, THZ-2-148-1, THZ-3-06-1, THZ-3-07-1, THZ-3-11-1, THZ-3-30-1, THZ-3-39-1, and THZ-3-46-1.

In certain embodiments, the kits are used for preventing and/or treating diseases associated with JNK kinase activity. In certain embodiments, the kits are used for preventing and/or treating a proliferative disease. In certain embodiments, the kits are used for preventing and/or treating cancer. In certain embodiments, the kits are used for preventing and/or treating a benign neoplasm. In certain embodiments, the kits are used for preventing and/or treating a neurodegenerative disease. In certain embodiments, the kits are used for preventing and/or treating a metabolic disorder. In certain embodiments, the kits are used for preventing and/or treating an inflammatory disease. In certain embodiments, the kits are used for preventing and/or treating a cardiovascular disease.

Methods of Treatment

The present invention provides methods for the prevention and treatment of various diseases, e.g., neurodegenerative diseases, metabolic disorders, inflammatory diseases, cardiovascular diseases, and proliferative diseases (e.g., cancer and benign neoplasms).

In certain embodiments, the methods of the present invention comprise administering to a subject in need thereof an effective amount of a compound of the present invention, or a pharmaceutical composition thereof.

In certain embodiments, the effective amount is a therapeutically effective amount. In certain embodiments, the effective amount is a prophylactically effective amount.

In certain embodiments, the subject administered the inventive compound, or composition as described herein, is an animal. The animal may be of either sex and may be of any stage of development. In certain embodiments, the animal is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the subject is a non-human, genetically engineered animal. In certain embodiments, the subject is a non-human transgenic animal, such as a transgenic mouse or transgenic pig.

In certain embodiments, the disease is a proliferative disease, e.g., cancer. In certain embodiments, the disease is benign neoplasm. In certain embodiments, the disease is a neurodegenerative disease. In certain embodiments, the disease is stroke. In certain embodiments, the disease is Parkinson's disease. In certain embodiments, the disease is Alzheimer's disease. In certain embodiments, the disease is a metabolic disorder. In certain embodiments, the disease is diabetes. In certain embodiments, the disease is an inflammatory disease. In certain embodiments, the disease is a cardiovascular disease, e.g., stroke.

In certain embodiments, the methods of the present invention comprise administering to a subject with a proliferative disease (e.g., cancer) an effective amount of a compound of the present invention, or the pharmaceutical composition thereof. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer [e.g., meningioma, glioblastomas, glioma (e.g., astrocytoma, oligodendroglioma), medulloblastoma]; bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endothelio sarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)]; lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), nonsmall cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer [e.g., squamous cell carcinoma (SCC), keratoacanthoma (KA), melanoma, basal cell carcinoma (BCC)]; small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the methods of the present invention comprise administering to a subject with a benign neoplasm an effective amount of a compound of the present invention, or the pharmaceutical composition thereof.

In certain embodiments, the methods of the present invention comprise administering to a subject with a neurodegenerative disease an effective amount of a compound of the present invention, or the pharmaceutical composition thereof. Exemplary neurodegenerative diseases include, but are not limited to, multiple sclerosis. Parkinson's disease, Huntington's disease, amyotrophic lateral sclerosis, Alzheimer's disease. In certain embodiments, the methods of the present invention comprise administering to a subject with Parkinson's disease an effective amount of a compound of the present invention, or the pharmaceutical composition thereof. In certain embodiments, the methods of the present invention comprise administering to a subject with Alzheimer's disease an effective amount of a compound of the present invention, or the pharmaceutical composition thereof.

In certain embodiments, the methods of the present invention comprise administering to a subject with a metabolic disorder (e.g., Type I or II diabetes, or an obesity-related condition or complication thereof) an effective amount of a compound of the present invention, or the pharmaceutical composition thereof. An "obesity-related condition" as used herein, includes, but is not limited to, a condition related to obesity, undesired weight gain (e.g., from medication-induced weight gain, from cessation of smoking) or an overeating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity and pre-obesity (e.g., being "over-weight") as defined by the World Health Organization. Obesity-related conditions include, but are not limited to, Type II diabetes mellitus; ischemic heart disease, arterial vascular disease, angina, myocardial infarction, stroke, migraines, congestive heart failure, deep vein thrombosis, pulmonary embolism, gall stones, gastroesophagael reflux disease, obesity hypoventilation syndrome, erectile dysfunction, urinary incontinence, liver injury, and chronic renal failure. In certain embodiments, the metabolic disorder is diabetes. For example, in certain embodiments, the methods of the present invention comprise administering to a subject with diabetes (i.e., Type I or II diabetes) an effective amount of a compound of the present invention, or the pharmaceutical composition thereof.

In certain embodiments, the methods of the present invention comprise administering to a subject with an inflammatory disease an effective amount of a compound of the present invention, or the pharmaceutical composition thereof. Inflammatory disease refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory diseases include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the methods of the present invention comprise administering to a subject with a cardiovascular disease an effective amount of a compound of the present invention, or the pharmaceutical composition thereof. Exemplary cardiovascular diseases include, but are not limited to, hypertension, circulatory shock, myocardial reperfusion injury, stroke, and atherosclerosis. In certain embodiments, the methods of the present invention comprise administering to a subject with stroke an effective amount of a compound of the present invention, or the pharmaceutical composition thereof.

In certain embodiments, the disease is a disease associated with JNK activity, e.g., a disease associated with aberrant or unwanted JNK activity. For example, in certain embodiments, the disease results from increased JNK activity. In certain embodiments, the methods of the present invention comprise administering to a subject with a JNK-associated disease an effective amount of a compound of the present invention, or a pharmaceutical composition thereof. Inhibition of JNK1 is associated with treatment of cancer, diabetes, and inflammatory diseases (e.g., inflammation). Increased JNK1 activity is also associated with obesity, i.e., inhibition of JNK1 or mouse knockout has been found to increase insulin sensitivity. Inhibition of JNK3 is associated with the treatment of neurodegenerative diseases. See Kyriakis et al., 2001; Zhang et al., 2005; and Hunot et al., 2004 for discussions of the association of JNK with various neurodegenerative diseases, e.g., Parkinson's and Alzheimer's diseases.

CDK7 is also called CDK catalytic kinase which usually catalyze the CDK1 and CDK2 for the phosphorylation of their substrate. For CDK1 and CDK2, they are activated in many cancers, e.g., colon cancer, liver cancer, and breast cancer. CDK7 is known to be responsible at least for RNAP II Ser 2 and Ser 5 phosphorylation. CDK7 has a lysine which has a very similar location as cysteine in JNK, and it envisioned that active JNK inhibitors of the present invention will also be active CDK7 inhibitors. Thus, in certain embodiments, the methods of the present invention comprise administering to a subject with a CDK7-associated disease an effective amount of a compound of the present invention, or a pharmaceutical composition thereof.

In certain embodiments, the methods of the present invention comprise administering to a subject with an IRAK1/4-associated disease an effective amount of a compound of the present invention, or a pharmaceutical composition thereof.

In certain embodiments, the methods of the present invention comprise administering to a subject with an EGFR-associated disease an effective amount of a compound of the present invention, or a pharmaceutical composition thereof.

In certain embodiments, the methods of the present invention comprise administering to a subject with a DDR1/2-associated disease an effective amount of a compound of the present invention, or a pharmaceutical composition thereof.

In certain embodiments, the methods of the present invention comprise administering to a subject with a c-Kit-associated disease an effective amount of a compound of the present invention, or a pharmaceutical composition thereof.

In certain embodiments, the methods of the present invention comprise administering to a subject with a PDGFR-associated disease an effective amount of a compound of the present invention, or a pharmaceutical composition thereof.

A proliferative disease may also be associated with inhibition of apoptosis of a cell in a biological sample or subject.

All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. In another aspect, the present invention provides methods of inhibiting cell growth in a biological sample or subject by contacting with the biological sample or administering to the subject an effective amount of a compound of the present invention, or a pharmaceutical composition thereof.

In still another aspect, the present invention provides methods of inducing apoptosis of a cell in a biological sample or a subject by contacting with the biological sample or administering to the subject an effective amount of a compound of the present invention, or a pharmaceutical composition thereof.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a benign neoplastic cell. In certain embodiments, the cell is an endothelial cell. In certain embodiments, the cell is an immune cell.

In certain embodiments, the compound is a JNK inhibitor. In certain embodiments, the compound is a JNK1 inhibitor. In certain embodiments, the compound is a JNK2 inhibitor. In certain embodiments, the compound is a JNK3 inhibitor. In certain embodiments, the compound is a CDK7 inhibitor. In certain embodiments, the compound is an IRAK1/4 inhibitor. In certain embodiments, the compound is an EGFR inhibitor. In certain embodiments, the compound is a DDR1/2 inhibitor. In certain embodiments, the compound is a c-Kit inhibitor. In certain embodiments, the compound is a PDGFR inhibitor.

In certain embodiments, the compound is a compound of the present invention.

Another aspect of the invention relates to methods of screening a library of compounds to identify one or more compounds that are useful in the treatment of a proliferative disease, in inhibiting cell growth, and/or in inducing apoptosis of a cell. In certain embodiments, the library of compounds is a library of compounds of the present invention. The methods of screening a library include providing at least two different compounds of the present invention, or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of the present invention, or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics. In certain embodiments, the methods of screening a library include providing at least two different compounds of the present invention, or pharmaceutically acceptable salts thereof, or pharmaceutical compositions thereof; and performing at least one assay using the different compounds of the present invention, or pharmaceutically acceptable salts thereof, or pharmaceutical compositions thereof, to detect one or more characteristics. In certain embodiments, the characteristic is a characteristic associated with proliferative diseases. In certain embodiments, the characteristic is a desired characteristic. In certain embodiments, the desired characteristic is usefulness in treating a proliferative disease, in inhibiting cell growth or cell proliferation, and/or in inducing apoptosis of a cell. In certain embodiments, the desired characteristic is anti-proliferation. In certain embodiments, the desired characteristic is anti-cancer. In certain embodiments, the desired characteristic is inhibition of a kinase. In certain embodiments, the desired characteristic is inhibition of JNK. In certain embodiments, the desired characteristic is inhibition of CDK7. In certain embodiments, the desired characteristic is inhibition of IRAK1/4. In certain embodiments, the desired characteristic is inhibition of EGFR. In certain embodiments, the desired characteristic is inhibition of DDR1/2. In certain embodiments, the desired characteristic is inhibition of c-Kit. In certain embodiments, the desired characteristic is inhibition of PDGFR. The characteristic to be detected may also be an undesired characteristic associated with the proliferative disease, cell growth or cell proliferation, and/or apoptosis of a cell. In certain embodiments, the undesired characteristic is induction of cell growth or cell proliferation. In certain embodiments, the undesired characteristic is inhibition of apoptosis of a cell.

The different compounds of the present invention may be provided from natural sources (see, e.g., Sternberg et al., Proc. Nat. Acad. Sci. USA, (1995) 92:1609-1613) or generated by synthetic methods such as combinatorial chemistry (see, e.g., Ecker et al., Bio/Technology, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the proliferative disease described herein. The assay may be an immunoassay, such as a sandwich-type assay, competitive binding assay, one-step direct test, two-step test, or blot assay. The step of performing at least one assay may be performed robotically or manually. In certain embodiments, the activity of a kinase is inhibited. In certain embodiments, the activity of JNK is inhibited. In certain embodiments, the activity of CDK is inhibited. In certain embodiments, the activity of CDK7 is inhibited. In certain embodiments, the expression of a kinase, such as JNK and CDK (e.g., CDK7), is down-regulated. In certain embodiments, apoptosis of a cell is induced.

Another aspect of the present invention relates to compounds described therein, or pharmaceutically acceptable salts, solvates, hydrates, polymorphs, co-crystals, tautomers, stereoisomers, isotopically labeled derivatives, prodrugs, or compositions thereof, for use in treating a proliferative disease in a subject in need thereof.

Still another aspect of the present invention relates to compounds described therein, or pharmaceutically acceptable salts, solvates, hydrates, polymorphs, co-crystals, tautomers, stereoisomers, isotopically labeled derivatives, prodrugs, or compositions thereof, for use in inhibiting cell growth in a biological sample or subject in need thereof.

In yet another aspect, the present invention provides compounds described therein, or pharmaceutically acceptable salts, solvates, hydrates, polymorphs, co-crystals, tautomers, stereoisomers, isotopically labeled derivatives, prodrugs, or compositions thereof, for use in inducing apoptosis of a cell in a biological sample or subject in need thereof.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of the Compounds

General Synthetic Methods

The compounds provided herein can be prepared from readily available starting materials using the following general methods and procedures. See, e.g., Scheme 1 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

All solvents and reagents were used as obtained. $^1$H NMR spectra were recorded with a Varian Inova 600 NMR spectrometer and referenced to dimethylsulfoxide. Chemical shifts are expressed in ppm. Mass spectra were measured with Waters Micromass ZQ using an ESI source coupled to a Waters 2525 HPLC system operating in reverse mode with a Waters Sunfire $C_{18}$ 5 μm, 4.6 mm×50 mm column. Purification of compounds was performed with either a Teledyne ISCO CombiFlash Rf system or a Waters Micromass ZQ preparative system. The purity was analyzed on the above-mentioned Waters LC-MS Symmetry ($C_{18}$ column, 4.6 mm×50 mm, 5 μM) using a gradient of 5-95% methanol in water containing 0.05% trifluoroacetic acid (TFA).

General processes for preparing compounds of the present invention, e.g., JNK-IN-5, JNK-IN-6, JNK-IN-7, JNK-IN-8, JNK-IN-9, JNK-IN-10, JNK-IN-11, and JNK-IN-12, are provided as further embodiments of the invention and are illustrated in Schemes 1.

Scheme 1. Exemplary synthesis of compounds of the present invention

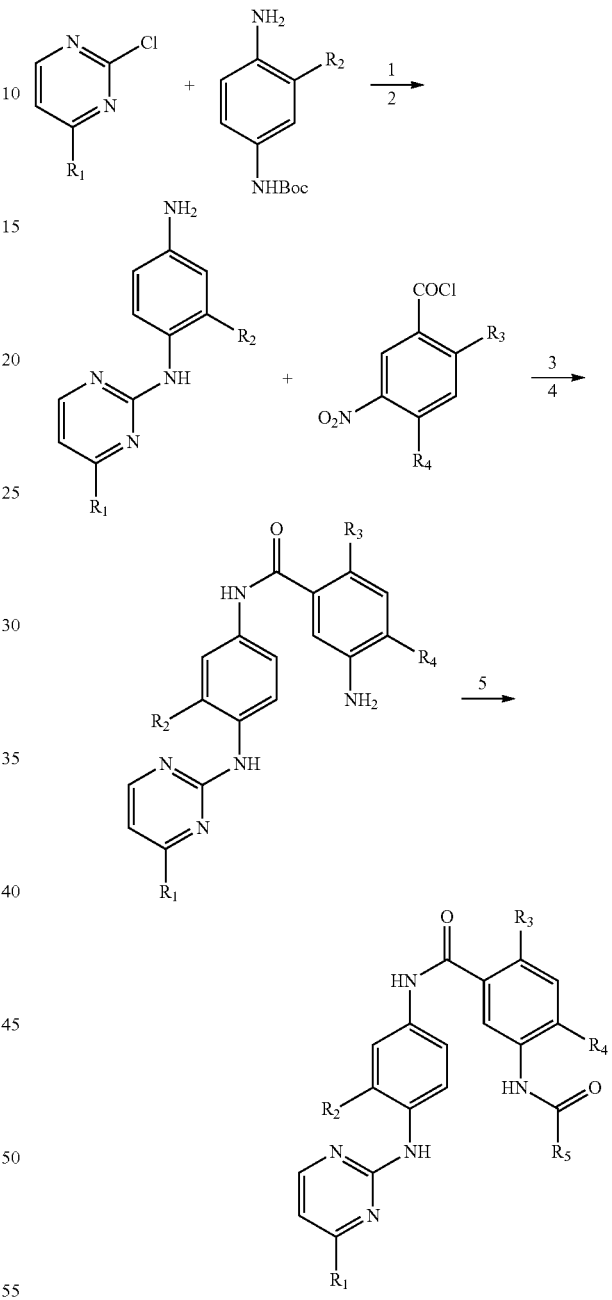

JNK-IN-5 $R_1$ = 3-pyridinyl, $R_2$ = H, $R_3$ = H, $R_4$ = H, $R_5$ = CH=CH$_2$
JNK-IN-6 $R_1$ = 3-pyridinyl, $R_2$ = H, $R_3$ = H, $R_4$ = H, $R_5$ = CH$_2$CH$_3$
JNK-IN-7 $R_1$ = 3-pyridinyl, $R_2$ = H, $R_3$ = H, $R_4$ = H, $R_5$ = CH=CHCH$_2$NMe$_2$
JNK-IN-8 $R_1$ = 3-pyridinyl, $R_2$ = CH$_3$, $R_3$ = H, $R_4$ = H, $R_5$ = CH=CHCH$_2$NMe$_2$
JNK-IN-9 $R_1$ = 3-pyridinyl, $R_2$ = H, $R_3$ = CH$_3$, $R_4$ = H, $R_5$ = CH=CHCH$_2$NMe$_2$
JNK-IN-10 $R_1$ = 3-pyridinyl, $R_2$ = H, $R_3$ = H, $R_4$ = CH$_3$, $R_5$ = CH=CHCH$_2$NMe$_2$
JNK-IN-11 R1 = 2-phenylpyrazoleo[1,5-a]pyridine, $R_2$ = $R_3$ = $R_4$ = H, $R_5$ = CH=CHCH$_2$NMe$_2$
JNK-IN-12 $R_1$ = benzothiazol-2-yl acetonitrile, $R_2$ = $R_3$ = $R_4$ = H, $R_5$ = CH=CHCH$_2$NMe$_2$ Reagents and conditions: (1) Pd$_2$(dba)$_3$, X-Phos, K$_2$CO$_3$, t-BuOH, 90° C.; (2) TFA, CH$_2$Cl$_2$; (3) pyridine, 90° C.; (4) SnCl$_2$; (5) acryloyl chloride or 4-bromobut-2-enoyl chloride, NHMe$_2$ or propionyl chloride.

Each of the compounds shown in Scheme 1 may be designated a different compound number. Table 1 illustrates the alternative compound designation numbers of these compounds. For example, JNK-IN-5 and THZ-2-117-1 are alternative compound numbers designating the same compound.

TABLE 1

Alternative compound designation numbers

| | |
|---|---|
| JNK-IN-5 | THZ-2-117-1 |
| JNK-IN-6 | THZ-3-15-1 |
| JNK-IN-7 | THZ-2-118-1 |
| JNK-IN-8 | THZ-2-140-2 |
| JNK-IN-9 | THZ-2-143-1 |
| JNK-IN-10 | THZ-2-145-1 |
| JNK-IN-11 | THZ-2-148-1 |
| JNK-IN-12 | THZ-3-07-1 |

Buchwald Coupling

To a solution of 4-substituted-2-chloropyrimide in t-butanol was added t-butyl-4-aminophenylcarbamate or t-butyl-3-aminophenylcarbamate (1.0 equiv.), $K_2CO_3$ (1.0 equiv.), X-Phos (0.1 equiv.) and $Pd_2(dba)_3$. After heating at 90° C. for 6 h, the reaction mixture was diluted with a mixture of chloroform and 2-propanol (4:1). The organic layer was washed with water (3×), dried over $MgSO_4$, filtered and concentrated under reduced pressure. The resulting crude product was used for the next step without further purification.

BOC Deprotection Using Trifluoroacetic Acid

To a stirred solution of the above crude product in $CH_2Cl_2$ was added TFA at room temperature. The reaction mixture was stirred for 2 h and concentrated under reduced pressure. The resulting crude product was purified by flash column chromatography with $CH_2Cl_2$/methanol (10/1) to provide the title compound.

Preparation of Nitrobenzamide

The free amine obtained from the BOC deprotection step was dissolved in pyridine and nitrobenzoyl chloride (1.2 equiv.) was added to this solution. After stirring for 2 h at 90° C., the reaction mixture was concentrated and the resulting crude product was used for the next step without further purification.

Reduction of the Bitro Compound with $SnCl_2$

The nitro compound obtained from a reaction of the aniline and nitrobenzoyl chloride was suspended in ethyl acetate/methanol (5:1) and treated with $SnCl_2$ (2.5 equiv.). After stirring for 2-5 h at 80° C., the reaction mixture was cooled to room temperature and poured into saturated aqueous $NaHCO_3$. The mixture was stirred for 10 min and the aqueous phase was then extracted with chloroform and 2-propanol (4:1). The combined organic layer was washed with water and brine, dried over $MgSO_4$, filtered through a pad of celite and concentrated under reduced pressure. The resulting crude product was purified by flash column chromatography with $CH_2Cl_2$/methanol (10/1) to provide the title compound.

Preparation of the Acrylamide

To a DMF solution of the aniline obtained in the reduction step was added N,N-diisopropylethylamine (1.2 equiv.). The reaction mixture was cooled to −60° C. and then treated with 4-chloro-but-2-enoyl chloride (5.0 equiv.) in $CH_2Cl_2$. The reaction mixture was stirred for 10 min at −60° C. and then treated with a solution of dimethylamine in THF. The reaction mixture was then warmed to room temperature, stirred for 1 h and concentrated under reduced pressure. The resulting crude product was purified by preparative HPLC to provide the title compound.

Analytical Data of Exemplary Compounds

JNK-IN-5: LC-MS: (M+H) 437, $^1$H NMR (600 MHz, DMSO-$d_6$) 10.34 (s, 1 H), 10.19 (s, 1 H), 9.71 (s, 1 H), 9.33 (s, 1 H), 8.72 (s, 1 H), 8.57 (d, J=4.8 Hz, 1 H), 8.49 (d, J=4.8 Hz, 1 H), 8.14 (s, 1 H), 7.90 (d, J=9.0 Hz, 1 H), 7.76 (d, J=9.0 Hz, 2 H), 7.68 (d, J=9.0 Hz, 2 H), 7.63 (d, J=7.8 Hz, 1 H), 7.58 (m, 1 H), 7.47 (m, 2 H), 6.44 (m, 1 H), 6.29 (d, J=16.2 Hz, 1 H), 5.76 (d, J=16.2 Hz, 1 H).

JNK-IN-6: LC-MS(M+H) 439, $^1$H NMR (600 MHz, DMSO-$d_6$) 10.12 (s, 1 H0, 10.04 (s, 1 H), 9.72 (s, 1 H), 9.33 (s, 1 H), 8.74 (d, J=4.8 Hz, 1 H), 8.58 (d, J=5.4 Hz, 1 H), 8.55 (dt, J=6.0, 1.8 Hz, 1 H), 8.07 (t, J=1.8 Hz, 1 H), 7.80 (d, J=7.2 Hz, 1 H), 7.74 (d, J=9.6 Hz, 2 H), 7.68 (d, J=9.6 Hz, 2 H), 7.64 (m, 1 H), 7.58 (m, 1 H), 7.47 (d, J=4.8 Hz, 1 H), 7.41 (t, J=7.8 Hz, 1 H), 2.35 (q, J=7.8 Hz, 2 H), 1.08 (t, J=7.8 Hz, 3 H).

JNK-IN-7: LC-MS: (M+H) 494, $^1$H NMR (600 MHz, DMSO-$d_6$) 10.53 (s, 1 H), 10.20 (s, 1 H), 9.94 (b, 1 H), 9.75 (s, 1 H), 9.35 (s, 1 H), 8.75 (d, J=4.8 Hz, 1 H), 8.59 (d, J=4.8 Hz, 1 H), 8.56 (dt, J=4.8, 7.8 Hz, 1 H), 8.17 (s, 1 H), 7.89 (d, J=9.0 Hz, 1 H), 7.77 (d, J=9.0 Hz, 2 H), 7.69 (d, J=9.0 Hz, 2 H), 7.65 (m, 2 H), 7.49 (m, 2 H), 6.76 (m, 1 H), 6.48 (d, J=15.6 Hz, 1 H), 3.96 (d, J=6.0 Hz, 2 H), 2.79 (s, 6 H).

JNKIN-8: LC-MS: (M+H) 508, $^1$H NMR (600 MHz, DMSO-$d_6$) 10.54 (s, 1 H), 10.20 (s, 1 H), 9.24 (s, 1 H), 8.95 (s, 1 H), 8.70 (d, J=3.0 Hz, 1 H), 8.47 (d, J=4.8 Hz, 1 H), 8.44 (d, J=7.8 Hz, 1 H), 8.17 (s, 1 H), 7.89 (d, J=7.8 Hz, 1 H), 7.77 (d, J=7.8 Hz, 1 H), 7.63 (d, J=1.8 Hz, 1 H), 7.49-7.44 (m, 2 H), 7.40 (d, J=5.4 Hz, 1 H), 6.76 (m, 1 H), 6.46 (d, J=15.6 Hz, 1 H), 3.94 (d, J=6.0 Hz, 2 H), 2.79 (s, 6 H), 2.23 (s, 3 H).

JNK-IN-9: LC-MS: (M+H) 508, $^1$H NMR (600 MHz, DMSO-$d_6$) 10.41, (s, 1 H), 10.22 (s, 1 H), 9.71 (s, 1 H), 9.33 (s, 1 H), 8.73 (d, J=3.6 Hz, 1 H), 8.58 (d, J=5.4 Hz, 1 H), 8.52 (d, J=7.8 Hz, 1 H), 7.75 (m 3 H), 7.67-7.61 (m, 4 H), 77.26 (d, J=8.4 Hz, 2 H), 6.73 (m, 1 H), 6.43 (d, J=15.6 Hz, 1 H), 3.94 (d, J=6.0 Hz, 2 H), 2.79 (s, 6 H), 2.32 (s, 3 H).

JNK-IN-10: LC-MS (M+H) 508, $^1$H NMR (600 MHz, DMSO-$d_6$), 10.12 (s, 1 H), 9.84 (s, 1 H), 9.74 (s, 1 H), 9.35 (s, 1 H), 8.76 (d, J=4.2 Hz, 1 H), 8.59 (m, 2 H), 8.05 (s, 1 H), 7.75 (m, 3 H), 7.67 (m, 3 H), 7.47 (d, J=5.4 Hz, 1 H), 7.37 (d, J=8.4 Hz, 1 H), 6.74 (m, 1 H), 6.57 (d, J=15.6 Hz, 1 H), 3.94 (d, J=6.0 Hz, 2 H), 2.79 (s, 6 H), 2.27 (s, 3 H).

JNK-IN-11: LC-MS: (M+H) 609, $^1$H NMR (600 MHz, DMSO-$d_6$) 10.52 (s, 1 H), 10.17 (s, 1 H), 9.53 (s, 1 H), 8.81 (d, J=7.2 Hz, 1 H), 8.47 (br, 1 H), 8.22 (d, J=5.4 Hz, 1 H), 8.16 (s, 1 H), 7.89 (d, J=8.4 Hz, 1 H), 7.67 (d, J=7.8 Hz, 1 H), 7.59 (m, 6 H), 7.47 (m, 5 H), 7.11 (m, 1 H), 6.77 (m, 1 H), 6.45 (m, 2 H), 3.95 (d, J=6.6 Hz, 1 2 H), 2.79 (s, 6 H).

JNK-IN-12: LC-MS (M+H) 589, $^1$H NMR (600 MHz, DMSO-$d_6$) 10.58 (s, 1 H), 10.43 (s, 1 H), 10.12 (s, 1 H), 8.23 (s, 1 H), 7.93 (d, J=8.4 Hz, 2 H), 7.84 (br, 2 H), 7.71 (d, J=8.4 Hz, 2 H), 7.65 (m, 1 H), 7.51 (m, 3 H), 7.36 (br, 1 H), 7.22 (br, 1 H), 6.78 (m, 1 H), 6.52 (br, 1 H), 6.47 (d, J=15.6 Hz, 1 H), 3.94 (d, J=6.0 Hz, 2 H), 2.79 (s, 6 H).

Example 2

Assays of the Compounds

Intact Protein Analysis

For each analysis, about 100 pmol JNK protein+/−inhibitor (JNK-IN-7) was injected onto a self-packed reversed phase column (1/32" O.D.×500 μm I.D., 5 cm of POROS 10R2 resin). After desalting, protein was eluted with an HPLC gradient (0-100% B in 4 minutes, A=0.2 M acetic acid in water, B=0.2 M acetic acid in acetonitrile, and flow rate=10 μL/min) into a QTRAP mass spectrometer (AB Sciex, Toronto, Canada) or an LTQ Orbitrap mass spectrometer (ThermoFisher Scientific, San Jose, Calif.). The QTRAP was operated in Q1 MS mode at unit resolution scanning at 2000 amu/sec. LTQ OrbitrapMS spectra were acquired in centroid mode using the electron multipliers for ion detection. Mass spectra were deconvoluted using MagTran 1.03b2 software.

Protease Digestion and NanoLC/MS Analysis of Peptide Fragments

JNK-IN-7 treated JNK (25 µg, about 620 pmol) was diluted with ammonium bicarbonate buffer at pH 8.0 and then reduced for 30 min at 56° C. with 10 mM DTT. After cooling for 5 min, the protein was alkylated with 22.5 mM iodoacetamide for 30 min at room temperature in the dark and digested overnight with 1.5 µg of trypsin at 37° C. In the morning, 1 µg of Glu-C was added, and the solution further incubated at 37° C. for 8 hr. Digested peptides (about 2 pmol) were injected onto a self-packed pre-column (4 cm POROS 10R2) and eluted into the mass spectrometer (LTQ OrbitrapVelos, ThermoFisher Scientific). Peptides were subjected to $MS^2$ by CAD (electron multiplier detection, relative collision energy 35%, q=0.25) as well as HCD (image current detection, resolution at m/z 400=7500, and relative collision energy=35%).

Cell-based Assays for c-Jun Phosphorylation

The cell based kinase assays for c-Jun phosphorylation carried out by using the LanthaScreen™ c-Jun (1-79) HeLa cell line (Life Technologies, Carlsbad, Calif.) which stably express GFP-c-Jun 1-79 and GFP-ATF2 19-106, respectively. Phosphorylation was determined by measuring the time resolved FRET (TR-FRET) between a terbium labeled phospho-c-Jun specific antibody and GFP. The cells were plated in white tissue culture treated 384 well plates at a density of 10,000 cell per well in 32 µL assay medium (Opti-MEM®, supplemented with 0.5% charcoal/dextran-treated FBS, 100 U/ml penicillin and 100 µg/ml streptomycin, 0.1 mM nonessential amino acids, 1 mM sodium pyruvate, 25 mM Hepes, pH 7.3, and lacking phenol red). After overnight incubation, cells were pretreated for 90 minutes with compound (at indicated concentration) diluted in 4 µL assay buffer followed by 30 min of stimulation with 5 ng/ml of TNF-α in 4 µL assay buffer (final assay volume was 40 µl). The medium was then removed by aspiration, and the cells were lysed by adding 20 µl of lysis buffer (20 mM Tris-HCl, pH 7.6, 5 mM EDTA, 1% Nonidet P-40 substitute, 5 mM NaF, 150 mM NaCl, and 1:100 protease and phosphatase inhibitor mix, SIGMA P8340 and P2850, respectively). The lysis buffer included 2 nM of the terbium-labeled anti-c-Jun (pSer73) detection antibodies (Life Technologies). After allowing the assay to equilibrate for 60 minutes at room temperature, TR-FRET emission ratios were determined on a BMG Pherastar fluorescence plate reader (BMG Labtech, Cary, N.C.) using the following parameters: excitation at 340 nm; emission at 520 nm and 490 nm; 100 µs lag time; 200 µs integration time; and emission ratio=$Em_{520}/Em_{490}$. All data were analyzed and plotted using Graphpad Prism 4.

High Throughput Microscopy

Cells were plated at 7500 cells/well in 96-well microscopy plates (Corning) in recommended media for 24 hours, and then starved in media lacking serum for 16 hours. Cells were pre-treated for 180 minutes with 10-fold stock solutions of JNK inhibitors and for 10 min with control compounds MK2206, PD0325901, SB239063, KIN040, and KIN208 and treated with 10-fold stock solutions of IGF-1, IL-6, TNF-α (all PeproTech), or anisomycin for 60 minutes. Cells were fixed in 2% paraformaldehyde for 10 min at room temperature and washed with PBS-T (Phosphate Buffered Saline, 0.1% Tween 20). Cells were permeabilized in methanol for 10 min at room temperature, washed with PBS-T, and blocked in Odyssey Blocking Buffer (LI-COR Biosciences) for 1 hour at room temperature. Cells were incubated overnight at 4° C. with antibody specific for Erk1/2(pT202/pY204), Akt(pS473), c-Jun(pS73), pP38(T180/Y182) and pSTAT3(Y705) (Cell Signaling Technology), pRSK1(S380) and pMSK1(S376) (Epitomics), and NF-κB (Santa Cruz Biotechnology) diluted 1:400 in Odyssey Blocking Buffer. Cells were washed three times in PBS-T and incubated with rabbit-specific secondary antibody labeled with Alexa Fluor 647 (Invitrogen) diluted 1:2000 in Odyssey Blocking Buffer. Cells were washed once in PBS-T and once in PBS and incubated in 250 ng/ml Hoechst 33342 (Invitrogen) and 1:1000 Whole Cell Stain (blue; Thermo Scientific) solution. Cells were washed twice with PBS and imaged in an imageWoRx high-throughput microscope (Applied Precision). Data were plotted using DataPflex.

Binding Kinetics Assay

A375 cells (ATCC® CRL-1619™) were pre-treated with 1 µM compound for the indicated amounts of time. Remove the medium and wash 3 times with PBS. Resuspend the cell pellet with 1 mL Lysis Buffer (1% NP-40, 1% CHAPS, 25 mM Tris, 150 mM NaCl, Phosphatase Inhibitor Cocktail, Roche 04906845001, and Protease Inhibitor Cocktail Roche 11836170001). Rotate end-to-end for 30 min at 4° C. Lysates were cleared by centrifugation at 14000 rpm for 15 min in the Eppendorf. The cleared lysates gel filtered into Kinase Buffer (0.1% NP-40, 20 mM HEPES, 150 mM NaCl, Phosphatase Inhibitor Cocktail, and Protease Inhibitor Cocktail) using Bio-Rad 10DG colums. The total protein concentration of the gel-filtered lysate should be around 5-15 mg/ml. Cell lysate was labeled with the probe from ActivX® at 5 µM for 1 hour. Samples were reduced with DTT, and cysteines were blocked with iodoacetamide and gel filtered to remove excess reagents and exchange the buffer. Add 1 volume of 2× Binding Buffer (2% Triton-100, 1% NP-40, 2 mM EDTA, and 2× PBS) and 50 µL streptavidin bead slurry and rotate end-to-end for 2 hours, centrifuge at 7000 rpm for 2 min. Wash 3 times with 1× Binding Buffer and 3 times with PBS. Add 30 µL 1× sample buffer to beads, and heat samples at 95° C. for 10 min. Run samples on an SDS-PAGE gel at 110 V. After transferred, the membrane was immunoblotted with JNK antibody (Cell signaling 9258).

Buffers

Lysis Buffer contained 50 mM Tris/HCl (pH 7.5), 1 mM EGTA, 1 mM EDTA, 1% (w/v) 1 mM sodium orthovanadate, 10 mM sodium (β-glycerophosphate, 50 mM NaF, 5 mM sodium pyrophosphate, 0.27 M sucrose, 1 mM Benzamidine, and 2 mM phenylmethanesulphonylfluoride (PMSF) and supplemented with 1% (v/v) Triton X-100. Kinase assay buffer contained 50 mM Tris/HCl (pH 7.5) and 0.1 mM EGTA.

Cell Culture, Treatments and Cell Lysis

HEK-293 cells stably expressing Interleukin Receptor 1 (HEK293-IL1R) were cultured in Dulbecco's Modified Eagle's medium (DMEM) supplemented with 10% FBS, 2 mM glutamine and 1× antimycotic/antibiotic solution. Cells were serum starved for 18 h before incubation with DMSO or different inhibitors, stimulated with 2 µM anisomycin (Sigma) for 1 h, and lysates were clarified by centrifugation for 10 min at 16000 g and 4° C.

Antibodies

Rabbit polyclonal antibodies against total pan JNK isoforms ((#9252), phospho-pan JNK isoforms (Thr183/Tyr185), (#4668), total p38 (#9212) or phospho-p38 MAPK (Thr180/Tyr182), (4631 resp.), total c-Jun (#9165), phospho-c-Jun (Ser63) (#9261), and phospho-MSK1 (Ser376) (#9591) were from Cell Signalling technology.

SDS-PAGE and Western Blot

Cell lysates (30 µg) were resolved by electrophoresis on SDS polyacrylamide gels (10%) or Novex 4-12% gradient gels, and electroblotted to nitrocellulose membranes. Membranes were blocked with 5% skimmed milk (w/v) in 50 mM Tris/HCl (pH 7.5) 0.15 M NaCl, and 0.1% (v/v) Tween (TBST Buffer). Primary antibodies were used at a concentration of 1 µg/ml, diluted in 5% skimmed milk in TBST, and incubated overnight at 4° C. Detection of immune-complexes was performed using horseradish-peroxidase-conjugated secondary antibodies (Pierce) and an enhanced-chemiluminescence reagent (in-house).

JNK2 Kinase Assays

Wild type JNK2 or mutant JNK2[Cys116Ser] was activated in a reaction mixture containing 2 µM JNK2, 200 nM MKK4, 200 nM MKK7 in kinase assay buffer containing 0.1 mM ATP, and 10 mM magnesium chloride. After incubation at 30 min at 30° C. the reaction mixture was snap frozen in aliquots. Activity of JNK2 was assessed in a total reaction volume of 50 µl containing 200 nM activated wild type JNK or mutant JNK2[Cys116Ser], in kinase buffer containing 0.1 mM [γ-32P]ATP (about 500-1000 cpm/pmol), 10 mM magnesium chloride, and 2 µM ATF2 (residues 19-96) as a substrate. Reactions were terminated by adding 20 mM EDTA. 40 µl of the reaction mixture was applied to P81 phosphocellulose paper which was washed in 50 mM phosphoric acid and phosphorylated ATF2 peptide bound to p81 paper quantified by Cerenkov counting.

Results

The JNK family of kinases constitutes a central node in the stress-activated MAPK signaling pathway and may provide potential targets for future drugs to treat cancer, inflammatory diseases and neurological diseases. With the exception of a 9 L analogue (FIG. 1; Crocker et al., 2011), achieving pharmacological inhibition of JNK in animal models has to a large extent been hampered by the lack of potent and selective inhibitors with suitable pharmacokinetic properties. To address these limitations, irreversible JNK inhibitors are developed that covalently modify a conserved cysteine residue. The major advantages of this approach is that sustained target inhibition can be achieved with only transient exposure of the target to the inhibitor which reduces the need to achieve pharmacological properties that would allow for sustained drug levels in vivo (Singh et al., 2010). A further advantage is that potent inhibition is completely dependent on covalent modification and therefore mutation of the reactive cysteine residue creates a version of JNK that are insensitive to the compounds. These mutant forms of JNK can then be used to establish the JNK-dependency of any observed inhibitor induced phenotype which provides a powerful control for specificity.

Structure-based drug design was used to develop ATP-site directed covalent inhibitors of JNK kinases that could target a unique cysteine conserved in all the JNK kinases. Cysteine-directed covalent inhibitors possess a number of potential advantages relative to non-covalent inhibitors such as ability to control kinase selectivity using both non-covalent and covalent recognition of the kinase and the ability to exhibit prolonged pharmacodynamics despite competition with high endogenous intracellular ATP concentrations. Selective cysteine-directed covalent inhibitors have been developed for a number of kinases including Rsk (FMK) (Cohen et al., 2005; and Nguyen, 2008), FGFRs (FIIN-1) (Zhou et al., 2010), Mek (Schirmer et al., 2006), Nek2 (Henise et al., 2011), and other kinases possessing a cysteine immediately proceeding the "DFG-motif" (hypothemycin and analogs) as well as several undergoing clinical investigation as inhibitors of EGFR (HKI-272, BIBW2992, CI1033, and EKB569) and BTK (AVL-292, and PCI32765) (Singh et al., 2010). Despite these efforts, only four different cysteine positions have been targeted in the ATP-site and there are at least 180 kinases that possess a cysteine that could theoretically be targeted by suitably designed inhibitors (Zhang et al., 2009). Here, provided in the present invention include the structure-based design, detailed biochemical and cellular characterization, and crystal structure analysis of JNK3 modified by covalent inhibitors that can irreversibly modify a conserved cysteine residue in JNK.

Figure 2A:
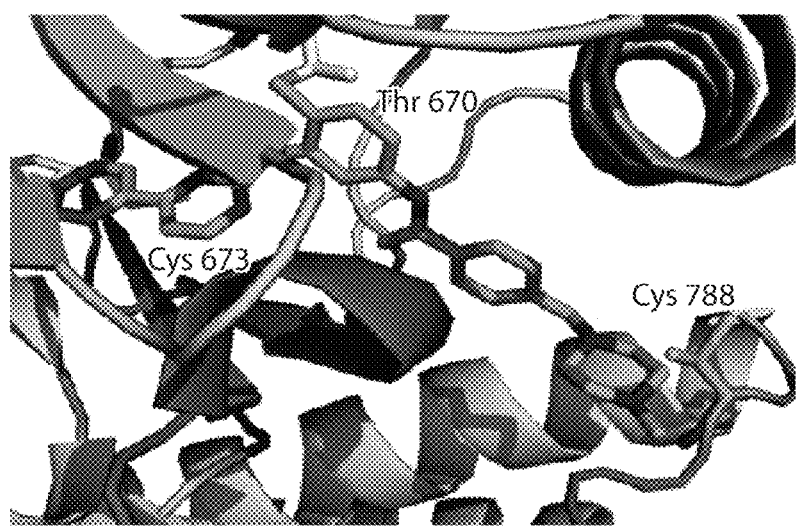
FIGS. 2A and 2B depict the crystal structure (PDB ID 1T46) of c-Kit (ribbons) complexed with imatinib (sticks) (FIG. 2A), and the crystal structure (PDB ID 1XBB) of Syk (ribbons) complexed with imatinib (sticks) (FIG. 2B).
Figure 2B:
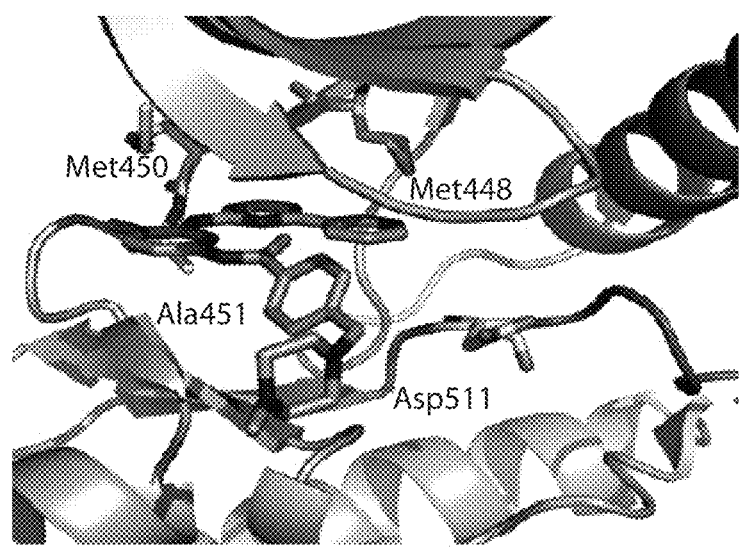
Figure 3:
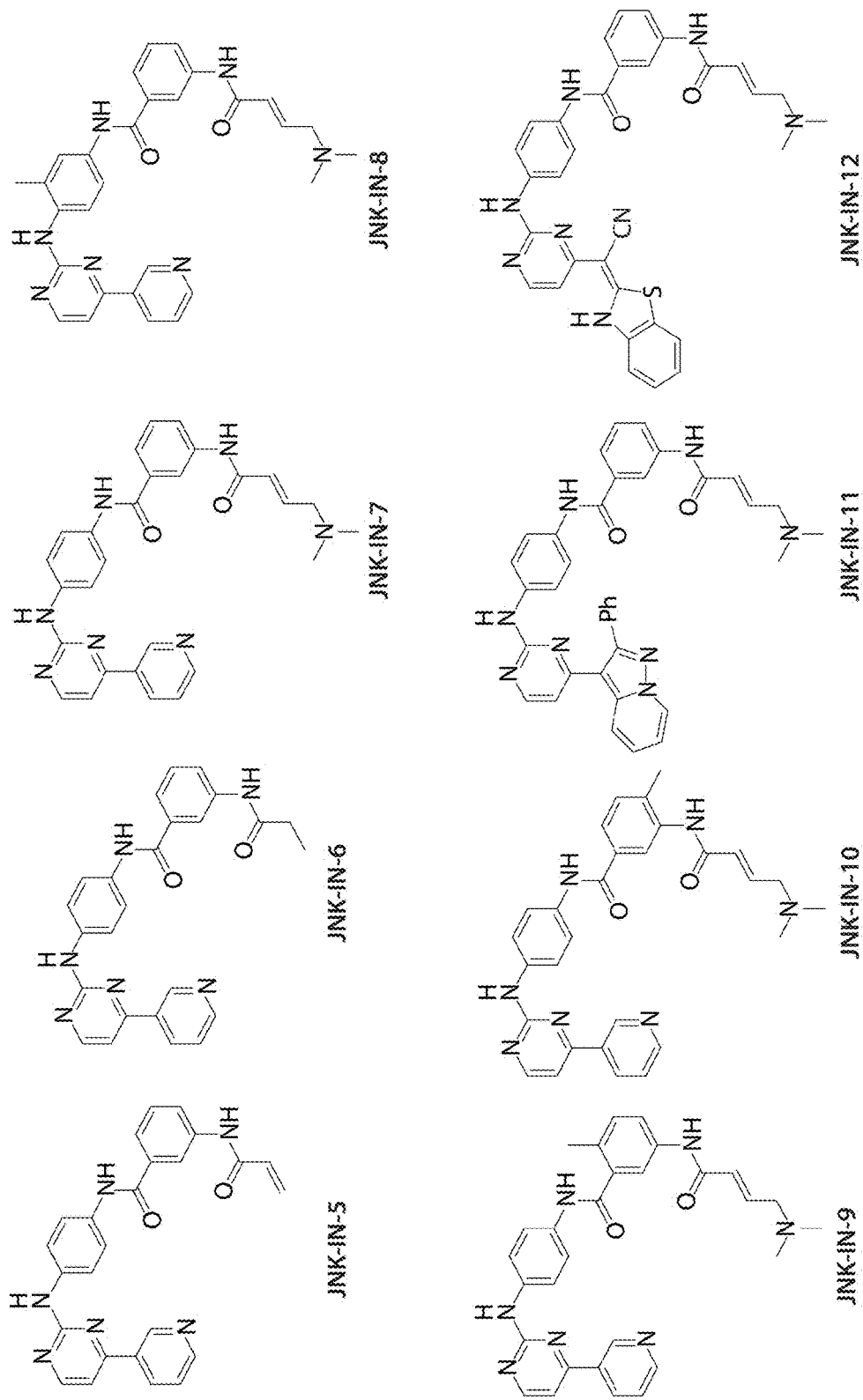
FIG. 3 shows the chemical structures of JNK inhibitors JNK-IN-5 to 12.

Most currently reported cysteine-directed covalent inhibitors are from the "type-1" (Liu et al., 2006) inhibitor class: they bind to the kinase in an "active" conformation with the activation loop in a conformation conducive to substrate binding. It is speculated whether "type-2" inhibitors which bind kinases in an "inactive" state with the activation loop in a conformation that blocks substrate from binding might also present a promising platform from which to design a new class of covalent inhibitors. Through an examination of kinases co-crystallized with type-2 inhibitors, it was noticed that both c-Kit (Leproult et al., 2011) and PDGFR possessed a cysteine immediately preceding the "DFG-motif" that marks the beginning of the activation loop and that might be exploited by a suitably designed type-2 inhibitor. It was decided to use the phenylaminopyrimidine core of imatinib as a scaffold for elaboration because this compound binds Abl, c-Kit and PDGFR in the type-2 conformation and because it possesses favorable drug properties. Measurement of the distance between methylpiperidine moiety of imatinib and Cys788 in c-Kit (PDB: 1T46) (Mol et al., 2004) (FIG. 2A) inspired the effort to replace the methylpiperzine moiety with an electrophilic acrylamide bearing a water-solubility enhancing dimethylamino group to generate JNK-IN-7 (FIG. 3). It was confirmed that these binding results translated into single digit micromolar $IC_{50}$ for inhibition of JNK kinase activity using the "Z"-lyte assay format (Table 2). This result was unanticipated because despite the large number of JNK inhibitors reported in the literature, there are no reports of "type-2" JNK inhibitors, and it was therefore not anticipated that imatinib could bind to JNK in an extended "type-2" conformation. However, there are a number of structurally related phenylaminopyrimidines such as 9 L (Kamenecka et al., 2010) and 30 (Alam et al., 2007) (FIG. 1) that bind to JNK in a type-1 conformation, and it was speculated that perhaps JNK-IN-7 was binding in an analogous fashion to JNK. In addition, it was hypothesized that imatinib might exploit an alternative "type-1" conformation when binding to JNK where the inhibitor assumes an U-shaped configuration as has been observed in a Syk-imatinib co-structure (PDB: 1XBB) (Atwell et al., 2004), (FIG. 2B). If JNK-IN-7 were to recognize JNK analogously to how imatinib binds to Syk, the acrylamide moiety of JNK-IN-7 would be placed within covalent bond forming distance of Cys116 of JNK1 and JNK2 and Cys154 of JNK3. To test these hypotheses, a number of analogs of JNK-IN-7 were prepared (FIG. 3). Shown in Table 2 are the JNK-inhibition $IC_{50}$ values and c-Jun phosphorylation-inhibition (in Hela and A375 cells) values of these compounds.

TABLE 2

Biochemical $IC_{50}$ for JNK inhibitors against JNK1, JNK2, and JNK3 and cellular $EC_{50}$ for inhibition of c-Jun phosphorylation in Hela and A375 cells

| Compound | $IC_{50}$ (nM) | | | p-c-Jun $EC_{50}$ (nM) | |
|---|---|---|---|---|---|
| | JNK1 | JNK2 | JNK3 | Hela | A375 |
| JNK-IN-5 | 2.11 | 1.93 | 0.96 | 118 | 32 |
| JNK-IN-6 | | | 148 | 6760 | 1905 |
| JNK-IN-7 | 1.54 | 1.99 | 0.75 | 130 | 244 |
| JNK-IN-8 | 4.67 | 18.7 | 0.98 | 486 | 338 |
| JNK-IN-9 | | | 0.5 | 104 | 117 |
| JNK-IN-10 | | | 0.5 | 173 | 141 |
| JNK-IN-11 | 1.34 | 0.5 | 0.5 | 48 | 8.6 |
| JNK-IN-12 | 13 | 11.3 | 11 | 605 | 134 |
| 5A | 10000* | | 200* | >10000 | >10000 |
| SP-600125 | | 110* | 190* | 7450 | 1985 |
| AS601245 | 150* | 220* | 70* | 2025 | 2400 |

*Literature values.

Figure 4:
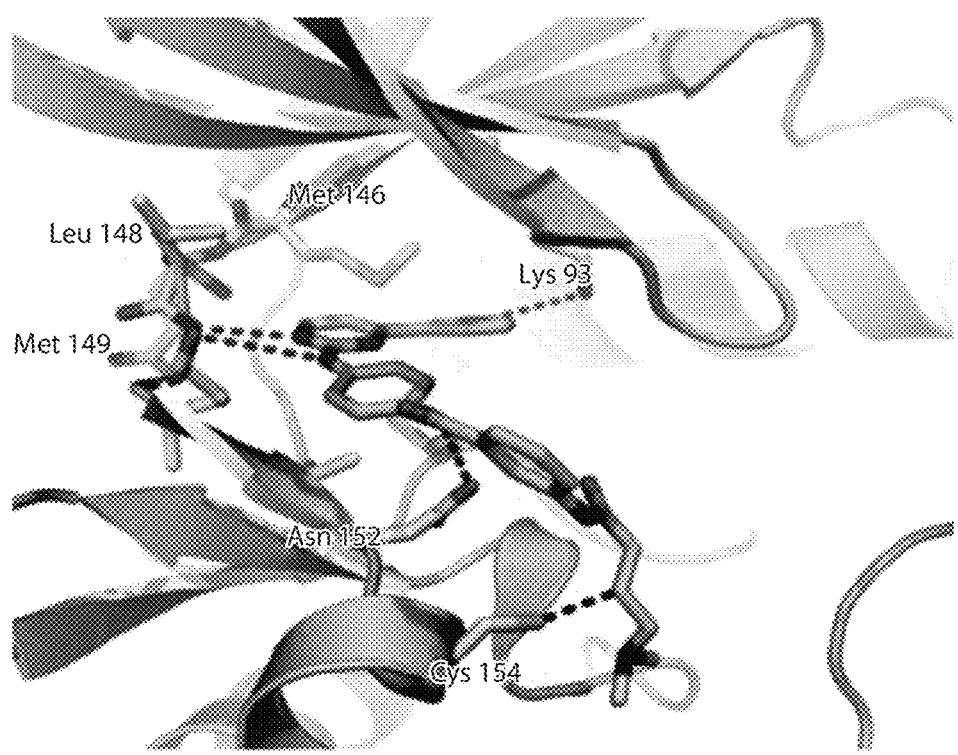
FIG. 4 depicts a docking result of JNK-IN-7 (sticks) with JNK3 (ribbons). Potential hydrogen-bonding interactions are indicated with dashed lines.
Figure 5A:
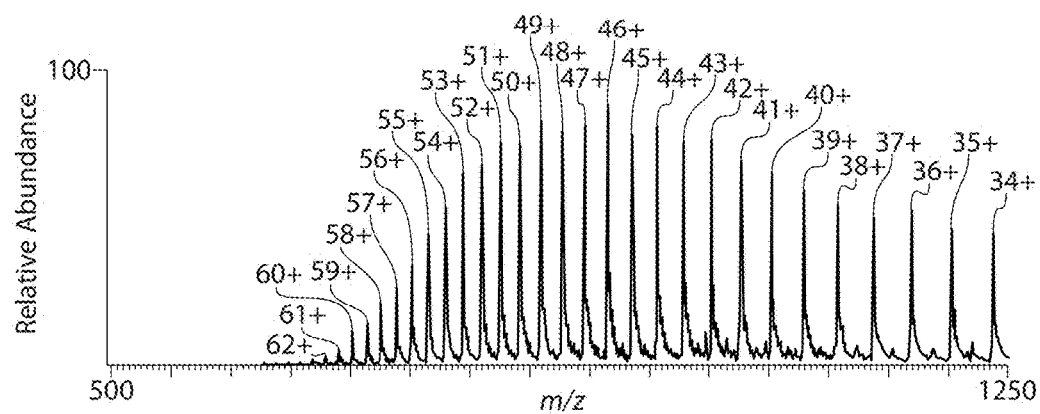
FIGS. 5A to 5C show the mass spectra obtained from analysis of untreated (FIG. 5A) or JNK-IN-7 treated (FIG. 5B) recombinant JNK3 kinase domain, and the HCD MS/MS spectrum of the peptide LMDANLC*QVIQME (JNK residues 148-160; C* indicates a labeled cysteine residue) (FIG. 5C). Identification of ions of type b and y are indicated with lines above and below the sequence, respectively.
Figure 5B:
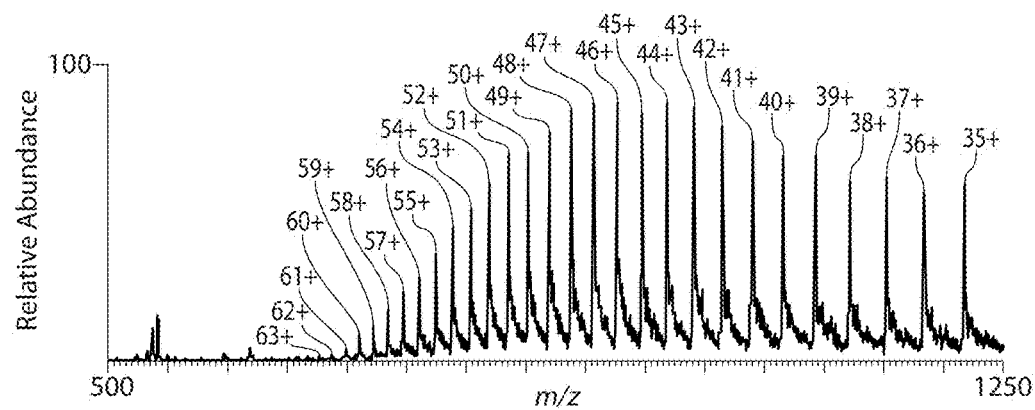
Figure 5C:
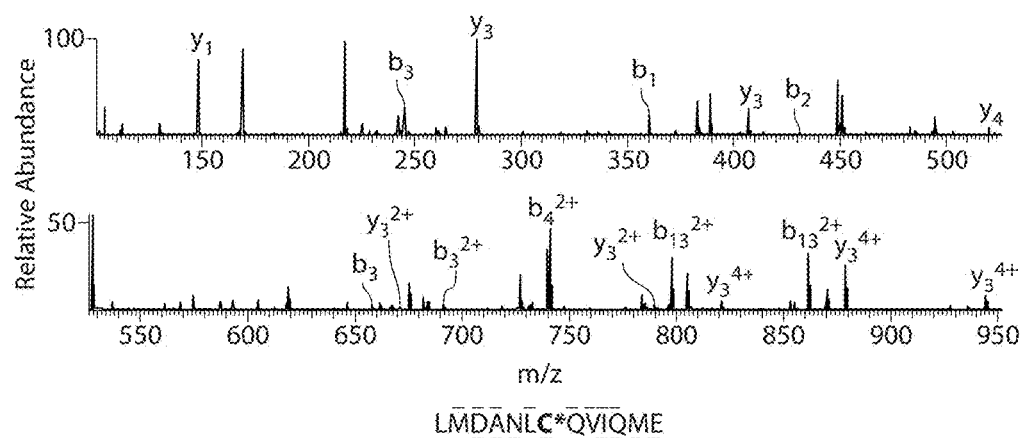

Dramatic improvement in $IC_{50}$ was observed when a 1,4-dianiline and 1,3-benzamide were incorporated as the linker segment between the pyrimidine and the acrylamide moiety as exemplified by JNK-IN-5 and JNK-IN-7. Molecular docking of JNK-IN-7 with JNK3 suggested that this significant improvement in potency was likely due to a more optimal placement of the acrylamide relative to Cys 154 which may result in more efficient covalent bond formation (FIG. 4). Incubation of JNK-IN-7 and JNK3 followed by electrospray mass spectrometry revealed the addition of a single molecule of inhibitor to the protein and labeling of Cys 154 (FIGS. 5A to 5C).

In order to investigate the importance of covalent bond formation to the potency of this class of inhibitor, JNK-IN-6 was prepared with an unreactive and approximately isosteric propyl amide group replacing the acrylamide of JNK-IN-5. As expected, this compound exhibited an almost 100-fold less potent biochemical $IC_{50}$ on JNK1, 2, and 3 (Table 2). A small collection of analogs of JNK-IN-7 bearing modifications was prepared that was expected to influence the selectivity relative to other kinases. Also prepared were three methylated analogs JNK-IN-8, JNK-IN-9, and JNK-IN-10, all of which retained the ability to potently inhibit JNK biochemical activity. The pyridine ring of JNK-IN-7 was replaced with substituents that had previously been reported in other JNK inhibitors including a bulky group 2-phenylpyrazolo[1,5-a]pyridine (Alam et al., 2007) and benzothiazol-2-yl acetonitrile (Gaillard et al., 2005). The influence of these changes on kinase selectivity is discussed in detail below.

Figure 6:
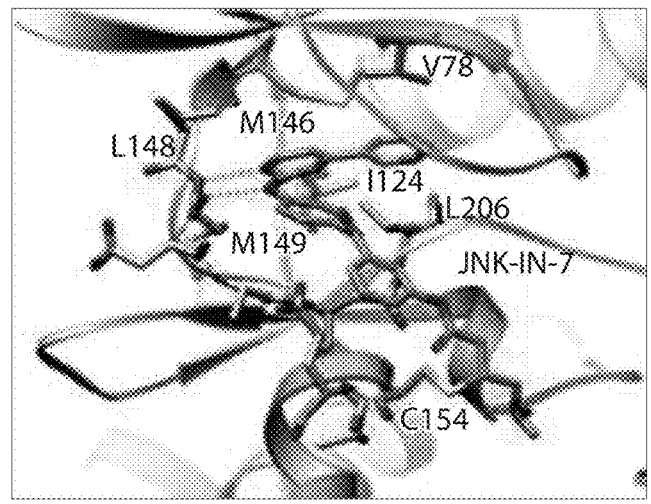
FIG. 6 depicts the crystal structure of JNK3 residues 39-402 modified at Cys-154 by JNK-IN-7. The covalent inhibitors and the key residues of JNK3 that are involved in hydrophobic and hydrogen bonding interactions with the covalent inhibitors are labeled and are shown in stick models. The hydrogen bonds between the kinase "hinge" residue Met-149 and the aminopyrimidine-motif of the covalent inhibitors are represented as dotted lines.
Figure 7:
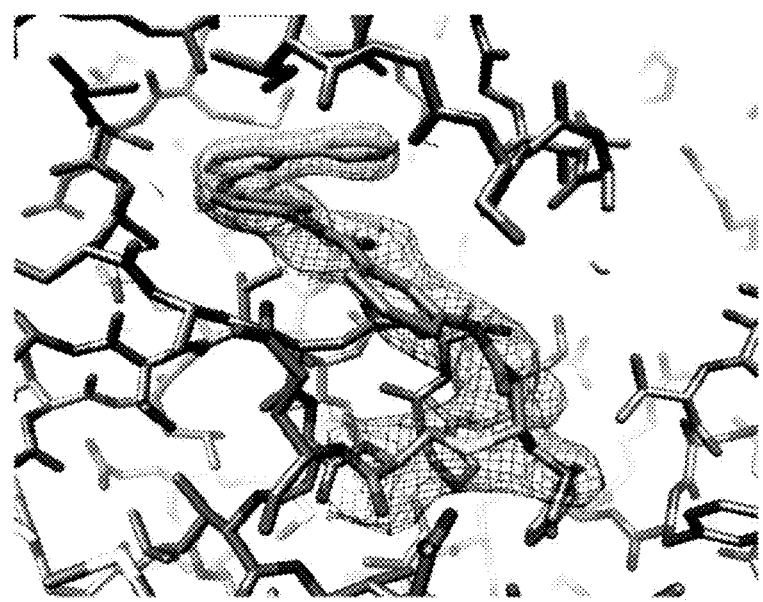
FIG. 7 is a 2Fo-Fc electron density map corresponding to the covalent inhibitor JNK-IN-7 (sticks). The map is contoured at 1σ and shows unambiguous electron densities of JNK-IN-7.

In order to validate the molecular modeling results and to provide a basis for further structure-based optimization efforts, JNK-IN-7 was co-crystallized with JNK3 de novo using the same JNK3 protein reported previously for 9 L (Kamenecka et al., 2010) (FIG. 6 and Table 3). The resulting 2.60 Å and 2.97 Å crystal structures were in good agreement with the docking model described above. Continuous electron density was visible to Cys154 consistent with covalent bond formation (FIG. 7). The inhibitor formed three hydrogen bonds with JNK3, two from the aminopyrimidine motif to the kinase hinge residues Leu148 and Met149 and a third from the amide NH to Asn152. This third hydrogen bond may be important for positioning the terminal ring and orienting the acrylamide moiety proximal to Cys 154 thereby facilitating covalent bond formation. The overall kinase conformation of JNK is remarkably similar to the reported 9 L crystal structure (average RSMD 2.40 Å) (Kamenecka et al., 2010) with the kinase assuming an active conformation. This demonstrates that the covalent inhibitor does not appear to trap an unusual conformation of the kinase. There is a small hydrophobic pocket adjacent to the aniline ortho position which may explain why there was tolerance for the "flag" methyl group in JNK-IN-8 which provided a crucial selectivity determinant. The pyridine moiety binds in a hydrophobic pocket and did not optimally fill this space which was consistent with the potency improvements realized by replacement with the larger moieties present in JNK-IN-11 and JNK-IN-12. Modification of the inhibitor in this region would clearly afford significant opportunities for modulating both inhibitor potency and selectivity.

TABLE 3

Data collection and refinement statistics for a co-crystal structure between JNK-IN-7 and the kinase domain of JNK3 (residues 39-402)

| | Space group | $P2_12_12$ |
|---|---|---|
| | Cell dimensions (Å) | a = 109.49, b = 156.26, c = 43.88, α = β = γ = 90 |
| | Asymmetric unit | 2 Molecules |
| | Resolution (Å) [1] | 156.26-2.97 (3.13-2.97) |
| | Unique reflections | 16,326 |
| | I/σI [1] | 13.2 (3.8) |
| | Completeness (%) [1] | 100.0 (100.0) |
| | $R_{sym}$ (I) [1, 2] | 0.13 (0.49) |
| Refinement | Resolution (Å) [1] | 27.62-2.97 (3.17-2.97) |
| | Number of reflections | 16,238 |
| | $R_{free}$ [1, 3] | 27.13 (35.33) |
| | $R_{cryst}$ [1, 4] | 20.01 (21.34) |
| R.m.s. deviation | Bond length (Å) | 0.010 |
| | Bond angle (°) | 1.18 |
| | B-factor, average (Å$^2$) | 46.15 |
| Number of atoms | Protein | 5536 |
| | Water | 220 |
| | Ligand (as modified cysteine) | 86 |

[1] Parentheses refer to statics for the highest resolution shell.

[2] $R_{sym} = \sum_{hkl}\sum_i |I_i(hkl) - \overline{I(hkl)}| / \sum_{hkl}\sum_i I_i(hkl)$

[3] $R_{free}$ is calculated with removal of 5.1% and 6.2% of the data for ZG-10 and THZ-2-118-1, respectively, as the test sets at the beginning of refinements.

[4] $R_{cryst} = \sum_{hkl} ||F_{obs}(hkl)| - |F_{calc}(hkl)|| / \sum_{hkl} |F_{obs}(hkl)|$ In parallel with biochemical evaluation, the ability of the compounds to inhibit JNK activity in cells was investigated using two independent assays formats. This is a critical issue because there are several reported JNK inhibitors with nanomolar biochemical potency that translate into micromolar cellular inhibitors. The most well characterized direct phosphorylation substrate of JNK is the transcription factor c-Jun. The first assay format is a high-throughput (HTS) compatible cellular assay capable of measuring changes in phosphorylation of c-Jun using the measurement of time resolved fluorescence resonance energy transfer (TR-FRET) between a stably expressed GFP-c-Jun (1-79) fusion protein and a terbium labeled anti pSer73 c-Jun antibody as readout (Robers et al., 2008; Carlson et al., 2009; and Stebbins et al., 2008). The second assay format consisted of treating serum starved A375 cells with test compounds followed by stimulation of the JNK kinase pathway with anisomycin and monitoring c-Jun phosphorylation by confocal microscopy with an anti-phospho Ser73 antibody (Millard et al., 2011; and Hendriks et al., 2010). With the exception of a few compounds, both assay formats provided a similar rank-order of $IC_{50}$'s for this compound series (Table 2). In agreement with the biochemical assays, JNK-IN-5 also provided the break-through in cellular potency and was capable of inhibiting of c-Jun phosphorylation with an $IC_{50}$ of about 100 nM in HeLa cells and about 30 nM in A375 cells. Introduction of the dimethyl group to yield JNK-IN-7 resulted in a 2-3-fold loss in potency for cellular JNK inhibition which was not predicted based upon the enzymatic assay. Introduction of methyl groups at the meta-position of the dianiline ring or to the meta and ortho positions of the benzamide resulted in compounds with cellular potency in the hundreds of nanomolar range. JNK-IN-11, the most potent cellular inhibitor of JNK activity in this series, incorporated the phenylpyrazoleo[1,5-a]pyridine motif and possessed an $IC_{50}$ of about 30 nM and about 10 nM in HeLa and A375 cells respectively. JNK-IN-6, the compound incapable of covalent bond formation, possessed an $IC_{50}$ 50-fold higher than its covalent analog JNK-IN-5 again underscoring the requirement for the acrylamide moiety to achieve potent cellular inhibition. In order to provide a direct comparison with published JNK inhibitors, SP600125, 5A, and AS601245 (FIG. 1) were tested in parallel in both assay formats. Surprisingly all these compounds exhibited IC$_{50}$'s in the micromolar range which suggests that covalent inhibition may be required to observe potent inhibition under the conditions investigated.

Figure 8:
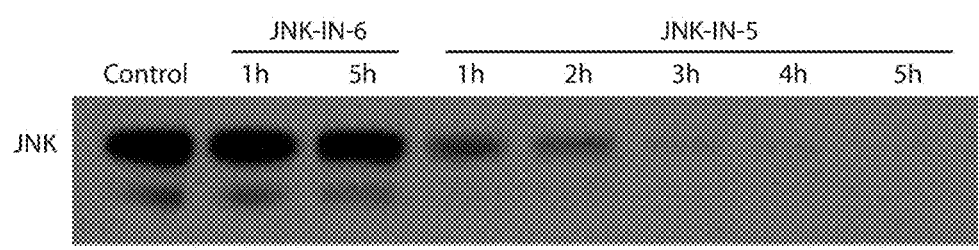
FIG. 8 shows the kinetics of labeling of JNK in JNK-IN-5, an irreversible JNK inhibitor, compared with JNK-IN-6, a reversible inhibitor. A375 cells were incubated with inhibitors for the indicated amount of time after which cell lysates were prepared and labeled with ATP-biotin. Biotinylated proteins were pulled down with streptavidin beads and material bound to the beads was eluted and separate by SDS-PAGE followed by Western blot analysis for JNK. Complete protection of JNK was achieved following a three-hour incubation with JNK-IN-5 while no protection of JNK labeling was achieved following incubation with JNK-IN-6.
Figure 14A:
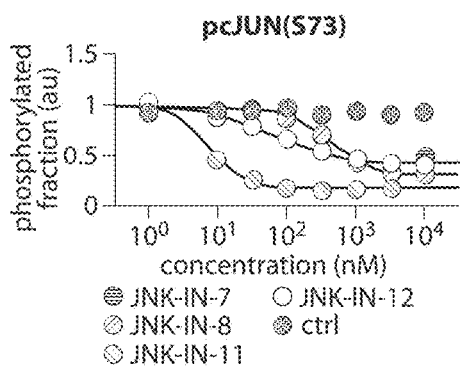
FIGS. 14A to 14H illustrate the evaluation of the cellular selectivity for the JNK inhibitors as monitored through inhibition of phosphorylation of key nodes on multiple signal transduction pathways. A375 cells were stimulated with anisomycin (FIGS. 14A and 14C to 14F), IGF-1 (FIG. 14B), IL-6 (FIG. 14G), and TNF-α (FIG. 14H) for sixty minutes. The output of multiple signaling pathways was measured using high throughput microscopy at multiple concentrations of four JNK inhibitors and a control compound specific to each pathway DMSO (FIG. 14A), MK2206 (allosteric Akt inhibitor, Haoyuan Chemexpress Co., Limited. Hirai, et al., 2010) (FIG. 14B), PD0325901 (allosteric Mek inhibitor, Haoyuan Chemexpress Co., Limited. Barrett, et al., 2008) (FIGS. 14C and 14D), SB239063 (ATP-competitive p38 inhibitor, Haoyuan Chemexpress Co., Limited. Underwood et al., 2000) (FIGS. 14E and 14F), KIN001-040 (ATP-competitive JAK1,2,3 inhibitor, Haoyuan Chemexpress Co., Limited. Thompson et al., 2002) (FIG. 14G), and KIN001-208 (IKK inhibitor VIII, Haoyuan Chemexpress Co., Limited., Murata, et al., 2004) (FIG. 14H).
Figure 14B:
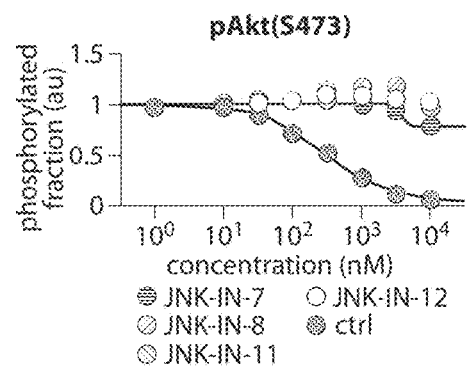
Figure 14C:
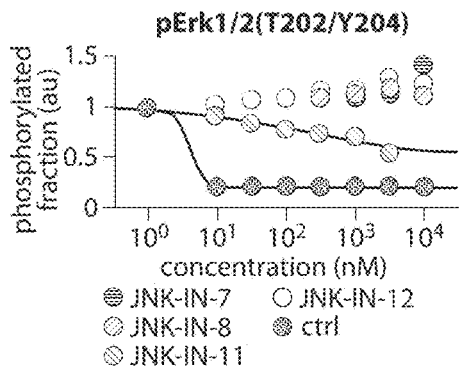
Figure 14D:
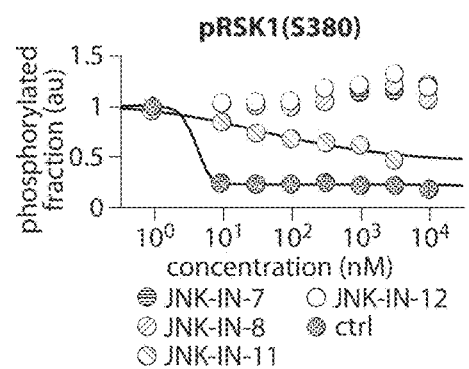
Figure 14E:
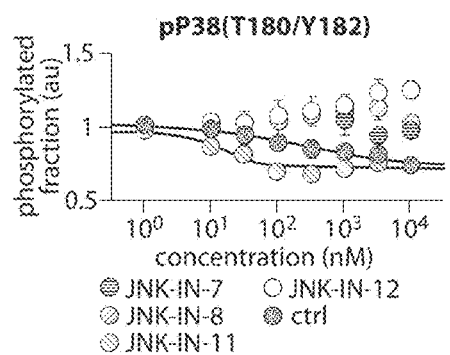
Figure 14F:
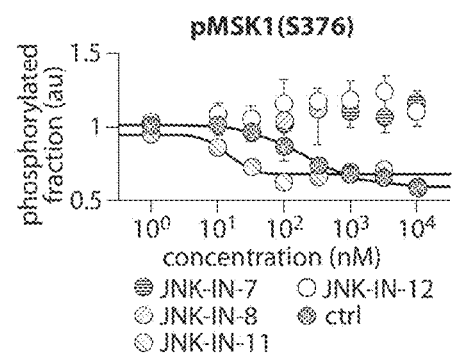
Figure 14G:
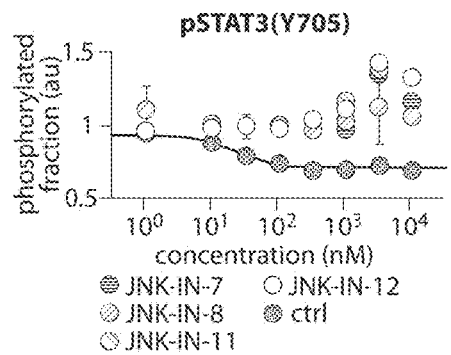
Figure 14H:
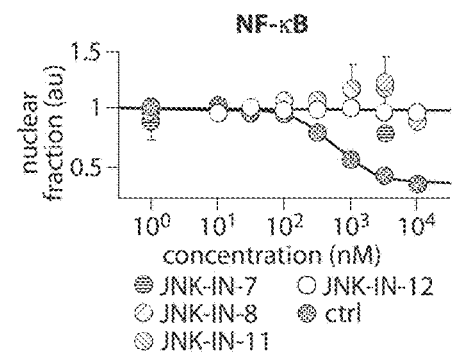

In order to evaluate the kinetics with which JNK-IN-5 could covalently modify JNK in cells, a pulse-chase assay was developed. A375 cells were treated with JNK-IN-5 for 1, 2, 3, 4, and 5 hours to allow for cell penetration and labeling of intracellular targets. Cell lysates were then prepared and labeled with ATP-biotin which contains a reactive acyl phosphate anhydride that reacts non-specifically with the catalytic lysine of kinases including JNK (Patricelli et al., 2007). Streptavidin affinity chromatography is then used to isolate all biotinylated proteins and JNK protein is detected following SDS-PAGE and Western blotting (FIG. 8). The amount of time that JNK-IN-5 must be incubated with cells to fully protect JNK from subsequent labeling by ATP-biotin provides a measure of the rate of intracellular covalent bond formation. It took approximately three hours for JNK-IN-5 to modify JNK to an undetectable level by this assay format. As a negative control, the non-covalent inhibitor JNK-IN-6 was subject to the same protocol and was demonstrated to be incapable of protecting JNK from labeling by ATP-biotin.

The kinase selectivity of several key compounds was first evaluated using a chemical proteomic approach named KiNativ which detects 260 kinases in A375 cells (ActivX Biosciences). To probe the intracellular targets of the compounds, A375 cells were incubated with the inhibitors and then looked for protection of labeling by an ATP-biotin probe that non-specifically labels conserved lysines on kinases and other nucleotide-dependent enzymes. This provided an important advantage relative to the in vitro kinase selectivity profiling because in vitro the short incubation times and presence of reactive thiols in the buffers can potentially cause false negatives for acrylamide-modified kinase inhibitors. Treatment of A375 cells with 1 µM of four of the irreversible JNK inhibitors resulted in the identification of JNK as the most potent and common target (FIG. 9). In contrast, the reversible inhibitor JNK-IN-6 did not inhibit JNK activity following the same live cell treatment. In addition to JNK1, JNK2, and JNK3, JNK-IN-7 also binds to IRAK1, PIP5K3, PI3KC3, and PIP4K2C. Since cysteine-directed covalent kinase inhibitors will sometimes cross-react with kinases that contain an equivalently placed cysteine, a sequence alignment was performed to identify all kinases which have a cysteine near JNK1 Cys116 (FIG. 10). Amongst the 40 kinases revealed through this analysis, only IRAK1 exhibited a detectable binding affinity to JNK-IN-7 based upon KinomeScan profiling. Since IRAK1 crystal structure is not available, the IRAK4 crystal structure (PDB: 3CGF) was examined which demonstrates that Cys276 is potentially located in a similar location relative to the reactive Cys154 of JNK3. Therefore covalent modification of IRAK1 by JNK-IN-7 is a possibility and indeed biochemical kinase assay afforded an IC$_{50}$ of about 10 nM against IRAK1. To evaluate whether IRAK1 is a bona fide intracellular target of JNK-IN-7, it was evaluated whether the compound could inhibit the E3-ligase activity of pellino, which provides an indirect measure of inhibition of IRAK1 kinase activity in cells. JNK-IN-7 inhibited Interleukin 1-stimulated Pellino 1 E3 ligase activity but required a relatively high concentration of 10 µM to achieve complete inhibition (Goh et al., 2011). Sequence alignments do not reveal obvious cysteine residues that could be covalently modified in PIP3K3C, PIP4K2C, and PIP5K3, but further work will be required to evaluate whether these are indeed functional targets of JNK-IN-7. Although JNK-IN-7 is a relatively selective JNK inhibitor in cells, introduction of the "flag" methyl to yield JNK-IN-8 resulted in a dramatic improvement in selectivity and eliminated binding to IRAK1, PIP3K3C, PIP4K2C, and PIP5K3. The dramatic selectivity improvement that results from introduction of this flag-methyl group has been previously reported for imatinib (Zimmermann et al., 1996). Replacement of the pyridine ring with bulkier substituents as exhibited by JNK-IN-11 resulted in a broadening of the selectivity profile as well as further enhancing the potency for inhibition of c-Jun phosphorylation in cells. JNK-IN-11 binds potently to JNKs, p38, PIP5K3, ZAK, ZC2, PIP5K3, and CK1 demonstrating that this compound class might be a valuable lead compound to develop selective inhibitors of these potential alternative targets. JNK-IN-12, bearing a benzothiazol-2-yl acetonitrile moiety, displayed a further broadened profile highlighting the value of KiNativ profiling in evaluating the full spectrum of intracellular targets.

To complement the KiNativ profiling, the in vitro kinase selectivity of several key compounds was comprehensively evaluated by two complementary approaches: a kinase-binding assays against a panel of 442 distinct kinases using the KINOMEscan methodology (DiscoverX) and a standard radioactivity-based enzymatic assays against a panel of 124 kinases (The National Centre for Protein Kinase Profiling in Dundee). Based upon the KINOMEscan results, JNK-IN-7, JNK-IN-8, and JNK-IN-12 possessed highly selective S scores (defined as the ratio number of kinases inhibited more than 90 percent at screening concentration of 1 µM) of 0.085, 0.031, and 0.025, respectively (FIG. 11). For example, JNK-IN-7 exhibited binding inhibition of 95% or more to approximately 14 kinases at the concentration of 1.0 µM. It was attempted to confirm all these potent binding targets using either an enzymatic kinase assay or through the measurement of a dissociation constant to the kinase in question. JNK-IN-7 was confirmed to have a K$_d$ or IC$_{50}$ of 100 nM or less against eight additional kinases (FIG. 12). JNK-IN-7 was next tested for its ability to inhibit the enzymatic activity of a panel of 121 kinases at a concentration of 1.0 µM. This analysis revealed 12 kinases that were inhibited more than 80% relative to the DMSO control and follow-up IC$_{50}$ determination revealed sub-200 nM IC$_{50}$ against of IRAK1, ERK8, and NUAK1 (FIG. 13). JNK-IN-12 bearing a benzothiazol-2-yl acetonitrile in place of the pyridine conferred an improved selectivity relative to JNK-IN-7. The KINOMEscan score for JNK-IN-12 was even smaller than JNK-IN-8, and follow-up enzymatic assays on the potent targets revealed IC$_{50}$'s of 37.6, 57.1, and 89.9 nM for IRAK1, HIPK4, and AKT2, respectively (FIG. 12). This high in vitro selectivity however differed markedly from the large number of targets detected by KiNativ. The introduction of phenylpyrazolo[1,5-a]pyridine to JNK-IN-11 resulted in a significant decrease in kinase selectivity as assessed by KINOMEscan (Score=0.125) and more than 30 additional kinases including different mutants of EGFR, c-Kit, DDR1, and Gsk3b (FIGS. 12 and 13). Consistent with the KiNativ profiling, JNK-IN-8 also exhibited exceptional selectivity based upon KinomeScan and enzymatic profiling. Further biochemical and binding assays failed to identify any target with an IC$_{50}$ or K$_d$ of less than 1.0 µM. Cumulatively these combined profiling technologies demonstrate that JNK-IN-8 is a remarkably selective covalent JNK inhibitor and is appropriate for interrogating JNK-dependent biological phenomena.

The profiling above provides an assessment of direct engagement with potential targets but does not address further perturbations that maybe induced as a consequence of these binding events. A confocal microscopy-based assay was therefore established using phospho-specific antibodies identical to that used to measure c-Jun phosphorylation, which would report on inhibition phosphorylation of sentinel nodes in other signaling pathways including Erk, p38, JNK, Akt, Stat, NFkB, and Rsk by high throughput microscopy (Table 4 and FIGS. 14A to 14H) (Millard, et al., 2011). JNK-IN-7, JNK-IN-8, and JNK-IN-12 exhibited only onpathway activity as monitored by inhibition of c-Jun phosphorylation. JNK-IN-11 was the only compound found to have off-pathway activity as exemplified by its ability to potently block phosphorylation of ERK, RSK1, MSK1, and p38 consistent with the substantially broadened kinase selectivity profile of this compound. Interestingly, JNK-IN-11 also provided the most complete inhibition of c-Jun phosphorylation which is likely due to its ability to inhibit additional pathways that ultimately signal to phospho-c-Jun.

TABLE 4

Cellular EC$_{50}$ values in nanomolar of four JNK inhibitors for inhibition of several signaling pathways as monitored by measuring inhibition of phosphorylation of Akt, Erk, Msk1, p38, RSK, STAT3, and c-Jun or NF-kB nuclear translocation using high-throughput microscopy

|  | NF-kB | pAkt | pErk | pMSK1 | pP38 | pRSK | pSTAT3 | pc-Jun |
|---|---|---|---|---|---|---|---|---|
| JNK-IN-7 | >10000 | >10000 | >10000 | >10000 | >10000 | >10000 | >10000 | 285 |
| JNK-IN-8 | >10000 | >10000 | >10000 | >10000 | >10000 | >10000 | >10000 | 425 |
| JNK-IN-11 | >10000 | >10000 | 19 | 14 | 15 | 20 | >10000 | <10 |
| JNK-IN-12 | >10000 | >10000 | >10000 | >10000 | >10000 | >10000 | >10000 | 125 |

Figure 15A:
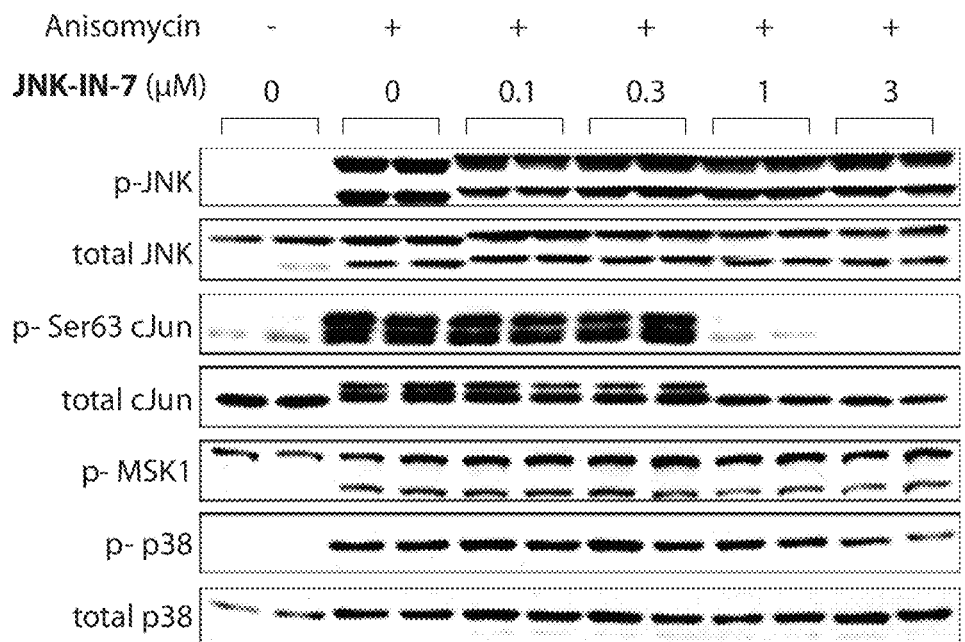
FIGS. 15A to 15C show results of a Western blot analysis of inhibition of JNK, c-Jun, MSK1, and p38 for JNK-IN-7
Figure 15B:
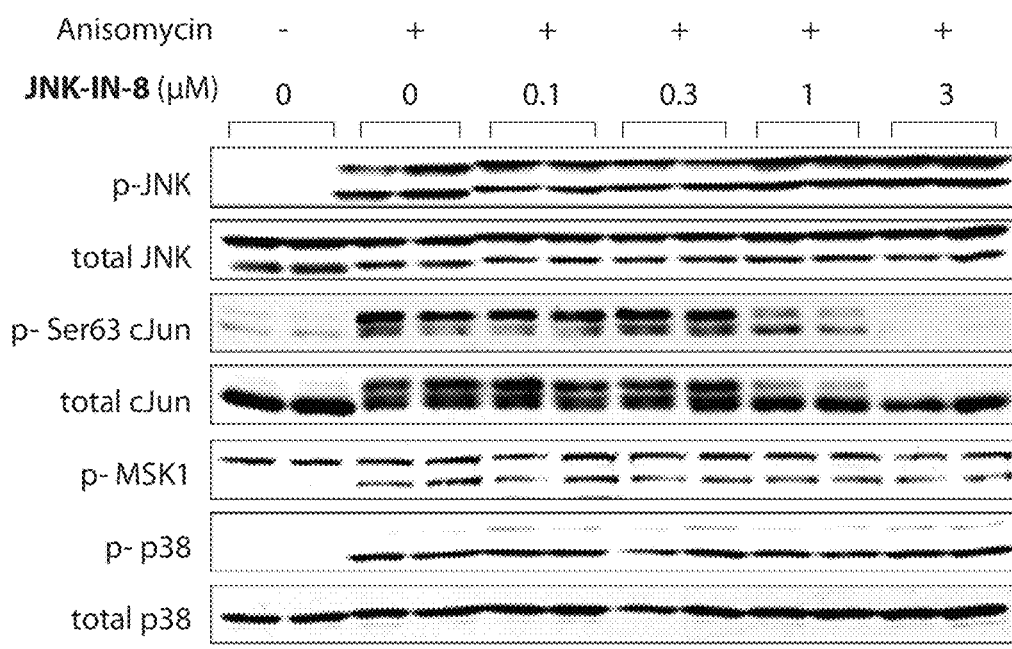
Figure 15C:
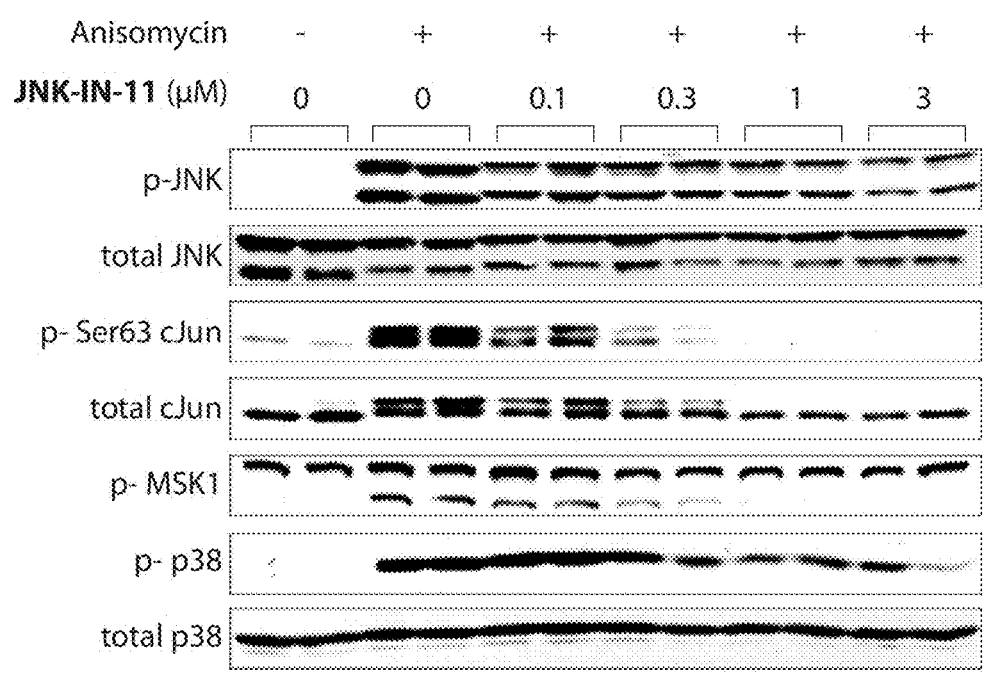
Figure 16A:
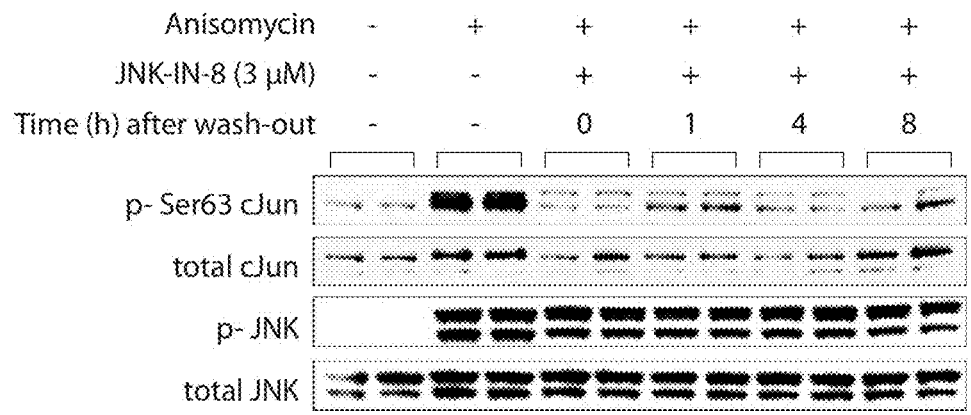
FIGS. 16A and 16B depict Western blot results. Inhibition of phosphorylation of c-Jun is not recovered following "washout" of JNK-IN-8. HEK293-ILR1 cells were treated with JNK-IN-8 for three hours, followed by extensive washout of inhibitor and stimulated with anisomycin for 1 h after the indicated hours (FIG. 16A). Cell lysates were prepared, resolved by SDS-PAGE, and p-c-Jun (Ser63) and p-JNK were monitored by Western blot.
Figure 16B:
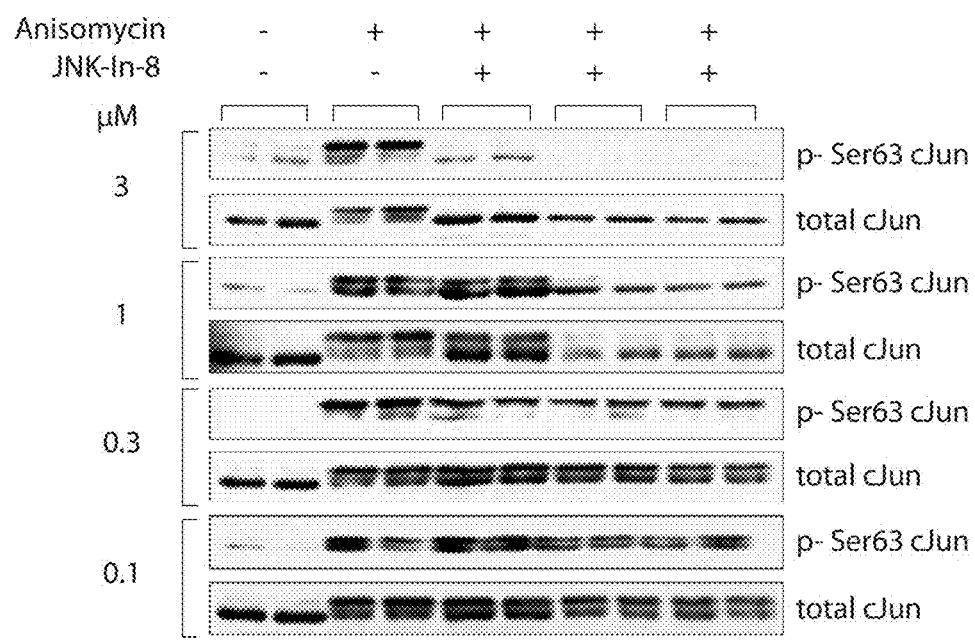

To further corroborate these results, what was also examined was the ability of the compounds to inhibit phosphorylation of JNK, c-Jun, MSK1, and p38 in HEK293-ILR1 cells following stimulation by anisomycin by traditional Western blotting (FIGS. 15A to 15C). All compounds, except the JNK-IN-11, were capable of inhibiting c-Jun phosphorylation without inhibiting MSK1 and p38 phosphorylation. The inhibition was not reversed by removal of JNK-IN-8 from cell culture medium (FIGS. 16A and 16B). The results are in good agreement with the relative potencies established using the immunostaining and kinase profiling approaches. Interestingly, a distinct reduction in electrophoretic mobility of JNK protein is apparent upon incubation with the inhibitors presumably as a consequence of covalent modification by the inhibitors.

Figure 17:
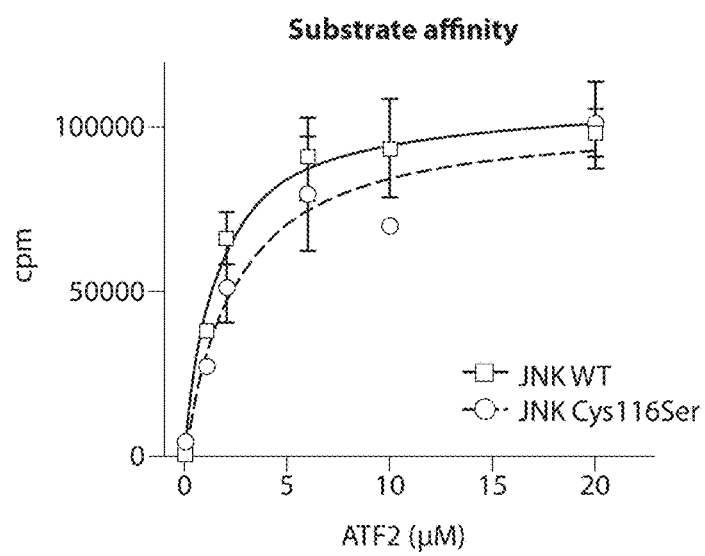
FIG. 17 shows curves for the determination of $K_m$ for ATF2 for JNK WT and JNK Cys116Ser.
Figure 18:
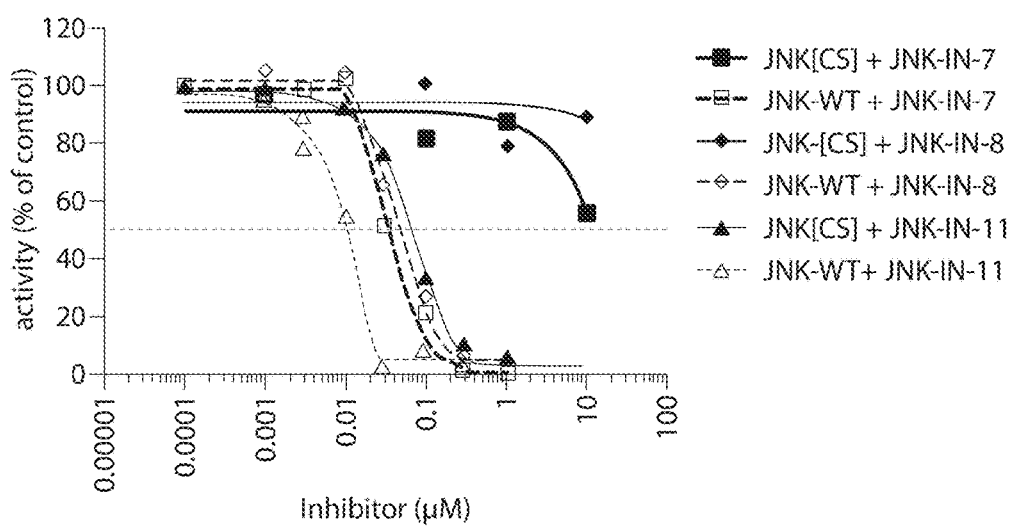
FIG. 18 shows that mutation of the conserved Cys116 to Ser increases the $IC_{50}$ for inhibition of JNK2 by over 100-fold for JNK-IN-7 and JNK-IN-8 but only by approximately 10-fold for JNK-IN-11.

In order to investigate the extent to which the observed cellular effects resulted from direct covalent modification of JNK1, JNK2, or JNK3 cysteine residues versus other potential intracellular targets, mutagenesis was used to engineer Cys to Ser mutant for JNK2. Cys116Ser JNK2 JNK2 was purified, and it was confirmed that activated wild type JNK2 and mutant JNK2[Cys116Ser] displayed similar K$_m$ and V$_{max}$ towards the ATF2 peptide substrate in vitro (FIG. 17). In the presence of inhibitors, the mutation resulted in a 10-fold increase in IC$_{50}$ for inhibition of JNK activity by JNK-IN-11, and remarkably, at least a 100-fold increase in IC$_{50}$ for JNK-IN-7 and JNK-IN-8 (FIG. 18). Overall, the results of the present invention demonstrate that JNK-IN-8 is an efficient, specific, and irreversible intracellular inhibitor of JNK kinase activity by a mechanism that depends on a conserved Cys in the ATP-binding motif.

Comparative Data

Table 5 demonstrates the dramatic effects changing the orientation of the C and D ring have on JNK activity. For example, "para-meta" compounds of the present invention, i.e., compounds comprising para NH groups on phenyl Ring C and meta NH(C=O) groups on phenyl Ring D, are surprisingly more active than compounds having the opposite structural configuration, i.e., "meta-para" compounds comprising meta-NH substituents on phenyl Ring C and para NH(C=O) groups on phenyl Ring D.

TABLE 5

IC$_{50}$ values in micromolars of compounds for certain kinase targets

| Structure | JNK1 | JNK2 | JNK3 | E50/A375 | CDK7 |
|---|---|---|---|---|---|
|  |  |  |  | >10000 |  |

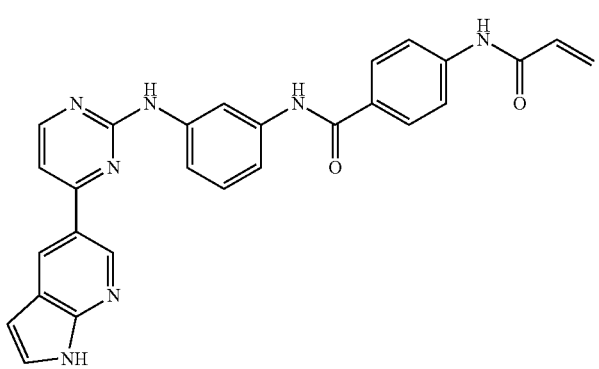 [SMILES: C=CC(=O)Nc1ccc(C(=O)Nc2cccc(Nc3nccc(-c4cnc5[nH]ccc5c4)n3)c2)cc1]

THZ-2-071-1 (meta-para)

TABLE 5-continued
IC$_{50}$ values in micromolars of compounds for certain kinase targets
| Structure | JNK1 | JNK2 | JNK3 | E50/A375 | CDK7 |
|---|---|---|---|---|---|
| 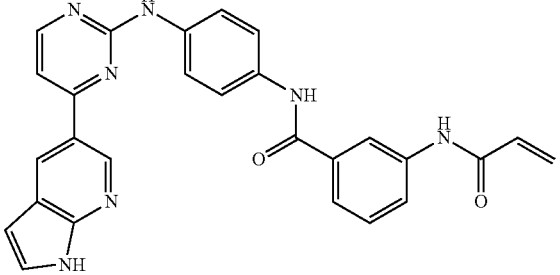<br>THZ-3-11-1 (para-meta) | | | 0.897 | | |
| 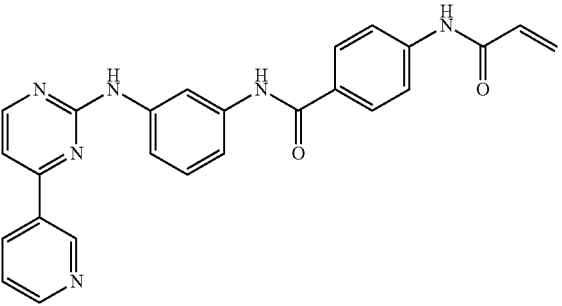 [SMILES: C=CC(=O)Nc1ccc(C(=O)Nc2cccc(Nc3nccc(-c4cccnc4)n3)c2)cc1]<br>ZG-9 (meta-para) | 1240 | 1720 | 184 | 5458 | |
| 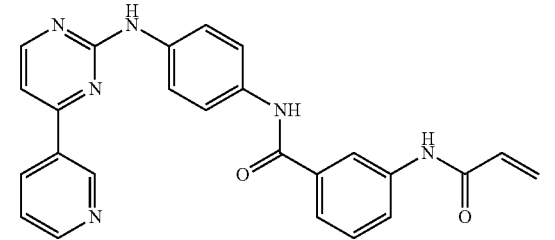 [SMILES: C=CC(=O)Nc1cccc(C(=O)Nc2ccc(Nc3nccc(-c4cccnc4)n3)cc2)c1]<br>JNK-IN-5 (para-meta) | 2.11 | 1.93 | 0.96 | 32 | |
| 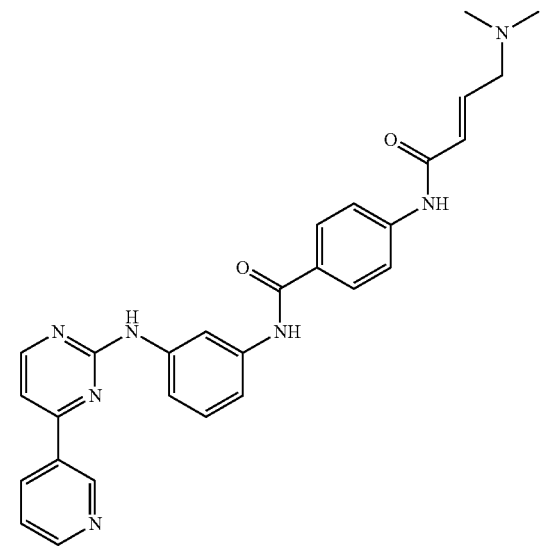 [SMILES: CN(C)C/C=C/C(=O)Nc1ccc(C(=O)Nc2cccc(Nc3nccc(-c4cccnc4)n3)c2)cc1]<br>ZG-10 (meta-para) | 809 | 1140 | 709 | 2400 | |

TABLE 5-continued
IC$_{50}$ values in micromolars of compounds for certain kinase targets
| Structure | JNK1 | JNK2 | JNK3 | E50/A375 | CDK7 |
|---|---|---|---|---|---|
| 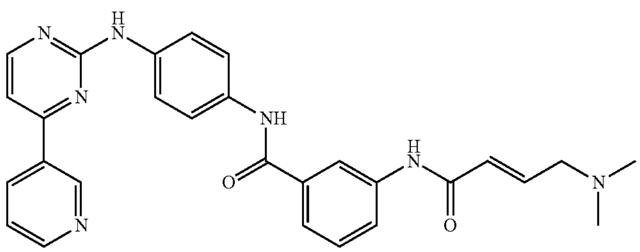 [SMILES: CN(C)C/C=C/C(=O)Nc1cccc(C(=O)Nc2ccc(Nc3nccc(-c4cccnc4)n3)cc2)c1] | 1.54 | 1.99 | 0.75 | 244 | |
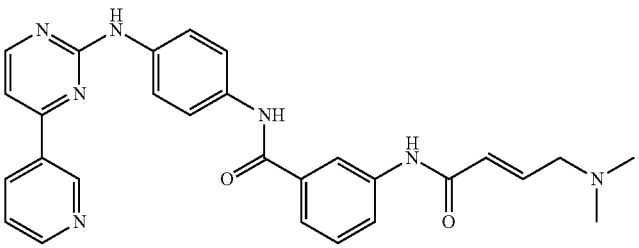
JNK-IN-7 (para-meta)
| | 7780 | 4230 | 7750 | | |
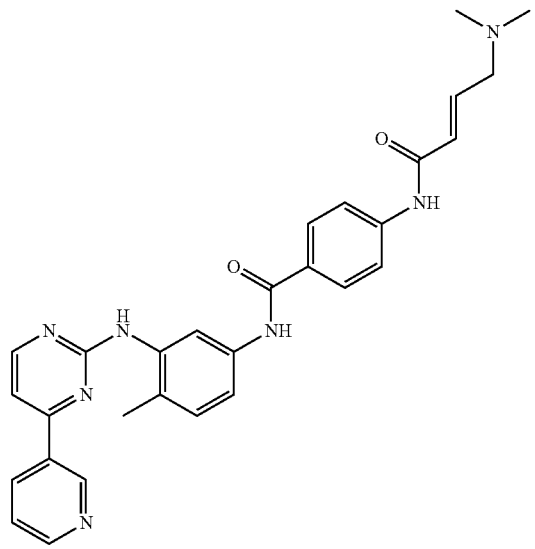 [SMILES: Cc1ccc(NC(=O)c2ccc(NC(=O)/C=C/CN(C)C)cc2)cc1Nc1nccc(-c2cccnc2)n1]
ZG-6 (meta-para)
| | 4.67 | 18.7 | <0.510 | 338 | |
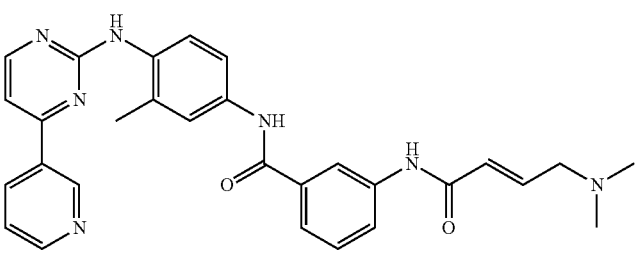 [SMILES: Cc1cc(NC(=O)c2cccc(NC(=O)/C=C/CN(C)C)c2)ccc1Nc1nccc(-c2cccnc2)n1]
JNK-IN-8 (para-meta)

TABLE 5-continued

IC₅₀ values in micromolars of compounds for certain kinase targets

| Structure | JNK1 | JNK2 | JNK3 | E50/A375 | CDK7 |
|---|---|---|---|---|---|
| 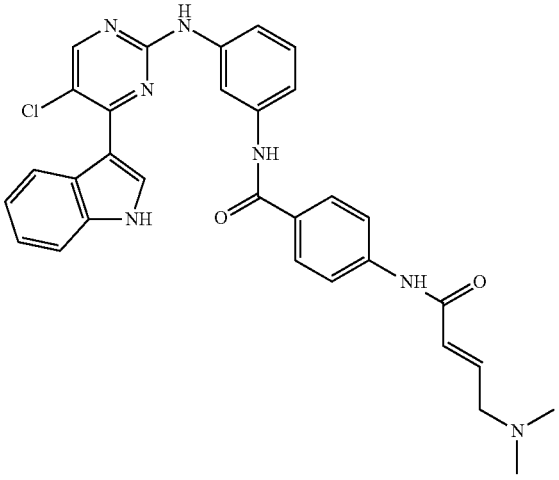 [SMILES: CN(C)C/C=C/C(=O)Nc1ccc(C(=O)Nc2cccc(Nc3ncc(Cl)c(-c4c[nH]c5ccccc45)n3)c2)cc1]<br>THZ-2-102-1 (meta-para) | 637 | 346 | 7110 | | |
| 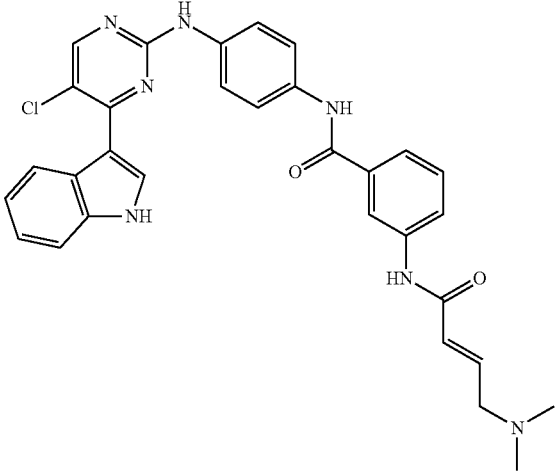 [SMILES: CN(C)C/C=C/C(=O)Nc1cccc(C(=O)Nc2ccc(Nc3ncc(Cl)c(-c4c[nH]c5ccccc45)n3)cc2)c1]<br>THZ-3-30-1 (para-meta) | 1.67 | 1.23 | 1.24 | | 0.0755 |

CONCLUSION

Molecular docking of JNK-IN-7 into the crystal structures of JNK3, provided a rational basis for structure-guided design of the appropriate linker-element that would serve to connect the phenylaminopyrimidine pharmacophore which is predicted to bind to the kinase-hinge segment with a reactive acrylamide moiety. It was discovered by the inventors of the present invention that the most critical feature to impart potent enzymatic and cellular JNK inhibition was for this linker segment to contain a 1,4-disposition of the dianiline moiety and a 1,3-disposition of terminal aminobenzoic acid moiety as exemplified by JNK-IN-7 and JNK-IN-8. A 2.97 Å co-structure between JNK-IN-7 and JNK3 fully corroborated the molecular modeling and demonstrated covalent bond formation with residue Cys 154 of JNK3. Extensive biochemical and cellular selectivity profiling allowed for identifying several additional kinase targets for JNK-IN-7 including IRAK1, MPSK1, NEK9, PIP3K3C, PIP4K2C, and PIP5K3. Interestingly most of these additional targets appear to require the acrylamide warhead to achieve efficient inhibition as they are not targeted by the non-acrylamide containing inhibitor JNK-IN-6. With the exception of IRAK1, these kinases do not appear to contain a reactive cysteine that is located in a similar position to Cys154 of JNK3. This suggests that JNK-IN-7 may use a different conformation to recognize these kinases and thereby access an alternative cysteine residue. Alternatively, JNK-IN-7 may form covalent adducts with reactive lysine residues. For example, the natural product inhibitor Wortmannin undergoes a Michael addition reaction with Lys833 of Pi3K, albeit with a different electrophilic moiety. It has been validated that JNK-IN-7 can indeed inhibit IRAK-1 dependent E3 ligase activity of pellino in cells albeit at higher concentrations (1-10 µM) and further optimization guided by the cell-based assay will be required to establish if more potent cellular inhibition of this target can be achieved (Goh et al., 2011). Two ways were discovered by the inventors of the present invention to further enhance the kinase selectivity of JNK-IN-7. The first was to introduce an ortho-methyl group which is analogous to the "flag" methyl group of imatinib or the ortho-methoxy group of the ALK inhibitor TAE684 (Galkin et al., 2007) and the polo-kinase inhibitor BI-2356 (Kothe et al., 2007). This modification was exemplified by JNK-IN-8, and the crystal structure of JNK-IN-7 predicts that this methyl group could possibly nestle into a small grove along the hinge segment between Asp150 and Ala151 of JNK3. The second was to replace the pyridine moiety with a geometrically more complex benzothiazol-2-yl acetonitrile moiety which was previously identified as a favorable pharmacophore for binding to the JNK ATP-site as exemplified by JNK-IN-12 (Gaillard et al., 2005). The functionality present in this portion of the inhibitor which is predicted to bind in proximity to the "gatekeeper" methionine provides a critical selectivity determinant for the inhibitors. For example, JNK-IN-11, which possesses a bulky 2-phenylpyrazolo[1,5-a]pyridine group, displays a dramatically broadened inhibition profile in both biochemical and cellular assays.

JNK-IN-12 appeared to bind to considerably more kinases based on the KiNativ technology relative to enzymatic or KinomeScan technology. Although there are several non overlapping targets detected by these different technologies, there may be cellular metabolism of the benzothiazol-2-yl acetonitrile moiety to yield species that bind to additional kinase targets. Further work will be required to establish whether the additional targets detected by KiNativ for JNK IN 7, JNK-IN-11, and JNK-IN-12 are indeed covalently modified and whether bona fide potent cellular inhibition is achieved.

Covalent inhibitors are typically designed by rational modification of scaffolds that are already potent non-covalent binders of the desired target protein. For example, the anilinoquinazoline scaffold provides a template for highly potent covalent and non covalent inhibitors of EGFR kinase (Smaill et al., 2000). A second approach is to start from relatively low affinity non-covalent binders and to allow covalent bond formation to drive affinity toward the desired target. For example, the pyrrolopyrimidine Rsk inhibitor CMK (Cohen et al., 2005) and the anilinopyrimidine T790M EGFR inhibitor WZ-4002 (Zhou et al., 2009) both gain approximately 100-fold potency for their respective targets by covalent bond formation. The covalent inhibitors described in this study fall into this second category of requiring covalent bond formation in order to achieve potent inhibition of JNK kinase activity. One major advantage of this second approach is that it is much easier to identify a relatively selective low affinity non-covalent scaffold as a starting point relative to a selective high affinity scaffold. The challenge with the second approach is that one has to discover a scaffold that will allow presentation of the electrophile with the ideal geometry to allow for covalent bond formation. This is especially true because the residence time for a low affinity non-covalent compound is typically short. As can be seen from the structure-activity relationship for JNK-IN-5 to 12, relatively minor changes can have dramatic consequences to the potency of inhibition. This is in sharp contrast to the general notion that a covalent inhibitor will always be exceptionally potent. Intracellularly there is a kinetic competition for modification of the desired target versus "off-targets" which maybe other proteins or engagement of cellular pathways that metabolize reactive electrophilies. In addition, proteins are continuously synthesized and degraded with varying kinetics which can allow for regeneration of unmodified protein. Therefore an effective covalent inhibitor must label its target protein rapidly relatively to competing labeling events and protein turn-over.

Two general approaches are favored to developing potent covalent inhibitors. The first is to generate small rationally designed libraries of electrophile modified inhibitors that can be used in cell-based screens to select for compounds with activity against the desired target. Simple molecular modeling based on known ATP-site recognition modes can be used to select where on the scaffold to modify with an electrophilic group. This approach was used to develop WZ-4002 a potent and selective inhibitor of the T790M "gatekeeper" mutation of EGFR. The disadvantage of this approach is that it requires considerable up-front synthetic effort and the cellular screening approach requires a relatively high efficiency inhibitor be present in the initial screening library. The second approach is to search for low affinity non-covalent scaffolds typically using a biochemical screening approach which allows for screening at high concentrations and then using structure-based drug design to prepare a small library of covalent inhibitors for optimization. The advantage of this approach is that there is large collection of known kinase inhibitors with known kinase selectivity profiles. The disadvantage of this approach is that it can be difficult to predict which scaffold allows for the correct trajectory for the electrophile relative to the protein nucleophile. Use of these and other strategies may provide an efficient means to generate first-in-class covalent inhibitors for the large number of kinases containing suitable cysteine and possibly lysine residues.

It was demonstrated that the KiNativ profiling methodology is a powerful tool for discovering and guiding the optimization of new covalent inhibitors. First it allows for an unbiased screen of the majority of available ATP-competitive targets in a cellular system of choice. Second by assessing selectivity in a cellular context, the native kinase conformation is accessed and the structure-activity relationships appear to correlate well with functional cellular assays. JNK-IN-8 achieves potent, selective, covalent, and irreversible inhibition of JNK in cells that reaches completion after approximately 3 hours (FIGS. 16A and 16B). It may be recommended that JNK-IN-8 be used at concentrations of approximately 1.0 µM and that preincubation time be approximately 3 h to inhibit cellular JNK activity.

REFERENCES CITED (1) Chang et al., Nature (2010) 410:37-40.
(2) Johnson et al., Science (2002) 298:1911-1912.
(3) Pearson et al., Endocr. Rev. (2001) 22:153-183.
(4) Raman et al., Oncogene. (2007) 26:3100-3112.
(5) Derijard et al., Cell (1994) 76:1025-1037.
(6) Pulverer et al., Nature (1991) 353:670-673.
(7) Kallunki et al., Genes Dev. (1994) 8:2996-3007.
(8) Sluss et al., Mol. Cell. Biol. (1994) 14:8376-8384.
(9) Mohit et al., Neuron (1995) 14:67-78
(10) Kyriakis et al., Physiol. Rev. (2001) 81:807-869.
(11) Zhang et al., Expert Opin. Invest. Drugs (2005) 14:1373-1383.
(12) Hunot et al., Proc. Natl. Acad. Sci. USA (2004) 101: 665-670.
(13) Aguirre et al., J. Biol. Chem. (2000) 275:9047-9054.
(14) Aguirre et al., J. Biol. Chem. (2002) 277:1531-1537.
(15) Hirosumi et al., Nature (2002) 420:333-336.
(16) Sabio et al., Trends Biochem. Sci. (2010) 35:490-496.
(17) Han et al., Arthritis Rheum. (2002) 46:818-823.
(18) Wong, Curr. Opin. Pharmacol. (2005) 5:264-271.
(19) Pelaia et al., J. Cell. Physiol. (2005) 202:642-653.

(20) Blease et al., *Expert Opin. Emerging Drugs* (2003) 8:71-81.
(21) Chialda et al., *Respir. Res.* (2005) 6:36-54.
(22) Osto et al., *Circulation* (2008) 118:2073-2080.
(23) Philip et al., *Mini-Reviews in Medicinal Chemistry* (2008) 8:755-766.
(24) Bennett et al., *Proc. Natl. Acad. Sci. USA* (2001) 98:13681.
(25) Bain et al., *Biochem. J.* (2007) 408:297-315.
(26) Inesta-Vaquera et al., *Biochemical and Biophysical Research Communications* (2010) 399:84-90.
(27) Gaillard et al., *J. Med. Chem.* (2005) 48:4596-4607.
(28) Cohen et al., *Science* (2005) 308:1318-1321.
(29) Nguyen, *Anti-Cancer Agents in Medicinal Chemistry* (2008) 8:710-716.
(30) Zhou et al., *Chemistry & Biology* (2010) 17:285-295.
(31) Schirmer et al., *Proc. Natl. Acad. Sci. USA* (2006) 103:4234-4239.
(32) Henise et al., *J. Med. Chem.* (2011) 54:4133-4146.
(33) Singh et al., *Current Opinion in Chemical Biology* (2010) 14:475-480.
(34) Zhang et al., *Cancer* (2009) 9:28-39.
(35) Liu et al., *Nature Chemical Biology* (2006) 2:358-364.
(36) Mol et al., *J. Biol. Chem.* (2004) 279:31655-31663
(37) Kamenecka et al., *J. Med. Chem.* (2010) 53:419-431.
(38) Alam et al., *J. Bioorg. Med. Chem. Lett.* (2007) 17:3463.
(39) Atwell et al., *J. Biol. Chem.* (2004) 279:55827-55832.
(40) Zimmwermann et al., *Bioorg. Med. Chem. Lett.* (1996) 6:1221-1226.
(41) Robers et al., *Anal. Biochem.* (2008) 372:189-197.
(42) Carlson et al., *J. Biomol. Screen.* (2009) 14:121-132.
(43) Stebbins et al., *Proc. Natl. Acad. Sci. USA* (2008) 105:16809-16813.
(44) Millard et al., *Nature Methods* (2011) 8:487-492.
(45) Hendriks et al., *Bioinformatics* (2010) 26:432-433.
(46) Patricelli et al., *Biochemistry* (2007) 46:350-358.
(47) Goh et al., Identification of the protein kinases that activate the E3 ubiquitin ligase Pellino 1 in the innate immune system. *Biochemical Journal* (published as Immediate Publication on Oct. 18, 2011).
(48) Crocker et al., *ACS Chem. Neurosci.* (2011) 2:207-212.
(49) Fabian et al., *Nature Biotechnology* (2005) 23:329-336.
(50) Goldstein et al., *Nat. Rev. Drug Discov.* (2008) 7:391-397.
(51) Leproult et al., *J. Med. Chem.* (2011) 54:1347-1355.
(52) Galkin et al., *Proc. Natl. Acad. Sci. USA* (2007) 104:270-275.
(53) Kothe et al., *Chem. Biol. Drug Des.* (2007) 70:540-546.
(54) Smaill et al., *J. Med. Chem.* (2000) 43:1380-1397.
(55) Zhou et al., *Nature* (2009) 462:1070-1074.
(56) Karaman et al., *Nat. Biotechnol.* (2008) 26:127-132.

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

All publications, including but not limited to journal articles, books, patents, and patent applications, cited in this specification are herein incorporated by reference as if each individual publication were specifically and individually indicated to be incorporated by reference herein as though fully set forth.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:
1. A compound of Formula (I):

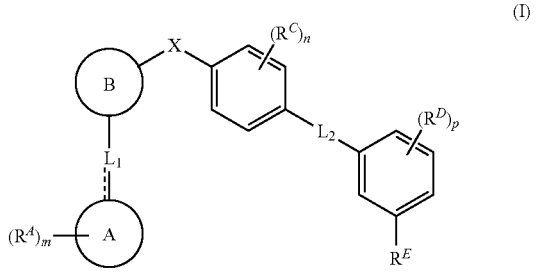

or a pharmaceutically acceptable salt thereof;
wherein:
Ring A is a carbocyclic, heterocyclic, heteroaryl, or aryl ring;
each instance of $R^A$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A1})_2$, and —$SR^{A1}$, wherein each occurrence of $R^{A1}$ is independently hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{A1}$ groups are joined to form an optionally substituted heterocyclic ring;
m is 0, 1, 2, 3, or 4;
Ring B is a group of the formula:

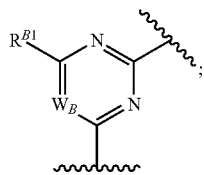

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1a}$, —$N(R^{B1a})_2$, and —$SR^{B1a}$, wherein each occurrence of $R^{B1a}$ is independently hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two $R^{B1a}$ groups are joined to form an optionally substituted heterocyclic ring;
$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B2a}$, —$N(R^{B2a})_2$, and —$SR^{B2a}$, wherein each occurrence of $R^{B2a}$ is independently hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two $R^{B2a}$ groups are joined to form an optionally substituted heterocyclic ring;
or $R^{B1}$ and $R^{B2}$ are joined to form an optionally substituted carbocyclyl, optionally substituted heterocyclyl, optionally substituted heteroaryl, or optionally substituted aryl ring;
$L_1$ is =$C(R^{L1a})$—, —O—, —S—, —$NR^{L1b}C$(=O)—, —C(=O)$NR^{L1b}$—, —SC(=O)—, —C(=O)S—, —OC(=O)—, —C(=O)O—, —$NR^{L1b}$C(=S)—, —C(=S)$NR^{L1b}$—, trans-CH=CH—, cis-CH=CH—, —S(=O)$_2$O—, —OS(=O)$_2$—, —S(=O)$_2NR^{L1b}$—, —$NR^{L1b}$S(=O)$_2$—, or an optionally substituted $C_{2-4}$ hydrocarbon chain, optionally wherein on methylene unit of the hydrocarbon chain is replaced with =$C(R^{L1a})$—, —O—, —S—, —$NR^{L1b}$—, —$NR^{L1b}$C(=O)—, —C(=O)$NR^{L1b}$—, —SC(=O)—, —C(=O)S—, —OC(=O)—, —C(=O)O—, —$NR^{L1b}$C(=S)—, —C(=S)$NR^{L1b}$—, trans-CH=CH—, cis-CH=CH—, —S(=O)$_2$O—, —OS(=O)$_2$—, —S(=O)$_2NR^{L1b}$—, or —$NR^{L1b}$S(=O)$_2$—, wherein $R^{L1a}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, or —$NO_2$, and $R^{L1b}$ is hydrogen, $C_{1-6}$ alkyl, or a nitrogen protecting group;
═ represents a single or double bond;
X is an optionally substituted $C_{1-4}$ hydrocarbon chain, optionally wherein one or more carbon units of the hydrocarbon chain is replaced with —O—, —S—, or —$NR^X$—, wherein $R^X$ is hydrogen, $C_{1-6}$ alkyl, or a nitrogen protecting group;
$L_2$ is a bond, —O—, —S—, —$NR^{L2a}$—, —$NR^{L2a}$C(=O)—, —C(=O)$NR^{L2a}$—, —SC(=O)—, —C(=O)S—, —OC(=O)—, —C(=O)O—, —$NR^{L2a}$C(=S)—, —C(=S)$NR^{L2a}$—, trans-$CR^{L2b}$=$CR^{L2b}$—, cis-$CR^{L2b}$=$CR^{L2b}$—, —C≡C—, —OC($R^{L2b}$)$_2$—, —C($R^{L2b}$)$_2$O—, —$NR^{L2a}$C($R^{L2b}$)$_2$—, —C($R^{L2b}$)$_2NR^{L2a}$—, —SC($R^{L2b}$)$_2$—, —C($R^{L2b}$)$_2$S—, —S(=O)$_2$O—, —OS(=O)$_2$—, —S(=O)$_2NR^{L2a}$—, —$NR^{L2a}$S(=O)$_2$—, or an optionally substituted $C_{1-4}$ hydrocarbon chain, optionally wherein one or more carbon units of the hydrocarbon chain is replaced with —O—, —S—, —$NR^{L2a}NR^{L2a}$C(=O)—, —C(=O)$NR^{L2a}$—, —SC(=O)—, —C(=O)S—, —OC(=O)—, —C(=O)O—, —$NR^{L2a}$C(=S)—, —C(=S)$NR^{L2a}$—, trans-$CR^{L2b}$=$CR^{L2b}$—, cis- $CR^{L2b}=CR^{L2b}-$, $-C\equiv C-$, $-S(=O)_2O-$, $-OS(=O)_2-$, $-S(=O)_2NR^{L2a}-$, or $-NR^{L2a}S(=O)_2-$, wherein $R^{L2a}$ is hydrogen, $C_{1-6}$ alkyl, or a nitrogen protecting group, and wherein each occurrence of $R^{L2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L2b}$ groups are joined to form an optionally substituted carbocyclic or optionally substituted heterocyclic ring;

each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C1}$, $-N(R^{C1})_2$, and $-SR^{C1}$, wherein each occurrence of $R^{C1}$ is independently hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{C1}$ groups are joined to form an optionally substituted heterocyclic ring;

n is 0, 1, 2, 3, or 4;

each instance of $R^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$, wherein each occurrence of $R^{D1}$ is independently hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{D1}$ groups are joined to form an optionally substituted heterocyclic ring;

p is 0, 1, 2, 3, or 4;

$R^E$ is a group of the formula:

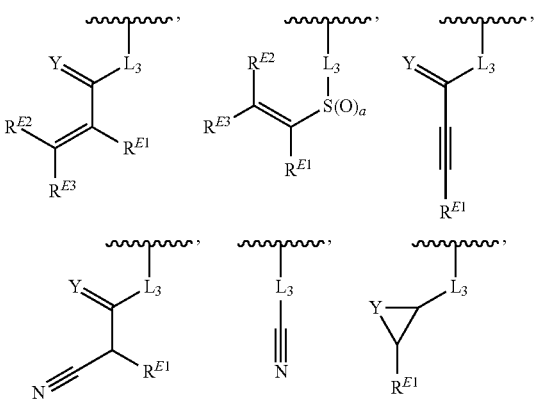

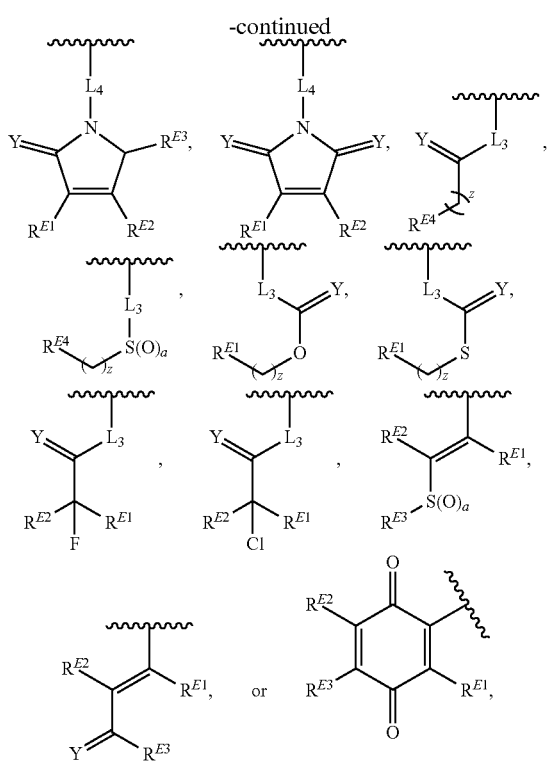

wherein:

$L_3$ is a bond, $-O-$, $-S-$, $-NR^{L3a}-$, $-NR^{L3a}C(=O)-$, $-C(=O)NR^{L3a}-$, $-SC(=O)-$, $-C(=O)S-$, $-OC(=O)-$, $-C(=O)O-$, $-NR^{L3a}C(=S)-$, $-C(=S)NR^{L3a}-$, trans-$CR^{L3b}=CR^{L3b}-$, cis-$CR^{L3b}=CR^{L3b}-$, $-C\equiv C-$, $-OC(R^{L3b})_2-$, $-C(R^{L3b})_2O-$, $-NR^{L3a}C(R^{L3b})_2-$, $-C(R^{L3b})_2NR^{L3a}-$, $-SC(R^{L3b})_2-$, $-S(=O)_2O-$, $-OS(=O)_2-$, $-S(=O)_2NR^{L3a}-$, $-NR^{L3a}S(=O)_2-$, or an optionally substituted $C_{1-4}$ hydrocarbon chain, optionally wherein one or more carbon units of the hydrocarbon chain is replaced with $-O-$, $-S-$, $-NR^{L3a}-$, $-NR^{L3a}C(=O)-$, $-C(=O)NR^{L3a}-$, $-SC(=O)-$, $-C(=O)S-$, $-OC(=O)-$, $-C(=O)O-$, $-NR^{L3a}C(=S)-$, $-C(=S)NR^{L3a}-$, trans-$CR^{L3b}=CR^{L3b}-$, cis-$CR^{L3b}=CR^{L3b}-$, $-C\equiv C-$, $-S(=O)_2O-$, $-OS(=O)_2-$, $-S(=O)_2NR^{L3a}-$, or $-NR^{L3a}S(=O)_2-$, wherein $R^{L3a}$ is hydrogen, $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L_4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-CH_2OR^{E1a}$, $-CH_2N(R^{E1a})_2$, $-CH_2SR^{E1a}$, $-OR^{E1a}$, $-N(R^{E1a})_2$, and $-SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of $R^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$ or $R^{E2}$ and $R^{E3}$ or $R^{E1}$ and $R^{E2}$ are joined to form an optionally substituted carbocyclic or optionally substituted heterocyclic ring;

$R^{E4}$ is a leaving group;

Y is O, S, or NR$^{E5}$, wherein $R^{E5}$ is hydrogen, C$_{1-6}$ alkyl, or a nitrogen protecting group;

a is 1 or 2; and z is 0, 1, 2, 3, 4, 5, or 6.

2. The compound of claim 1, wherein L$_1$ is the group =C(R$^{L1a}$)— attached to Ring A by the double bond, and attached to Ring B by the single bond.

3. The compound of claim 1, wherein

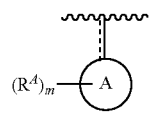

is of the formula:

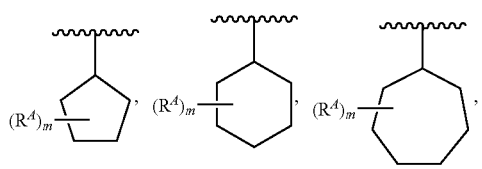

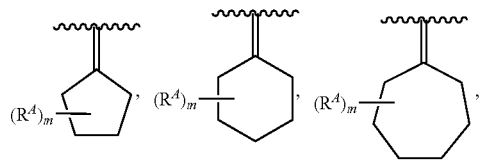

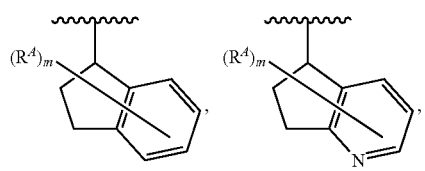

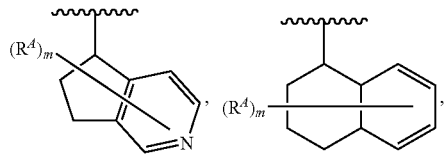

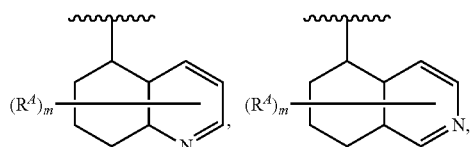

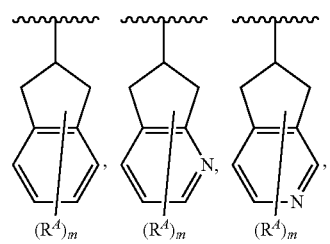

4. The compound of claim 1, wherein

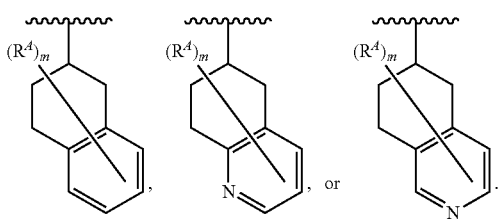

is of the formula:

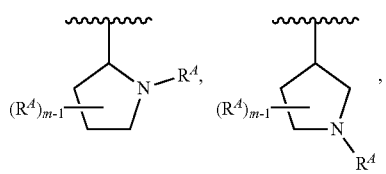

-continued
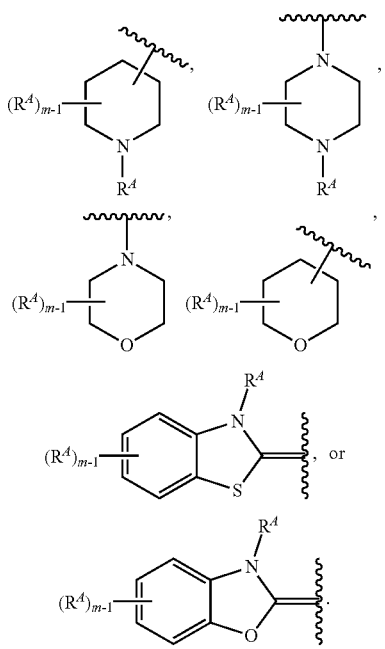
5. The compound of claim 1, wherein
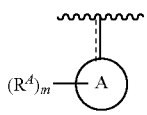
is of the formula:
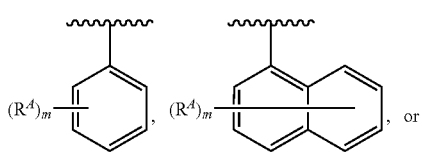
6. The compound of claim 1, wherein
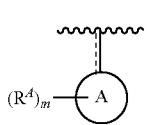
is of the formula:
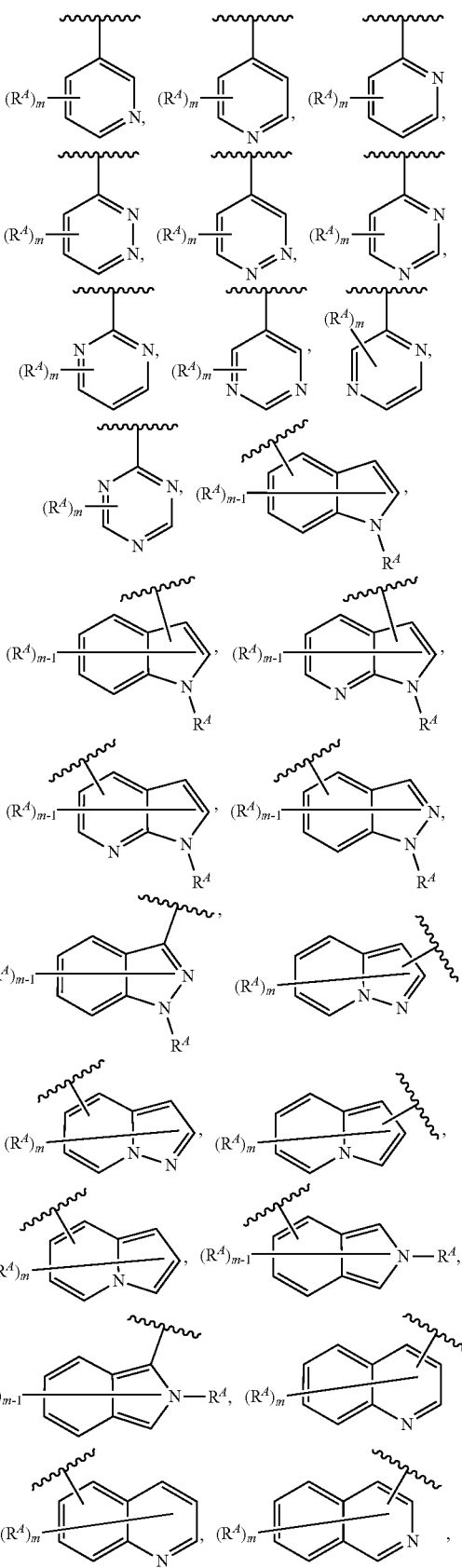

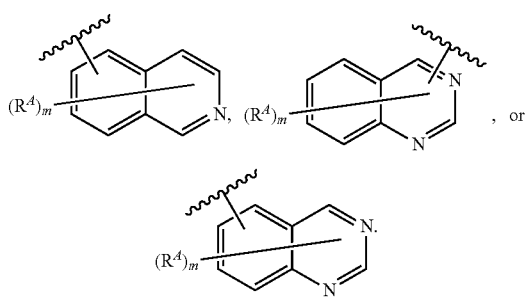

7. The compound of claim 1, wherein $W_B$ is $CR^{B2}$; and Ring B is a group of formula:

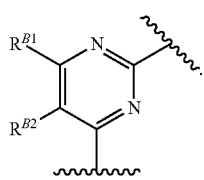

8. The compound of claim 1, wherein X is —$NR^X$—.

9. The compound of claim 1, wherein $L_2$ is —$NR^{L2a}C(=O)$—.

10. The compound of claim 1, wherein $R^E$ is a group of formula:

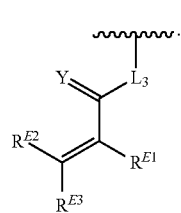

11. The compound of claim 10, wherein Y is O; $L_3$ is —$NR^{L3a}$—; $R^{E1}$ is hydrogen; $R^{E2}$ is hydrogen; and $R^{E3}$ is —$CH_2N(R^{E3a})_2$.

12. The compound of claim 1, wherein the compound is of formula:

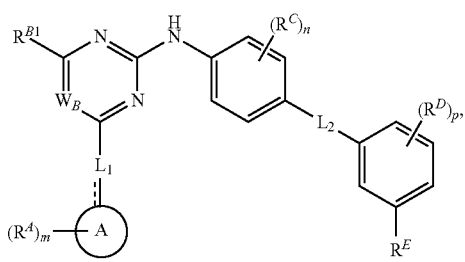

or a pharmaceutically acceptable salt thereof.

13. The compound of claim 1, wherein the compound is of formula:

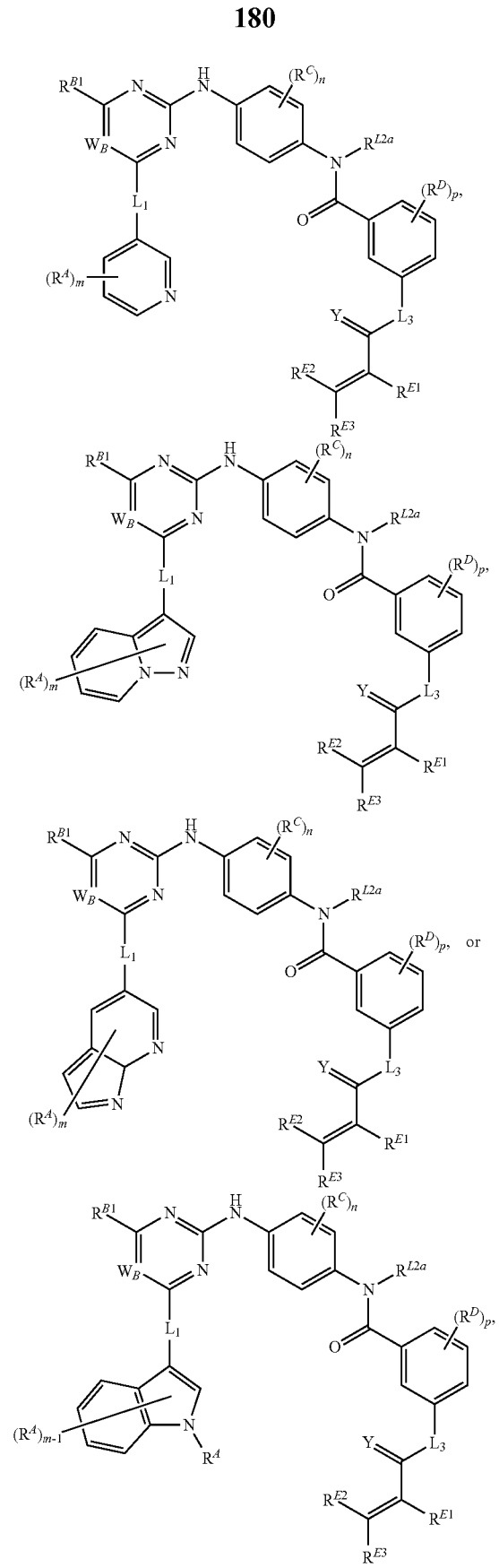

or a pharmaceutically acceptable salt thereof.

14. The compound of claim 1, wherein the compound is of formula:

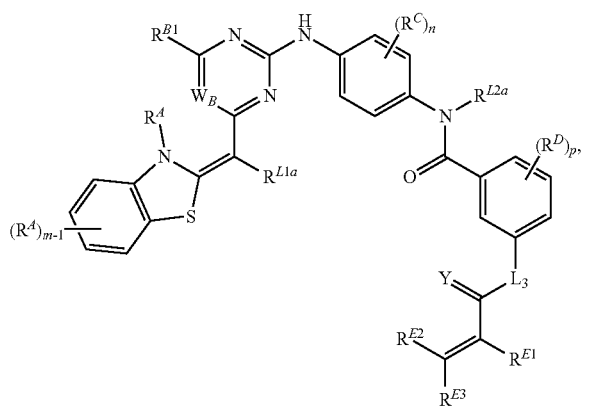

or a pharmaceutically acceptable salt thereof.

15. The compound of claim 1, wherein the compound is of formula:

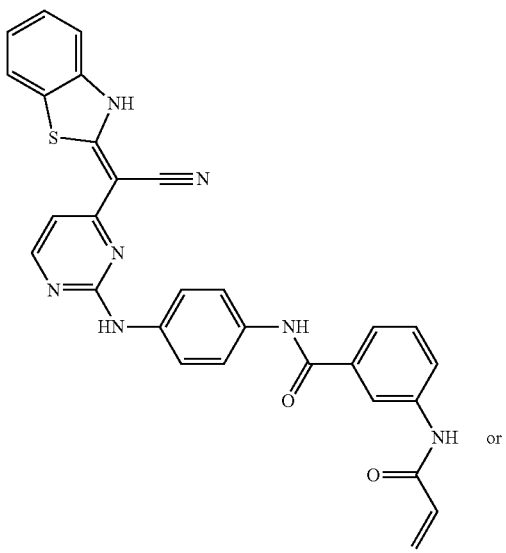

(THZ-3-06-1)

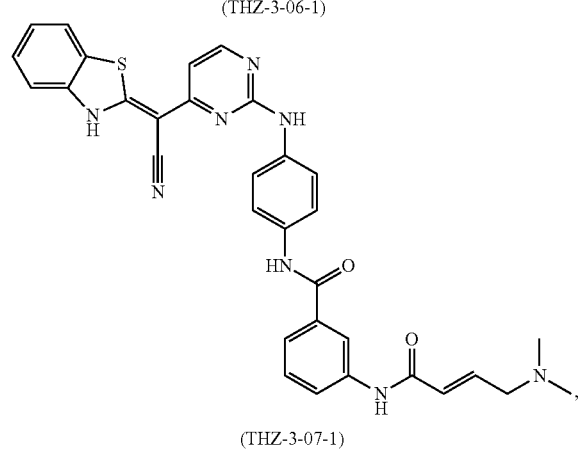

(THZ-3-07-1)

or a pharmaceutically acceptable salt thereof.

16. A pharmaceutical composition comprising a compound of claim 1, or a pharmaceutically acceptable salt thereof, and a pharmaceutically acceptable excipient.

17. A method of treating a proliferative disease, neurodegenerative disease, stroke, inflammatory disease, or metabolic disorder comprising administering to a subject in need thereof an effective amount of a compound of claim 1, or a pharmaceutically acceptable salt thereof.

18. A method of screening a library of compounds of claim 1 to identify one or more compounds that are useful in the treatment of a proliferative disease in a subject, the method comprising:

providing at least two different compounds of claim 1, or pharmaceutically acceptable salts thereof; and performing at least one assay using the different compounds, or pharmaceutically acceptable salts thereof, to detect one or more characteristics associated with the proliferative disease.

19. A kit comprising:

a container comprising a compound of claim 1, or a pharmaceutically acceptable salt thereof; and instructions for administering to a subject the compound, or the pharmaceutically acceptable salt thereof.

20. The compound of claim 1, wherein Ring A is a monocyclic or bicyclic, heteroaryl ring.

21. The compound of claim 1, wherein

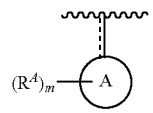

is of the formula:

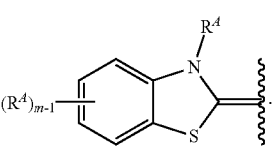

22. The compound of claim 1, wherein each instance of $R^A$ is independently hydrogen, halogen, or optionally substituted alkyl.

23. The compound of claim 7, wherein $R^{B1}$ is hydrogen, halogen, or optionally substituted alkyl; and $R^{B2}$ is hydrogen, halogen, or optionally substituted alkyl.

24. The compound of claim 1, wherein $L_2$ is —C(=O)NR$^{L2a}$—.

25. The compound of claim 1, wherein each instance of $R^C$ is independently hydrogen, halogen, or optionally substituted alkyl.

26. The compound of claim 1, wherein each instance of $R^D$ is independently hydrogen, halogen, or optionally substituted alkyl.

27. The compound of claim 10, wherein Y is O; $L_3$ is —NR$^{L3a}$—; and each of $R^{E1}$, $R^{E2}$, and $R^{E3}$ is hydrogen.

28. The compound of claim 1, wherein the compound is of formula:

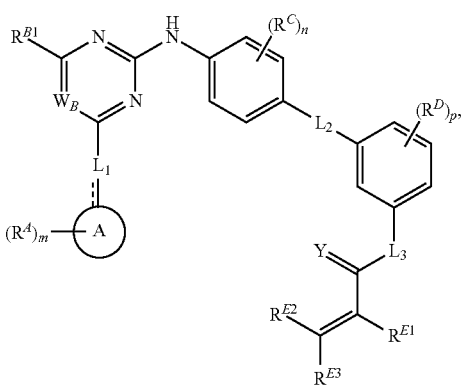

or a pharmaceutically acceptable salt thereof.

29. The compound of claim 1, wherein the compound is of formula:

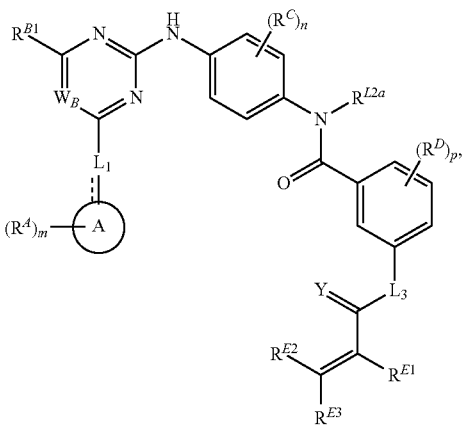

or a pharmaceutically acceptable salt thereof.

30. The compound of claim 1, wherein Ring A is a monocyclic or bicyclic, heterocyclic ring.

31. The compound of claim 2, wherein Ring A is a monocyclic or bicyclic, heteroaryl ring.

32. The compound of claim 2, wherein Ring A is a monocyclic or bicyclic, heterocyclic ring.

33. The method of claim 17, wherein the method is a method of treating a proliferative disease.

34. The method of claim 33, wherein the proliferative disease is cancer.

35. The method of claim 33, wherein the proliferative disease is melanoma, lung cancer, cervical cancer, or kidney cancer.

36. The method of claim 17, wherein the method is a method of treating a neurodegenerative disease, wherein the neurodegenerative disease is Parkinson's disease or Alzheimer's disease.

37. The method of claim 17, wherein the method is a method of treating an inflammatory disease, wherein the inflammatory disease is rheumatoid arthritis.

38. The method of claim 17, wherein the method is a method of treating a metabolic disorder, wherein the metabolic disorder is diabetes.

39. The method of claim 17, wherein the compound is of formula:

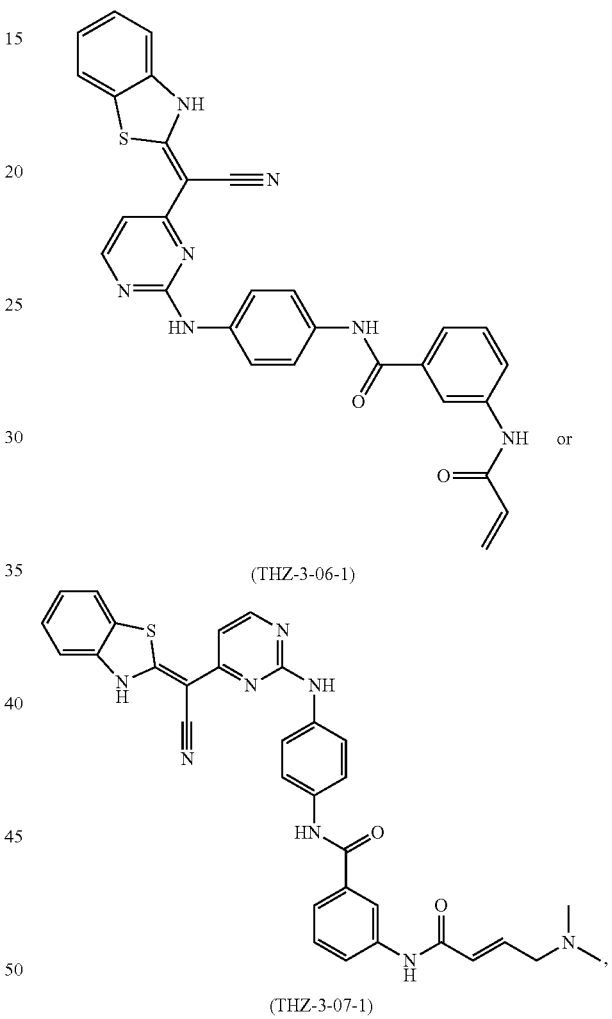

or a pharmaceutically acceptable salt thereof.

* * * * *

UNITED STATES PATENT AND TRADEMARK OFFICE
CERTIFICATE OF CORRECTION

PATENT NO. : 10,144,730 B2
APPLICATION NO. : 15/188545
DATED : December 4, 2018
INVENTOR(S) : Gray et al.

It is certified that error appears in the above-identified patent and that said Letters Patent is hereby corrected as shown below:

In the Claims

In Claim 1, at Column 172, Line 32, the text: "on methylene" should be replaced with: --one methylene--.

In Claim 3, at Column 176, Lines 20-25, the formula should read:

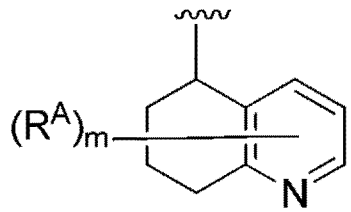

In Claim 3, at Column 176, Lines 20-25, the formula should read:

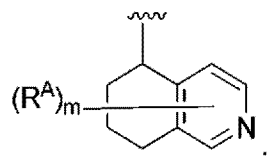

In Claim 4, at Column 177, Lines 10-15, the formula should read:

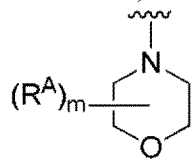

Signed and Sealed this
Thirty-first Day of December, 2019

Andrei Iancu
*Director of the United States Patent and Trademark Office*

In Claim 4, at Column 177, Lines 10-15, the formula should read:
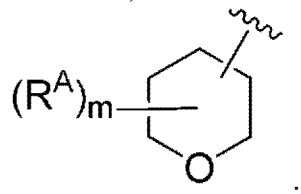
.